US005889174A

United States Patent [19]
Warren et al.

[11] Patent Number: 5,889,174
[45] Date of Patent: Mar. 30, 1999

[54] NUCLEOTIDE SEQUENCES ENCODING PESTICIDAL PROTEINS

[75] Inventors: Gregory W. Warren; Michael G. Koziel, both of Cary; Martha A. Mullins, Raleigh; Gordon J. Nye, Apex; Brian Carr; Nalini M. Desai, both of Cary; Kristy Kostichka; Juan J. Estruch, both of Durham, all of N.C.

[73] Assignee: Novartis Finance Corporation, New York, N.Y.

[21] Appl. No.: 470,567

[22] Filed: Jun. 6, 1995

Related U.S. Application Data

[60] Division of Ser. No. 463,483, Jun. 5, 1995, which is a continuation-in-part of Ser. No. 314,594, Sep. 28, 1994, abandoned, which is a continuation-in-part of Ser. No. 218,018, Mar. 23, 1994, abandoned, which is a continuation-in-part of Ser. No. 37,057, Mar. 25, 1993, abandoned.

[51] Int. Cl.$^6$ ............................ C12N 15/31; C12P 21/02; C07K 14/32
[52] U.S. Cl. ...................... 536/23.71; 436/69.1; 536/23.7
[58] Field of Search .......................... 435/69.1; 536/23.7, 536/23.71

[56] References Cited

U.S. PATENT DOCUMENTS

| | | | |
|---|---|---|---|
| 3,632,747 | 1/1972 | Satohiro et al. | 424/93.46 |
| 3,651,215 | 3/1972 | Satohiro et al. | 424/93.46 |
| 4,996,155 | 2/1991 | Sick et al. | 435/252.3 X |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO90/13651 | 11/1970 | WIPO . |
| WO88/08880 | 11/1988 | WIPO . |
| WO91/16432 | 10/1991 | WIPO . |
| WO91/16434 | 10/1991 | WIPO . |
| WO 94/21795 | 9/1994 | WIPO . |

OTHER PUBLICATIONS

Bernier et al., "*Bacillus thuringiensis* Strains A20 and A29 and Insecticidal Compounds Therefrom, and Compositions Containing These Compounds", Abstract No. 227249, *New Zealand Patent Office Journal*, 80(6):798, (1988).
Hofte, H., et al., "Insecticidal Crystal Proteins of *Bacillus thruingiensis*", *Microbiological Reviews*, 53(2):242–255 (1989).
Koziel, M.G., et al., "Field Performance of Elite Tansgenic Maize Plants Expressing an Insecticidal Protein Derived from *Bacillus thuringiensis*", *Bio/Technology*, 11:194–200 (1993).
Krieg, A., "Thuricin, a Bacteriocin Produced by *Bacillus thuringiensis*", *J. Invert. Path.*, 15:291 (1970).
Krieg, A., "Concerning Alpha–exotoxin Produced by Vegetative Cells of *Bacillus thuringiensis* and *Bacillus cereus*", *J. Invert. Path.*, 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).
Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.
Myers, P.S., et al., "Localization of a Mosquito–Larval Toxin of *Bacillus sphaericus* 1593", *Appl. Environ. Microbiol.*, 39(1):1205–1211 (1980).
Porter, A.G., et al., "Mosquitocidal Toxins of Bacilli and Their Genetic Manipulation for Effective Biological Control of Mosquitoes", *Microbiological Reviews*, 57(4):838–861 (1993).
Sekar, V., "The Insecticidal Crystal Protein Gene is Expressed in Vegetative Cells of *Bacillus thuringiensis* var. temebropmos", *Current Microbiology*, 17:347–349.
Shivakumar, A.G., et al., Abstract, :Cloned Crystal Protein Genes Express Vegetatively in *Bacillus subtilis*, *Plasmid*, 16(3):230 (1986).
Thanabalu, T., et al., "Proteolytic Processing of the Mosquitocidal Toxin from *Bacillus sphaericus* SSII–1", *J. Bacteriol.*, 174(15):5051–5056 (1992).
Yoshisue, H., et al., "Effects of *Bacillus thuringiensis* var. israelensis 20 kDa Protein on Production of the Bti 130–kDa Crystal Protein in *Escherichia coli*", *Bioscience, Biotechnology, and Biochemistry*, 56(9):1429–1433 (1992).
Arellano, A., et al., "Evidence of a New *Bacillus thuriengiensis* Toxin Active Against the Australian Sheep Blowfly *Lucilla cuprina*", *Proceedings and Abstracts of the 5th International Colloquium on Invertebrate Pathology and Microbial Control, Adelaide, Austrailia*, 20–24 Aug., 1990, p. 291.
Beecher, Douglas J., et al., "A Novel Bicomponent Hemolysin from *Bacillus cereus*", *Inspection and Immunity*, 58(7):2220–2227 (1990).
Faust, R.M., "Bacterial Diseases", In: *Insect Diseases*, G. Cantwell, ed., Marcel Dekker, NY 1974, pp. 90–102.
Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.
Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

(List continued on next page.)

Primary Examiner—Johnny F. Railey, II
Attorney, Agent, or Firm—Gary M. Pace; J. T. Meigs

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

11 Claims, 1 Drawing Sheet

OTHER PUBLICATIONS

Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", *Can. J. Zool.*, 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).

Jellis et al., "*Bacillus thuringiensis* δ–Endotoxin Variants and Insecticidal Compositions", Abstract No. 228108, *New Zealand Patent Office Journal*, 81(3):359, (1992).

Schurter et al., "Genetic Manifpulation of *B.thuringiensis* and *B.cereus* Vectors and Insecticidal Composition", Abstract No. 229191, *New Zealand Patent Office Journal*, 81(3):363, (1992).

Tayabali et al., "Semiautomated Quantification of Cytotoxic Damage Induced in Cultured Insect Cells Exposed to Commercial *Bacillus thuringiensis* Biopesticides", *Journal of Applied Toxicology*, 15(5): 365–373 (1995).

Thanabalu et al., "Cytotoxicity and ADP–Ribosylating Activity of the Mosquitocidal Toxin from *Bacillus sphaericus* SSII–1: Possible Roles of the 27– and 70–Kilodalton Peptides", *Journal of Bacteriology*, 175(8): 2314–2320 (1993).

Vaithlingam et al., "Anti–Coleopteran Toxin and Gene", Abstract No. 226442, *New Zealand Patent Office Journal*, 80(7):931, (1991).

Wahisaka et al., "*Bacillus thuringiensis* Mutant and Bacterial Insecticide", Abstract No. 199725, *New Zealand Patent Office Journal*, (1982).

Walther et al., "Analysis of Mosquito Larvicidal Potential Exhibited by Vegetative Cells of *Bacillus thuringiensis* subsp. israelensis", *Applied and Environmental Microbiology*, 52(4): 650–653 (1986).

Ward et al., "*Bacillus thuringiensis* var. israelensis δ–Endotoxin Cloning and Expression of the Toxin in Sporogenic and Asporogenic Strains of *Bacillus subtilis*", *Journal of Molecular Biology*, 191(1): 13–22 (1986).

Chambers et al., Isolation and Characterization of a Novel Isecticidal Crystal Protein Gene from *Bacillus thuringiensis* subsp. aizawai, Journal of Bacteriology, vol. 173, No. 13, Jul. 1991, pp. 3966–3976.

Gleave, et al., Screening by Poymerase Chain Reaction of *Bacillus thuringiensis* Serotypes for the Presence of cryV–like Insecticidal Protein Genes and Characterization of a cryV Gene Cloned from *B. thuringiensis* subsp. kurstaki, Applied and Environmental Microbiology, vol. 59, No. 5, May 1993, pp. 1683–168.

Kostichka, et al. Cloning of a cryV–type Isecticidal Protein Gene from *Bacillus thuringiensis*: the cry–V encoded Protein Is Expressed Early in Stationary Phase, Journal of Bacteriology, vol. 178, No. 7, Apr. 1996, pp. 2141–2144.

Mettus et al., Applied and Environmental Microbiology 56(4):1128–1134 (1990).

Sekar et al., Proc. Natl. Acad. Sci. USA 84:7036–7040 (1987).

Figure 1

Characterization of pCIB6022

| | Activity vs. WCRW |
|---|---|
| pCIB6022 (VIP2A(a) — VIP1A(a); sites C, X, S, RI, B, RV, C) | +++ |
| pCIB6203 | — |
| pCIB6023 | — |
| pCIB6206 | — |
| pCIB6024 | — |

Functional Complementation of VIP Clones

| | |
|---|---|
| pCIB6203 + pCIB6023 | +++ |
| pCIB6203 + pCIB6206 | +++ |
| pCIB6023 + pCIB6024 | +++ |

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 6049 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: CDS
( B ) LOCATION: 1082..2467
( D ) OTHER INFORMATION: /product="VIP2A(a)"

( i x ) FEATURE:
( A ) NAME/KEY: misc_feature
( B ) LOCATION: 2475..5126
( D ) OTHER INFORMATION: /note= "Coding sequence for the 100 kd VIP1A(a) protein. This coding sequence is repeated in SEQ ID NO:4 and translated separately."

( x i ) SEQUENCE DESCRIPTION: SEQ ID NO:1:

ATCGATACAA TGTTGTTTTA CTTAGACCGG TAGTCTCTGT AATTTGTTTA ATGCTATATT 60

CTTTACTTTG ATACATTTTA ATAGCCATTT CAACCTTATC AGTATGTTTT TGTGGTCTTC 120

CTCCTTTTTT TCCACGAGCT CTAGCTGCGT TTAATCCTGT TTTGGTACGT TCGCTAATAA 180

TATCTCTTTC TAATTCTGCA ATACTTGCCA TCATTCGAAA GAAGAATTTC CCCATAGCAT 240

TAGAGGTATC AATGTTGTCA TGAATAGAAA TAAAATCTAC ACCTAGCTCT TTGAATTTTT 300

CACTTAACTC AATTAGGTGT TTTGTAGAGC GAGAAATTCG ATCAAGTTTG TAAACAACTA 360

TCTTATCGCC TTTACGTAAT ACTTTTAGCA ACTCTTCGAG TTGAGGGCGC TCTTTTTTTA 420

TTCCTGTTAT TTTCTCCTGA TATAGCCTTT CTACACCATA TTGTTGCAAA GCATCTATTT 480

GCATATCGAG ATTTTGTTCT TCTGTGCTGA CACGAGCATA ACCAAAAATC AAATTGGTTT 540

CACTTCCTAT CTAAATATAT CTATTAAAAT AGCACCAAAA ACCTTATTAA ATTAAAATAA 600

GGAACTTTGT TTTTGGATAT GGATTTTGGT ACTCAATATG GATGAGTTTT TAACGCTTTT 660

GTTAAAAAAC AAACAAGTGC CATAAACGGT CGTTTTTGGG ATGACATAAT AAATAATCTG 720

TTTGATTAAC CTAACCTTGT ATCCTTACAG CCCAGTTTTA TTTGTACTTC AACTGACTGA 780

ATATGAAAAC AACATGAAGG TTTCATAAAA TTTATATATT TTCCATAACG GATGCTCTAT 840

CTTTAGGTTA TAGTTAAATT ATAAGAAAAA AACAAACGGA GGGAGTGAAA AAAAGCATCT 900

```
TCTCTATAAT TTTACAGGCT CTTTAATAAG AAGGGGGGAG ATTAGATAAT AAATATGAAT      960

ATCTATCTAT AATTGTTTGC TTCTACAATA ACTTATCTAA CTTTCATATA CAACAACAAA     1020

ACAGACTAAA TCCAGATTGT ATATTCATTT TCAGTTGTTC CTTTATAAAA TAATTTCATA     1080
```

| A ATG | AAA | AGA | ATG | GAG | GGA | AAG | TTG | TTT | ATG | GTG | TCA | AAA | AAA | TTA | 1126 |
|---|---|---|---|---|---|---|---|---|---|---|---|---|---|---|---|
| Met | Lys | Arg | Met | Glu | Gly | Lys | Leu | Phe | Met | Val | Ser | Lys | Lys | Leu | |
| 1 | | | | 5 | | | | | 10 | | | | | 15 | |

| CAA | GTA | GTT | ACT | AAA | ACT | GTA | TTG | CTT | AGT | ACA | GTT | TTC | TCT | ATA | TCT | 1174 |
|---|---|---|---|---|---|---|---|---|---|---|---|---|---|---|---|---|
| Gln | Val | Val | Thr | Lys | Thr | Val | Leu | Leu | Ser | Thr | Val | Phe | Ser | Ile | Ser | |
| | | | | 20 | | | | | 25 | | | | | 30 | | |

| TTA | TTA | AAT | AAT | GAA | GTG | ATA | AAA | GCT | GAA | CAA | TTA | AAT | ATA | AAT | TCT | 1222 |
|---|---|---|---|---|---|---|---|---|---|---|---|---|---|---|---|---|
| Leu | Leu | Asn | Asn | Glu | Val | Ile | Lys | Ala | Glu | Gln | Leu | Asn | Ile | Asn | Ser | |
| | | | 35 | | | | | 40 | | | | | 45 | | | |

| CAA | AGT | AAA | TAT | ACT | AAC | TTG | CAA | AAT | CTA | AAA | ATC | ACT | GAC | AAG | GTA | 1270 |
|---|---|---|---|---|---|---|---|---|---|---|---|---|---|---|---|---|
| Gln | Ser | Lys | Tyr | Thr | Asn | Leu | Gln | Asn | Leu | Lys | Ile | Thr | Asp | Lys | Val | |
| | | 50 | | | | | 55 | | | | | 60 | | | | |

| GAG | GAT | TTT | AAA | GAA | GAT | AAG | GAA | AAA | GCG | AAA | GAA | TGG | GGG | AAA | GAA | 1318 |
|---|---|---|---|---|---|---|---|---|---|---|---|---|---|---|---|---|
| Glu | Asp | Phe | Lys | Glu | Asp | Lys | Glu | Lys | Ala | Lys | Glu | Trp | Gly | Lys | Glu | |
| | 65 | | | | | 70 | | | | | 75 | | | | | |

| AAA | GAA | AAA | GAG | TGG | AAA | CTA | ACT | GCT | ACT | GAA | AAA | GGA | AAA | ATG | AAT | 1366 |
|---|---|---|---|---|---|---|---|---|---|---|---|---|---|---|---|---|
| Lys | Glu | Lys | Glu | Trp | Lys | Leu | Thr | Ala | Thr | Glu | Lys | Gly | Lys | Met | Asn | |
| 80 | | | | | 85 | | | | | 90 | | | | | 95 | |

| AAT | TTT | TTA | GAT | AAT | AAA | AAT | GAT | ATA | AAG | ACA | AAT | TAT | AAA | GAA | ATT | 1414 |
|---|---|---|---|---|---|---|---|---|---|---|---|---|---|---|---|---|
| Asn | Phe | Leu | Asp | Asn | Lys | Asn | Asp | Ile | Lys | Thr | Asn | Tyr | Lys | Glu | Ile | |
| | | | | 100 | | | | | 105 | | | | | 110 | | |

| ACT | TTT | TCT | ATG | GCA | GGC | TCA | TTT | GAA | GAT | GAA | ATA | AAA | GAT | TTA | AAA | 1462 |
|---|---|---|---|---|---|---|---|---|---|---|---|---|---|---|---|---|
| Thr | Phe | Ser | Met | Ala | Gly | Ser | Phe | Glu | Asp | Glu | Ile | Lys | Asp | Leu | Lys | |
| | | | 115 | | | | | 120 | | | | | 125 | | | |

| GAA | ATT | GAT | AAG | ATG | TTT | GAT | AAA | ACC | AAT | CTA | TCA | AAT | TCT | ATT | ATC | 1510 |
|---|---|---|---|---|---|---|---|---|---|---|---|---|---|---|---|---|
| Glu | Ile | Asp | Lys | Met | Phe | Asp | Lys | Thr | Asn | Leu | Ser | Asn | Ser | Ile | Ile | |
| | | 130 | | | | | 135 | | | | | 140 | | | | |

| ACC | TAT | AAA | AAT | GTG | GAA | CCG | ACA | ACA | ATT | GGA | TTT | AAT | AAA | TCT | TTA | 1558 |
|---|---|---|---|---|---|---|---|---|---|---|---|---|---|---|---|---|
| Thr | Tyr | Lys | Asn | Val | Glu | Pro | Thr | Thr | Ile | Gly | Phe | Asn | Lys | Ser | Leu | |
| | 145 | | | | | 150 | | | | | 155 | | | | | |

| ACA | GAA | GGT | AAT | ACG | ATT | AAT | TCT | GAT | GCA | ATG | GCA | CAG | TTT | AAA | GAA | 1606 |
|---|---|---|---|---|---|---|---|---|---|---|---|---|---|---|---|---|
| Thr | Glu | Gly | Asn | Thr | Ile | Asn | Ser | Asp | Ala | Met | Ala | Gln | Phe | Lys | Glu | |
| 160 | | | | | 165 | | | | | 170 | | | | | 175 | |

| CAA | TTT | TTA | GAT | AGG | GAT | ATT | AAG | TTT | GAT | AGT | TAT | CTA | GAT | ACG | CAT | 1654 |
|---|---|---|---|---|---|---|---|---|---|---|---|---|---|---|---|---|
| Gln | Phe | Leu | Asp | Arg | Asp | Ile | Lys | Phe | Asp | Ser | Tyr | Leu | Asp | Thr | His | |
| | | | | 180 | | | | | 185 | | | | | 190 | | |

| TTA | ACT | GCT | CAA | CAA | GTT | TCC | AGT | AAA | GAA | AGA | GTT | ATT | TTG | AAG | GTT | 1702 |
|---|---|---|---|---|---|---|---|---|---|---|---|---|---|---|---|---|
| Leu | Thr | Ala | Gln | Gln | Val | Ser | Ser | Lys | Glu | Arg | Val | Ile | Leu | Lys | Val | |
| | | | 195 | | | | | 200 | | | | | 205 | | | |

| ACG | GTT | CCG | AGT | GGG | AAA | GGT | TCT | ACT | ACT | CCA | ACA | AAA | GCA | GGT | GTC | 1750 |
|---|---|---|---|---|---|---|---|---|---|---|---|---|---|---|---|---|
| Thr | Val | Pro | Ser | Gly | Lys | Gly | Ser | Thr | Thr | Pro | Thr | Lys | Ala | Gly | Val | |
| | | 210 | | | | | 215 | | | | | 220 | | | | |

| ATT | TTA | AAT | AAT | AGT | GAA | TAC | AAA | ATG | CTC | ATT | GAT | AAT | GGG | TAT | ATG | 1798 |
|---|---|---|---|---|---|---|---|---|---|---|---|---|---|---|---|---|
| Ile | Leu | Asn | Asn | Ser | Glu | Tyr | Lys | Met | Leu | Ile | Asp | Asn | Gly | Tyr | Met | |
| | 225 | | | | | 230 | | | | | 235 | | | | | |

| GTC | CAT | GTA | GAT | AAG | GTA | TCA | AAA | GTG | GTG | AAA | AAA | GGG | GTG | GAG | TGC | 1846 |
|---|---|---|---|---|---|---|---|---|---|---|---|---|---|---|---|---|
| Val | His | Val | Asp | Lys | Val | Ser | Lys | Val | Val | Lys | Lys | Gly | Val | Glu | Cys | |
| 240 | | | | | 245 | | | | | 250 | | | | | 255 | |

| TTA | CAA | ATT | GAA | GGG | ACT | TTA | AAA | AAG | AGT | CTT | GAC | TTT | AAA | AAT | GAT | 1894 |
|---|---|---|---|---|---|---|---|---|---|---|---|---|---|---|---|---|
| Leu | Gln | Ile | Glu | Gly | Thr | Leu | Lys | Lys | Ser | Leu | Asp | Phe | Lys | Asn | Asp | |
| | | | | 260 | | | | | 265 | | | | | 270 | | |

| ATA | AAT | GCT | GAA | GCG | CAT | AGC | TGG | GGT | ATG | AAG | AAT | TAT | GAA | GAG | TGG | 1942 |
|---|---|---|---|---|---|---|---|---|---|---|---|---|---|---|---|---|
| Ile | Asn | Ala | Glu | Ala | His | Ser | Trp | Gly | Met | Lys | Asn | Tyr | Glu | Glu | Trp | |
| | | | 275 | | | | | 280 | | | | | 285 | | | |

| GCT | AAA | GAT | TTA | ACC | GAT | TCG | CAA | AGG | GAA | GCT | TTA | GAT | GGG | TAT | GCT | 1990 |
|---|---|---|---|---|---|---|---|---|---|---|---|---|---|---|---|---|

| | | | | | | | | | | | | | | |
|---|---|---|---|---|---|---|---|---|---|---|---|---|---|---|
| Ala | Lys | Asp | Leu | Thr | Asp | Ser | Gln | Arg | Glu | Ala | Leu | Asp | Gly | Tyr | Ala |
| | | 290 | | | | | 295 | | | | | 300 | | | |

```
AGG  CAA  GAT  TAT  AAA  GAA  ATC  AAT  AAT  TAT  TTA  AGA  AAT  CAA  GGC  GGA      2038
Arg  Gln  Asp  Tyr  Lys  Glu  Ile  Asn  Asn  Tyr  Leu  Arg  Asn  Gln  Gly  Gly
     305                     310                     315

AGT  GGA  AAT  GAA  AAA  CTA  GAT  GCT  CAA  ATA  AAA  AAT  ATT  TCT  GAT  GCT      2086
Ser  Gly  Asn  Glu  Lys  Leu  Asp  Ala  Gln  Ile  Lys  Asn  Ile  Ser  Asp  Ala
320                     325                     330                     335

TTA  GGG  AAG  AAA  CCA  ATA  CCG  GAA  AAT  ATT  ACT  GTG  TAT  AGA  TGG  TGT      2134
Leu  Gly  Lys  Lys  Pro  Ile  Pro  Glu  Asn  Ile  Thr  Val  Tyr  Arg  Trp  Cys
               340                     345                     350

GGC  ATG  CCG  GAA  TTT  GGT  TAT  CAA  ATT  AGT  GAT  CCG  TTA  CCT  TCT  TTA      2182
Gly  Met  Pro  Glu  Phe  Gly  Tyr  Gln  Ile  Ser  Asp  Pro  Leu  Pro  Ser  Leu
               355                     360                     365

AAA  GAT  TTT  GAA  GAA  CAA  TTT  TTA  AAT  ACA  ATC  AAA  GAA  GAC  AAA  GGA      2230
Lys  Asp  Phe  Glu  Glu  Gln  Phe  Leu  Asn  Thr  Ile  Lys  Glu  Asp  Lys  Gly
          370                     375                     380

TAT  ATG  AGT  ACA  AGC  TTA  TCG  AGT  GAA  CGT  CTT  GCA  GCT  TTT  GGA  TCT      2278
Tyr  Met  Ser  Thr  Ser  Leu  Ser  Ser  Glu  Arg  Leu  Ala  Ala  Phe  Gly  Ser
     385                     390                     395

AGA  AAA  ATT  ATA  TTA  CGA  TTA  CAA  GTT  CCG  AAA  GGA  AGT  ACG  GGT  GCG      2326
Arg  Lys  Ile  Ile  Leu  Arg  Leu  Gln  Val  Pro  Lys  Gly  Ser  Thr  Gly  Ala
400                     405                     410                     415

TAT  TTA  AGT  GCC  ATT  GGT  GGA  TTT  GCA  AGT  GAA  AAA  GAG  ATC  CTA  CTT      2374
Tyr  Leu  Ser  Ala  Ile  Gly  Gly  Phe  Ala  Ser  Glu  Lys  Glu  Ile  Leu  Leu
               420                     425                     430

GAT  AAA  GAT  AGT  AAA  TAT  CAT  ATT  GAT  AAA  GTA  ACA  GAG  GTA  ATT  ATT      2422
Asp  Lys  Asp  Ser  Lys  Tyr  His  Ile  Asp  Lys  Val  Thr  Glu  Val  Ile  Ile
          435                     440                     445

AAA  GGT  GTT  AAG  CGA  TAT  GTA  GTG  GAT  GCA  ACA  TTA  TTA  ACA  AAT           2467
Lys  Gly  Val  Lys  Arg  Tyr  Val  Val  Asp  Ala  Thr  Leu  Leu  Thr  Asn
     450                     455                     460
```

```
TAAGGAGATG  AAAAATATGA  AGAAAAAGTT  AGCAAGTGTT  GTAACGTGTA  CGTTATTAGC    2527
TCCTATGTTT  TTGAATGGAA  ATGTGAATGC  TGTTTACGCA  GACAGCAAAA  CAAATCAAAT    2587
TTCTACAACA  CAGAAAAATC  AACAGAAAGA  GATGGACCGA  AAAGGATTAC  TTGGGTATTA    2647
TTTCAAGGA   AAAGATTTTA  GTAATCTTAC  TATGTTTGCA  CCGACACGTG  ATAGTACTCT    2707
TATTTATGAT  CAACAAACAG  CAAATAAACT  ATTAGATAAA  AACAACAAG   AATATCAGTC    2767
TATTCGTTGG  ATTGGTTTGA  TTCAGAGTAA  AGAAACGGGA  GATTTCACAT  TTAACTTATC    2827
TGAGGATGAA  CAGGCAATTA  TAGAAATCAA  TGGGAAAATT  ATTTCTAATA  AAGGGAAAGA    2887
AAAGCAAGTT  GTCCATTTAG  AAAAAGGAAA  ATTAGTTCCA  ATCAAAATAG  AGTATCAATC    2947
AGATACAAAA  TTTAATATTG  ACAGTAAAAC  ATTTAAAGAA  CTTAAATTAT  TTAAAATAGA    3007
TAGTCAAAAC  CAACCCCAGC  AAGTCCAGCA  AGATGAACTG  AGAAATCCTG  AATTTAACAA    3067
GAAAGAATCA  CAGGAATTCT  TAGCGAAACC  ATCGAAAATA  AATCTTTTCA  CTCAAAAAAT    3127
GAAAAGGGAA  ATTGATGAAG  ACACGGATAC  GGATGGGGAC  TCTATTCCTG  ACCTTTGGGA    3187
AGAAAATGGG  TATACGATTC  ACAATAGAAT  CGCTGTAAAG  TGGGACGATT  CTCTAGCAAG    3247
TAAAGGGTAT  ACGAAATTTG  TTTCAAATCC  ACTAGAAAGT  CACACAGTTG  GTGATCCTTA    3307
TACAGATTAT  GAAAAGGCAG  CAAGAGATCT  AGATTTGTCA  AATGCAAAGG  AAACGTTTAA    3367
CCCATTGGTA  GCTGCTTTTC  CAAGTGTGAA  TGTTAGTATG  GAAAAGGTGA  TATTATCACC    3427
AAATGAAAAT  TTATCCAATA  GTGTAGAGTC  TCATTCATCC  ACGAATTGGT  CTTATACAAA    3487
TACAGAAGGT  GCTTCTGTTG  AAGCGGGGAT  TGGACCAAAA  GGTATTTCGT  TCGGAGTTAG    3547
CGTAAACTAT  CAACACTCTG  AAACAGTTGC  ACAAGAATGG  GGAACATCTA  CAGGAAATAC    3607
```

```
TTCGCAATTC  AATACGGCTT  CAGCGGGATA  TTTAAATGCA  AATGTTCGAT  ATAACAATGT   3667
AGGAACTGGT  GCCATCTACG  ATGTAAAACC  TACAACAAGT  TTTGTATTAA  ATAACGATAC   3727
TATCGCAACT  ATTACGGCGA  AATCTAATTC  TACAGCCTTA  AATATATCTC  CTGGAGAAAG   3787
TTACCCGAAA  AAAGGACAAA  ATGGAATCGC  AATAACATCA  ATGGATGATT  TTAATTCCCA   3847
TCCGATTACA  TTAAATAAAA  AACAAGTAGA  TAATCTGCTA  AATAATAAAC  CTATGATGTT   3907
GGAAACAAAC  CAAACAGATG  GTGTTTATAA  GATAAAAGAT  ACACATGGAA  ATATAGTAAC   3967
TGGCGGAGAA  TGGAATGGTG  TCATACAACA  AATCAAGGCT  AAAACAGCGT  CTATTATTGT   4027
GGATGATGGG  GAACGTGTAG  CAGAAAAACG  TGTAGCGGCA  AAAGATTATG  AAAATCCAGA   4087
AGATAAAACA  CCGTCTTTAA  CTTAAAAGA   TGCCCTGAAG  CTTTCATATC  CAGATGAAAT   4147
AAAAGAAATA  GAGGGATTAT  TATATTATAA  AAACAAACCG  ATATACGAAT  CGAGCGTTAT   4207
GACTTACTTA  GATGAAAATA  CAGCAAAAGA  AGTGACCAAA  CAATTAAATG  ATACCACTGG   4267
GAAATTTAAA  GATGTAAGTC  ATTTATATGA  TGTAAAACTG  ACTCCAAAAA  TGAATGTTAC   4327
AATCAAATTG  TCTATACTTT  ATGATAATGC  TGAGTCTAAT  GATAACTCAA  TTGGTAAATG   4387
GACAAACACA  AATATTGTTT  CAGGTGGAAA  TAACGGAAAA  AAACAATATT  CTTCTAATAA   4447
TCCGGATGCT  AATTTGACAT  TAAATACAGA  TGCTCAAGAA  AAATTAAATA  AAAATCGTGA   4507
CTATTATATA  AGTTTATATA  TGAAGTCAGA  AAAAAACACA  CAATGTGAGA  TTACTATAGA   4567
TGGGGAGATT  TATCCGATCA  CTACAAAAAC  AGTGAATGTG  AATAAAGACA  ATTACAAAAG   4627
ATTAGATATT  ATAGCTCATA  ATATAAAAAG  TAATCCAATT  TCTTCACTTC  ATATTAAAAC   4687
GAATGATGAA  ATAACTTTAT  TTTGGGATGA  TATTTCTATA  ACAGATGTAG  CATCAATAAA   4747
ACCGGAAAAT  TTAACAGATT  CAGAAATTAA  ACAGATTTAT  AGTAGGTATG  GTATTAAGTT   4807
AGAAGATGGA  ATCCTTATTG  ATAAAAAGG   TGGGATTCAT  TATGGTGAAT  TTATTAATGA   4867
AGCTAGTTTT  AATATTGAAC  CATTGCAAAA  TTATGTGACC  AAATATGAAG  TTACTTATAG   4927
TAGTGAGTTA  GGACCAAACG  TGAGTGACAC  ACTTGAAAGT  GATAAAATTT  ACAAGGATGG   4987
GACAATTAAA  TTTGATTTTA  CCAAATATAG  TAAAAATGAA  CAAGGATTAT  TTTATGACAG   5047
TGGATTAAAT  TGGGACTTTA  AAATTAATGC  TATTACTTAT  GATGGTAAAG  AGATGAATGT   5107
TTTTCATAGA  TATAATAAAT  AGTTATTATA  TCTATGAAGC  TGGTGCTAAA  GATAGTGTAA   5167
AAGTTAATAT  ACTGTAGGAT  TGTAATAAAA  GTAATGGAAT  TGATATCGTA  CTTTGGAGTG   5227
GGGGATACTT  TGTAAATAGT  TCTATCAGAA  ACATTAGACT  AAGAAAAGTT  ACTACCCCCA   5287
CTTGAAAATG  AAGATTCAAC  TGATTACAAA  CAACCTGTTA  AATATTATAA  GGTTTTAACA   5347
AAATATTAAA  CTCTTTATGT  TAATACTGTA  ATATAAAGAG  TTTAATTGTA  TTCAAATGAA   5407
GCTTTCCCAC  AAAATTAGAC  TGATTATCTA  ATGAAATAAT  CAGTCTAATT  TTGTAGAACA   5467
GGTCTGGTAT  TATTGTACGT  GGTCACTAAA  AGATATCTAA  TATTATTGGG  CAAGGCGTTC   5527
CATGATTGAA  TCCTCGAATG  TCTTGCCCTT  TCATTTATT   TAAGAAGGAT  TGTGGAGAAA   5587
TTATGGTTTA  GATAATGAAG  AAAGACTTCA  CTTCTAATTT  TGATGTTAA   ATAAATCAAA   5647
ATTTGGCGAT  TCACATTGTT  TAATCCACTG  ATAAACATA   CTGGAGTGTT  CTTAAAAAAT   5707
CAGCTTTTTT  CTTTATAAAA  TTTTGCTTAG  CGTACGAAAT  TCGTGTTTTG  TTGGTGGGAC   5767
CCCATGCCCA  TCAACTTAAG  AGTAAATTAG  TAATGAACTT  TCGTTCATCT  GGATTAAAAT   5827
AACCTCAAAT  TAGGACATGT  TTTTAAAAAT  AAGCAGACCA  AATAAGCCTA  GAATAGGTAT   5887
CATTTTTAAA  AATTATGCTG  CTTTCTTTTG  TTTTCCAAAT  CCATTATACT  CATAAGCAAC   5947
ACCCATAATG  TCAAAGACTG  TTTTTGTCTC  ATATCGATAA  GCTTGATATC  GAATTCCTGC   6007
```

AGCCCGGGGG ATCCACTAGT TCTAGAGCGG CCGCCACCGC GG                                        6049

(2) INFORMATION FOR SEQ ID NO:2:

(i) SEQUENCE CHARACTERISTICS:
        (A) LENGTH: 462 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Arg Met Glu Gly Lys Leu Phe Met Val Ser Lys Lys Leu Gln
 1               5                  10                  15
Val Val Thr Lys Thr Val Leu Leu Ser Thr Val Phe Ser Ile Ser Leu
                20                  25                  30
Leu Asn Asn Glu Val Ile Lys Ala Glu Gln Leu Asn Ile Asn Ser Gln
            35                  40                  45
Ser Lys Tyr Thr Asn Leu Gln Asn Leu Lys Ile Thr Asp Lys Val Glu
        50                  55                  60
Asp Phe Lys Glu Asp Glu Lys Ala Lys Glu Trp Gly Lys Glu Lys
 65                  70                  75                  80
Glu Lys Glu Trp Lys Leu Thr Ala Thr Glu Lys Gly Lys Met Asn Asn
                85                  90                  95
Phe Leu Asp Asn Lys Asn Asp Ile Lys Thr Asn Tyr Lys Glu Ile Thr
               100                 105                 110
Phe Ser Met Ala Gly Ser Phe Glu Asp Glu Ile Lys Asp Leu Lys Glu
               115                 120                 125
Ile Asp Lys Met Phe Asp Lys Thr Asn Leu Ser Asn Ser Ile Ile Thr
       130                 135                 140
Tyr Lys Asn Val Glu Pro Thr Thr Ile Gly Phe Asn Lys Ser Leu Thr
145                 150                 155                 160
Glu Gly Asn Thr Ile Asn Ser Asp Ala Met Ala Gln Phe Lys Glu Gln
               165                 170                 175
Phe Leu Asp Arg Asp Ile Lys Phe Asp Ser Tyr Leu Asp Thr His Leu
               180                 185                 190
Thr Ala Gln Gln Val Ser Ser Lys Glu Arg Val Ile Leu Lys Val Thr
           195                 200                 205
Val Pro Ser Gly Lys Gly Ser Thr Thr Pro Thr Lys Ala Gly Val Ile
    210                 215                 220
Leu Asn Asn Ser Glu Tyr Lys Met Leu Ile Asp Asn Gly Tyr Met Val
225                 230                 235                 240
His Val Asp Lys Val Ser Lys Val Val Lys Lys Gly Val Glu Cys Leu
                245                 250                 255
Gln Ile Glu Gly Thr Leu Lys Lys Ser Leu Asp Phe Lys Asn Asp Ile
            260                 265                 270
Asn Ala Glu Ala His Ser Trp Gly Met Lys Asn Tyr Glu Glu Trp Ala
        275                 280                 285
Lys Asp Leu Thr Asp Ser Gln Arg Glu Ala Leu Asp Gly Tyr Ala Arg
    290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Ile Lys Asn Ile Ser Asp Ala Leu
                325                 330                 335
Gly Lys Lys Pro Ile Pro Glu Asn Ile Thr Val Tyr Arg Trp Cys Gly
            340                 345                 350
```

| Met | Pro | Glu<br>355 | Phe | Gly | Tyr | Gln | Ile<br>360 | Ser | Asp | Pro | Leu | Pro<br>365 | Ser | Leu | Lys |
|---|---|---|---|---|---|---|---|---|---|---|---|---|---|---|---|
| Asp | Phe<br>370 | Glu | Glu | Gln | Phe | Leu<br>375 | Asn | Thr | Ile | Lys | Glu<br>380 | Asp | Lys | Gly | Tyr |
| Met<br>385 | Ser | Thr | Ser | Leu | Ser<br>390 | Ser | Glu | Arg | Leu | Ala<br>395 | Ala | Phe | Gly | Ser | Arg<br>400 |
| Lys | Ile | Ile | Leu | Arg<br>405 | Leu | Gln | Val | Pro | Lys<br>410 | Gly | Ser | Thr | Gly | Ala<br>415 | Tyr |
| Leu | Ser | Ala | Ile<br>420 | Gly | Gly | Phe | Ala | Ser<br>425 | Glu | Lys | Glu | Ile | Leu<br>430 | Leu | Asp |
| Lys | Asp | Ser<br>435 | Lys | Tyr | His | Ile | Asp<br>440 | Lys | Val | Thr | Glu | Val<br>445 | Ile | Ile | Lys |
| Gly | Val<br>450 | Lys | Arg | Tyr | Val | Val<br>455 | Asp | Ala | Thr | Leu | Leu<br>460 | Thr | Asn | | |

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..20
        (D) OTHER INFORMATION: /note= "Signal peptide for vacuolar
            targetting"

(xi) SEQUENCE DESCRIPTION: SEQ ID NO:3:

| Ser<br>1 | Ser | Ser | Ser | Phe<br>5 | Ala | Asp | Ser | Asn | Pro<br>10 | Ile | Arg | Val | Thr | Asp<br>15 | Arg |
|---|---|---|---|---|---|---|---|---|---|---|---|---|---|---|---|
| Ala | Ala | Ser | Thr<br>20 | | | | | | | | | | | | |

(2) INFORMATION FOR SEQ ID NO:4:

(i) SEQUENCE CHARACTERISTICS:
        (A) LENGTH: 2655 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus cereus
        (B) STRAIN: AB78
        (C) INDIVIDUAL ISOLATE: NRRL B- 21058

-continued

| | | | | | | | | | | | | | | | | |
|---|---|---|---|---|---|---|---|---|---|---|---|---|---|---|---|---|
| TTA | GCT | CCT | ATG | TTT | TTG | AAT | GGA | AAT | GTG | AAT | GCT | GTT | TAC | GCA | GAC | 96 |
| Leu | Ala | Pro | Met | Phe | Leu | Asn | Gly | Asn | Val | Asn | Ala | Val | Tyr | Ala | Asp | |
| | 480 | | | | 485 | | | | 490 | | | | | | | |
| AGC | AAA | ACA | AAT | CAA | ATT | TCT | ACA | ACA | CAG | AAA | AAT | CAA | CAG | AAA | GAG | 144 |
| Ser | Lys | Thr | Asn | Gln | Ile | Ser | Thr | Thr | Gln | Lys | Asn | Gln | Gln | Lys | Glu | |
| 495 | | | | | 500 | | | | | 505 | | | | | 510 | |
| ATG | GAC | CGA | AAA | GGA | TTA | CTT | GGG | TAT | TAT | TTC | AAA | GGA | AAA | GAT | TTT | 192 |
| Met | Asp | Arg | Lys | Gly | Leu | Leu | Gly | Tyr | Tyr | Phe | Lys | Gly | Lys | Asp | Phe | |
| | | | | 515 | | | | | 520 | | | | | 525 | | |
| AGT | AAT | CTT | ACT | ATG | TTT | GCA | CCG | ACA | CGT | GAT | AGT | ACT | CTT | ATT | TAT | 240 |
| Ser | Asn | Leu | Thr | Met | Phe | Ala | Pro | Thr | Arg | Asp | Ser | Thr | Leu | Ile | Tyr | |
| | | | 530 | | | | | 535 | | | | | 540 | | | |
| GAT | CAA | CAA | ACA | GCA | AAT | AAA | CTA | TTA | GAT | AAA | AAA | CAA | CAA | GAA | TAT | 288 |
| Asp | Gln | Gln | Thr | Ala | Asn | Lys | Leu | Leu | Asp | Lys | Lys | Gln | Gln | Glu | Tyr | |
| | | | 545 | | | | | 550 | | | | | 555 | | | |
| CAG | TCT | ATT | CGT | TGG | ATT | GGT | TTG | ATT | CAG | AGT | AAA | GAA | ACG | GGA | GAT | 336 |
| Gln | Ser | Ile | Arg | Trp | Ile | Gly | Leu | Ile | Gln | Ser | Lys | Glu | Thr | Gly | Asp | |
| 560 | | | | | 565 | | | | | 570 | | | | | | |
| TTC | ACA | TTT | AAC | TTA | TCT | GAG | GAT | GAA | CAG | GCA | ATT | ATA | GAA | ATC | AAT | 384 |
| Phe | Thr | Phe | Asn | Leu | Ser | Glu | Asp | Glu | Gln | Ala | Ile | Ile | Glu | Ile | Asn | |
| 575 | | | | | 580 | | | | | 585 | | | | | 590 | |
| GGG | AAA | ATT | ATT | TCT | AAT | AAA | GGG | AAA | GAA | AAG | CAA | GTT | GTC | CAT | TTA | 432 |
| Gly | Lys | Ile | Ile | Ser | Asn | Lys | Gly | Lys | Glu | Lys | Gln | Val | Val | His | Leu | |
| | | | | 595 | | | | | 600 | | | | | 605 | | |
| GAA | AAA | GGA | AAA | TTA | GTT | CCA | ATC | AAA | ATA | GAG | TAT | CAA | TCA | GAT | ACA | 480 |
| Glu | Lys | Gly | Lys | Leu | Val | Pro | Ile | Lys | Ile | Glu | Tyr | Gln | Ser | Asp | Thr | |
| | | | 610 | | | | | 615 | | | | | 620 | | | |
| AAA | TTT | AAT | ATT | GAC | AGT | AAA | ACA | TTT | AAA | GAA | CTT | AAA | TTA | TTT | AAA | 528 |
| Lys | Phe | Asn | Ile | Asp | Ser | Lys | Thr | Phe | Lys | Glu | Leu | Lys | Leu | Phe | Lys | |
| | | 625 | | | | | 630 | | | | | 635 | | | | |
| ATA | GAT | AGT | CAA | AAC | CAA | CCC | CAG | CAA | GTC | CAG | CAA | GAT | GAA | CTG | AGA | 576 |
| Ile | Asp | Ser | Gln | Asn | Gln | Pro | Gln | Gln | Val | Gln | Gln | Asp | Glu | Leu | Arg | |
| | 640 | | | | | 645 | | | | | 650 | | | | | |
| AAT | CCT | GAA | TTT | AAC | AAG | AAA | GAA | TCA | CAG | GAA | TTC | TTA | GCG | AAA | CCA | 624 |
| Asn | Pro | Glu | Phe | Asn | Lys | Lys | Glu | Ser | Gln | Glu | Phe | Leu | Ala | Lys | Pro | |
| 655 | | | | | 660 | | | | | 665 | | | | | 670 | |
| TCG | AAA | ATA | AAT | CTT | TTC | ACT | CAA | AAA | ATG | AAA | AGG | GAA | ATT | GAT | GAA | 672 |
| Ser | Lys | Ile | Asn | Leu | Phe | Thr | Gln | Lys | Met | Lys | Arg | Glu | Ile | Asp | Glu | |
| | | | | 675 | | | | | 680 | | | | | 685 | | |
| GAC | ACG | GAT | ACG | GAT | GGG | GAC | TCT | ATT | CCT | GAC | CTT | TGG | GAA | GAA | AAT | 720 |
| Asp | Thr | Asp | Thr | Asp | Gly | Asp | Ser | Ile | Pro | Asp | Leu | Trp | Glu | Glu | Asn | |
| | | | | 690 | | | | | 695 | | | | | 700 | | |
| GGG | TAT | ACG | ATT | CAA | AAT | AGA | ATC | GCT | GTA | AAG | TGG | GAC | GAT | TCT | CTA | 768 |
| Gly | Tyr | Thr | Ile | Gln | Asn | Arg | Ile | Ala | Val | Lys | Trp | Asp | Asp | Ser | Leu | |
| | | 705 | | | | | 710 | | | | | 715 | | | | |
| GCA | AGT | AAA | GGG | TAT | ACG | AAA | TTT | GTT | TCA | AAT | CCA | CTA | GAA | AGT | CAC | 816 |
| Ala | Ser | Lys | Gly | Tyr | Thr | Lys | Phe | Val | Ser | Asn | Pro | Leu | Glu | Ser | His | |
| | 720 | | | | | 725 | | | | | 730 | | | | | |
| ACA | GTT | GGT | GAT | CCT | TAT | ACA | GAT | TAT | GAA | AAG | GCA | GCA | AGA | GAT | CTA | 864 |
| Thr | Val | Gly | Asp | Pro | Tyr | Thr | Asp | Tyr | Glu | Lys | Ala | Ala | Arg | Asp | Leu | |
| 735 | | | | | 740 | | | | | 745 | | | | | 750 | |
| GAT | TTG | TCA | AAT | GCA | AAG | GAA | ACG | TTT | AAC | CCA | TTG | GTA | GCT | GCT | TTT | 912 |
| Asp | Leu | Ser | Asn | Ala | Lys | Glu | Thr | Phe | Asn | Pro | Leu | Val | Ala | Ala | Phe | |
| | | | | 755 | | | | | 760 | | | | | 765 | | |
| CCA | AGT | GTG | AAT | GTT | AGT | ATG | GAA | AAG | GTG | ATA | TTA | TCA | CCA | AAT | GAA | 960 |
| Pro | Ser | Val | Asn | Val | Ser | Met | Glu | Lys | Val | Ile | Leu | Ser | Pro | Asn | Glu | |
| | | | 770 | | | | | 775 | | | | | 780 | | | |
| AAT | TTA | TCC | AAT | AGT | GTA | GAG | TCT | CAT | TCA | TCC | ACG | AAT | TGG | TCT | TAT | 1008 |
| Asn | Leu | Ser | Asn | Ser | Val | Glu | Ser | His | Ser | Ser | Thr | Asn | Trp | Ser | Tyr | |
| | 785 | | | | | 790 | | | | | 795 | | | | | |

-continued

| | | | | | | | | | | | | | | | | |
|---|---|---|---|---|---|---|---|---|---|---|---|---|---|---|---|---|
| ACA | AAT | ACA | GAA | GGT | GCT | TCT | GTT | GAA | GCG | GGG | ATT | GGA | CCA | AAA | GGT | 1056 |
| Thr | Asn | Thr | Glu | Gly | Ala | Ser | Val | Glu | Ala | Gly | Ile | Gly | Pro | Lys | Gly | |
| | 800 | | | | | 805 | | | | | 810 | | | | | |
| ATT | TCG | TTC | GGA | GTT | AGC | GTA | AAC | TAT | CAA | CAC | TCT | GAA | ACA | GTT | GCA | 1104 |
| Ile | Ser | Phe | Gly | Val | Ser | Val | Asn | Tyr | Gln | His | Ser | Glu | Thr | Val | Ala | |
| 815 | | | | | 820 | | | | | 825 | | | | | 830 | |
| CAA | GAA | TGG | GGA | ACA | TCT | ACA | GGA | AAT | ACT | TCG | CAA | TTC | AAT | ACG | GCT | 1152 |
| Gln | Glu | Trp | Gly | Thr | Ser | Thr | Gly | Asn | Thr | Ser | Gln | Phe | Asn | Thr | Ala | |
| | | | | 835 | | | | | 840 | | | | | 845 | | |
| TCA | GCG | GGA | TAT | TTA | AAT | GCA | AAT | GTT | CGA | TAT | AAC | AAT | GTA | GGA | ACT | 1200 |
| Ser | Ala | Gly | Tyr | Leu | Asn | Ala | Asn | Val | Arg | Tyr | Asn | Asn | Val | Gly | Thr | |
| | | | 850 | | | | | 855 | | | | | 860 | | | |
| GGT | GCC | ATC | TAC | GAT | GTA | AAA | CCT | ACA | ACA | AGT | TTT | GTA | TTA | AAT | AAC | 1248 |
| Gly | Ala | Ile | Tyr | Asp | Val | Lys | Pro | Thr | Thr | Ser | Phe | Val | Leu | Asn | Asn | |
| | | 865 | | | | | 870 | | | | | 875 | | | | |
| GAT | ACT | ATC | GCA | ACT | ATT | ACG | GCG | AAA | TCT | AAT | TCT | ACA | GCC | TTA | AAT | 1296 |
| Asp | Thr | Ile | Ala | Thr | Ile | Thr | Ala | Lys | Ser | Asn | Ser | Thr | Ala | Leu | Asn | |
| 880 | | | | | 885 | | | | | 890 | | | | | | |
| ATA | TCT | CCT | GGA | GAA | AGT | TAC | CCG | AAA | AAA | GGA | CAA | AAT | GGA | ATC | GCA | 1344 |
| Ile | Ser | Pro | Gly | Glu | Ser | Tyr | Pro | Lys | Lys | Gly | Gln | Asn | Gly | Ile | Ala | |
| 895 | | | | | 900 | | | | | 905 | | | | | 910 | |
| ATA | ACA | TCA | ATG | GAT | GAT | TTT | AAT | TCC | CAT | CCG | ATT | ACA | TTA | AAT | AAA | 1392 |
| Ile | Thr | Ser | Met | Asp | Asp | Phe | Asn | Ser | His | Pro | Ile | Thr | Leu | Asn | Lys | |
| | | | | 915 | | | | | 920 | | | | | 925 | | |
| AAA | CAA | GTA | GAT | AAT | CTG | CTA | AAT | AAT | AAA | CCT | ATG | ATG | TTG | GAA | ACA | 1440 |
| Lys | Gln | Val | Asp | Asn | Leu | Leu | Asn | Asn | Lys | Pro | Met | Met | Leu | Glu | Thr | |
| | | | 930 | | | | | 935 | | | | | 940 | | | |
| AAC | CAA | ACA | GAT | GGT | GTT | TAT | AAG | ATA | AAA | GAT | ACA | CAT | GGA | AAT | ATA | 1488 |
| Asn | Gln | Thr | Asp | Gly | Val | Tyr | Lys | Ile | Lys | Asp | Thr | His | Gly | Asn | Ile | |
| | | 945 | | | | | 950 | | | | | 955 | | | | |
| GTA | ACT | GGC | GGA | GAA | TGG | AAT | GGT | GTC | ATA | CAA | CAA | ATC | AAG | GCT | AAA | 1536 |
| Val | Thr | Gly | Gly | Glu | Trp | Asn | Gly | Val | Ile | Gln | Gln | Ile | Lys | Ala | Lys | |
| 960 | | | | | 965 | | | | | 970 | | | | | | |
| ACA | GCG | TCT | ATT | ATT | GTG | GAT | GAT | GGG | GAA | CGT | GTA | GCA | GAA | AAA | CGT | 1584 |
| Thr | Ala | Ser | Ile | Ile | Val | Asp | Asp | Gly | Glu | Arg | Val | Ala | Glu | Lys | Arg | |
| 975 | | | | | 980 | | | | | 985 | | | | | 990 | |
| GTA | GCG | GCA | AAA | GAT | TAT | GAA | AAT | CCA | GAA | GAT | AAA | ACA | CCG | TCT | TTA | 1632 |
| Val | Ala | Ala | Lys | Asp | Tyr | Glu | Asn | Pro | Glu | Asp | Lys | Thr | Pro | Ser | Leu | |
| | | | | 995 | | | | | 1000 | | | | | 1005 | | |
| ACT | TTA | AAA | GAT | GCC | CTG | AAG | CTT | TCA | TAT | CCA | GAT | GAA | ATA | AAA | GAA | 1680 |
| Thr | Leu | Lys | Asp | Ala | Leu | Lys | Leu | Ser | Tyr | Pro | Asp | Glu | Ile | Lys | Glu | |
| | | | | 1010 | | | | | 1015 | | | | | 1020 | | |
| ATA | GAG | GGA | TTA | TTA | TAT | TAT | AAA | AAC | AAA | CCG | ATA | TAC | GAA | TCG | AGC | 1728 |
| Ile | Glu | Gly | Leu | Leu | Tyr | Tyr | Lys | Asn | Lys | Pro | Ile | Tyr | Glu | Ser | Ser | |
| | | | | 1025 | | | | | 1030 | | | | | 1035 | | |
| GTT | ATG | ACT | TAC | TTA | GAT | GAA | AAT | ACA | GCA | AAA | GAA | GTG | ACC | AAA | CAA | 1776 |
| Val | Met | Thr | Tyr | Leu | Asp | Glu | Asn | Thr | Ala | Lys | Glu | Val | Thr | Lys | Gln | |
| | | | 1040 | | | | | 1045 | | | | | 1050 | | | |
| TTA | AAT | GAT | ACC | ACT | GGG | AAA | TTT | AAA | GAT | GTA | AGT | CAT | TTA | TAT | GAT | 1824 |
| Leu | Asn | Asp | Thr | Thr | Gly | Lys | Phe | Lys | Asp | Val | Ser | His | Leu | Tyr | Asp | |
| 1055 | | | | | 1060 | | | | | 1065 | | | | | 1070 | |
| GTA | AAA | CTG | ACT | CCA | AAA | ATG | AAT | GTT | ACA | ATC | AAA | TTG | TCT | ATA | CTT | 1872 |
| Val | Lys | Leu | Thr | Pro | Lys | Met | Asn | Val | Thr | Ile | Lys | Leu | Ser | Ile | Leu | |
| | | | | 1075 | | | | | 1080 | | | | | 1085 | | |
| TAT | GAT | AAT | GCT | GAG | TCT | AAT | GAT | AAC | TCA | ATT | GGT | AAA | TGG | ACA | AAC | 1920 |
| Tyr | Asp | Asn | Ala | Glu | Ser | Asn | Asp | Asn | Ser | Ile | Gly | Lys | Trp | Thr | Asn | |
| | | | 1090 | | | | | 1095 | | | | | 1100 | | | |
| ACA | AAT | ATT | GTT | TCA | GGT | GGA | AAT | AAC | GGA | AAA | AAA | CAA | TAT | TCT | TCT | 1968 |
| Thr | Asn | Ile | Val | Ser | Gly | Gly | Asn | Asn | Gly | Lys | Lys | Gln | Tyr | Ser | Ser | |
| | | 1105 | | | | | 1110 | | | | | 1115 | | | | |

| | | | | | | | | | | | | | | | |
|---|---|---|---|---|---|---|---|---|---|---|---|---|---|---|---|
| AAT | AAT | CCG | GAT | GCT | AAT | TTG | ACA | TTA | AAT | ACA | GAT | GCT | CAA | GAA | AAA | 2016
| Asn | Asn | Pro | Asp | Ala | Asn | Leu | Thr | Leu | Asn | Thr | Asp | Ala | Gln | Glu | Lys |
| | | 1120 | | | | 1125 | | | | | 1130 | | | | |

```
AAT AAT CCG GAT GCT AAT TTG ACA TTA AAT ACA GAT GCT CAA GAA AAA    2016
Asn Asn Pro Asp Ala Asn Leu Thr Leu Asn Thr Asp Ala Gln Glu Lys
         1120                1125                1130

TTA AAT AAA AAT CGT GAC TAT TAT ATA AGT TTA TAT ATG AAG TCA GAA    2064
Leu Asn Lys Asn Arg Asp Tyr Tyr Ile Ser Leu Tyr Met Lys Ser Glu
1135                1140                1145                1150

AAA AAC ACA CAA TGT GAG ATT ACT ATA GAT GGG GAG ATT TAT CCG ATC    2112
Lys Asn Thr Gln Cys Glu Ile Thr Ile Asp Gly Glu Ile Tyr Pro Ile
                1155                1160                1165

ACT ACA AAA ACA GTG AAT GTG AAT AAA GAC AAT TAC AAA AGA TTA GAT    2160
Thr Thr Lys Thr Val Asn Val Asn Lys Asp Asn Tyr Lys Arg Leu Asp
            1170                1175                1180

ATT ATA GCT CAT AAT ATA AAA AGT AAT CCA ATT TCT TCA CTT CAT ATT    2208
Ile Ile Ala His Asn Ile Lys Ser Asn Pro Ile Ser Ser Leu His Ile
                1185                1190                1195

AAA ACG AAT GAT GAA ATA ACT TTA TTT TGG GAT GAT ATT TCT ATA ACA    2256
Lys Thr Asn Asp Glu Ile Thr Leu Phe Trp Asp Asp Ile Ser Ile Thr
        1200                1205                1210

GAT GTA GCA TCA ATA AAA CCG GAA AAT TTA ACA GAT TCA GAA ATT AAA    2304
Asp Val Ala Ser Ile Lys Pro Glu Asn Leu Thr Asp Ser Glu Ile Lys
1215                1220                1225                1230

CAG ATT TAT AGT AGG TAT GGT ATT AAG TTA GAA GAT GGA ATC CTT ATT    2352
Gln Ile Tyr Ser Arg Tyr Gly Ile Lys Leu Glu Asp Gly Ile Leu Ile
                1235                1240                1245

GAT AAA AAA GGT GGG ATT CAT TAT GGT GAA TTT ATT AAT GAA GCT AGT    2400
Asp Lys Lys Gly Gly Ile His Tyr Gly Glu Phe Ile Asn Glu Ala Ser
            1250                1255                1260

TTT AAT ATT GAA CCA TTG CAA AAT TAT GTG ACC AAA TAT GAA GTT ACT    2448
Phe Asn Ile Glu Pro Leu Gln Asn Tyr Val Thr Lys Tyr Glu Val Thr
        1265                1270                1275

TAT AGT AGT GAG TTA GGA CCA AAC GTG AGT GAC ACA CTT GAA AGT GAT    2496
Tyr Ser Ser Glu Leu Gly Pro Asn Val Ser Asp Thr Leu Glu Ser Asp
1280                1285                1290

AAA ATT TAC AAG GAT GGG ACA ATT AAA TTT GAT TTT ACC AAA TAT AGT    2544
Lys Ile Tyr Lys Asp Gly Thr Ile Lys Phe Asp Phe Thr Lys Tyr Ser
1295                1300                1305                1310

AAA AAT GAA CAA GGA TTA TTT TAT GAC AGT GGA TTA AAT TGG GAC TTT    2592
Lys Asn Glu Gln Gly Leu Phe Tyr Asp Ser Gly Leu Asn Trp Asp Phe
                1315                1320                1325

AAA ATT AAT GCT ATT ACT TAT GAT GGT AAA GAG ATG AAT GTT TTT CAT    2640
Lys Ile Asn Ala Ile Thr Tyr Asp Gly Lys Glu Met Asn Val Phe His
            1330                1335                1340

AGA TAT AAT AAA TAG                                                2655
Arg Tyr Asn Lys
            1345
```

(2) INFORMATION FOR SEQ ID NO:5:

(i) SEQUENCE CHARACTERISTICS:
        (A) LENGTH: 884 amino acids
        (B) TYPE: amino acid
        (D) TOPOLOGY: linear (ii) MOLECULE TYPE: protein (xi) SEQUENCE DESCRIPTION: SEQ ID NO:5:

```
Met Lys Asn Met Lys Lys Lys Leu Ala Ser Val Val Thr Cys Thr Leu
 1               5                   10                  15

Leu Ala Pro Met Phe Leu Asn Gly Asn Val Asn Ala Val Tyr Ala Asp
                20                  25                  30

Ser Lys Thr Asn Gln Ile Ser Thr Thr Gln Lys Asn Gln Gln Lys Glu
```

-continued

```
                        35                          40                          45

Met   Asp   Arg   Lys   Gly   Leu   Leu   Gly   Tyr   Tyr   Phe   Lys   Gly   Lys   Asp   Phe
            50                        55                        60

Ser   Asn   Leu   Thr   Met   Phe   Ala   Pro   Thr   Arg   Asp   Ser   Thr   Leu   Ile   Tyr
65                            70                        75                                  80

Asp   Gln   Gln   Thr   Ala   Asn   Lys   Leu   Leu   Asp   Lys   Lys   Gln   Gln   Glu   Tyr
                        85                        90                                  95

Gln   Ser   Ile   Arg   Trp   Ile   Gly   Leu   Ile   Gln   Ser   Lys   Glu   Thr   Gly   Asp
                  100                       105                       110

Phe   Thr   Phe   Asn   Leu   Ser   Glu   Asp   Glu   Gln   Ala   Ile   Ile   Glu   Ile   Asn
            115                       120                       125

Gly   Lys   Ile   Ile   Ser   Asn   Lys   Gly   Lys   Glu   Lys   Gln   Val   Val   His   Leu
      130                       135                       140

Glu   Lys   Gly   Lys   Leu   Val   Pro   Ile   Lys   Ile   Glu   Tyr   Gln   Ser   Asp   Thr
145                       150                       155                                   160

Lys   Phe   Asn   Ile   Asp   Ser   Lys   Thr   Phe   Lys   Glu   Leu   Lys   Leu   Phe   Lys
                        165                       170                       175

Ile   Asp   Ser   Gln   Asn   Gln   Pro   Gln   Val   Gln   Gln   Asp   Glu   Leu   Arg
                  180                       185                       190

Asn   Pro   Glu   Phe   Asn   Lys   Lys   Glu   Ser   Gln   Glu   Phe   Leu   Ala   Lys   Pro
            195                       200                       205

Ser   Lys   Ile   Asn   Leu   Phe   Thr   Gln   Lys   Met   Lys   Arg   Glu   Ile   Asp   Glu
      210                       215                       220

Asp   Thr   Asp   Thr   Asp   Gly   Asp   Ser   Ile   Pro   Asp   Leu   Trp   Glu   Glu   Asn
225                       230                       235                                   240

Gly   Tyr   Thr   Ile   Gln   Asn   Arg   Ile   Ala   Val   Lys   Trp   Asp   Asp   Ser   Leu
                        245                       250                       255

Ala   Ser   Lys   Gly   Tyr   Thr   Lys   Phe   Val   Ser   Asn   Pro   Leu   Glu   Ser   His
                  260                       265                       270

Thr   Val   Gly   Asp   Pro   Tyr   Thr   Asp   Tyr   Glu   Lys   Ala   Ala   Arg   Asp   Leu
            275                       280                       285

Asp   Leu   Ser   Asn   Ala   Lys   Glu   Thr   Phe   Asn   Pro   Leu   Val   Ala   Ala   Phe
      290                       295                       300

Pro   Ser   Val   Asn   Val   Ser   Met   Glu   Lys   Val   Ile   Leu   Ser   Pro   Asn   Glu
305                       310                       315                                   320

Asn   Leu   Ser   Asn   Ser   Val   Glu   Ser   His   Ser   Ser   Thr   Asn   Trp   Ser   Tyr
                        325                       330                       335

Thr   Asn   Thr   Glu   Gly   Ala   Ser   Val   Ala   Gly   Ile   Gly   Pro   Lys   Gly
                  340                       345                       350

Ile   Ser   Phe   Gly   Val   Ser   Val   Asn   Tyr   Gln   His   Ser   Glu   Thr   Val   Ala
            355                       360                       365

Gln   Glu   Trp   Gly   Thr   Ser   Thr   Gly   Asn   Thr   Ser   Gln   Phe   Asn   Thr   Ala
      370                       375                       380

Ser   Ala   Gly   Tyr   Leu   Asn   Ala   Asn   Val   Arg   Tyr   Asn   Asn   Val   Gly   Thr
385                       390                       395                                   400

Gly   Ala   Ile   Tyr   Asp   Val   Lys   Pro   Thr   Thr   Ser   Phe   Val   Leu   Asn   Asn
                        405                       410                       415

Asp   Thr   Ile   Ala   Thr   Ile   Thr   Ala   Lys   Ser   Asn   Ser   Thr   Ala   Leu   Asn
                  420                       425                       430

Ile   Ser   Pro   Gly   Glu   Ser   Tyr   Pro   Lys   Lys   Gly   Gln   Asn   Gly   Ile   Ala
            435                       440                       445

Ile   Thr   Ser   Met   Asp   Asp   Phe   Asn   Ser   His   Pro   Ile   Thr   Leu   Asn   Lys
      450                       455                       460
```

| | | | | | | | | | | | | | | |
|---|---|---|---|---|---|---|---|---|---|---|---|---|---|---|
| Lys 465 | Gln | Val | Asp | Asn | Leu 470 | Leu | Asn | Asn | Lys 475 | Pro | Met | Met | Leu | Glu Thr 480 |
| Asn | Gln | Thr | Asp | Gly 485 | Val | Tyr | Lys | Ile | Lys 490 | Asp | Thr | His | Gly | Asn Ile 495 |
| Val | Thr | Gly | Gly 500 | Glu | Trp | Asn | Gly | Val 505 | Ile | Gln | Gln | Ile | Lys 510 | Ala Lys |
| Thr | Ala | Ser 515 | Ile | Ile | Val | Asp | Asp 520 | Gly | Glu | Arg | Val | Ala 525 | Glu | Lys Arg |
| Val | Ala | Ala 530 | Lys | Asp | Tyr | Glu 535 | Asn | Pro | Glu | Asp | Lys 540 | Thr | Pro | Ser Leu |
| Thr 545 | Leu | Lys | Asp | Ala | Leu 550 | Lys | Leu | Ser | Tyr | Pro 555 | Asp | Glu | Ile | Lys Glu 560 |
| Ile | Glu | Gly | Leu | Leu 565 | Tyr | Tyr | Lys | Asn | Lys 570 | Pro | Ile | Tyr | Glu 575 | Ser Ser |
| Val | Met | Thr | Tyr 580 | Leu | Asp | Glu | Asn | Thr 585 | Ala | Lys | Glu | Val | Thr 590 | Lys Gln |
| Leu | Asn | Asp 595 | Thr | Thr | Gly | Lys | Phe 600 | Lys | Asp | Val | Ser | His 605 | Leu | Tyr Asp |
| Val | Lys 610 | Leu | Thr | Pro | Lys | Met 615 | Asn | Val | Thr | Ile | Lys 620 | Leu | Ser | Ile Leu |
| Tyr 625 | Asp | Asn | Ala | Glu | Ser 630 | Asn | Asp | Asn | Ser | Ile 635 | Gly | Lys | Trp | Thr Asn 640 |
| Thr | Asn | Ile | Val | Ser 645 | Gly | Gly | Asn | Asn | Gly 650 | Lys | Lys | Gln | Tyr | Ser Ser 655 |
| Asn | Asn | Pro | Asp 660 | Ala | Asn | Leu | Thr | Leu 665 | Asn | Thr | Asp | Ala | Gln 670 | Glu Lys |
| Leu | Asn | Lys 675 | Asn | Arg | Asp | Tyr | Tyr 680 | Ile | Ser | Leu | Tyr | Met 685 | Lys | Ser Glu |
| Lys | Asn 690 | Thr | Gln | Cys | Glu | Ile 695 | Thr | Ile | Asp | Gly | Glu 700 | Ile | Tyr | Pro Ile |
| Thr 705 | Thr | Lys | Thr | Val | Asn 710 | Val | Asn | Lys | Asp | Asn 715 | Tyr | Lys | Arg | Leu Asp 720 |
| Ile | Ile | Ala | His | Asn 725 | Ile | Lys | Ser | Asn | Pro 730 | Ile | Ser | Ser | Leu | His Ile 735 |
| Lys | Thr | Asn | Asp 740 | Glu | Ile | Thr | Leu | Phe 745 | Trp | Asp | Asp | Ile | Ser 750 | Ile Thr |
| Asp | Val | Ala 755 | Ser | Ile | Lys | Pro | Glu 760 | Asn | Leu | Thr | Asp | Ser 765 | Glu | Ile Lys |
| Gln | Ile 770 | Tyr | Ser | Arg | Tyr | Gly 775 | Ile | Lys | Leu | Glu | Asp 780 | Gly | Ile | Leu Ile |
| Asp 785 | Lys | Lys | Gly | Gly | Ile 790 | His | Tyr | Gly | Glu | Phe 795 | Ile | Asn | Glu | Ala Ser 800 |
| Phe | Asn | Ile | Glu | Pro 805 | Leu | Gln | Asn | Tyr | Val 810 | Thr | Lys | Tyr | Glu 815 | Val Thr |
| Tyr | Ser | Ser | Glu 820 | Leu | Gly | Pro | Asn | Val 825 | Ser | Asp | Thr | Leu | Glu 830 | Ser Asp |
| Lys | Ile | Tyr 835 | Lys | Asp | Gly | Thr | Ile 840 | Lys | Phe | Asp | Phe | Thr 845 | Lys | Tyr Ser |
| Lys | Asn 850 | Glu | Gln | Gly | Leu | Phe 855 | Tyr | Asp | Ser | Gly | Leu 860 | Asn | Trp | Asp Phe |
| Lys 865 | Ile | Asn | Ala | Ile | Thr 870 | Tyr | Asp | Gly | Lys | Glu 875 | Met | Asn | Val | Phe His 880 |
| Arg | Tyr | Asn | Lys | | | | | | | | | | | |

(2) INFORMATION FOR SEQ ID NO:6:

(i) SEQUENCE CHARACTERISTICS:
        (A) LENGTH: 2004 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus cereus
&nb -continued

```
                          1080                            1085                            1090
TCT  AAT  TCT  ACA  GCC  TTA  AAT  ATA  TCT  CCT  GGA  GAA  AGT  TAC  CCG  AAA          672
Ser  Asn  Ser  Thr  Ala  Leu  Asn  Ile  Ser  Pro  Gly  Glu  Ser  Tyr  Pro  Lys
          1095                      1100                           1105

AAA  GGA  CAA  AAT  GGA  ATC  GCA  ATA  ACA  TCA  ATG  GAT  GAT  TTT  AAT  TCC          720
Lys  Gly  Gln  Asn  Gly  Ile  Ala  Ile  Thr  Ser  Met  Asp  Asp  Phe  Asn  Ser
1110                               1115                          1120

CAT  CCG  ATT  ACA  TTA  AAT  AAA  AAA  CAA  GTA  GAT  AAT  CTG  CTA  AAT  AAT          768
His  Pro  Ile  Thr  Leu  Asn  Lys  Lys  Gln  Val  Asp  Asn  Leu  Leu  Asn  Asn
1125                          1130                          1135                     1140

AAA  CCT  ATG  ATG  TTG  GAA  ACA  AAC  CAA  ACA  GAT  GGT  GTT  TAT  AAG  ATA          816
Lys  Pro  Met  Met  Leu  Glu  Thr  Asn  Gln  Thr  Asp  Gly  Val  Tyr  Lys  Ile
                              1145                          1150                     1155

AAA  GAT  ACA  CAT  GGA  AAT  ATA  GTA  ACT  GGC  GGA  GAA  TGG  AAT  GGT  GTC          864
Lys  Asp  Thr  His  Gly  Asn  Ile  Val  Thr  Gly  Gly  Glu  Trp  Asn  Gly  Val
                         1160                          1165                          1170

ATA  CAA  CAA  ATC  AAG  GCT  AAA  ACA  GCG  TCT  ATT  ATT  GTG  GAT  GAT  GGG          912
Ile  Gln  Gln  Ile  Lys  Ala  Lys  Thr  Ala  Ser  Ile  Ile  Val  Asp  Asp  Gly
                    1175                          1180                          1185

GAA  CGT  GTA  GCA  GAA  AAA  CGT  GTA  GCG  GCA  AAA  GAT  TAT  GAA  AAT  CCA          960
Glu  Arg  Val  Ala  Glu  Lys  Arg  Val  Ala  Ala  Lys  Asp  Tyr  Glu  Asn  Pro
               1190                          1195                          1200

GAA  GAT  AAA  ACA  CCG  TCT  TTA  ACT  TTA  AAA  GAT  GCC  CTG  AAG  CTT  TCA         1008
Glu  Asp  Lys  Thr  Pro  Ser  Leu  Thr  Leu  Lys  Asp  Ala  Leu  Lys  Leu  Ser
1205                          1210                          1215                     1220

TAT  CCA  GAT  GAA  ATA  AAA  GAA  ATA  GAG  GGA  TTA  TTA  TAT  TAT  AAA  AAC         1056
Tyr  Pro  Asp  Glu  Ile  Lys  Glu  Ile  Glu  Gly  Leu  Leu  Tyr  Tyr  Lys  Asn
                              1225                          1230                     1235

AAA  CCG  ATA  TAC  GAA  TCG  AGC  GTT  ATG  ACT  TAC  TTA  GAT  GAA  AAT  ACA         1104
Lys  Pro  Ile  Tyr  Glu  Ser  Ser  Val  Met  Thr  Tyr  Leu  Asp  Glu  Asn  Thr
                         1240                          1245                          1250

GCA  AAA  GAA  GTG  ACC  AAA  CAA  TTA  AAT  GAT  ACC  ACT  GGG  AAA  TTT  AAA         1152
Ala  Lys  Glu  Val  Thr  Lys  Gln  Leu  Asn  Asp  Thr  Thr  Gly  Lys  Phe  Lys
                    1255                          1260                          1265

GAT  GTA  AGT  CAT  TTA  TAT  GAT  GTA  AAA  CTG  ACT  CCA  AAA  ATG  AAT  GTT         1200
Asp  Val  Ser  His  Leu  Tyr  Asp  Val  Lys  Leu  Thr  Pro  Lys  Met  Asn  Val
               1270                          1275                          1280

ACA  ATC  AAA  TTG  TCT  ATA  CTT  TAT  GAT  AAT  GCT  GAG  TCT  AAT  GAT  AAC         1248
Thr  Ile  Lys  Leu  Ser  Ile  Leu  Tyr  Asp  Asn  Ala  Glu  Ser  Asn  Asp  Asn
1285                          1290                          1295                     1300

TCA  ATT  GGT  AAA  TGG  ACA  AAC  ACA  AAT  ATT  GTT  TCA  GGT  GGA  AAT  AAC         1296
Ser  Ile  Gly  Lys  Trp  Thr  Asn  Thr  Asn  Ile  Val  Ser  Gly  Gly  Asn  Asn
                              1305                          1310                     1315

GGA  AAA  AAA  CAA  TAT  TCT  TCT  AAT  AAT  CCG  GAT  GCT  AAT  TTG  ACA  TTA         1344
Gly  Lys  Lys  Gln  Tyr  Ser  Ser  Asn  Asn  Pro  Asp  Ala  Asn  Leu  Thr  Leu
                         1320                          1325                          1330

AAT  ACA  GAT  GCT  CAA  GAA  AAA  TTA  AAT  AAA  AAT  CGT  GAC  TAT  TAT  ATA         1392
Asn  Thr  Asp  Ala  Gln  Glu  Lys  Leu  Asn  Lys  Asn  Arg  Asp  Tyr  Tyr  Ile
          1335                          1340                          1345

AGT  TTA  TAT  ATG  AAG  TCA  GAA  AAA  AAC  ACA  CAA  TGT  GAG  ATT  ACT  ATA         1440
Ser  Leu  Tyr  Met  Lys  Ser  Glu  Lys  Asn  Thr  Gln  Cys  Glu  Ile  Thr  Ile
          1350                          1355                          1360

GAT  GGG  GAG  ATT  TAT  CCG  ATC  ACT  ACA  AAA  ACA  GTG  AAT  GTG  AAT  AAA         1488
Asp  Gly  Glu  Ile  Tyr  Pro  Ile  Thr  Thr  Lys  Thr  Val  Asn  Val  Asn  Lys
1365                          1370                          1375                     1380

GAC  AAT  TAC  AAA  AGA  TTA  GAT  ATT  ATA  GCT  CAT  AAT  ATA  AAA  AGT  AAT         1536
Asp  Asn  Tyr  Lys  Arg  Leu  Asp  Ile  Ile  Ala  His  Asn  Ile  Lys  Ser  Asn
                         1385                          1390                          1395

CCA  ATT  TCT  TCA  CTT  CAT  ATT  AAA  ACG  AAT  GAT  GAA  ATA  ACT  TTA  TTT         1584
Pro  Ile  Ser  Ser  Leu  His  Ile  Lys  Thr  Asn  Asp  Glu  Ile  Thr  Leu  Phe
```

|  | 1400 | | | | | 1405 | | | | | 1410 | | | | |
|---|---|---|---|---|---|---|---|---|---|---|---|---|---|---|---|
| TGG | GAT | GAT | ATT | TCT | ATA | ACA | GAT | GTA | GCA | TCA | ATA | AAA | CCG | GAA | AAT | 1632 |
| Trp | Asp | Asp | Ile | Ser | Ile | Thr | Asp | Val | Ala | Ser | Ile | Lys | Pro | Glu | Asn | |
| | 1415 | | | | | 1420 | | | | | 1425 | | | | | |
| TTA | ACA | GAT | TCA | GAA | ATT | AAA | CAG | ATT | TAT | AGT | AGG | TAT | GGT | ATT | AAG | 1680 |
| Leu | Thr | Asp | Ser | Glu | Ile | Lys | Gln | Ile | Tyr | Ser | Arg | Tyr | Gly | Ile | Lys | |
| | 1430 | | | | | 1435 | | | | | 1440 | | | | | |
| TTA | GAA | GAT | GGA | ATC | CTT | ATT | GAT | AAA | AAA | GGT | GGG | ATT | CAT | TAT | GGT | 1728 |
| Leu | Glu | Asp | Gly | Ile | Leu | Ile | Asp | Lys | Lys | Gly | Gly | Ile | His | Tyr | Gly | |
| 1445 | | | | | 1450 | | | | | 1455 | | | | | 1460 | |
| GAA | TTT | ATT | AAT | GAA | GCT | AGT | TTT | AAT | ATT | GAA | CCA | TTG | CCA | AAT | TAT | 1776 |
| Glu | Phe | Ile | Asn | Glu | Ala | Ser | Phe | Asn | Ile | Glu | Pro | Leu | Pro | Asn | Tyr | |
| | | | | 1465 | | | | | 1470 | | | | | 1475 | | |
| GTG | ACC | AAA | TAT | GAA | GTT | ACT | TAT | AGT | AGT | GAG | TTA | GGA | CCA | AAC | GTG | 1824 |
| Val | Thr | Lys | Tyr | Glu | Val | Thr | Tyr | Ser | Ser | Glu | Leu | Gly | Pro | Asn | Val | |
| | | | 1480 | | | | | 1485 | | | | | 1490 | | | |
| AGT | GAC | ACA | CTT | GAA | AGT | GAT | AAA | ATT | TAC | AAG | GAT | GGG | ACA | ATT | AAA | 1872 |
| Ser | Asp | Thr | Leu | Glu | Ser | Asp | Lys | Ile | Tyr | Lys | Asp | Gly | Thr | Ile | Lys | |
| | | 1495 | | | | | 1500 | | | | | 1505 | | | | |
| TTT | GAT | TTT | ACC | AAA | TAT | AGT | AAA | AAT | GAA | CAA | GGA | TTA | TTT | TAT | GAC | 1920 |
| Phe | Asp | Phe | Thr | Lys | Tyr | Ser | Lys | Asn | Glu | Gln | Gly | Leu | Phe | Tyr | Asp | |
| | 1510 | | | | | 1515 | | | | | 1520 | | | | | |
| AGT | GGA | TTA | AAT | TGG | GAC | TTT | AAA | ATT | AAT | GCT | ATT | ACT | TAT | GAT | GGT | 1968 |
| Ser | Gly | Leu | Asn | Trp | Asp | Phe | Lys | Ile | Asn | Ala | Ile | Thr | Tyr | Asp | Gly | |
| 1525 | | | | | 1530 | | | | | 1535 | | | | | 1540 | |
| AAA | GAG | ATG | AAT | GTT | TTT | CAT | AGA | TAT | AAT | AAA | TAG | | | | | 2004 |
| Lys | Glu | Met | Asn | Val | Phe | His | Arg | Tyr | Asn | Lys | | | | | | |
| | | | | 1545 | | | | | 1550 | | | | | | | |

(2) INFORMATION FOR SEQ ID NO:7:

(i) SEQUENCE CHARACTERISTICS:
        (A) LENGTH: 667 amino acids
        (B) TYPE: amino acid
        (D) TOPOLOGY: linear (ii) MOLECULE TYPE: protein (xi) SEQUENCE DESCRIPTION: SEQ ID NO:7:

| Met | Lys | Arg | Glu | Ile | Asp | Glu | Asp | Thr | Asp | Thr | Asp | Gly | Asp | Ser | Ile |
|---|---|---|---|---|---|---|---|---|---|---|---|---|---|---|---|
| 1 | | | | 5 | | | | | 10 | | | | | 15 | |
| Pro | Asp | Leu | Trp | Glu | Glu | Asn | Gly | Tyr | Thr | Ile | Gln | Asn | Arg | Ile | Ala |
| | | | 20 | | | | | 25 | | | | | 30 | | |
| Val | Lys | Trp | Asp | Asp | Ser | Leu | Ala | Ser | Lys | Gly | Tyr | Thr | Lys | Phe | Val |
| | | | 35 | | | | | 40 | | | | | 45 | | |
| Ser | Asn | Pro | Leu | Glu | Ser | His | Thr | Val | Gly | Asp | Pro | Tyr | Thr | Asp | Tyr |
| | | 50 | | | | | 55 | | | | | 60 | | | |
| Glu | Lys | Ala | Ala | Arg | Asp | Leu | Asp | Leu | Ser | Asn | Ala | Lys | Glu | Thr | Phe |
| 65 | | | | | 70 | | | | | 75 | | | | | 80 |
| Asn | Pro | Leu | Val | Ala | Ala | Phe | Pro | Ser | Val | Asn | Val | Ser | Met | Glu | Lys |
| | | | | 85 | | | | | 90 | | | | | 95 | |
| Val | Ile | Leu | Ser | Pro | Asn | Glu | Asn | Leu | Ser | Asn | Ser | Val | Glu | Ser | His |
| | | | | 100 | | | | | 105 | | | | | 110 | |
| Ser | Ser | Thr | Asn | Trp | Ser | Tyr | Thr | Asn | Thr | Glu | Gly | Ala | Ser | Val | Glu |
| | | | 115 | | | | | 120 | | | | | 125 | | |
| Ala | Gly | Ile | Gly | Pro | Lys | Gly | Ile | Ser | Phe | Gly | Val | Ser | Val | Asn | Tyr |
| | | | 130 | | | | | 135 | | | | | 140 | | |
| Gln | His | Ser | Glu | Thr | Val | Ala | Gln | Glu | Trp | Gly | Thr | Ser | Thr | Gly | Asn |
| 145 | | | | | 150 | | | | | 155 | | | | | 160 |

| | | | | | | | | | | | | | | |
|---|---|---|---|---|---|---|---|---|---|---|---|---|---|---|
| Thr | Ser | Gln | Phe | Asn 165 | Thr | Ala | Ser | Ala | Gly 170 | Tyr | Leu | Asn | Ala 175 | Asn | Val |
| Arg | Tyr | Asn | Asn 180 | Val | Gly | Thr | Gly | Ala 185 | Ile | Tyr | Asp | Val | Lys 190 | Pro | Thr |
| Thr | Ser | Phe 195 | Val | Leu | Asn | Asn | Asp 200 | Thr | Ile | Ala | Thr | Ile 205 | Thr | Ala | Lys |
| Ser | Asn 210 | Ser | Thr | Ala | Leu | Asn 215 | Ile | Ser | Pro | Gly | Glu 220 | Ser | Tyr | Pro | Lys |
| Lys 225 | Gly | Gln | Asn | Gly | Ile 230 | Ala | Ile | Thr | Ser | Met 235 | Asp | Asp | Phe | Asn | Ser 240 |
| His | Pro | Ile | Thr | Leu 245 | Asn | Lys | Lys | Gln | Val 250 | Asp | Asn | Leu | Leu 255 | Asn | Asn |
| Lys | Pro | Met | Met 260 | Leu | Glu | Thr | Asn | Gln 265 | Thr | Asp | Gly | Val | Tyr 270 | Lys | Ile |
| Lys | Asp | Thr 275 | His | Gly | Asn | Ile | Val 280 | Thr | Gly | Gly | Glu | Trp 285 | Asn | Gly | Val |
| Ile | Gln 290 | Gln | Ile | Lys | Ala | Lys 295 | Thr | Ala | Ser | Ile | Ile 300 | Val | Asp | Asp | Gly |
| Glu 305 | Arg | Val | Ala | Glu | Lys 310 | Arg | Val | Ala | Ala | Lys 315 | Asp | Tyr | Glu | Asn | Pro 320 |
| Glu | Asp | Lys | Thr | Pro 325 | Ser | Leu | Thr | Leu | Lys 330 | Asp | Ala | Leu | Lys 335 | Leu | Ser |
| Tyr | Pro | Asp | Glu 340 | Ile | Lys | Glu | Ile | Glu 345 | Gly | Leu | Leu | Tyr | Tyr 350 | Lys | Asn |
| Lys | Pro | Ile 355 | Tyr | Glu | Ser | Ser | Val 360 | Met | Thr | Tyr | Leu | Asp 365 | Glu | Asn | Thr |
| Ala | Lys 370 | Glu | Val | Thr | Lys | Gln 375 | Leu | Asn | Asp | Thr | Thr 380 | Gly | Lys | Phe | Lys |
| Asp 385 | Val | Ser | His | Leu | Tyr 390 | Asp | Val | Lys | Leu | Thr 395 | Pro | Lys | Met | Asn | Val 400 |
| Thr | Ile | Lys | Leu | Ser 405 | Ile | Leu | Tyr | Asp | Asn 410 | Ala | Glu | Ser | Asn | Asp 415 | Asn |
| Ser | Ile | Gly | Lys 420 | Trp | Thr | Asn | Thr | Asn 425 | Ile | Val | Ser | Gly | Gly 430 | Asn | Asn |
| Gly | Lys | Lys 435 | Gln | Tyr | Ser | Ser | Asn 440 | Asn | Pro | Asp | Ala | Asn 445 | Leu | Thr | Leu |
| Asn | Thr 450 | Asp | Ala | Gln | Glu | Lys 455 | Leu | Asn | Lys | Asn | Arg 460 | Asp | Tyr | Tyr | Ile |
| Ser 465 | Leu | Tyr | Met | Lys | Ser 470 | Glu | Lys | Asn | Thr | Gln 475 | Cys | Glu | Ile | Thr | Ile 480 |
| Asp | Gly | Glu | Ile | Tyr 485 | Pro | Ile | Thr | Thr | Lys 490 | Thr | Val | Asn | Val | Asn 495 | Lys |
| Asp | Asn | Tyr | Lys 500 | Arg | Leu | Asp | Ile | Ile 505 | Ala | His | Asn | Ile | Lys 510 | Ser | Asn |
| Pro | Ile | Ser 515 | Ser | Leu | His | Ile | Lys 520 | Thr | Asn | Asp | Glu | Ile 525 | Thr | Leu | Phe |
| Trp | Asp 530 | Asp | Ile | Ser | Ile | Thr 535 | Asp | Val | Ala | Ser | Ile 540 | Lys | Pro | Glu | Asn |
| Leu 545 | Thr | Asp | Ser | Glu | Ile 550 | Lys | Gln | Ile | Tyr | Ser 555 | Arg | Tyr | Gly | Ile | Lys 560 |
| Leu | Glu | Asp | Gly | Ile 565 | Leu | Ile | Asp | Lys | Lys 570 | Gly | Gly | Ile | His | Tyr 575 | Gly |
| Glu | Phe | Ile | Asn 580 | Glu | Ala | Ser | Phe | Asn 585 | Ile | Glu | Pro | Leu | Pro 590 | Asn | Tyr |

```
Val  Thr  Lys  Tyr  Glu  Val  Thr  Tyr  Ser  Ser  Glu  Leu  Gly  Pro  Asn  Val
          595                      600                     605

Ser  Asp  Thr  Leu  Glu  Ser  Asp  Lys  Ile  Tyr  Lys  Asp  Gly  Thr  Ile  Lys
          610                      615                     620

Phe  Asp  Phe  Thr  Lys  Tyr  Ser  Lys  Asn  Glu  Gln  Gly  Leu  Phe  Tyr  Asp
625                           630                     635                     640

Ser  Gly  Leu  Asn  Trp  Asp  Phe  Lys  Ile  Asn  Ala  Ile  Thr  Tyr  Asp  Gly
                    645                      650                     655

Lys  Glu  Met  Asn  Val  Phe  His  Arg  Tyr  Asn  Lys
               660                      665
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: Peptide
        ( B ) LOCATION: 1..16
        ( D ) OTHER INFORMATION: /note= "N-terminal sequence of
        protein purified from strain AB78"

( x i ) SEQUENCE DESCRIPTION: SEQ ID NO:8:

```
Lys  Arg  Glu  Ile  Asp  Glu  Asp  Thr  Asp  Thr  Asx  Gly  Asp  Ser  Ile  Pro
1                   5                        10                      15
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..21
        ( D ) OTHER INFORMATION: /note= "Oligonucleotide probe based
        on amino acids 3 to 9 of SEQ ID NO:8, using codon usage
        of Bacillus thuringiensis"

( x i ) SEQUENCE DESCRIPTION: SEQ ID NO:9:

```
GAAATTGATC AAGATACNGA T                                              21
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single (D) TOPOLOGY: linear (ii) MOLECULE TYPE: peptide (iii) HYPOTHETICAL: NO (v) FRAGMENT TYPE: N-terminal (vi) ORIGINAL SOURCE:
    (A) ORGANISM: Bacillus thuringiensis
    (B) STRAIN: AB88

(ix) FEATURE:
    (A) NAME/KEY: Peptide
    (B) LOCATION: 1..14
    (D) OTHER INFORMATION: /note= "N-terminal amino acid
        sequence of protein known as anion exchange fraction 23
        (smaller)"

(xi) SEQUENCE DESCRIPTION: SEQ ID NO:10:

Xaa Glu Pro Phe Val Ser Ala Xaa Xaa Xaa Gln Xaa Xaa Xaa
1               5                   10

(2) INFORMATION FOR SEQ ID NO:11:

(i) SEQUENCE CHARACTERISTICS:
      (A) LENGTH: 13 amino acids
      (B) TYPE: amino acid
      (C) STRANDEDNESS: single
      (D) TOPOLOGY: linear (vi) ORIGINAL SOURCE:
      (A) ORGANISM: Bacillus thuringiensis (xi) SEQUENCE DESCRIPTION: SEQ ID NO:11:

Xaa Glu Tyr Glu Asn Val Glu Pro Phe Val Ser Ala Xaa
1               5                   10

(2) INFORMATION FOR SEQ ID NO:12:

(i) SEQUENCE CHARACTERISTICS:
      (A) LENGTH: 14 amino acids
      (B) TYPE: amino acid
      (C) STRANDEDNESS: single
      (D) TOPOLOGY: linear (vi) ORIGINAL SOURCE:
      (A) ORGANISM: Bacillus thurigiensis (xi) SEQUENCE DESCRIPTION: SEQ ID NO:12:

Met Asn Lys Asn Asn Thr Lys Leu Pro Thr Arg Ala Leu Pro
1               5                   10

(2) INFORMATION FOR SEQ ID NO:13:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (iii) HYPOTHETICAL: NO (v) FRAGMENT TYPE: N-terminal (vi) ORIGINAL SOURCE:
      (A) ORGANISM: Bacillus thuringiensis
      (B) STRAIN: AB88

(ix) FEATURE:
      (A) NAME/KEY: Peptide
      (B) LOCATION: 1..15

(D) OTHER INFORMATION: /note= "N-terminal amino acid sequence of 35 kDa VIP active against Agrotis ipsilon"

(x i) SEQUENCE DESCRIPTION: SEQ ID NO:13:

```
Ala  Leu  Ser  Glu  Asn  Thr  Gly  Lys  Asp  Gly  Gly  Tyr  Ile  Val  Pro
 1              5                        10                            15
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (v i) ORIGINAL SOURCE:
        (A) ORGANISM: Bacillus thuringiensis (x i) SEQUENCE DESCRIPTION: SEQ ID NO:14:

```
Met  Asp  Asn  Asn  Pro  Asn  Ile  Asn  Glu
 1              5
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: N-terminal (i x) FEATURE:
        (A) NAME/KEY: Peptide
        (B) LOCATION: 1..9
        (D) OTHER INFORMATION: /note= "N-terminal sequence of 80 kDa delta- endotoxin"

(x i) SEQUENCE DESCRIPTION: SEQ ID NO:15:

```
Met  Asp  Asn  Asn  Pro  Asn  Ile  Asn  Glu
 1              5
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: N-terminal (v i) ORIGINAL SOURCE:
        (A) ORGANISM: Bacillus thuringiensis (i x) FEATURE:
        (A) NAME/KEY: Peptide
        (B) LOCATION: 1..11
        (D) OTHER INFORMATION: /note= "N-terminal sequence from 60 kDa delta- endotoxin"

(x i) SEQUENCE DESCRIPTION: SEQ ID NO:16:

```
Met  Asn  Val  Leu  Asn  Ser  Gly  Arg  Thr  Thr  Ile
 1              5                        10
```

( 2 ) INFORMATION FOR SEQ ID NO:17:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2652
( D ) OTHER INFORMATION: /note= "Maize optimized DNA sequence for 100 kd VIP1A(a) protein from AB78"

( x i ) SEQUENCE DESCRIPTION: SEQ ID NO:17:

```
ATGAAGAACA TGAAGAAGAA GCTGGCCAGC GTGGTGACCT GCACCCTGCT GGCCCCCATG    60
TTCCTGAACG GCAACGTGAA CGCCGTGTAC GCCGACAGCA AGACCAACCA GATCAGCACC   120
ACCCAGAAGA ACCAGCAGAA GGAGATGGAC CGCAAGGGCC TGCTGGGCTA CTACTTCAAG   180
GGCAAGGACT TCAGCAACCT GACCATGTTC GCCCCCACGC GTGACAGCAC CCTGATCTAC   240
GACCAGCAGA CCGCCAACAA GCTGCTGGAC AAGAAGCAGC AGGAGTACCA GAGCATCCGC   300
TGGATCGGCC TGATCCAGAG CAAGGAGACC GGCGACTTCA CCTTCAACCT GAGCGAGGAC   360
GAGCAGGCCA TCATCGAGAT CAACGGCAAG ATCATCAGCA ACAAGGGCAA GGAGAAGCAG   420
GTGGTGCACC TGGAGAAGGG CAAGCTGGTG CCCATCAAGA TCGAGTACCA GAGCGACACC   480
AAGTTCAACA TCGACAGCAA GACCTTCAAG GAGCTGAAGC TTTTCAAGAT CGACAGCCAG   540
AACCAGCCCC AGCAGGTGCA GCAGGACGAG CTGCGCAACC CCGAGTTCAA CAAGAAGGAG   600
AGCCAGGAGT TCCTGGCCAA GCCCAGCAAG ATCAACCTGT TCACCCAGCA GATGAAGCGC   660
GAGATCGACG AGGACACCGA CACCGACGGC GACAGCATCC CCGACCTGTG GGAGGAGAAC   720
GGCTACACCA TCCAGAACCG CATCGCCGTG AAGTGGGACG ACAGCCTGGC TAGCAAGGGC   780
TACACCAAGT TCGTGAGCAA CCCCCTGGAG AGCCACACCG TGGGCGACCC CTACACCGAC   840
TACGAGAAGG CCGCCCGCGA CCTGGACCTG AGCAACGCCA AGGAGACCTT CAACCCCCTG   900
GTGGCCGCCT TCCCCAGCGT GAACGTGAGC ATGGAGAAGG TGATCCTGAG CCCCAACGAG   960
AACCTGAGCA ACAGCGTGGA GAGCCACTCG AGCACCAACT GGAGCTACAC CAACACCGAG  1020
GGCGCCAGCG TGGAGGCCGG CATCGGTCCC AAGGGCATCA GCTTCGGCGT GAGCGTGAAC  1080
TACCAGCACA GCGAGACCGT GGCCCAGGAG TGGGGCACCA GCACCGGCAA CACCAGCCAG  1140
TTCAACACCG CCAGCGCCGG CTACCTGAAC GCCAACGTGC GCTACAACAA CGTGGGCACC  1200
GGCGCCATCT ACGACGTGAA GCCCACCACC AGCTTCGTGC TGAACAACGA CACCATCGCC  1260
ACCATCACCG CCAAGTCGAA TTCCACCGCC CTGAACATCA GCCCCGGCGA GAGCTACCCC  1320
AAGAAGGGCC AGAACGGCAT CGCCATCACC AGCATGGACG ACTTCAACAG CCACCCCATC  1380
ACCCTGAACA AGAAGCAGGT GGACAACCTG CTGAACAACA AGCCCATGAT GCTGGAGACC  1440
AACCAGACCG ACGGCGTCTA CAAGATCAAG GACACCCACG GCAACATCGT GACCGGCGGC  1500
GAGTGGAACG GCGTGATCCA GCAGATCAAG GCCAAGACCG CCAGCATCAT CGTCGACGAC  1560
GGCGAGCGCG TGGCCGAGAA GCGCGTGGCC GCCAAGGACT ACGAGAACCC CGAGGACAAG  1620
ACCCCCAGCC TGACCCTGAA GGACGCCCTG AAGCTGAGCT ACCCCGACGA GATCAAGGAG  1680
ATCGAGGGCC TGCTGTACTA CAAGAACAAG CCCATCTACG AGAGCAGCGT GATGACCTAT  1740
```

```
CTAGACGAGA ACACCGCCAA GGAGGTGACC AAGCAGCTGA ACGACACCAC CGGCAAGTTC 1800
AAGGACGTGA GCCACCTGTA CGACGTGAAG CTGACCCCCA AGATGAACGT GACCATCAAG 1860
CTGAGCATCC TGTACGACAA CGCCGAGAGC AACGACAACA GCATCGGCAA GTGGACCAAC 1920
ACCAACATCG TGAGCGGCGG CAACAACGGC AAGAAGCAGT ACAGCAGCAA CAACCCCGAC 1980
GCCAACCTGA CCCTGAACAC CGACGCCCAG GAGAAGCTGA ACAAGAACCG CGACTACTAC 2040
ATCAGCCTGT ACATGAAGAG CGAGAAGAAC ACCCAGTGCG AGATCACCAT CGACGGCGAG 2100
ATATACCCCA TCACCACCAA GACCGTGAAC GTGAACAAGG ACAACTACAA GCGCCTGGAC 2160
ATCATCGCCC ACAACATCAA GAGCAACCCC ATCAGCAGCC TGCACATCAA GACCAACGAC 2220
GAGATCACCC TGTTCTGGGA CGACATATCG ATTACCGACG TCGCCAGCAT CAAGCCCGAG 2280
AACCTGACCG ACAGCGAGAT CAAGCAGATA TACAGTCGCT ACGGCATCAA GCTGGAGGAC 2340
GGCATCCTGA TCGACAAGAA GGGCGGCATC CACTACGGCG AGTTCATCAA CGAGGCCAGC 2400
TTCAACATCG AGCCCCTGCA GAACTACGTG ACCAAGTACG AGGTGACCTA CAGCAGCGAG 2460
CTGGGCCCCA ACGTGAGCGA CACCCTGGAG AGCGACAAGA TTTACAAGGA CGGCACCATC 2520
AAGTTCGACT TCACCAAGTA CAGCAAGAAC GAGCAGGGCC TGTTCTACGA CAGCGGCCTG 2580
AACTGGGACT TCAAGATCAA CGCCATCACC TACGACGGCA AGGAGATGAA CGTGTTCCAC 2640
CGCTACAACA AGTAG 2655
```

( 2 ) INFORMATION FOR SEQ ID NO:18:

( i ) SEQUENCE CHARACTERISTICS:
( A ) LENGTH: 2004 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2004
( D ) OTHER INFORMATION: /note= "Maize optimized DNA sequence for VIP1A(a) 80 kd protein from AB78"

( x i ) SEQUENCE DESCRIPTION: SEQ ID NO:18:

```
ATGAAGCGCG AGATCGACGA GGACACCGAC ACCGACGGCG ACAGCATCCC CGACCTGTGG 60
GAGGAGAACG GCTACACCAT CCAGAACCGC ATCGCCGTGA AGTGGGACGA CAGCCTGGCT 120
AGCAAGGGCT ACACCAAGTT CGTGAGCAAC CCCCTGGAGA GCCACACCGT GGGCGACCCC 180
TACACCGACT ACGAGAAGGC CGCCCGCGAC CTGGACCTGA GCAACGCCAA GGAGACCTTC 240
AACCCCCTGG TGGCCGCCTT CCCCAGCGTG AACGTGAGCA TGGAGAAGGT GATCCTGAGC 300
CCCAACGAGA ACCTGAGCAA CAGCGTGGAG AGCCACTCGA GCACCAACTG GAGCTACACC 360
AACACCGAGG GCGCCAGCGT GGAGGCCGGC ATCGGTCCCA AGGGCATCAG CTTCGGCGTG 420
AGCGTGAACT ACCAGCACAG CGAGACCGTG GCCCAGGAGT GGGGCACCAG CACCGGCAAC 480
ACCAGCCAGT TCAACACCGC CAGCGCCGGC TACCTGAACG CCAACGTGCG CTACAACAAC 540
GTGGGCACCG GCGCCATCTA CGACGTGAAG CCCACCACCA GCTTCGTGCT GAACAACGAC 600
ACCATCGCCA CCATCACCGC CAAGTCGAAT TCCACCGCCC TGAACATCAG CCCCGGCGAG 660
AGCTACCCCA AGAAGGGCCA GAACGGCATC GCCATCACCA GCATGGACGA CTTCAACAGC 720
```

-continued

| | | | | | | |
|---|---|---|---|---|---|---|
| CACCCCATCA | CCCTGAACAA | GAAGCAGGTG | GACAACCTGC | TGAACAACAA | GCCCATGATG | 780 |
| CTGGAGACCA | ACCAGACCGA | CGGCGTCTAC | AAGATCAAGG | ACACCCACGG | CAACATCGTG | 840 |
| ACCGGCGGCG | AGTGGAACGG | CGTGATCCAG | CAGATCAAGG | CCAAGACCGC | CAGCATCATC | 900 |
| GTCGACGACG | GCGAGCGCGT | GGCCGAGAAG | CGCGTGGCCG | CCAAGGACTA | CGAGAACCCC | 960 |
| GAGGACAAGA | CCCCCAGCCT | GACCCTGAAG | GACGCCCTGA | AGCTGAGCTA | CCCCGACGAG | 1020 |
| ATCAAGGAGA | TCGAGGGCCT | GCTGTACTAC | AAGAACAAGC | CCATCTACGA | GAGCAGCGTG | 1080 |
| ATGACCTATC | TAGACGAGAA | CACCGCCAAG | GAGGTGACCA | AGCAGCTGAA | CGACACCACC | 1140 |
| GGCAAGTTCA | AGGACGTGAG | CCACCTGTAC | GACGTGAAGC | TGACCCCCAA | GATGAACGTG | 1200 |
| ACCATCAAGC | TGAGCATCCT | GTACGACAAC | GCCGAGAGCA | ACGACAACAG | CATCGGCAAG | 1260 |
| TGGACCAACA | CCAACATCGT | GAGCGGCGGC | AACAACGGCA | AGAAGCAGTA | CAGCAGCAAC | 1320 |
| AACCCCGACG | CCAACCTGAC | CCTGAACACC | GACGCCCAGG | AGAAGCTGAA | CAAGAACCGC | 1380 |
| GACTACTACA | TCAGCCTGTA | CATGAAGAGC | GAGAAGAACA | CCCAGTGCGA | GATCACCATC | 1440 |
| GACGGCGAGA | TATACCCCAT | CACCACCAAG | ACCGTGAACG | TGAACAAGGA | CAACTACAAG | 1500 |
| CGCCTGGACA | TCATCGCCCA | CAACATCAAG | AGCAACCCCA | TCAGCAGCCT | GCACATCAAG | 1560 |
| ACCAACGACG | AGATCACCCT | GTTCTGGGAC | GACATATCGA | TTACCGACGT | CGCCAGCATC | 1620 |
| AAGCCCGAGA | ACCTGACCGA | CAGCGAGATC | AAGCAGATAT | ACAGTCGCTA | CGGCATCAAG | 1680 |
| CTGGAGGACG | GCATCCTGAT | CGACAAGAAG | GGCGGCATCC | ACTACGGCGA | GTTCATCAAC | 1740 |
| GAGGCCAGCT | TCAACATCGA | GCCCCTGCAG | AACTACGTGA | CCAAGTACGA | GGTGACCTAC | 1800 |
| AGCAGCGAGC | TGGGCCCCAA | CGTGAGCGAC | ACCCTGGAGA | GCGACAAGAT | TTACAAGGAC | 1860 |
| GGCACCATCA | AGTTCGACTT | CACCAAGTAC | AGCAAGAACG | AGCAGGGCCT | GTTCTACGAC | 1920 |
| AGCGGCCTGA | ACTGGGACTT | CAAGATCAAC | GCCATCACCT | ACGACGGCAA | GGAGATGAAC | 1980 |
| GTGTTCCACC | GCTACAACAA | GTAG | | | | 2004 |

( 2 ) INFORMATION FOR SEQ ID NO:19:

( i ) SEQUENCE CHARACTERISTICS:
( A ) LENGTH: 4074 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1386
( D ) OTHER INFORMATION: /product="VIP2A(b) from Btt"

( i x ) FEATURE:
( A ) NAME/KEY: CDS
( B ) LOCATION: 1394..3895
( D ) OTHER INFORMATION: /product="VIP1A(b) from Btt"

( i x ) FEATURE:
( A ) NAME/KEY: misc_feature
( B ) LOCATION: 1..4074
( D ) OTHER INFORMATION: /note= "Cloned DNA sequence from Btt which contains the genes for both VIP1A(b) and VIP2A(b)"

( x i ) SEQUENCE DESCRIPTION: SEQ ID NO:19:

```
ATG CAA AGA ATG GAG GGA AAG TTG TTT GTG GTG TCA AAA ACA TTA CAA      48
Met Gln Arg Met Glu Gly Lys Leu Phe Val Val Ser Lys Thr Leu Gln
        670                 675                 680

GTA GTT ACT AGA ACT GTA TTG CTT AGT ACA GTT TAC TCT ATA ACT TTA      96
Val Val Thr Arg Thr Val Leu Leu Ser Thr Val Tyr Ser Ile Thr Leu
```

-continued

|     |     |     | 685 |     |     |     |     |     | 690 |     |     |     |     |     | 695 |      |
|-----|-----|-----|-----|-----|-----|-----|-----|-----|-----|-----|-----|-----|-----|-----|-----|------|
| TTA | AAT | AAT | GTA | GTG | ATA | AAA | GCT | GAC | CAA | TTA | AAT | ATA | AAT | TCT | CAA | 144  |
| Leu | Asn | Asn | Val | Val | Ile | Lys | Ala | Asp | Gln | Leu | Asn | Ile | Asn | Ser | Gln |      |
| 700 |     |     |     |     | 705 |     |     |     |     | 710 |     |     |     |     | 715 |      |
| AGT | AAA | TAT | ACT | AAC | TTG | CAA | AAT | CTA | AAA | ATC | CCT | GAT | AAT | GCA | GAG | 192  |
| Ser | Lys | Tyr | Thr | Asn | Leu | Gln | Asn | Leu | Lys | Ile | Pro | Asp | Asn | Ala | Glu |      |
|     |     |     |     | 720 |     |     |     |     | 725 |     |     |     |     | 730 |     |      |
| GAT | TTT | AAA | GAA | GAT | AAG | GGG | AAA | GCG | AAA | GAA | TGG | GGG | AAA | GAG | AAA | 240  |
| Asp | Phe | Lys | Glu | Asp | Lys | Gly | Lys | Ala | Lys | Glu | Trp | Gly | Lys | Glu | Lys |      |
|     |     |     | 735 |     |     |     |     | 740 |     |     |     |     | 745 |     |     |      |
| GGG | GAA | GAG | TGG | AGG | CCT | CCT | GCT | ACT | GAG | AAA | GGA | GAA | ATG | AAT | AAT | 288  |
| Gly | Glu | Glu | Trp | Arg | Pro | Pro | Ala | Thr | Glu | Lys | Gly | Glu | Met | Asn | Asn |      |
|     |     | 750 |     |     |     |     | 755 |     |     |     |     | 760 |     |     |     |      |
| TTT | TTA | GAT | AAT | AAA | AAT | GAT | ATA | AAG | ACC | AAT | TAT | AAA | GAA | ATT | ACT | 336  |
| Phe | Leu | Asp | Asn | Lys | Asn | Asp | Ile | Lys | Thr | Asn | Tyr | Lys | Glu | Ile | Thr |      |
|     | 765 |     |     |     |     | 770 |     |     |     |     | 775 |     |     |     |     |      |
| TTT | TCT | ATG | GCA | GGT | TCA | TGT | GAA | GAT | GAA | ATA | AAA | GAT | TTA | GAA | GAA | 384  |
| Phe | Ser | Met | Ala | Gly | Ser | Cys | Glu | Asp | Glu | Ile | Lys | Asp | Leu | Glu | Glu |      |
| 780 |     |     |     |     | 785 |     |     |     |     | 790 |     |     |     |     | 795 |      |
| ATT | GAT | AAG | ATC | TTT | GAT | AAA | GCC | AAT | CTC | TCG | AGT | TCT | ATT | ATC | ACC | 432  |
| Ile | Asp | Lys | Ile | Phe | Asp | Lys | Ala | Asn | Leu | Ser | Ser | Ser | Ile | Ile | Thr |      |
|     |     |     |     | 800 |     |     |     |     | 805 |     |     |     |     | 810 |     |      |
| TAT | AAA | AAT | GTG | GAA | CCA | GCA | ACA | ATT | GGA | TTT | AAT | AAA | TCT | TTA | ACA | 480  |
| Tyr | Lys | Asn | Val | Glu | Pro | Ala | Thr | Ile | Gly | Phe | Asn | Lys | Ser | Leu | Thr |      |
|     |     |     | 815 |     |     |     |     | 820 |     |     |     |     | 825 |     |     |      |
| GAA | GGT | AAT | ACG | ATT | AAT | TCT | GAT | GCA | ATG | GCA | CAG | TTT | AAA | GAA | CAA | 528  |
| Glu | Gly | Asn | Thr | Ile | Asn | Ser | Asp | Ala | Met | Ala | Gln | Phe | Lys | Glu | Gln |      |
|     |     | 830 |     |     |     |     | 835 |     |     |     |     | 840 |     |     |     |      |
| TTT | TTA | GGT | AAG | GAT | ATG | AAG | TTT | GAT | AGT | TAT | CTA | GAT | ACT | CAT | TTA | 576  |
| Phe | Leu | Gly | Lys | Asp | Met | Lys | Phe | Asp | Ser | Tyr | Leu | Asp | Thr | His | Leu |      |
|     | 845 |     |     |     |     | 850 |     |     |     |     | 855 |     |     |     |     |      |
| ACT | GCT | CAA | CAA | GTT | TCC | AGT | AAA | AAA | AGA | GTT | ATT | TTG | AAG | GTT | ACG | 624  |
| Thr | Ala | Gln | Gln | Val | Ser | Ser | Lys | Lys | Arg | Val | Ile | Leu | Lys | Val | Thr |      |
| 860 |     |     |     |     | 865 |     |     |     |     | 870 |     |     |     |     | 875 |      |
| GTT | CCG | AGT | GGG | AAA | GGT | TCT | ACT | ACT | CCA | ACA | AAA | GCA | GGT | GTC | ATT | 672  |
| Val | Pro | Ser | Gly | Lys | Gly | Ser | Thr | Thr | Pro | Thr | Lys | Ala | Gly | Val | Ile |      |
|     |     |     |     | 880 |     |     |     |     | 885 |     |     |     |     | 890 |     |      |
| TTA | AAC | AAT | AAT | GAA | TAC | AAA | ATG | CTC | ATT | GAT | AAT | GGG | TAT | GTG | CTC | 720  |
| Leu | Asn | Asn | Asn | Glu | Tyr | Lys | Met | Leu | Ile | Asp | Asn | Gly | Tyr | Val | Leu |      |
|     |     |     | 895 |     |     |     |     | 900 |     |     |     |     | 905 |     |     |      |
| CAT | GTA | GAT | AAG | GTA | TCA | AAA | GTA | GTA | AAA | AAA | GGG | ATG | GAG | TGC | TTA | 768  |
| His | Val | Asp | Lys | Val | Ser | Lys | Val | Val | Lys | Lys | Gly | Met | Glu | Cys | Leu |      |
|     |     | 910 |     |     |     |     | 915 |     |     |     |     | 920 |     |     |     |      |
| CAA | GTT | GAA | GGG | ACT | TTA | AAA | AAG | AGT | CTC | GAC | TTT | AAA | AAT | GAT | ATA | 816  |
| Gln | Val | Glu | Gly | Thr | Leu | Lys | Lys | Ser | Leu | Asp | Phe | Lys | Asn | Asp | Ile |      |
|     | 925 |     |     |     |     | 930 |     |     |     |     | 935 |     |     |     |     |      |
| AAT | GCT | GAA | GCG | CAT | AGC | TGG | GGG | ATG | AAA | ATT | TAT | GAA | GAC | TGG | GCT | 864  |
| Asn | Ala | Glu | Ala | His | Ser | Trp | Gly | Met | Lys | Ile | Tyr | Glu | Asp | Trp | Ala |      |
| 940 |     |     |     |     | 945 |     |     |     |     | 950 |     |     |     |     | 955 |      |
| AAA | AAT | TTA | ACC | GCT | TCG | CAA | AGG | GAA | GCT | TTA | GAT | GGG | TAT | GCT | AGG | 912  |
| Lys | Asn | Leu | Thr | Ala | Ser | Gln | Arg | Glu | Ala | Leu | Asp | Gly | Tyr | Ala | Arg |      |
|     |     |     |     | 960 |     |     |     |     | 965 |     |     |     |     | 970 |     |      |
| CAA | GAT | TAT | AAA | GAA | ATC | AAT | AAT | TAT | TTG | CGC | AAT | CAA | GGC | GGG | AGT | 960  |
| Gln | Asp | Tyr | Lys | Glu | Ile | Asn | Asn | Tyr | Leu | Arg | Asn | Gln | Gly | Gly | Ser |      |
|     |     |     | 975 |     |     |     |     | 980 |     |     |     |     | 985 |     |     |      |
| GGA | AAT | GAA | AAG | CTG | GAT | GCC | CAA | TTA | AAA | AAT | ATT | TCT | GAT | GCT | TTA | 1008 |
| Gly | Asn | Glu | Lys | Leu | Asp | Ala | Gln | Leu | Lys | Asn | Ile | Ser | Asp | Ala | Leu |      |
|     |     | 990 |     |     |     |     | 995 |     |     |     |     | 1000|     |     |     |      |
| GGG | AAG | AAA | CCC | ATA | CCA | GAA | AAT | ATT | ACC | GTG | TAT | AGA | TGG | TGT | GGC | 1056 |
| Gly | Lys | Lys | Pro | Ile | Pro | Glu | Asn | Ile | Thr | Val | Tyr | Arg | Trp | Cys | Gly |      |

-continued

|  | 1005 | | | | | 1010 | | | | | 1015 | | | | |  |
|---|---|---|---|---|---|---|---|---|---|---|---|---|---|---|---|---|
| ATG | CCG | GAA | TTT | GGT | TAT | CAA | ATT | AGT | GAT | CCG | TTA | CCT | TCT | TTA | AAA | 1104 |
| Met | Pro | Glu | Phe | Gly | Tyr | Gln | Ile | Ser | Asp | Pro | Leu | Pro | Ser | Leu | Lys | |
| 1020 | | | | | 1025 | | | | | 1030 | | | | | 1035 | |
| GAT | TTT | GAA | GAA | CAA | TTT | TTA | AAT | ACA | ATT | AAA | GAA | GAC | AAA | GGG | TAT | 1152 |
| Asp | Phe | Glu | Glu | Gln | Phe | Leu | Asn | Thr | Ile | Lys | Glu | Asp | Lys | Gly | Tyr | |
| | | | | 1040 | | | | | 1045 | | | | | 1050 | | |
| ATG | AGT | ACA | AGC | TTA | TCG | AGT | GAA | CGT | CTT | GCA | GCT | TTT | GGA | TCT | AGA | 1200 |
| Met | Ser | Thr | Ser | Leu | Ser | Ser | Glu | Arg | Leu | Ala | Ala | Phe | Gly | Ser | Arg | |
| | | | 1055 | | | | | 1060 | | | | | 1065 | | | |
| AAA | ATT | ATA | TTA | CGC | TTA | CAA | GTT | CCG | AAA | GGA | AGT | ACG | GGG | GCG | TAT | 1248 |
| Lys | Ile | Ile | Leu | Arg | Leu | Gln | Val | Pro | Lys | Gly | Ser | Thr | Gly | Ala | Tyr | |
| | | 1070 | | | | | 1075 | | | | | 1080 | | | | |
| TTA | AGT | GCC | ATT | GGT | GGA | TTT | GCA | AGT | GAA | AAA | GAG | ATC | CTA | CTT | GAT | 1296 |
| Leu | Ser | Ala | Ile | Gly | Gly | Phe | Ala | Ser | Glu | Lys | Glu | Ile | Leu | Leu | Asp | |
| | 1085 | | | | | 1090 | | | | | 1095 | | | | | |
| AAA | GAT | AGT | AAA | TAT | CAT | ATT | GAT | AAA | GCA | ACA | GAG | GTA | ATC | ATT | AAA | 1344 |
| Lys | Asp | Ser | Lys | Tyr | His | Ile | Asp | Lys | Ala | Thr | Glu | Val | Ile | Ile | Lys | |
| 1100 | | | | | 1105 | | | | | 1110 | | | | | 1115 | |
| GGT | GTT | AAG | CGA | TAT | GTA | GTG | GAT | GCA | ACA | TTA | TTA | ACA | AAT | | | 1386 |
| Gly | Val | Lys | Arg | Tyr | Val | Val | Asp | Ala | Thr | Leu | Leu | Thr | Asn | | | |
| | | | | 1120 | | | | | 1125 | | | | | | | |
| TAAGGAG | ATG | AAA | AAT | ATG | AAG | AAA | AAG | TTA | GCA | AGT | GTT | GTA | ACC | TGT | | 1435 |
| | Met | Lys | Asn | Met | Lys | Lys | Lys | Leu | Ala | Ser | Val | Val | Thr | Cys | | |
| | 1 | | | | 5 | | | | | 10 | | | | | | |
| ATG | TTA | TTA | GCT | CCT | ATG | TTT | TTG | AAT | GGA | AAT | GTG | AAT | GCT | GTT | AAC | 1483 |
| Met | Leu | Leu | Ala | Pro | Met | Phe | Leu | Asn | Gly | Asn | Val | Asn | Ala | Val | Asn | |
| 15 | | | | | 20 | | | | | 25 | | | | | 30 | |
| GCG | GAT | AGT | AAA | ATA | AAT | CAG | ATT | TCT | ACA | ACG | CAG | GAA | AAC | CAA | CAG | 1531 |
| Ala | Asp | Ser | Lys | Ile | Asn | Gln | Ile | Ser | Thr | Thr | Gln | Glu | Asn | Gln | Gln | |
| | | | | 35 | | | | | 40 | | | | | 45 | | |
| AAA | GAG | ATG | GAC | CGA | AAG | GGA | TTA | TTG | GGA | TAT | TAT | TTC | AAA | GGA | AAA | 1579 |
| Lys | Glu | Met | Asp | Arg | Lys | Gly | Leu | Leu | Gly | Tyr | Tyr | Phe | Lys | Gly | Lys | |
| | | | 50 | | | | | 55 | | | | | 60 | | | |
| GAT | TTT | AAT | AAT | CTT | ACT | ATG | TTT | GCA | CCG | ACA | CGT | GAT | AAT | ACC | CTT | 1627 |
| Asp | Phe | Asn | Asn | Leu | Thr | Met | Phe | Ala | Pro | Thr | Arg | Asp | Asn | Thr | Leu | |
| | | 65 | | | | | 70 | | | | | 75 | | | | |
| ATG | TAT | GAC | CAA | CAA | ACA | GCG | AAT | GCA | TTA | TTA | GAT | AAA | AAA | CAA | CAA | 1675 |
| Met | Tyr | Asp | Gln | Gln | Thr | Ala | Asn | Ala | Leu | Leu | Asp | Lys | Lys | Gln | Gln | |
| | 80 | | | | | 85 | | | | | 90 | | | | | |
| GAA | TAT | CAG | TCC | ATT | CGT | TGG | ATT | GGT | TTG | ATT | CAG | CGT | AAA | GAA | ACG | 1723 |
| Glu | Tyr | Gln | Ser | Ile | Arg | Trp | Ile | Gly | Leu | Ile | Gln | Arg | Lys | Glu | Thr | |
| 95 | | | | | 100 | | | | | 105 | | | | | 110 | |
| GGC | GAT | TTC | ACA | TTT | AAC | TTA | TCA | AAG | GAT | GAA | CAG | GCA | ATT | ATA | GAA | 1771 |
| Gly | Asp | Phe | Thr | Phe | Asn | Leu | Ser | Lys | Asp | Glu | Gln | Ala | Ile | Ile | Glu | |
| | | | | 115 | | | | | 120 | | | | | 125 | | |
| ATC | GAT | GGG | AAA | ATC | ATT | TCT | AAT | AAA | GGG | AAA | GAA | AAG | CAA | GTT | GTC | 1819 |
| Ile | Asp | Gly | Lys | Ile | Ile | Ser | Asn | Lys | Gly | Lys | Glu | Lys | Gln | Val | Val | |
| | | | 130 | | | | | 135 | | | | | 140 | | | |
| CAT | TTA | GAA | AAA | GAA | AAA | TTA | GTT | CCA | ATC | AAA | ATA | GAG | TAT | CAA | TCA | 1867 |
| His | Leu | Glu | Lys | Glu | Lys | Leu | Val | Pro | Ile | Lys | Ile | Glu | Tyr | Gln | Ser | |
| | | | 145 | | | | | 150 | | | | | 155 | | | |
| GAT | ACG | AAA | TTT | AAT | ATT | GAT | AGT | AAA | ACA | TTT | AAA | GAA | CTT | AAA | TTA | 1915 |
| Asp | Thr | Lys | Phe | Asn | Ile | Asp | Ser | Lys | Thr | Phe | Lys | Glu | Leu | Lys | Leu | |
| | | 160 | | | | | 165 | | | | | 170 | | | | |
| TTT | AAA | ATA | GAT | AGT | CAA | AAC | CAA | TCT | CAA | CAA | GTT | CAA | CTG | AGA | AAC | 1963 |
| Phe | Lys | Ile | Asp | Ser | Gln | Asn | Gln | Ser | Gln | Gln | Val | Gln | Leu | Arg | Asn | |
| 175 | | | | | 180 | | | | | 185 | | | | | 190 | |
| CCT | GAA | TTT | AAC | AAA | AAA | GAA | TCA | CAG | GAA | TTT | TTA | GCA | AAA | GCA | TCA | 2011 |
| Pro | Glu | Phe | Asn | Lys | Lys | Glu | Ser | Gln | Glu | Phe | Leu | Ala | Lys | Ala | Ser | |

|     |     |     |     |     |     | 195 |     |     |     |     |     | 200 |     |     |     |     | 205 |     |      |
|-----|-----|-----|-----|-----|-----|-----|-----|-----|-----|-----|-----|-----|-----|-----|-----|-----|-----|-----|------|

```
AAA  ACA  AAC  CTT  TTT  AAG  CAA  AAA  ATG  AAA  AGA  GAT  ATT  GAT  GAA  GAT              2059
Lys  Thr  Asn  Leu  Phe  Lys  Gln  Lys  Met  Lys  Arg  Asp  Ile  Asp  Glu  Asp
               210                      215                      220

ACG  GAT  ACA  GAT  GGA  GAC  TCC  ATT  CCT  GAT  CTT  TGG  GAA  GAA  AAT  GGG              2107
Thr  Asp  Thr  Asp  Gly  Asp  Ser  Ile  Pro  Asp  Leu  Trp  Glu  Glu  Asn  Gly
               225                      230                      235

TAC  ACG  ATT  CAA  AAT  AAA  GTT  GCT  GTC  AAA  TGG  GAT  GAT  TCG  CTA  GCA              2155
Tyr  Thr  Ile  Gln  Asn  Lys  Val  Ala  Val  Lys  Trp  Asp  Asp  Ser  Leu  Ala
               240                      245                      250

AGT  AAG  GGA  TAT  ACA  AAA  TTT  GTT  TCG  AAT  CCA  TTA  GAC  AGC  CAC  ACA              2203
Ser  Lys  Gly  Tyr  Thr  Lys  Phe  Val  Ser  Asn  Pro  Leu  Asp  Ser  His  Thr
255                 260                      265                      270

GTT  GGC  GAT  CCC  TAT  ACT  GAT  TAT  GAA  AAG  GCC  GCA  AGG  GAT  TTA  GAT              2251
Val  Gly  Asp  Pro  Tyr  Thr  Asp  Tyr  Glu  Lys  Ala  Ala  Arg  Asp  Leu  Asp
                    275                      280                      285

TTA  TCA  AAT  GCA  AAG  GAA  ACG  TTC  AAC  CCA  TTG  GTA  GCT  GCT  TTT  CCA              2299
Leu  Ser  Asn  Ala  Lys  Glu  Thr  Phe  Asn  Pro  Leu  Val  Ala  Ala  Phe  Pro
               290                      295                      300

AGT  GTG  AAT  GTT  AGT  ATG  GAA  AAG  GTG  ATA  TTA  TCA  CCA  AAT  GAA  AAT              2347
Ser  Val  Asn  Val  Ser  Met  Glu  Lys  Val  Ile  Leu  Ser  Pro  Asn  Glu  Asn
          305                      310                      315

TTA  TCC  AAT  AGT  GTA  GAG  TCT  CAT  TCA  TCC  ACG  AAT  TGG  TCT  TAT  ACG              2395
Leu  Ser  Asn  Ser  Val  Glu  Ser  His  Ser  Ser  Thr  Asn  Trp  Ser  Tyr  Thr
320                      325                      330

AAT  ACA  GAA  GGA  GCT  TCC  ATT  GAA  GCT  GGT  GGC  GGT  CCA  TTA  GGC  CTT              2443
Asn  Thr  Glu  Gly  Ala  Ser  Ile  Glu  Ala  Gly  Gly  Gly  Pro  Leu  Gly  Leu
335                      340                      345                 350

TCT  TTT  GGC  GTG  AGT  GTT  ACT  TAT  CAA  CAC  TCT  GAA  ACA  GTT  GCA  CAA              2491
Ser  Phe  Gly  Val  Ser  Val  Thr  Tyr  Gln  His  Ser  Glu  Thr  Val  Ala  Gln
               355                      360                      365

GAA  TGG  GGA  ACA  TCT  ACA  GGA  AAT  ACT  TCA  CAA  TTC  AAT  ACG  GCT  TCA              2539
Glu  Trp  Gly  Thr  Ser  Thr  Gly  Asn  Thr  Ser  Gln  Phe  Asn  Thr  Ala  Ser
               370                      375                      380

GCG  GGA  TAT  TTA  AAT  GCA  AAT  GTT  CGG  TAT  AAC  AAT  GTA  GGG  ACT  GGT              2587
Ala  Gly  Tyr  Leu  Asn  Ala  Asn  Val  Arg  Tyr  Asn  Asn  Val  Gly  Thr  Gly
          385                      390                      395

GCC  ATC  TAT  GAT  GTA  AAA  CCT  ACA  ACA  AGT  TTT  GTA  TTA  AAT  AAC  AAT              2635
Ala  Ile  Tyr  Asp  Val  Lys  Pro  Thr  Thr  Ser  Phe  Val  Leu  Asn  Asn  Asn
400                      405                      410

ACC  ATC  GCA  ACG  ATT  ACA  GCA  AAA  TCA  AAT  TCA  ACA  GCT  TTA  CGT  ATA              2683
Thr  Ile  Ala  Thr  Ile  Thr  Ala  Lys  Ser  Asn  Ser  Thr  Ala  Leu  Arg  Ile
415                      420                      425                 430

TCT  CCG  GGG  GAT  AGT  TAT  CCA  GAA  ATA  GGA  GAA  AAC  GCT  ATT  GCG  ATT              2731
Ser  Pro  Gly  Asp  Ser  Tyr  Pro  Glu  Ile  Gly  Glu  Asn  Ala  Ile  Ala  Ile
               435                      440                      445

ACA  TCT  ATG  GAT  GAT  TTT  AAT  TCT  CAT  CCA  ATT  ACA  TTA  AAT  AAA  CAA              2779
Thr  Ser  Met  Asp  Asp  Phe  Asn  Ser  His  Pro  Ile  Thr  Leu  Asn  Lys  Gln
               450                      455                      460

CAG  GTA  AAT  CAA  TTG  ATA  AAT  AAT  AAG  CCA  ATT  ATG  CTA  GAG  ACA  GAC              2827
Gln  Val  Asn  Gln  Leu  Ile  Asn  Asn  Lys  Pro  Ile  Met  Leu  Glu  Thr  Asp
          465                      470                      475

CAA  ACA  GAT  GGT  GTT  TAT  AAA  ATA  AGA  GAT  ACA  CAT  GGA  AAT  ATT  GTA              2875
Gln  Thr  Asp  Gly  Val  Tyr  Lys  Ile  Arg  Asp  Thr  His  Gly  Asn  Ile  Val
     480                      485                      490

ACT  GGT  GGA  GAA  TGG  AAT  GGT  GTA  ACA  CAA  CAA  ATT  AAA  GCA  AAA  ACA              2923
Thr  Gly  Gly  Glu  Trp  Asn  Gly  Val  Thr  Gln  Gln  Ile  Lys  Ala  Lys  Thr
495                      500                      505                 510

GCG  TCT  ATT  ATT  GTG  GAT  GAC  GGG  AAA  CAG  GTA  GCA  GAA  AAA  CGT  GTG              2971
Ala  Ser  Ile  Ile  Val  Asp  Asp  Gly  Lys  Gln  Val  Ala  Glu  Lys  Arg  Val
```

```
                             515                          520                             525
GCG  GCA  AAA  GAT  TAT  GGT  CAT  CCA  GAA  GAT  AAA  ACA  CCA  CCT  TTA  ACT    3019
Ala  Ala  Lys  Asp  Tyr  Gly  His  Pro  Glu  Asp  Lys  Thr  Pro  Pro  Leu  Thr
               530                     535                    540

TTA  AAA  GAT  ACC  CTG  AAG  CTT  TCA  TAC  CCA  GAT  GAA  ATA  AAA  GAA  ACT    3067
Leu  Lys  Asp  Thr  Leu  Lys  Leu  Ser  Tyr  Pro  Asp  Glu  Ile  Lys  Glu  Thr
               545                     550                    555

AAT  GGA  TTG  TTG  TAC  TAT  GAT  GAC  AAA  CCA  ATC  TAT  GAA  TCG  AGT  GTC    3115
Asn  Gly  Leu  Leu  Tyr  Tyr  Asp  Asp  Lys  Pro  Ile  Tyr  Glu  Ser  Ser  Val
               560                     565                    570

ATG  ACT  TAT  CTG  GAT  GAA  AAT  ACG  GCA  AAA  GAA  GTC  AAA  AAA  CAA  ATA    3163
Met  Thr  Tyr  Leu  Asp  Glu  Asn  Thr  Ala  Lys  Glu  Val  Lys  Lys  Gln  Ile
575                           580                    585                    590

AAT  GAT  ACA  ACC  GGA  AAA  TTT  AAG  GAT  GTA  AAT  CAC  TTA  TAT  GAT  GTA    3211
Asn  Asp  Thr  Thr  Gly  Lys  Phe  Lys  Asp  Val  Asn  His  Leu  Tyr  Asp  Val
                         595                     600                    605

AAA  CTG  ACT  CCA  AAA  ATG  AAT  TTT  ACG  ATT  AAA  ATG  GCT  TCC  TTG  TAT    3259
Lys  Leu  Thr  Pro  Lys  Met  Asn  Phe  Thr  Ile  Lys  Met  Ala  Ser  Leu  Tyr
               610                     615                    620

GAT  GGG  GCT  GAA  AAT  AAT  CAT  AAC  TCT  TTA  GGA  ACC  TGG  TAT  TTA  ACA    3307
Asp  Gly  Ala  Glu  Asn  Asn  His  Asn  Ser  Leu  Gly  Thr  Trp  Tyr  Leu  Thr
               625                     630                    635

TAT  AAT  GTT  GCT  GGT  GGA  AAT  ACT  GGG  AAG  AGA  CAA  TAT  CGT  TCA  GCT    3355
Tyr  Asn  Val  Ala  Gly  Gly  Asn  Thr  Gly  Lys  Arg  Gln  Tyr  Arg  Ser  Ala
               640                     645                    650

CAT  TCT  TGT  GCA  CAT  GTA  GCT  CTA  TCT  TCA  GAA  GCG  AAA  AAG  AAA  CTA    3403
His  Ser  Cys  Ala  His  Val  Ala  Leu  Ser  Ser  Glu  Ala  Lys  Lys  Lys  Leu
655                           660                    665                    670

AAT  CAA  AAT  GCG  AAT  TAC  TAT  CTT  AGC  ATG  TAT  ATG  AAG  GCT  GAT  TCT    3451
Asn  Gln  Asn  Ala  Asn  Tyr  Tyr  Leu  Ser  Met  Tyr  Met  Lys  Ala  Asp  Ser
                         675                     680                    685

ACT  ACG  GAA  CCT  ACA  ATA  GAA  GTA  GCT  GGG  GAA  AAA  TCT  GCA  ATA  ACA    3499
Thr  Thr  Glu  Pro  Thr  Ile  Glu  Val  Ala  Gly  Glu  Lys  Ser  Ala  Ile  Thr
                    690                     695                    700

AGT  AAA  AAA  GTA  AAA  TTA  AAT  AAT  CAA  AAT  TAT  CAA  AGA  GTT  GAT  ATT    3547
Ser  Lys  Lys  Val  Lys  Leu  Asn  Asn  Gln  Asn  Tyr  Gln  Arg  Val  Asp  Ile
               705                     710                    715

TTA  GTG  AAA  AAT  TCT  GAA  AGA  AAT  CCA  ATG  GAT  AAA  ATA  TAT  ATA  AGA    3595
Leu  Val  Lys  Asn  Ser  Glu  Arg  Asn  Pro  Met  Asp  Lys  Ile  Tyr  Ile  Arg
720                           725                    730

GGA  AAT  GGC  ACG  ACA  AAT  GTT  TAT  GGG  GAT  GAT  GTT  ACT  ATC  CCA  GAG    3643
Gly  Asn  Gly  Thr  Thr  Asn  Val  Tyr  Gly  Asp  Asp  Val  Thr  Ile  Pro  Glu
735                           740                    745                    750

GTA  TCA  GCT  ATA  AAT  CCG  GCT  AGT  CTA  TCA  GAT  GAA  GAA  ATT  CAA  GAA    3691
Val  Ser  Ala  Ile  Asn  Pro  Ala  Ser  Leu  Ser  Asp  Glu  Glu  Ile  Gln  Glu
                         755                     760                    765

ATA  TTT  AAA  GAC  TCA  ACT  ATT  GAA  TAT  GGA  AAT  CCT  AGT  TTC  GTT  GCT    3739
Ile  Phe  Lys  Asp  Ser  Thr  Ile  Glu  Tyr  Gly  Asn  Pro  Ser  Phe  Val  Ala
                    770                     775                    780

GAT  GCC  GTA  ACA  TTT  AAA  AAT  ATA  AAA  CCT  TTA  CAA  AAT  TAT  GTA  AAG    3787
Asp  Ala  Val  Thr  Phe  Lys  Asn  Ile  Lys  Pro  Leu  Gln  Asn  Tyr  Val  Lys
               785                     790                    795

GAA  TAT  GAA  ATA  TAT  CAT  AAA  TCT  CAT  CGA  TAT  GAA  AAG  AAA  ACG  GTC    3835
Glu  Tyr  Glu  Ile  Tyr  His  Lys  Ser  His  Arg  Tyr  Glu  Lys  Lys  Thr  Val
          800                     805                    810

TTT  GAT  ATC  ATG  GGT  GTT  CAT  TAT  GAG  TAT  AGT  ATA  GCT  AGG  GAA  CAA    3883
Phe  Asp  Ile  Met  Gly  Val  His  Tyr  Glu  Tyr  Ser  Ile  Ala  Arg  Glu  Gln
815                           820                    825                    830

AAG  AAA  GCC  GCA  TAATTTTAAA  AATAAAACTC  GTTAGAGTTT  ATTTAGCATG             3935
Lys  Lys  Ala  Ala
```

```
GTATTTTTAA GAATAATCAA TATGTTGAAC CGTTTGTAGC TGTTTTGGAA GGGAATTTCA      3995

TTTTATTTGG TCTCTTAAGT TGATGGGCAT GGGATATGTT CAGCATCCAA GCGTTTNGGG      4055

GGTTANAAAA TCCAATTTT                                                   4074
```

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Gln Arg Met Glu Gly Lys Leu Phe Val Val Ser Lys Thr Leu Gln
 1               5                  10                 15

Val Val Thr Arg Thr Val Leu Leu Ser Thr Val Tyr Ser Ile Thr Leu
                20                  25                 30

Leu Asn Asn Val Val Ile Lys Ala Asp Gln Leu Asn Ile Asn Ser Gln
            35                  40                 45

Ser Lys Tyr Thr Asn Leu Gln Asn Leu Lys Ile Pro Asp Asn Ala Glu
    50                  55                  60

Asp Phe Lys Glu Asp Lys Gly Lys Ala Lys Glu Trp Gly Lys Glu Lys
65                  70                  75                  80

Gly Glu Glu Trp Arg Pro Pro Ala Thr Glu Lys Gly Glu Met Asn Asn
                85                  90                  95

Phe Leu Asp Asn Lys Asn Asp Ile Lys Thr Asn Tyr Lys Glu Ile Thr
               100                 105                 110

Phe Ser Met Ala Gly Ser Cys Glu Asp Glu Ile Lys Asp Leu Glu Glu
           115                 120                 125

Ile Asp Lys Ile Phe Asp Lys Ala Asn Leu Ser Ser Ser Ile Ile Thr
    130                 135                 140

Tyr Lys Asn Val Glu Pro Ala Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Gly Lys Asp Met Lys Phe Asp Ser Tyr Leu Asp Thr His Leu
            180                 185                 190

Thr Ala Gln Gln Val Ser Ser Lys Lys Arg Val Ile Leu Lys Val Thr
    195                 200                 205

Val Pro Ser Gly Lys Gly Ser Thr Thr Pro Thr Lys Ala Gly Val Ile
210                 215                 220

Leu Asn Asn Asn Glu Tyr Lys Met Leu Ile Asp Asn Gly Tyr Val Leu
225                 230                 235                 240

His Val Asp Lys Val Ser Lys Val Val Lys Lys Gly Met Glu Cys Leu
                245                 250                 255

Gln Val Glu Gly Thr Leu Lys Lys Ser Leu Asp Phe Lys Asn Asp Ile
            260                 265                 270

Asn Ala Glu Ala His Ser Trp Gly Met Lys Ile Tyr Glu Asp Trp Ala
    275                 280                 285

Lys Asn Leu Thr Ala Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Leu Lys Asn Ile Ser Asp Ala Leu
                325                 330                 335
```

Gly Lys Lys Pro Ile Pro Glu Asn Ile Thr Val Tyr Arg Trp Cys Gly
                340             345                 350

Met Pro Glu Phe Gly Tyr Gln Ile Ser Asp Pro Leu Pro Ser Leu Lys
        355             360             365

Asp Phe Glu Glu Gln Phe Leu Asn Thr Ile Lys Glu Asp Lys Gly Tyr
    370             375             380

Met Ser Thr Ser Leu Ser Ser Glu Arg Leu Ala Ala Phe Gly Ser Arg
385             390             395                         400

Lys Ile Ile Leu Arg Leu Gln Val Pro Lys Gly Ser Thr Gly Ala Tyr
            405             410             415

Leu Ser Ala Ile Gly Gly Phe Ala Ser Glu Lys Glu Ile Leu Leu Asp
            420             425             430

Lys Asp Ser Lys Tyr His Ile Asp Lys Ala Thr Glu Val Ile Ile Lys
        435             440             445

Gly Val Lys Arg Tyr Val Val Asp Ala Thr Leu Leu Thr Asn
450             455             460

( 2 ) INFORMATION FOR SEQ ID NO:21:

( i ) SEQUENCE CHARACTERISTICS:
        ( A ) LENGTH: 834 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

Met Lys Asn Met Lys Lys Leu Ala Ser Val Val Thr Cys Met Leu
1               5               10              15

Leu Ala Pro Met Phe Leu Asn Gly Asn Val Asn Ala Val Asn Ala Asp
            20              25              30

Ser Lys Ile Asn Gln Ile Ser Thr Thr Gln Glu Asn Gln Gln Lys Glu
        35              40              45

Met Asp Arg Lys Gly Leu Leu Gly Tyr Tyr Phe Lys Gly Lys Asp Phe
    50              55              60

Asn Asn Leu Thr Met Phe Ala Pro Thr Arg Asp Asn Thr Leu Met Tyr
65              70              75                          80

Asp Gln Gln Thr Ala Asn Ala Leu Leu Asp Lys Lys Gln Gln Glu Tyr
            85              90              95

Gln Ser Ile Arg Trp Ile Gly Leu Ile Gln Arg Lys Glu Thr Gly Asp
            100             105             110

Phe Thr Phe Asn Leu Ser Lys Asp Glu Gln Ala Ile Ile Glu Ile Asp
            115             120             125

Gly Lys Ile Ile Ser Asn Lys Gly Lys Glu Lys Gln Val Val His Leu
    130             135             140

Glu Lys Glu Lys Leu Val Pro Ile Lys Ile Glu Tyr Gln Ser Asp Thr
145                 150             155                     160

Lys Phe Asn Ile Asp Ser Lys Thr Phe Lys Glu Leu Lys Leu Phe Lys
            165             170             175

Ile Asp Ser Gln Asn Gln Ser Gln Gln Val Gln Leu Arg Asn Pro Glu
            180             185             190

Phe Asn Lys Lys Glu Ser Gln Glu Phe Leu Ala Lys Ala Ser Lys Thr
        195             200             205

Asn Leu Phe Lys Gln Lys Met Lys Arg Asp Ile Asp Glu Asp Thr Asp
    210             215             220

Thr Asp Gly Asp Ser Ile Pro Asp Leu Trp Glu Glu Asn Gly Tyr Thr

-continued

```
225                     230                     235                     240
Ile Gln Asn Lys Val Ala Val Lys Trp Asp Ser Leu Ala Ser Lys
                245                     250                     255
Gly Tyr Thr Lys Phe Val Ser Asn Pro Leu Asp Ser His Thr Val Gly
                260                     265                     270
Asp Pro Tyr Thr Asp Tyr Glu Lys Ala Ala Arg Asp Leu Asp Leu Ser
                275                     280                     285
Asn Ala Lys Glu Thr Phe Asn Pro Leu Val Ala Ala Phe Pro Ser Val
                290                     295                     300
Asn Val Ser Met Glu Lys Val Ile Leu Ser Pro Asn Glu Asn Leu Ser
305                     310                     315                     320
Asn Ser Val Glu Ser His Ser Ser Thr Asn Trp Ser Tyr Thr Asn Thr
                        325                     330                     335
Glu Gly Ala Ser Ile Glu Ala Gly Gly Pro Leu Gly Leu Ser Phe
                340                     345                     350
Gly Val Ser Val Thr Tyr Gln His Ser Glu Thr Val Ala Gln Glu Trp
                355                     360                     365
Gly Thr Ser Thr Gly Asn Thr Ser Gln Phe Asn Thr Ala Ser Ala Gly
                370                     375                     380
Tyr Leu Asn Ala Asn Val Arg Tyr Asn Asn Val Gly Thr Gly Ala Ile
385                     390                     395                     400
Tyr Asp Val Lys Pro Thr Thr Ser Phe Val Leu Asn Asn Asn Thr Ile
                405                     410                     415
Ala Thr Ile Thr Ala Lys Ser Asn Ser Thr Ala Leu Arg Ile Ser Pro
                420                     425                     430
Gly Asp Ser Tyr Pro Glu Ile Gly Glu Asn Ala Ile Ala Ile Thr Ser
                435                     440                     445
Met Asp Asp Phe Asn Ser His Pro Ile Thr Leu Asn Lys Gln Gln Val
        450                     455                     460
Asn Gln Leu Ile Asn Asn Lys Pro Ile Met Leu Glu Thr Asp Gln Thr
465                     470                     475                     480
Asp Gly Val Tyr Lys Ile Arg Asp Thr His Gly Asn Ile Val Thr Gly
                        485                     490                     495
Gly Glu Trp Asn Gly Val Thr Gln Gln Ile Lys Ala Lys Thr Ala Ser
                500                     505                     510
Ile Ile Val Asp Asp Gly Lys Gln Val Ala Glu Lys Arg Val Ala Ala
                515                     520                     525
Lys Asp Tyr Gly His Pro Glu Asp Lys Thr Pro Pro Leu Thr Leu Lys
                530                     535                     540
Asp Thr Leu Lys Leu Ser Tyr Pro Asp Glu Ile Lys Glu Thr Asn Gly
545                     550                     555                     560
Leu Leu Tyr Tyr Asp Asp Lys Pro Ile Tyr Glu Ser Ser Val Met Thr
                565                     570                     575
Tyr Leu Asp Glu Asn Thr Ala Lys Glu Val Lys Lys Gln Ile Asn Asp
                580                     585                     590
Thr Thr Gly Lys Phe Lys Asp Val Asn His Leu Tyr Asp Val Lys Leu
                595                     600                     605
Thr Pro Lys Met Asn Phe Thr Ile Lys Met Ala Ser Leu Tyr Asp Gly
                610                     615                     620
Ala Glu Asn Asn His Asn Ser Leu Gly Thr Trp Tyr Leu Thr Tyr Asn
625                     630                     635                     640
Val Ala Gly Gly Asn Thr Gly Lys Arg Gln Tyr Arg Ser Ala His Ser
                        645                     650                     655
```

-continued

Cys Ala His Val Ala Leu Ser Ser Glu Ala Lys Lys Lys Leu Asn Gln
660 665 670

Asn Ala Asn Tyr Tyr Leu Ser Met Tyr Met Lys Ala Asp Ser Thr Thr
675 680 685

Glu Pro Thr Ile Glu Val Ala Gly Glu Lys Ser Ala Ile Thr Ser Lys
690 695 700

Lys Val Lys Leu Asn Asn Gln Asn Tyr Gln Arg Val Asp Ile Leu Val
705 710 715 720

Lys Asn Ser Glu Arg Asn Pro Met Asp Lys Ile Tyr Ile Arg Gly Asn
725 730 735

Gly Thr Thr Asn Val Tyr Gly Asp Asp Val Thr Ile Pro Glu Val Ser
740 745 750

Ala Ile Asn Pro Ala Ser Leu Ser Asp Glu Glu Ile Gln Glu Ile Phe
755 760 765

Lys Asp Ser Thr Ile Glu Tyr Gly Asn Pro Ser Phe Val Ala Asp Ala
770 775 780

Val Thr Phe Lys Asn Ile Lys Pro Leu Gln Asn Tyr Val Lys Glu Tyr
785 790 795 800

Glu Ile Tyr His Lys Ser His Arg Tyr Glu Lys Lys Thr Val Phe Asp
805 810 815

Ile Met Gly Val His Tyr Glu Tyr Ser Ile Ala Arg Glu Gln Lys Lys
820 825 830

Ala Ala ( 2 ) INFORMATION FOR SEQ ID NO:22:

( i ) SEQUENCE CHARACTERISTICS:
( A ) LENGTH: 4041 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..4038
( D ) OTHER INFORMATION: /product="VIP1A(a)/VIP2A(a) fusion product"

( x i ) SEQUENCE DESCRIPTION: SEQ ID NO:22:

ATG AAA AGA ATG GAG GGA AAG TTG TTT ATG GTG TCA AAA AAA TTA CAA 48
Met Lys Arg Met Glu Gly Lys Leu Phe Met Val Ser Lys Lys Leu Gln
835 840 845 850

GTA GTT ACT AAA ACT GTA TTG CTT AGT ACA GTT TTC TCT ATA TCT TTA 96
Val Val Thr Lys Thr Val Leu Leu Ser Thr Val Phe Ser Ile Ser Leu
855 860 865

TTA AAT AAT GAA GTG ATA AAA GCT GAA CAA TTA AAT ATA AAT TCT CAA 144
Leu Asn Asn Glu Val Ile Lys Ala Glu Gln Leu Asn Ile Asn Ser Gln
870 875 880

AGT AAA TAT ACT AAC TTG CAA AAT CTA AAA ATC ACT GAC AAG GTA GAG 192
Ser Lys Tyr Thr Asn Leu Gln Asn Leu Lys Ile Thr Asp Lys Val Glu
885 890 895

GAT TTT AAA GAA GAT AAG GAA AAA GCG AAA GAA TGG GGG AAA GAA AAA 240
Asp Phe Lys Glu Asp Lys Glu Lys Ala Lys Glu Trp Gly Lys Glu Lys
900 905 910

GAA AAA GAG TGG AAA CTA ACT GCT ACT GAA AAA GGA AAA ATG AAT AAT 288
Glu Lys Glu Trp Lys Leu Thr Ala Thr Glu Lys Gly Lys Met Asn Asn
915 920 925 930

TTT TTA GAT AAT AAA AAT GAT ATA AAG ACA AAT TAT AAA GAA ATT ACT 336
Phe Leu Asp Asn Lys Asn Asp Ile Lys Thr Asn Tyr Lys Glu Ile Thr

|     |     |     |     | 935 |     |     |     | 940 |     |     |     | 945 |     |     |     |      |
|-----|-----|-----|-----|-----|-----|-----|-----|-----|-----|-----|-----|-----|-----|-----|-----|------|
| TTT | TCT | ATG | GCA | GGC | TCA | TTT | GAA | GAT | GAA | ATA | AAA | GAT | TTA | AAA | GAA | 384  |
| Phe | Ser | Met | Ala | Gly | Ser | Phe | Glu | Asp | Glu | Ile | Lys | Asp | Leu | Lys | Glu |      |
|     |     |     | 950 |     |     |     | 955 |     |     |     | 960 |     |     |     |     |      |
| ATT | GAT | AAG | ATG | TTT | GAT | AAA | ACC | AAT | CTA | TCA | AAT | TCT | ATT | ATC | ACC | 432  |
| Ile | Asp | Lys | Met | Phe | Asp | Lys | Thr | Asn | Leu | Ser | Asn | Ser | Ile | Ile | Thr |      |
|     |     | 965 |     |     |     | 970 |     |     |     | 975 |     |     |     |     |     |      |
| TAT | AAA | AAT | GTG | GAA | CCG | ACA | ACA | ATT | GGA | TTT | AAT | AAA | TCT | TTA | ACA | 480  |
| Tyr | Lys | Asn | Val | Glu | Pro | Thr | Thr | Ile | Gly | Phe | Asn | Lys | Ser | Leu | Thr |      |
|     | 980 |     |     |     |     | 985 |     |     |     |     | 990 |     |     |     |     |      |
| GAA | GGT | AAT | ACG | ATT | AAT | TCT | GAT | GCA | ATG | GCA | CAG | TTT | AAA | GAA | CAA | 528  |
| Glu | Gly | Asn | Thr | Ile | Asn | Ser | Asp | Ala | Met | Ala | Gln | Phe | Lys | Glu | Gln |      |
| 995 |     |     |     |     | 1000|     |     |     |     | 1005|     |     |     |     | 1010|      |
| TTT | TTA | GAT | AGG | GAT | ATT | AAG | TTT | GAT | AGT | TAT | CTA | GAT | ACG | CAT | TTA | 576  |
| Phe | Leu | Asp | Arg | Asp | Ile | Lys | Phe | Asp | Ser | Tyr | Leu | Asp | Thr | His | Leu |      |
|     |     |     |     | 1015|     |     |     |     | 1020|     |     |     |     | 1025|     |      |
| ACT | GCT | CAA | CAA | GTT | TCC | AGT | AAA | GAA | AGA | GTT | ATT | TTG | AAG | GTT | ACG | 624  |
| Thr | Ala | Gln | Gln | Val | Ser | Ser | Lys | Glu | Arg | Val | Ile | Leu | Lys | Val | Thr |      |
|     |     |     | 1030|     |     |     |     | 1035|     |     |     |     | 1040|     |     |      |
| GTT | CCG | AGT | GGG | AAA | GGT | TCT | ACT | ACT | CCA | ACA | AAA | GCA | GGT | GTC | ATT | 672  |
| Val | Pro | Ser | Gly | Lys | Gly | Ser | Thr | Thr | Pro | Thr | Lys | Ala | Gly | Val | Ile |      |
|     |     |     | 1045|     |     |     |     | 1050|     |     |     |     | 1055|     |     |      |
| TTA | AAT | AAT | AGT | GAA | TAC | AAA | ATG | CTC | ATT | GAT | AAT | GGG | TAT | ATG | GTC | 720  |
| Leu | Asn | Asn | Ser | Glu | Tyr | Lys | Met | Leu | Ile | Asp | Asn | Gly | Tyr | Met | Val |      |
|     |     |     | 1060|     |     |     |     | 1065|     |     |     |     | 1070|     |     |      |
| CAT | GTA | GAT | AAG | GTA | TCA | AAA | GTG | GTG | AAA | AAA | GGG | GTG | GAG | TGC | TTA | 768  |
| His | Val | Asp | Lys | Val | Ser | Lys | Val | Val | Lys | Lys | Gly | Val | Glu | Cys | Leu |      |
| 1075|     |     |     |     | 1080|     |     |     |     | 1085|     |     |     |     | 1090|      |
| CAA | ATT | GAA | GGG | ACT | TTA | AAA | AAG | AGT | CTT | GAC | TTT | AAA | AAT | GAT | ATA | 816  |
| Gln | Ile | Glu | Gly | Thr | Leu | Lys | Lys | Ser | Leu | Asp | Phe | Lys | Asn | Asp | Ile |      |
|     |     |     |     | 1095|     |     |     |     | 1100|     |     |     |     | 1105|     |      |
| AAT | GCT | GAA | GCG | CAT | AGC | TGG | GGT | ATG | AAG | AAT | TAT | GAA | GAG | TGG | GCT | 864  |
| Asn | Ala | Glu | Ala | His | Ser | Trp | Gly | Met | Lys | Asn | Tyr | Glu | Glu | Trp | Ala |      |
|     |     |     |     | 1110|     |     |     |     | 1115|     |     |     |     | 1120|     |      |
| AAA | GAT | TTA | ACC | GAT | TCG | CAA | AGG | GAA | GCT | TTA | GAT | GGG | TAT | GCT | AGG | 912  |
| Lys | Asp | Leu | Thr | Asp | Ser | Gln | Arg | Glu | Ala | Leu | Asp | Gly | Tyr | Ala | Arg |      |
|     |     |     | 1125|     |     |     |     | 1130|     |     |     |     | 1135|     |     |      |
| CAA | GAT | TAT | AAA | GAA | ATC | AAT | AAT | TAT | TTA | AGA | AAT | CAA | GGC | GGA | AGT | 960  |
| Gln | Asp | Tyr | Lys | Glu | Ile | Asn | Asn | Tyr | Leu | Arg | Asn | Gln | Gly | Gly | Ser |      |
|     |     |     | 1140|     |     |     |     | 1145|     |     |     |     | 1150|     |     |      |
| GGA | AAT | GAA | AAA | CTA | GAT | GCT | CAA | ATA | AAA | AAT | ATT | TCT | GAT | GCT | TTA | 1008 |
| Gly | Asn | Glu | Lys | Leu | Asp | Ala | Gln | Ile | Lys | Asn | Ile | Ser | Asp | Ala | Leu |      |
| 1155|     |     |     |     | 1160|     |     |     |     | 1165|     |     |     |     | 1170|      |
| GGG | AAG | AAA | CCA | ATA | CCG | GAA | AAT | ATT | ACT | GTG | TAT | AGA | TGG | TGT | GGC | 1056 |
| Gly | Lys | Lys | Pro | Ile | Pro | Glu | Asn | Ile | Thr | Val | Tyr | Arg | Trp | Cys | Gly |      |
|     |     |     | 1175|     |     |     |     | 1180|     |     |     |     | 1185|     |     |      |
| ATG | CCG | GAA | TTT | GGT | TAT | CAA | ATT | AGT | GAT | CCG | TTA | CCT | TCT | TTA | AAA | 1104 |
| Met | Pro | Glu | Phe | Gly | Tyr | Gln | Ile | Ser | Asp | Pro | Leu | Pro | Ser | Leu | Lys |      |
|     |     |     | 1190|     |     |     |     | 1195|     |     |     |     | 1200|     |     |      |
| GAT | TTT | GAA | GAA | CAA | TTT | TTA | AAT | ACA | ATC | AAA | GAA | GAC | AAA | GGA | TAT | 1152 |
| Asp | Phe | Glu | Glu | Gln | Phe | Leu | Asn | Thr | Ile | Lys | Glu | Asp | Lys | Gly | Tyr |      |
|     |     |     | 1205|     |     |     |     | 1210|     |     |     |     | 1215|     |     |      |
| ATG | AGT | ACA | AGC | TTA | TCG | AGT | GAA | CGT | CTT | GCA | GCT | TTT | GGA | TCT | AGA | 1200 |
| Met | Ser | Thr | Ser | Leu | Ser | Ser | Glu | Arg | Leu | Ala | Ala | Phe | Gly | Ser | Arg |      |
|     |     |     | 1220|     |     |     |     | 1225|     |     |     |     | 1230|     |     |      |
| AAA | ATT | ATA | TTA | CGA | TTA | CAA | GTT | CCG | AAA | GGA | AGT | ACG | GGT | GCG | TAT | 1248 |
| Lys | Ile | Ile | Leu | Arg | Leu | Gln | Val | Pro | Lys | Gly | Ser | Thr | Gly | Ala | Tyr |      |
|     |     |     | 1235|     |     |     |     | 1240|     |     |     |     | 1245|     |     | 1250 |
| TTA | AGT | GCC | ATT | GGT | GGA | TTT | GCA | AGT | GAA | AAA | GAG | ATC | CTA | CTT | GAT | 1296 |
| Leu | Ser | Ala | Ile | Gly | Gly | Phe | Ala | Ser | Glu | Lys | Glu | Ile | Leu | Leu | Asp |      |

```
                          1 2 5 5                       1 2 6 0                       1 2 6 5

AAA  GAT  AGT  AAA  TAT  CAT  ATT  GAT  AAA  GTA  ACA  GAG  GTA  ATT  ATT  AAA      1 3 4 4
Lys  Asp  Ser  Lys  Tyr  His  Ile  Asp  Lys  Val  Thr  Glu  Val  Ile  Ile  Lys
               1 2 7 0                 1 2 7 5                      1 2 8 0

GGT  GTT  AAG  CGA  TAT  GTA  GTG  GAT  GCA  ACA  TTA  TTA  ACA  AAT  ATG  AAA      1 3 9 2
Gly  Val  Lys  Arg  Tyr  Val  Val  Asp  Ala  Thr  Leu  Leu  Thr  Asn  Met  Lys
               1 2 8 5                 1 2 9 0                      1 2 9 5

AAT  ATG  AAG  AAA  AAG  TTA  GCA  AGT  GTT  GTA  ACG  TGT  ACG  TTA  TTA  GCT      1 4 4 0
Asn  Met  Lys  Lys  Lys  Leu  Ala  Ser  Val  Val  Thr  Cys  Thr  Leu  Leu  Ala
     1 3 0 0                      1 3 0 5                 1 3 1 0

CCT  ATG  TTT  TTG  AAT  GGA  AAT  GTG  AAT  GCT  GTT  TAC  GCA  GAC  AGC  AAA      1 4 8 8
Pro  Met  Phe  Leu  Asn  Gly  Asn  Val  Asn  Ala  Val  Tyr  Ala  Asp  Ser  Lys
1 3 1 5                      1 3 2 0                 1 3 2 5                1 3 3 0

ACA  AAT  CAA  ATT  TCT  ACA  ACA  CAG  AAA  AAT  CAA  CAG  AAA  GAG  ATG  GAC      1 5 3 6
Thr  Asn  Gln  Ile  Ser  Thr  Thr  Gln  Lys  Asn  Gln  Gln  Lys  Glu  Met  Asp
                    1 3 3 5                      1 3 4 0                    1 3 4 5

CGA  AAA  GGA  TTA  CTT  GGG  TAT  TAT  TTC  AAA  GGA  AAA  GAT  TTT  AGT  AAT      1 5 8 4
Arg  Lys  Gly  Leu  Leu  Gly  Tyr  Tyr  Phe  Lys  Gly  Lys  Asp  Phe  Ser  Asn
                    1 3 5 0                      1 3 5 5                    1 3 6 0

CTT  ACT  ATG  TTT  GCA  CCG  ACA  CGT  GAT  AGT  ACT  CTT  ATT  TAT  GAT  CAA      1 6 3 2
Leu  Thr  Met  Phe  Ala  Pro  Thr  Arg  Asp  Ser  Thr  Leu  Ile  Tyr  Asp  Gln
               1 3 6 5                 1 3 7 0                      1 3 7 5

CAA  ACA  GCA  AAT  AAA  CTA  TTA  GAT  AAA  AAA  CAA  CAA  GAA  TAT  CAG  TCT      1 6 8 0
Gln  Thr  Ala  Asn  Lys  Leu  Leu  Asp  Lys  Lys  Gln  Gln  Glu  Tyr  Gln  Ser
     1 3 8 0                      1 3 8 5                 1 3 9 0

ATT  CGT  TGG  ATT  GGT  TTG  ATT  CAG  AGT  AAA  GAA  ACG  GGA  GAT  TTC  ACA      1 7 2 8
Ile  Arg  Trp  Ile  Gly  Leu  Ile  Gln  Ser  Lys  Glu  Thr  Gly  Asp  Phe  Thr
1 3 9 5                      1 4 0 0                 1 4 0 5                1 4 1 0

TTT  AAC  TTA  TCT  GAG  GAT  GAA  CAG  GCA  ATT  ATA  GAA  ATC  AAT  GGG  AAA      1 7 7 6
Phe  Asn  Leu  Ser  Glu  Asp  Glu  Gln  Ala  Ile  Ile  Glu  Ile  Asn  Gly  Lys
                    1 4 1 5                      1 4 2 0                    1 4 2 5

ATT  ATT  TCT  AAT  AAA  GGG  AAA  GAA  AAG  CAA  GTT  GTC  CAT  TTA  GAA  AAA      1 8 2 4
Ile  Ile  Ser  Asn  Lys  Gly  Lys  Glu  Lys  Gln  Val  Val  His  Leu  Glu  Lys
               1 4 3 0                      1 4 3 5                 1 4 4 0

GGA  AAA  TTA  GTT  CCA  ATC  AAA  ATA  GAG  TAT  CAA  TCA  GAT  ACA  AAA  TTT      1 8 7 2
Gly  Lys  Leu  Val  Pro  Ile  Lys  Ile  Glu  Tyr  Gln  Ser  Asp  Thr  Lys  Phe
          1 4 4 5                      1 4 5 0                 1 4 5 5

AAT  ATT  GAC  AGT  AAA  ACA  TTT  AAA  GAA  CTT  AAA  TTA  TTT  AAA  ATA  GAT      1 9 2 0
Asn  Ile  Asp  Ser  Lys  Thr  Phe  Lys  Glu  Leu  Lys  Leu  Phe  Lys  Ile  Asp
     1 4 6 0                      1 4 6 5                 1 4 7 0

AGT  CAA  AAC  CAA  CCC  CAG  CAA  GTC  CAG  CAA  GAT  GAA  CTG  AGA  AAT  CCT      1 9 6 8
Ser  Gln  Asn  Gln  Pro  Gln  Gln  Val  Gln  Gln  Asp  Glu  Leu  Arg  Asn  Pro
1 4 7 5                      1 4 8 0                 1 4 8 5                1 4 9 0

GAA  TTT  AAC  AAG  AAA  GAA  TCA  CAG  GAA  TTC  TTA  GCG  AAA  CCA  TCG  AAA      2 0 1 6
Glu  Phe  Asn  Lys  Lys  Glu  Ser  Gln  Glu  Phe  Leu  Ala  Lys  Pro  Ser  Lys
                    1 4 9 5                      1 5 0 0                    1 5 0 5

ATA  AAT  CTT  TTC  ACT  CAA  AAA  ATG  AAA  AGG  GAA  ATT  GAT  GAA  GAC  ACG      2 0 6 4
Ile  Asn  Leu  Phe  Thr  Gln  Lys  Met  Lys  Arg  Glu  Ile  Asp  Glu  Asp  Thr
               1 5 1 0                      1 5 1 5                 1 5 2 0

GAT  ACG  GAT  GGG  GAC  TCT  ATT  CCT  GAC  CTT  TGG  GAA  GAA  AAT  GGG  TAT      2 1 1 2
Asp  Thr  Asp  Gly  Asp  Ser  Ile  Pro  Asp  Leu  Trp  Glu  Glu  Asn  Gly  Tyr
          1 5 2 5                      1 5 3 0                 1 5 3 5

ACG  ATT  CAA  AAT  AGA  ATC  GCT  GTA  AAG  TGG  GAC  GAT  TCT  CTA  GCA  AGT      2 1 6 0
Thr  Ile  Gln  Asn  Arg  Ile  Ala  Val  Lys  Trp  Asp  Asp  Ser  Leu  Ala  Ser
     1 5 4 0                      1 5 4 5                 1 5 5 0

AAA  GGG  TAT  ACG  AAA  TTT  GTT  TCA  AAT  CCA  CTA  GAA  AGT  CAC  ACA  GTT      2 2 0 8
Lys  Gly  Tyr  Thr  Lys  Phe  Val  Ser  Asn  Pro  Leu  Glu  Ser  His  Thr  Val
1 5 5 5                      1 5 6 0                 1 5 6 5                1 5 7 0

GGT  GAT  CCT  TAT  ACA  GAT  TAT  GAA  AAG  GCA  GCA  AGA  GAT  CTA  GAT  TTG      2 2 5 6
Gly  Asp  Pro  Tyr  Thr  Asp  Tyr  Glu  Lys  Ala  Ala  Arg  Asp  Leu  Asp  Leu
```

-continued

```
                          1575                          1580                          1585
TCA AAT GCA AAG GAA ACG TTT AAC CCA TTG GTA GCT GCT TTT CCA AGT                      2304
Ser Asn Ala Lys Glu Thr Phe Asn Pro Leu Val Ala Ala Phe Pro Ser
            1590                1595                1600

GTG AAT GTT AGT ATG GAA AAG GTG ATA TTA TCA CCA AAT GAA AAT TTA                      2352
Val Asn Val Ser Met Glu Lys Val Ile Leu Ser Pro Asn Glu Asn Leu
        1605                1610                1615

TCC AAT AGT GTA GAG TCT CAT TCA TCC ACG AAT TGG TCT TAT ACA AAT                      2400
Ser Asn Ser Val Glu Ser His Ser Ser Thr Asn Trp Ser Tyr Thr Asn
        1620                1625                1630

ACA GAA GGT GCT TCT GTT GAA GCG GGG ATT GGA CCA AAA GGT ATT TCG                      2448
Thr Glu Gly Ala Ser Val Glu Ala Gly Ile Gly Pro Lys Gly Ile Ser
1635                1640                1645                1650

TTC GGA GTT AGC GTA AAC TAT CAA CAC TCT GAA ACA GTT GCA CAA GAA                      2496
Phe Gly Val Ser Val Asn Tyr Gln His Ser Glu Thr Val Ala Gln Glu
                1655                1660                1665

TGG GGA ACA TCT ACA GGA AAT ACT TCG CAA TTC AAT ACG GCT TCA GCG                      2544
Trp Gly Thr Ser Thr Gly Asn Thr Ser Gln Phe Asn Thr Ala Ser Ala
            1670                1675                1680

GGA TAT TTA AAT GCA AAT GTT CGA TAT AAC AAT GTA GGA ACT GGT GCC                      2592
Gly Tyr Leu Asn Ala Asn Val Arg Tyr Asn Asn Val Gly Thr Gly Ala
        1685                1690                1695

ATC TAC GAT GTA AAA CCT ACA ACA AGT TTT GTA TTA AAT AAC GAT ACT                      2640
Ile Tyr Asp Val Lys Pro Thr Thr Ser Phe Val Leu Asn Asn Asp Thr
        1700                1705                1710

ATC GCA ACT ATT ACG GCG AAA TCT AAT TCT ACA GCC TTA AAT ATA TCT                      2688
Ile Ala Thr Ile Thr Ala Lys Ser Asn Ser Thr Ala Leu Asn Ile Ser
1715                1720                1725                1730

CCT GGA GAA AGT TAC CCG AAA AAA GGA CAA AAT GGA ATC GCA ATA ACA                      2736
Pro Gly Glu Ser Tyr Pro Lys Lys Gly Gln Asn Gly Ile Ala Ile Thr
                1735                1740                1745

TCA ATG GAT GAT TTT AAT TCC CAT CCG ATT ACA TTA AAT AAA AAA CAA                      2784
Ser Met Asp Asp Phe Asn Ser His Pro Ile Thr Leu Asn Lys Lys Gln
            1750                1755                1760

GTA GAT AAT CTG CTA AAT AAT AAA CCT ATG ATG TTG GAA ACA AAC CAA                      2832
Val Asp Asn Leu Leu Asn Asn Lys Pro Met Met Leu Glu Thr Asn Gln
        1765                1770                1775

ACA GAT GGT GTT TAT AAG ATA AAA GAT ACA CAT GGA AAT ATA GTA ACT                      2880
Thr Asp Gly Val Tyr Lys Ile Lys Asp Thr His Gly Asn Ile Val Thr
1780                1785                1790

GGC GGA GAA TGG AAT GGT GTC ATA CAA CAA ATC AAG GCT AAA ACA GCG                      2928
Gly Gly Glu Trp Asn Gly Val Ile Gln Gln Ile Lys Ala Lys Thr Ala
1795                1800                1805                1810

TCT ATT ATT GTG GAT GAT GGG GAA CGT GTA GCA GAA AAA CGT GTA GCG                      2976
Ser Ile Ile Val Asp Asp Gly Glu Arg Val Ala Glu Lys Arg Val Ala
                1815                1820                1825

GCA AAA GAT TAT GAA AAT CCA GAA GAT AAA ACA CCG TCT TTA ACT TTA                      3024
Ala Lys Asp Tyr Glu Asn Pro Glu Asp Lys Thr Pro Ser Leu Thr Leu
            1830                1835                1840

AAA GAT GCC CTG AAG CTT TCA TAT CCA GAT GAA ATA AAA GAA ATA GAG                      3072
Lys Asp Ala Leu Lys Leu Ser Tyr Pro Asp Glu Ile Lys Glu Ile Glu
        1845                1850                1855

GGA TTA TTA TAT TAT AAA AAC AAA CCG ATA TAC GAA TCG AGC GTT ATG                      3120
Gly Leu Leu Tyr Tyr Lys Asn Lys Pro Ile Tyr Glu Ser Ser Val Met
1860                1865                1870

ACT TAC TTA GAT GAA AAT ACA GCA AAA GAA GTG ACC AAA CAA TTA AAT                      3168
Thr Tyr Leu Asp Glu Asn Thr Ala Lys Glu Val Thr Lys Gln Leu Asn
1875                1880                1885                1890

GAT ACC ACT GGG AAA TTT AAA GAT GTA AGT CAT TTA TAT GAT GTA AAA                      3216
Asp Thr Thr Gly Lys Phe Lys Asp Val Ser His Leu Tyr Asp Val Lys
```

```
                                   1895                        1900                          1905
CTG  ACT  CCA  AAA  ATG  AAT  GTT  ACA  ATC  AAA  TTG  TCT  ATA  CTT  TAT  GAT      3264
Leu  Thr  Pro  Lys  Met  Asn  Val  Thr  Ile  Lys  Leu  Ser  Ile  Leu  Tyr  Asp
               1910                     1915                    1920

AAT  GCT  GAG  TCT  AAT  GAT  AAC  TCA  ATT  GGT  AAA  TGG  ACA  AAC  ACA  AAT      3312
Asn  Ala  Glu  Ser  Asn  Asp  Asn  Ser  Ile  Gly  Lys  Trp  Thr  Asn  Thr  Asn
               1925                     1930                    1935

ATT  GTT  TCA  GGT  GGA  AAT  AAC  GGA  AAA  AAA  CAA  TAT  TCT  TCT  AAT  AAT      3360
Ile  Val  Ser  Gly  Gly  Asn  Asn  Gly  Lys  Lys  Gln  Tyr  Ser  Ser  Asn  Asn
               1940                     1945                    1950

CCG  GAT  GCT  AAT  TTG  ACA  TTA  AAT  ACA  GAT  GCT  CAA  GAA  AAA  TTA  AAT      3408
Pro  Asp  Ala  Asn  Leu  Thr  Leu  Asn  Thr  Asp  Ala  Gln  Glu  Lys  Leu  Asn
1955                     1960                    1965                         1970

AAA  AAT  CGT  GAC  TAT  TAT  ATA  AGT  TTA  TAT  ATG  AAG  TCA  GAA  AAA  AAC      3456
Lys  Asn  Arg  Asp  Tyr  Tyr  Ile  Ser  Leu  Tyr  Met  Lys  Ser  Glu  Lys  Asn
               1975                     1980                    1985

ACA  CAA  TGT  GAG  ATT  ACT  ATA  GAT  GGG  GAG  ATT  TAT  CCG  ATC  ACT  ACA      3504
Thr  Gln  Cys  Glu  Ile  Thr  Ile  Asp  Gly  Glu  Ile  Tyr  Pro  Ile  Thr  Thr
               1990                     1995                    2000

AAA  ACA  GTG  AAT  GTG  AAT  AAA  GAC  AAT  TAC  AAA  AGA  TTA  GAT  ATT  ATA      3552
Lys  Thr  Val  Asn  Val  Asn  Lys  Asp  Asn  Tyr  Lys  Arg  Leu  Asp  Ile  Ile
               2005                     2010                    2015

GCT  CAT  AAT  ATA  AAA  AGT  AAT  CCA  ATT  TCT  TCA  CTT  CAT  ATT  AAA  ACG      3600
Ala  His  Asn  Ile  Lys  Ser  Asn  Pro  Ile  Ser  Ser  Leu  His  Ile  Lys  Thr
               2020                     2025                    2030

AAT  GAT  GAA  ATA  ACT  TTA  TTT  TGG  GAT  GAT  ATT  TCT  ATA  ACA  GAT  GTA      3648
Asn  Asp  Glu  Ile  Thr  Leu  Phe  Trp  Asp  Asp  Ile  Ser  Ile  Thr  Asp  Val
2035                     2040                    2045                         2050

GCA  TCA  ATA  AAA  CCG  GAA  AAT  TTA  ACA  GAT  TCA  GAA  ATT  AAA  CAG  ATT      3696
Ala  Ser  Ile  Lys  Pro  Glu  Asn  Leu  Thr  Asp  Ser  Glu  Ile  Lys  Gln  Ile
               2055                     2060                    2065

TAT  AGT  AGG  TAT  GGT  ATT  AAG  TTA  GAA  GAT  GGA  ATC  CTT  ATT  GAT  AAA      3744
Tyr  Ser  Arg  Tyr  Gly  Ile  Lys  Leu  Glu  Asp  Gly  Ile  Leu  Ile  Asp  Lys
               2070                     2075                    2080

AAA  GGT  GGG  ATT  CAT  TAT  GGT  GAA  TTT  ATT  AAT  GAA  GCT  AGT  TTT  AAT      3792
Lys  Gly  Gly  Ile  His  Tyr  Gly  Glu  Phe  Ile  Asn  Glu  Ala  Ser  Phe  Asn
               2085                     2090                    2095

ATT  GAA  CCA  TTG  CAA  AAT  TAT  GTG  ACC  AAA  TAT  GAA  GTT  ACT  TAT  AGT      3840
Ile  Glu  Pro  Leu  Gln  Asn  Tyr  Val  Thr  Lys  Tyr  Glu  Val  Thr  Tyr  Ser
2100                     2105                    2110

AGT  GAG  TTA  GGA  CCA  AAC  GTG  AGT  GAC  ACA  CTT  GAA  AGT  GAT  AAA  ATT      3888
Ser  Glu  Leu  Gly  Pro  Asn  Val  Ser  Asp  Thr  Leu  Glu  Ser  Asp  Lys  Ile
2115                     2120                    2125                         2130

TAC  AAG  GAT  GGG  ACA  ATT  AAA  TTT  GAT  TTT  ACC  AAA  TAT  AGT  AAA  AAT      3936
Tyr  Lys  Asp  Gly  Thr  Ile  Lys  Phe  Asp  Phe  Thr  Lys  Tyr  Ser  Lys  Asn
               2135                     2140                    2145

GAA  CAA  GGA  TTA  TTT  TAT  GAC  AGT  GGA  TTA  AAT  TGG  GAC  TTT  AAA  ATT      3984
Glu  Gln  Gly  Leu  Phe  Tyr  Asp  Ser  Gly  Leu  Asn  Trp  Asp  Phe  Lys  Ile
               2150                     2155                    2160

AAT  GCT  ATT  ACT  TAT  GAT  GGT  AAA  GAG  ATG  AAT  GTT  TTT  CAT  AGA  TAT      4032
Asn  Ala  Ile  Thr  Tyr  Asp  Gly  Lys  Glu  Met  Asn  Val  Phe  His  Arg  Tyr
               2165                     2170                    2175

AAT  AAA  TAG                                                                        4041
Asn  Lys
     2180
```

( 2 ) INFORMATION FOR SEQ ID NO:23:

( i ) SEQUENCE CHARACTERISTICS:
        ( A ) LENGTH: 1346 amino acids
        ( B ) TYPE: amino acid (D) TOPOLOGY: linear (ii) MOLECULE TYPE: protein (xi) SEQUENCE DESCRIPTION: SEQ ID NO:23:

| Met | Lys | Arg | Met | Glu | Gly | Lys | Leu | Phe | Met | Val | Ser | Lys | Lys | Leu | Gln |
|---|---|---|---|---|---|---|---|---|---|---|---|---|---|---|---|
| 1 | | | | 5 | | | | | 10 | | | | | 15 | |

| Val | Val | Thr | Lys | Thr | Val | Leu | Leu | Ser | Thr | Val | Phe | Ser | Ile | Ser | Leu |
|---|---|---|---|---|---|---|---|---|---|---|---|---|---|---|---|
| | | | 20 | | | | | 25 | | | | | 30 | | |

| Leu | Asn | Asn | Glu | Val | Ile | Lys | Ala | Glu | Gln | Leu | Asn | Ile | Asn | Ser | Gln |
|---|---|---|---|---|---|---|---|---|---|---|---|---|---|---|---|
| | | 35 | | | | | 40 | | | | | 45 | | | |

| Ser | Lys | Tyr | Thr | Asn | Leu | Gln | Asn | Leu | Lys | Ile | Thr | Asp | Lys | Val | Glu |
|---|---|---|---|---|---|---|---|---|---|---|---|---|---|---|---|
| | 50 | | | | | 55 | | | | | 60 | | | | |

| Asp | Phe | Lys | Glu | Asp | Lys | Glu | Lys | Ala | Lys | Glu | Trp | Gly | Lys | Glu | Lys |
|---|---|---|---|---|---|---|---|---|---|---|---|---|---|---|---|
| 65 | | | | | 70 | | | | | 75 | | | | | 80 |

| Glu | Lys | Glu | Trp | Lys | Leu | Thr | Ala | Thr | Glu | Lys | Gly | Lys | Met | Asn | Asn |
|---|---|---|---|---|---|---|---|---|---|---|---|---|---|---|---|
| | | | | 85 | | | | | 90 | | | | | 95 | |

| Phe | Leu | Asp | Asn | Lys | Asn | Asp | Ile | Lys | Thr | Asn | Tyr | Lys | Glu | Ile | Thr |
|---|---|---|---|---|---|---|---|---|---|---|---|---|---|---|---|
| | | | 100 | | | | | 105 | | | | | 110 | | |

| Phe | Ser | Met | Ala | Gly | Ser | Phe | Glu | Asp | Glu | Ile | Lys | Asp | Leu | Lys | Glu |
|---|---|---|---|---|---|---|---|---|---|---|---|---|---|---|---|
| | | | 115 | | | | | 120 | | | | | 125 | | |

| Ile | Asp | Lys | Met | Phe | Asp | Lys | Thr | Asn | Leu | Ser | Asn | Ser | Ile | Ile | Thr |
|---|---|---|---|---|---|---|---|---|---|---|---|---|---|---|---|
| | | | 130 | | | | | 135 | | | | | 140 | | |

| Tyr | Lys | Asn | Val | Glu | Pro | Thr | Thr | Ile | Gly | Phe | Asn | Lys | Ser | Leu | Thr |
|---|---|---|---|---|---|---|---|---|---|---|---|---|---|---|---|
| 145 | | | | | 150 | | | | | 155 | | | | | 160 |

| Glu | Gly | Asn | Thr | Ile | Asn | Ser | Asp | Ala | Met | Ala | Gln | Phe | Lys | Glu | Gln |
|---|---|---|---|---|---|---|---|---|---|---|---|---|---|---|---|
| | | | | 165 | | | | | 170 | | | | | 175 | |

| Phe | Leu | Asp | Arg | Asp | Ile | Lys | Phe | Asp | Ser | Tyr | Leu | Asp | Thr | His | Leu |
|---|---|---|---|---|---|---|---|---|---|---|---|---|---|---|---|
| | | | 180 | | | | | 185 | | | | | 190 | | |

| Thr | Ala | Gln | Gln | Val | Ser | Ser | Lys | Glu | Arg | Val | Ile | Leu | Lys | Val | Thr |
|---|---|---|---|---|---|---|---|---|---|---|---|---|---|---|---|
| | | | 195 | | | | | 200 | | | | | 205 | | |

| Val | Pro | Ser | Gly | Lys | Gly | Ser | Thr | Thr | Pro | Thr | Lys | Ala | Gly | Val | Ile |
|---|---|---|---|---|---|---|---|---|---|---|---|---|---|---|---|
| | 210 | | | | | 215 | | | | | 220 | | | | |

| Leu | Asn | Asn | Ser | Glu | Tyr | Lys | Met | Leu | Ile | Asp | Asn | Gly | Tyr | Met | Val |
|---|---|---|---|---|---|---|---|---|---|---|---|---|---|---|---|
| 225 | | | | | 230 | | | | | 235 | | | | | 240 |

| His | Val | Asp | Lys | Val | Ser | Lys | Val | Val | Lys | Lys | Gly | Val | Glu | Cys | Leu |
|---|---|---|---|---|---|---|---|---|---|---|---|---|---|---|---|
| | | | | 245 | | | | | 250 | | | | | 255 | |

| Gln | Ile | Glu | Gly | Thr | Leu | Lys | Lys | Ser | Leu | Asp | Phe | Lys | Asn | Asp | Ile |
|---|---|---|---|---|---|---|---|---|---|---|---|---|---|---|---|
| | | | 260 | | | | | 265 | | | | | 270 | | |

| Asn | Ala | Glu | Ala | His | Ser | Trp | Gly | Met | Lys | Asn | Tyr | Glu | Glu | Trp | Ala |
|---|---|---|---|---|---|---|---|---|---|---|---|---|---|---|---|
| | | 275 | | | | | 280 | | | | | 285 | | | |

| Lys | Asp | Leu | Thr | Asp | Ser | Gln | Arg | Glu | Ala | Leu | Asp | Gly | Tyr | Ala | Arg |
|---|---|---|---|---|---|---|---|---|---|---|---|---|---|---|---|
| | 290 | | | | | 295 | | | | | 300 | | | | |

| Gln | Asp | Tyr | Lys | Glu | Ile | Asn | Asn | Tyr | Leu | Arg | Asn | Gln | Gly | Gly | Ser |
|---|---|---|---|---|---|---|---|---|---|---|---|---|---|---|---|
| 305 | | | | | 310 | | | | | 315 | | | | | 320 |

| Gly | Asn | Glu | Lys | Leu | Asp | Ala | Gln | Ile | Lys | Asn | Ile | Ser | Asp | Ala | Leu |
|---|---|---|---|---|---|---|---|---|---|---|---|---|---|---|---|
| | | | | 325 | | | | | 330 | | | | | 335 | |

| Gly | Lys | Lys | Pro | Ile | Pro | Glu | Asn | Ile | Thr | Val | Tyr | Arg | Trp | Cys | Gly |
|---|---|---|---|---|---|---|---|---|---|---|---|---|---|---|---|
| | | | 340 | | | | | 345 | | | | | 350 | | |

| Met | Pro | Glu | Phe | Gly | Tyr | Gln | Ile | Ser | Asp | Pro | Leu | Pro | Ser | Leu | Lys |
|---|---|---|---|---|---|---|---|---|---|---|---|---|---|---|---|
| | | 355 | | | | | 360 | | | | | 365 | | | |

| Asp | Phe | Glu | Glu | Gln | Phe | Leu | Asn | Thr | Ile | Lys | Glu | Asp | Lys | Gly | Tyr |
|---|---|---|---|---|---|---|---|---|---|---|---|---|---|---|---|
| | 370 | | | | | 375 | | | | | 380 | | | | |

| Met | Ser | Thr | Ser | Leu | Ser | Ser | Glu | Arg | Leu | Ala | Ala | Phe | Gly | Ser | Arg |
|---|---|---|---|---|---|---|---|---|---|---|---|---|---|---|---|
| 385 | | | | | 390 | | | | | 395 | | | | | 400 |

```
Lys Ile Ile Leu Arg Leu Gln Val Pro Lys Gly Ser Thr Gly Ala Tyr
                405                 410                 415
Leu Ser Ala Ile Gly Gly Phe Ala Ser Glu Lys Glu Ile Leu Leu Asp
            420             425                 430
Lys Asp Ser Lys Tyr His Ile Asp Lys Val Thr Glu Val Ile Ile Lys
            435             440                 445
Gly Val Lys Arg Tyr Val Val Asp Ala Thr Leu Leu Thr Asn Met Lys
        450             455                 460
Asn Met Lys Lys Lys Leu Ala Ser Val Val Thr Cys Thr Leu Leu Ala
465                 470                 475                 480
Pro Met Phe Leu Asn Gly Asn Val Asn Ala Val Tyr Ala Asp Ser Lys
                485                 490                 495
Thr Asn Gln Ile Ser Thr Thr Gln Lys Asn Gln Lys Glu Met Asp
            500             505                 510
Arg Lys Gly Leu Leu Gly Tyr Tyr Phe Lys Gly Lys Asp Phe Ser Asn
            515             520                 525
Leu Thr Met Phe Ala Pro Thr Arg Asp Ser Thr Leu Ile Tyr Asp Gln
    530             535                 540
Gln Thr Ala Asn Lys Leu Leu Asp Lys Lys Gln Gln Glu Tyr Gln Ser
545                 550                 555                 560
Ile Arg Trp Ile Gly Leu Ile Gln Ser Lys Glu Thr Gly Asp Phe Thr
                565                 570                 575
Phe Asn Leu Ser Glu Asp Glu Gln Ala Ile Ile Glu Ile Asn Gly Lys
                580                 585                 590
Ile Ile Ser Asn Lys Gly Lys Glu Lys Gln Val Val His Leu Glu Lys
            595                 600                 605
Gly Lys Leu Val Pro Ile Lys Ile Glu Tyr Gln Ser Asp Thr Lys Phe
    610                 615                 620
Asn Ile Asp Ser Lys Thr Phe Lys Glu Leu Lys Leu Phe Lys Ile Asp
625                 630                 635                 640
Ser Gln Asn Gln Pro Gln Gln Val Gln Gln Asp Glu Leu Arg Asn Pro
                645                 650                 655
Glu Phe Asn Lys Lys Glu Ser Gln Glu Phe Leu Ala Lys Pro Ser Lys
            660                 665                 670
Ile Asn Leu Phe Thr Gln Lys Met Lys Arg Glu Ile Asp Glu Asp Thr
            675                 680                 685
Asp Thr Asp Gly Asp Ser Ile Pro Asp Leu Trp Glu Glu Asn Gly Tyr
    690                 695                 700
Thr Ile Gln Asn Arg Ile Ala Val Lys Trp Asp Asp Ser Leu Ala Ser
705                 710                 715                 720
Lys Gly Tyr Thr Lys Phe Val Ser Asn Pro Leu Glu Ser His Thr Val
                725                 730                 735
Gly Asp Pro Tyr Thr Asp Tyr Glu Lys Ala Ala Arg Asp Leu Asp Leu
            740                 745                 750
Ser Asn Ala Lys Glu Thr Phe Asn Pro Leu Val Ala Ala Phe Pro Ser
            755                 760                 765
Val Asn Val Ser Met Glu Lys Val Ile Leu Ser Pro Asn Glu Asn Leu
    770                 775                 780
Ser Asn Ser Val Glu Ser His Ser Ser Thr Asn Trp Ser Tyr Thr Asn
785                 790                 795                 800
Thr Glu Gly Ala Ser Val Glu Ala Gly Ile Gly Pro Lys Gly Ile Ser
                805                 810                 815
Phe Gly Val Ser Val Asn Tyr Gln His Ser Glu Thr Val Ala Gln Glu
```

```
                        820                      825                      830
Trp  Gly  Thr  Ser  Thr  Gly  Asn  Thr  Ser  Gln  Phe  Asn  Thr  Ala  Ser  Ala
              835                      840                      845
Gly  Tyr  Leu  Asn  Ala  Asn  Val  Arg  Tyr  Asn  Asn  Val  Gly  Thr  Gly  Ala
     850                      855                      860
Ile  Tyr  Asp  Val  Lys  Pro  Thr  Thr  Ser  Phe  Val  Leu  Asn  Asn  Asp  Thr
865                      870                      875                      880
Ile  Ala  Thr  Ile  Thr  Ala  Lys  Ser  Asn  Ser  Thr  Ala  Leu  Asn  Ile  Ser
               885                      890                      895
Pro  Gly  Glu  Ser  Tyr  Pro  Lys  Lys  Gly  Gln  Asn  Gly  Ile  Ala  Ile  Thr
               900                      905                      910
Ser  Met  Asp  Asp  Phe  Asn  Ser  His  Pro  Ile  Thr  Leu  Asn  Lys  Lys  Gln
               915                      920                      925
Val  Asp  Asn  Leu  Leu  Asn  Asn  Lys  Pro  Met  Met  Leu  Glu  Thr  Asn  Gln
     930                      935                      940
Thr  Asp  Gly  Val  Tyr  Lys  Ile  Lys  Asp  Thr  His  Gly  Asn  Ile  Val  Thr
945                      950                      955                      960
Gly  Gly  Glu  Trp  Asn  Gly  Val  Ile  Gln  Gln  Ile  Lys  Ala  Lys  Thr  Ala
               965                      970                      975
Ser  Ile  Ile  Val  Asp  Asp  Gly  Glu  Arg  Val  Ala  Glu  Lys  Arg  Val  Ala
               980                      985                      990
Ala  Lys  Asp  Tyr  Glu  Asn  Pro  Glu  Asp  Lys  Thr  Pro  Ser  Leu  Thr  Leu
     995                      1000                     1005
Lys  Asp  Ala  Leu  Lys  Leu  Ser  Tyr  Pro  Asp  Glu  Ile  Lys  Glu  Ile  Glu
     1010                     1015                     1020
Gly  Leu  Leu  Tyr  Tyr  Lys  Asn  Lys  Pro  Ile  Tyr  Glu  Ser  Ser  Val  Met
1025                     1030                     1035                     1040
Thr  Tyr  Leu  Asp  Glu  Asn  Thr  Ala  Lys  Glu  Val  Thr  Lys  Gln  Leu  Asn
               1045                     1050                     1055
Asp  Thr  Thr  Gly  Lys  Phe  Lys  Asp  Val  Ser  His  Leu  Tyr  Asp  Val  Lys
               1060                     1065                     1070
Leu  Thr  Pro  Lys  Met  Asn  Val  Thr  Ile  Lys  Leu  Ser  Ile  Leu  Tyr  Asp
               1075                     1080                     1085
Asn  Ala  Glu  Ser  Asn  Asp  Asn  Ser  Ile  Gly  Lys  Trp  Thr  Asn  Thr  Asn
               1090                     1095                     1100
Ile  Val  Ser  Gly  Gly  Asn  Asn  Gly  Lys  Lys  Gln  Tyr  Ser  Ser  Asn  Asn
1105                     1110                     1115                     1120
Pro  Asp  Ala  Asn  Leu  Thr  Leu  Asn  Thr  Asp  Ala  Gln  Glu  Lys  Leu  Asn
               1125                     1130                     1135
Lys  Asn  Arg  Asp  Tyr  Tyr  Ile  Ser  Leu  Tyr  Met  Lys  Ser  Glu  Lys  Asn
               1140                     1145                     1150
Thr  Gln  Cys  Glu  Ile  Thr  Ile  Asp  Gly  Glu  Ile  Tyr  Pro  Ile  Thr  Thr
               1155                     1160                     1165
Lys  Thr  Val  Asn  Val  Asn  Lys  Asp  Asn  Tyr  Lys  Arg  Leu  Asp  Ile  Ile
     1170                     1175                     1180
Ala  His  Asn  Ile  Lys  Ser  Asn  Pro  Ile  Ser  Ser  Leu  His  Ile  Lys  Thr
1185                     1190                     1195                     1200
Asn  Asp  Glu  Ile  Thr  Leu  Phe  Trp  Asp  Asp  Ile  Ser  Ile  Thr  Asp  Val
               1205                     1210                     1215
Ala  Ser  Ile  Lys  Pro  Glu  Asn  Leu  Thr  Asp  Ser  Glu  Ile  Lys  Gln  Ile
               1220                     1225                     1230
Tyr  Ser  Arg  Tyr  Gly  Ile  Lys  Leu  Glu  Asp  Gly  Ile  Leu  Ile  Asp  Lys
               1235                     1240                     1245
```

-continued

Lys Gly Gly Ile His Tyr Gly Glu Phe Ile Asn Glu Ala Ser Phe Asn
1250 1255 1260

Ile Glu Pro Leu Gln Asn Tyr Val Thr Lys Tyr Glu Val Thr Tyr Ser
1265 1270 1275 1280

Ser Glu Leu Gly Pro Asn Val Ser Asp Thr Leu Glu Ser Asp Lys Ile
1285 1290 1295

Tyr Lys Asp Gly Thr Ile Lys Phe Asp Phe Thr Lys Tyr Ser Lys Asn
1300 1305 1310

Glu Gln Gly Leu Phe Tyr Asp Ser Gly Leu Asn Trp Asp Phe Lys Ile
1315 1320 1325

Asn Ala Ile Thr Tyr Asp Gly Lys Glu Met Asn Val Phe His Arg Tyr
1330 1335 1340

Asn Lys
1345

( 2 ) INFORMATION FOR SEQ ID NO:24:

( i ) SEQUENCE CHARACTERISTICS:
( A ) LENGTH: 1399 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..1386
( D ) OTHER INFORMATION: /note= "Maize optimized DNA sequence for VIP2A(a) protein from AB78"

( x i ) SEQUENCE DESCRIPTION: SEQ ID NO:24:

ATGAAGCGCA TGGAGGGCAA GCTGTTCATG GTGAGCAAGA AGCTCCAGGT GGTGACCAAG 60

ACCGTGCTGC TGAGCACCGT GTTCAGCATC AGCCTGCTGA ACAACGAGGT GATCAAGGCC 120

GAGCAGCTGA ACATCAACAG CCAGAGCAAG TACACCAACC TCCAGAACCT GAAGATCACC 180

GACAAGGTGG AGGACTTCAA GGAGGACAAG GAGAAGGCCA AGGAGTGGGG CAAGGAGAAG 240

GAGAAGGAGT GGAAGCTTAC CGCCACCGAG AAGGGCAAGA TGAACAACTT CCTGGACAAC 300

AAGAACGACA TCAAGACCAA CTACAAGGAG ATCACCTTCA GCATGGCCGG CAGCTTCGAG 360

GACGAGATCA AGGACCTGAA GGAGATCGAC AAGATGTTCG ACAAGACCAA CCTGAGCAAC 420

AGCATCATCA CCTACAAGAA CGTGGAGCCC ACCACCATCG GCTTCAACAA GAGCCTGACC 480

GAGGGCAACA CCATCAACAG CGACGCCATG GCCCAGTTCA AGGAGCAGTT CCTGGACCGC 540

GACATCAAGT TCGACAGCTA CCTGGACACC CACCTGACCG CCCAGCAGGT GAGCAGCAAG 600

GAGCGCGTGA TCCTGAAGGT GACCGTCCCC AGCGGCAAGG GCAGCACCAC CCCCACCAAG 660

GCCGGCGTGA TCCTGAACAA CAGCGAGTAC AAGATGCTGA TCGACAACGG CTACATGGTG 720

CACGTGGACA AGGTGAGCAA GGTGGTGAAG AAGGGCGTGG AGTGCCTCCA GATCGAGGGC 780

ACCCTGAAGA AGAGTCTAGA CTTCAAGAAC GACATCAACG CCGAGGCCCA CAGCTGGGGC 840

ATGAAGAACT ACGAGGAGTG GGCCAAGGAC CTGACCGACA GCCAGCGCGA GGCCCTGGAC 900

GGCTACGCCC GCCAGGACTA CAAGGAGATC AACAACTACC TGCGCAACCA GGGCGGCAGC 960

GGCAACGAGA AGCTGGACGC CCAGATCAAG AACATCAGCG ACGCCCTGGG CAAGAAGCCC 1020

ATCCCCGAGA ACATCACCGT GTACCGCTGG TGCGGCATGC CCGAGTTCGG CTACCAGATC 1080

AGCGACCCCC TGCCCAGCCT GAAGGACTTC GAGGAGCAGT TCCTGAACAC CATCAAGGAG 1140

GACAAGGGCT ACATGAGCAC CAGCCTGAGC AGCGAGCGCC TGGCCGCCTT CGGCAGCCGC 1200

| | | | | | |
|---|---|---|---|---|---|
| AAGATCATCC | TGCGCCTGCA | GGTGCCCAAG | GGCAGCACCG | GCGCCTACCT | GAGCGCCATC | 1260
| GGCGGCTTCG | CCAGCGAGAA | GGAGATCCTG | CTGGACAAGG | ACAGCAAGTA | CCACATCGAC | 1320
| AAGGTGACCG | AGTGATCAT | CAAGGGCGTG | AAGCGCTACG | TGGTGGACGC | CACCCTGCTG | 1380
| ACCAACTAGA | TCTGAGCTC | | | | | 1399

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note= "Secretion signal peptide to
            secrete VIP2 out of a cell"

( x i ) SEQUENCE DESCRIPTION: SEQ ID NO:25:

```
Gly Trp Ser Trp Ile Phe Leu Phe Leu Leu Ser Gly Ala Ala Gly Val
1               5                   10                  15

His Cys Leu
```

( 2 ) INFORMATION FOR SEQ ID NO:26:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..2655
( D ) OTHER INFORMATION: /note= "maize optimized DNA sequence encoding VIP1A(a)"

( x i ) SEQUENCE DESCRIPTION: SEQ ID NO:26:

```
ATGAAGAACA TGAAGAAGAA GCTGGCCAGC GTGGTGACCT GCACCCTGCT GGCCCCCATG      60

TTCCTGAACG GCAACGTGAA CGCCGTGTAC GCCGACAGCA AGACCAACCA GATCAGCACC     120

ACCCAGAAGA ACCAGCAGAA GGAGATGGAC CGCAAGGGCC TGCTGGGCTA CTACTTCAAG     180

GGCAAGGACT TCAGCAACCT GACCATGTTC GCCCCCACGC GTGACAGCAC CCTGATCTAC     240

GACCAGCAGA CCGCCAACAA GCTGCTGGAC AAGAAGCAGC AGGAGTACCA GAGCATCCGC     300

TGGATCGGCC TGATCCAGAG CAAGGAGACC GGCGACTTCA CCTTCAACCT GAGCGAGGAC     360

GAGCAGGCCA TCATCGAGAT CAACGGCAAG ATCATCAGCA ACAAGGGCAA GGAGAAGCAG     420

GTGGTGCACC TGGAGAAGGG CAAGCTGGTG CCCATCAAGA TCGAGTACCA GAGCGACACC     480

AAGTTCAACA TCGACAGCAA GACCTTCAAG GAGCTGAAGC TTTTCAAGAT CGACAGCCAG     540

AACCAGCCCC AGCAGGTGCA GCAGGACGAG CTGCGCAACC CCGAGTTCAA CAAGAAGGAG     600

AGCCAGGAGT TCCTGGCCAA GCCCAGCAAG ATCAACCTGT TCACCCAGCA GATGAAGCGC     660

GAGATCGACG AGGACACCGA CACCGACGGC GACAGCATCC CCGACCTGTG GGAGGAGAAC     720

GGCTACACCA TCCAGAACCG CATCGCCGTG AAGTGGGACG ACAGCCTGGC TAGCAAGGGC     780
```

-continued

| | | | | | | |
|---|---|---|---|---|---|---|
| TACACCAAGT | TCGTGAGCAA | CCCCCTGGAG | AGCCACACCG | TGGGCGACCC | CTACACCGAC | 840 |
| TACGAGAAGG | CCGCCCGCGA | CCTGGACCTG | AGCAACGCCA | AGGAGACCTT | CAACCCCCTG | 900 |
| GTGGCCGCCT | TCCCCAGCGT | GAACGTGAGC | ATGGAGAAGG | TGATCCTGAG | CCCCAACGAG | 960 |
| AACCTGAGCA | ACAGCGTGGA | GAGCCACTCG | AGCACCAACT | GGAGCTACAC | CAACACCGAG | 1020 |
| GGCGCCAGCG | TGGAGGCCGG | CATCGGTCCC | AAGGGCATCA | GCTTCGGCGT | GAGCGTGAAC | 1080 |
| TACCAGCACA | GCGAGACCGT | GGCCCAGGAG | TGGGGCACCA | GCACCGGCAA | CACCAGCCAG | 1140 |
| TTCAACACCG | CCAGCGCCGG | CTACCTGAAC | GCCAACGTGC | GCTACAACAA | CGTGGGCACC | 1200 |
| GGCGCCATCT | ACGACGTGAA | GCCCACCACC | AGCTTCGTGC | TGAACAACGA | CACCATCGCC | 1260 |
| ACCATCACCG | CCAAGTCGAA | TTCCACCGCC | CTGAACATCA | GCCCCGGCGA | GAGCTACCCC | 1320 |
| AAGAAGGGCC | AGAACGGCAT | CGCCATCACC | AGCATGGACG | ACTTCAACAG | CCACCCCATC | 1380 |
| ACCCTGAACA | AGAAGCAGGT | GGACAACCTG | CTGAACAACA | AGCCCATGAT | GCTGGAGACC | 1440 |
| AACCAGACCG | ACGGCGTCTA | CAAGATCAAG | GACACCCACG | GCAACATCGT | GACGGGCGGC | 1500 |
| GAGTGGAACG | GCGTGATCCA | GCAGATCAAG | GCCAAGACCG | CCAGCATCAT | CGTCGACGAC | 1560 |
| GGCGAGCGCG | TGGCCGAGAA | GCGCGTGGCC | GCCAAGGACT | ACGAGAACCC | CGAGGACAAG | 1620 |
| ACCCCCAGCC | TGACCCTGAA | GGACGCCCTG | AAGCTGAGCT | ACCCCGACGA | GATCAAGGAG | 1680 |
| ATCGAGGGCT | TGCTGTACTA | CAAGAACAAG | CCCATCTACG | AGAGCAGCGT | GATGACCTAT | 1740 |
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | AGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:27:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature ( B ) LOCATION: 1..1389
( D ) OTHER INFORMATION: /note= "maize optimized DNA sequence encoding VIP2A(a)"

( x i ) SEQUENCE DESCRIPTION: SEQ ID NO:27:

```
ATGAAGCGCA TGGAGGGCAA GCTGTTCATG GTGAGCAAGA AGCTCCAGGT GGTGACCAAG    60
ACCGTGCTGC TGAGCACCGT GTTCAGCATC AGCCTGCTGA ACAACGAGGT GATCAAGGCC   120
GAGCAGCTGA ACATCAACAG CCAGAGCAAG TACACCAACC TCCAGAACCT GAAGATCACC   180
GACAAGGTGG AGGACTTCAA GGAGGACAAG GAGAAGGCCA AGGAGTGGGG CAAGGAGAAG   240
GAGAAGGAGT GGAAGCTTAC CGCCACCGAG AAGGGCAAGA TGAACAACTT CCTGGACAAC   300
AAGAACGACA TCAAGACCAA CTACAAGGAG ATCACCTTCA GCATAGCCGG CAGCTTCGAG   360
GACGAGATCA AGGACCTGAA GGAGATCGAC AAGATGTTCG ACAAGACCAA CCTGAGCAAC   420
AGCATCATCA CCTACAAGAA CGTGGAGCCC ACCACCATCG GCTTCAACAA GAGCCTGACC   480
GAGGGCAACA CCATCAACAG CGACGCCATG GCCCAGTTCA AGGAGCAGTT CCTGGACCGC   540
GACATCAAGT TCGACAGCTA CCTGGACACC CACCTGACCG CCCAGCAGGT GAGCAGCAAG   600
GAGCGCGTGA TCCTGAAGGT GACCGTCCCC AGCGGCAAGG GCAGCACCAC CCCCACCAAG   660
GCCGGCGTGA TCCTGAACAA CAGCGAGTAC AAGATGCTGA TCGACAACGG CTACATGGTG   720
CACGTGGACA AGGTGAGCAA GGTGGTGAAG AAGGGCGTGG AGTGCCTCCA GATCGAGGGC   780
ACCCTGAAGA AGAGTCTAGA CTTCAAGAAC GACATCAACG CCGAGGCCCA CAGCTGGGGC   840
ATGAAGAACT ACGAGGAGTG GGCCAAGGAC CTGACCGACA GCCAGCGCGA GGCCCTGGAC   900
GGCTACGCCC GCCAGGACTA CAAGGAGATC AACAACTACC TGCGCAACCA GGGCGGCAGC   960
GGCAACGAGA AGCTGGACGC CCAGATCAAG AACATCAGCG ACGCCCTGGG CAAGAAGCCC  1020
ATCCCCGAGA ACATCACCGT GTACCGCTGG TGCGGCATGC CCGAGTTCGG CTACCAGATC  1080
AGCGACCCCC TGCCCAGCCT GAAGGACTTC GAGGAGCAGT TCCTGAACAC CATCAAGGAG  1140
GACAAGGGCT ACATGAGCAC CAGCCTGAGC AGCGAGCGCC TGGCCGCCTT CGGCAGCCGC  1200
AAGATCATCC TGCGCCTGCA GGTGCCCAAG GGCAGCACTG GTGCCTACCT GAGCGCCATC  1260
GGCGGCTTCG CCAGCGAGAA GGAGATCCTG CTGGATAAGG ACAGCAAGTA CCACATCGAC  1320
AAGGTGACCG AGGTGATCAT CAAGGGCGTG AAGCGCTACG TGGTGGACGC CACCCTGCTG  1380
ACCAACTAG                                                          1389
```

( 2 ) INFORMATION FOR SEQ ID NO:28:

( i ) SEQUENCE CHARACTERISTICS:
( A ) LENGTH: 2378 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: CDS
( B ) LOCATION: 9..2375
( D ) OTHER INFORMATION: /note= "Native DNA sequence encoding VIP3A(a) protein from AB88 as contained in pCIB7104"

( x i ) SEQUENCE DESCRIPTION: SEQ ID NO:28:

```
AGATGAAC ATG AAC AAG AAT AAT ACT AAA TTA AGC ACA AGA GCC TTA CCA    50
         Met Asn Lys Asn Asn Thr Lys Leu Ser Thr Arg Ala Leu Pro
          1               5                  10
```

-continued

| | | | | | | | | | | | | | | | | |
|---|---|---|---|---|---|---|---|---|---|---|---|---|---|---|---|---|
| AGT | TTT | ATT | GAT | TAT | TTT | AAT | GGC | ATT | TAT | GGA | TTT | GCC | ACT | GGT | ATC | 98 |
| Ser | Phe | Ile | Asp | Tyr | Phe | Asn | Gly | Ile | Tyr | Gly | Phe | Ala | Thr | Gly | Ile | |
| 15 | | | | 20 | | | | | 25 | | | | | 30 | | |
| AAA | GAC | ATT | ATG | AAC | ATG | ATT | TTT | AAA | ACG | GAT | ACA | GGT | GGT | GAT | CTA | 146 |
| Lys | Asp | Ile | Met | Asn | Met | Ile | Phe | Lys | Thr | Asp | Thr | Gly | Gly | Asp | Leu | |
| | | | 35 | | | | 40 | | | | | | 45 | | | |
| ACC | CTA | GAC | GAA | ATT | TTA | AAG | AAT | CAG | CAG | TTA | CTA | AAT | GAT | ATT | TCT | 194 |
| Thr | Leu | Asp | Glu | Ile | Leu | Lys | Asn | Gln | Gln | Leu | Leu | Asn | Asp | Ile | Ser | |
| | | | 50 | | | | 55 | | | | | 60 | | | | |
| GGT | AAA | TTG | GAT | GGG | GTG | AAT | GGA | AGC | TTA | AAT | GAT | CTT | ATC | GCA | CAG | 242 |
| Gly | Lys | Leu | Asp | Gly | Val | Asn | Gly | Ser | Leu | Asn | Asp | Leu | Ile | Ala | Gln | |
| | | 65 | | | | 70 | | | | | 75 | | | | | |
| GGA | AAC | TTA | AAT | ACA | GAA | TTA | TCT | AAG | GAA | ATA | TTA | AAA | ATT | GCA | AAT | 290 |
| Gly | Asn | Leu | Asn | Thr | Glu | Leu | Ser | Lys | Glu | Ile | Leu | Lys | Ile | Ala | Asn | |
| | 80 | | | | | 85 | | | | | 90 | | | | | |
| GAA | CAA | AAT | CAA | GTT | TTA | AAT | GAT | GTT | AAT | AAC | AAA | CTC | GAT | GCG | ATA | 338 |
| Glu | Gln | Asn | Gln | Val | Leu | Asn | Asp | Val | Asn | Asn | Lys | Leu | Asp | Ala | Ile | |
| 95 | | | | 100 | | | | | 105 | | | | | 110 | | |
| AAT | ACG | ATG | CTT | CGG | GTA | TAT | CTA | CCT | AAA | ATT | ACC | TCT | ATG | TTG | AGT | 386 |
| Asn | Thr | Met | Leu | Arg | Val | Tyr | Leu | Pro | Lys | Ile | Thr | Ser | Met | Leu | Ser | |
| | | | | 115 | | | | | 120 | | | | | 125 | | |
| GAT | GTA | ATG | AAA | CAA | AAT | TAT | GCG | CTA | AGT | CTG | CAA | ATA | GAA | TAC | TTA | 434 |
| Asp | Val | Met | Lys | Gln | Asn | Tyr | Ala | Leu | Ser | Leu | Gln | Ile | Glu | Tyr | Leu | |
| | | | 130 | | | | 135 | | | | | 140 | | | | |
| AGT | AAA | CAA | TTG | CAA | GAG | ATT | TCT | GAT | AAG | TTG | GAT | ATT | ATT | AAT | GTA | 482 |
| Ser | Lys | Gln | Leu | Gln | Glu | Ile | Ser | Asp | Lys | Leu | Asp | Ile | Ile | Asn | Val | |
| | | 145 | | | | | 150 | | | | | 155 | | | | |
| AAT | GTA | CTT | ATT | AAC | TCT | ACA | CTT | ACT | GAA | ATT | ACA | CCT | GCG | TAT | CAA | 530 |
| Asn | Val | Leu | Ile | Asn | Ser | Thr | Leu | Thr | Glu | Ile | Thr | Pro | Ala | Tyr | Gln | |
| | 160 | | | | | 165 | | | | | 170 | | | | | |
| AGG | ATT | AAA | TAT | GTG | AAC | GAA | AAA | TTT | GAG | GAA | TTA | ACT | TTT | GCT | ACA | 578 |
| Arg | Ile | Lys | Tyr | Val | Asn | Glu | Lys | Phe | Glu | Glu | Leu | Thr | Phe | Ala | Thr | |
| 175 | | | | | 180 | | | | | 185 | | | | | 190 | |
| GAA | ACT | AGT | TCA | AAA | GTA | AAA | AAG | GAT | GGC | TCT | CCT | GCA | GAT | ATT | CTT | 626 |
| Glu | Thr | Ser | Ser | Lys | Val | Lys | Lys | Asp | Gly | Ser | Pro | Ala | Asp | Ile | Leu | |
| | | | | 195 | | | | | 200 | | | | | 205 | | |
| GAT | GAG | TTA | ACT | GAG | TTA | ACT | GAA | CTA | GCG | AAA | AGT | GTA | ACA | AAA | AAT | 674 |
| Asp | Glu | Leu | Thr | Glu | Leu | Thr | Glu | Leu | Ala | Lys | Ser | Val | Thr | Lys | Asn | |
| | | | 210 | | | | 215 | | | | | 220 | | | | |
| GAT | GTG | GAT | GGT | TTT | GAA | TTT | TAC | CTT | AAT | ACA | TTC | CAC | GAT | GTA | ATG | 722 |
| Asp | Val | Asp | Gly | Phe | Glu | Phe | Tyr | Leu | Asn | Thr | Phe | His | Asp | Val | Met | |
| | | 225 | | | | 230 | | | | | 235 | | | | | |
| GTA | GGA | AAT | AAT | TTA | TTC | GGG | CGT | TCA | GCT | TTA | AAA | ACT | GCA | TCG | GAA | 770 |
| Val | Gly | Asn | Asn | Leu | Phe | Gly | Arg | Ser | Ala | Leu | Lys | Thr | Ala | Ser | Glu | |
| | 240 | | | | | 245 | | | | | 250 | | | | | |
| TTA | ATT | ACT | AAA | GAA | AAT | GTG | AAA | ACA | AGT | GGC | AGT | GAG | GTC | GGA | AAT | 818 |
| Leu | Ile | Thr | Lys | Glu | Asn | Val | Lys | Thr | Ser | Gly | Ser | Glu | Val | Gly | Asn | |
| 255 | | | | | 260 | | | | | 265 | | | | | 270 | |
| GTT | TAT | AAC | TTC | TTA | ATT | GTA | TTA | ACA | GCT | CTG | CAA | GCC | CAA | GCT | TTT | 866 |
| Val | Tyr | Asn | Phe | Leu | Ile | Val | Leu | Thr | Ala | Leu | Gln | Ala | Gln | Ala | Phe | |
| | | | | 275 | | | | | 280 | | | | | 285 | | |
| CTT | ACT | TTA | ACA | ACA | TGC | CGA | AAA | TTA | TTA | GGC | TTA | GCA | GAT | ATT | GAT | 914 |
| Leu | Thr | Leu | Thr | Thr | Cys | Arg | Lys | Leu | Leu | Gly | Leu | Ala | Asp | Ile | Asp | |
| | | | 290 | | | | 295 | | | | | 300 | | | | |
| TAT | ACT | TCT | ATT | ATG | AAT | GAA | CAT | TTA | AAT | AAG | GAA | AAA | GAG | GAA | TTT | 962 |
| Tyr | Thr | Ser | Ile | Met | Asn | Glu | His | Leu | Asn | Lys | Glu | Lys | Glu | Glu | Phe | |
| | | 305 | | | | 310 | | | | | 315 | | | | | |
| AGA | GTA | AAC | ATC | CTC | CCT | ACA | CTT | TCT | AAT | ACT | TTT | TCT | AAT | CCT | AAT | 1010 |
| Arg | Val | Asn | Ile | Leu | Pro | Thr | Leu | Ser | Asn | Thr | Phe | Ser | Asn | Pro | Asn | |
| | 320 | | | | | 325 | | | | | 330 | | | | | |

| | | | | | | | | | | | | | | | | |
|---|---|---|---|---|---|---|---|---|---|---|---|---|---|---|---|---|
| TAT | GCA | AAA | GTT | AAA | GGA | AGT | GAT | GAA | GAT | GCA | AAG | ATG | ATT | GTG | GAA | 1058 |
| Tyr | Ala | Lys | Val | Lys | Gly | Ser | Asp | Glu | Asp | Ala | Lys | Met | Ile | Val | Glu | |
| 335 | | | | 340 | | | | | 345 | | | | | | 350 | |
| GCT | AAA | CCA | GGA | CAT | GCA | TTG | ATT | GGG | TTT | GAA | ATT | AGT | AAT | GAT | TCA | 1106 |
| Ala | Lys | Pro | Gly | His | Ala | Leu | Ile | Gly | Phe | Glu | Ile | Ser | Asn | Asp | Ser | |
| | | | | 355 | | | | 360 | | | | | 365 | | | |
| ATT | ACA | GTA | TTA | AAA | GTA | TAT | GAG | GCT | AAG | CTA | AAA | CAA | AAT | TAT | CAA | 1154 |
| Ile | Thr | Val | Leu | Lys | Val | Tyr | Glu | Ala | Lys | Leu | Lys | Gln | Asn | Tyr | Gln | |
| | | | 370 | | | | 375 | | | | | 380 | | | | |
| GTC | GAT | AAG | GAT | TCC | TTA | TCG | GAA | GTT | ATT | TAT | GGT | GAT | ATG | GAT | AAA | 1202 |
| Val | Asp | Lys | Asp | Ser | Leu | Ser | Glu | Val | Ile | Tyr | Gly | Asp | Met | Asp | Lys | |
| | | 385 | | | | | 390 | | | | | 395 | | | | |
| TTA | TTG | TGC | CCA | GAT | CAA | TCT | GAA | CAA | ATC | TAT | TAT | ACA | AAT | AAC | ATA | 1250 |
| Leu | Leu | Cys | Pro | Asp | Gln | Ser | Glu | Gln | Ile | Tyr | Tyr | Thr | Asn | Asn | Ile | |
| | 400 | | | | | 405 | | | | | 410 | | | | | |
| GTA | TTT | CCA | AAT | GAA | TAT | GTA | ATT | ACT | AAA | ATT | GAT | TTC | ACT | AAA | AAA | 1298 |
| Val | Phe | Pro | Asn | Glu | Tyr | Val | Ile | Thr | Lys | Ile | Asp | Phe | Thr | Lys | Lys | |
| 415 | | | | | 420 | | | | | 425 | | | | | 430 | |
| ATG | AAA | ACT | TTA | AGA | TAT | GAG | GTA | ACA | GCG | AAT | TTT | TAT | GAT | TCT | TCT | 1346 |
| Met | Lys | Thr | Leu | Arg | Tyr | Glu | Val | Thr | Ala | Asn | Phe | Tyr | Asp | Ser | Ser | |
| | | | | 435 | | | | 440 | | | | | 445 | | | |
| ACA | GGA | GAA | ATT | GAC | TTA | AAT | AAG | AAA | AAA | GTA | GAA | TCA | AGT | GAA | GCG | 1394 |
| Thr | Gly | Glu | Ile | Asp | Leu | Asn | Lys | Lys | Lys | Val | Glu | Ser | Ser | Glu | Ala | |
| | | | 450 | | | | 455 | | | | | 460 | | | | |
| GAG | TAT | AGA | ACG | TTA | AGT | GCT | AAT | GAT | GAT | GGG | GTG | TAT | ATG | CCG | TTA | 1442 |
| Glu | Tyr | Arg | Thr | Leu | Ser | Ala | Asn | Asp | Asp | Gly | Val | Tyr | Met | Pro | Leu | |
| | | 465 | | | | | 470 | | | | | 475 | | | | |
| GGT | GTC | ATC | AGT | GAA | ACA | TTT | TTG | ACT | CCG | ATT | AAT | GGG | TTT | GGC | CTC | 1490 |
| Gly | Val | Ile | Ser | Glu | Thr | Phe | Leu | Thr | Pro | Ile | Asn | Gly | Phe | Gly | Leu | |
| | 480 | | | | | 485 | | | | | 490 | | | | | |
| CAA | GCT | GAT | GAA | AAT | TCA | AGA | TTA | ATT | ACT | TTA | ACA | TGT | AAA | TCA | TAT | 1538 |
| Gln | Ala | Asp | Glu | Asn | Ser | Arg | Leu | Ile | Thr | Leu | Thr | Cys | Lys | Ser | Tyr | |
| 495 | | | | | 500 | | | | | 505 | | | | | 510 | |
| TTA | AGA | GAA | CTA | CTG | CTA | GCA | ACA | GAC | TTA | AGC | AAT | AAA | GAA | ACT | AAA | 1586 |
| Leu | Arg | Glu | Leu | Leu | Leu | Ala | Thr | Asp | Leu | Ser | Asn | Lys | Glu | Thr | Lys | |
| | | | | 515 | | | | 520 | | | | | 525 | | | |
| TTG | ATC | GTC | CCG | CCA | AGT | GGT | TTT | ATT | AGC | AAT | ATT | GTA | GAG | AAC | GGG | 1634 |
| Leu | Ile | Val | Pro | Pro | Ser | Gly | Phe | Ile | Ser | Asn | Ile | Val | Glu | Asn | Gly | |
| | | | 530 | | | | 535 | | | | | 540 | | | | |
| TCC | ATA | GAA | GAG | GAC | AAT | TTA | GAG | CCG | TGG | AAA | GCA | AAT | AAT | AAG | AAT | 1682 |
| Ser | Ile | Glu | Glu | Asp | Asn | Leu | Glu | Pro | Trp | Lys | Ala | Asn | Asn | Lys | Asn | |
| | | 545 | | | | | 550 | | | | | 555 | | | | |
| GCG | TAT | GTA | GAT | CAT | ACA | GGC | GGA | GTG | AAT | GGA | ACT | AAA | GCT | TTA | TAT | 1730 |
| Ala | Tyr | Val | Asp | His | Thr | Gly | Gly | Val | Asn | Gly | Thr | Lys | Ala | Leu | Tyr | |
| | 560 | | | | | 565 | | | | | 570 | | | | | |
| GTT | CAT | AAG | GAC | GGA | GGA | ATT | TCA | CAA | TTT | ATT | GGA | GAT | AAG | TTA | AAA | 1778 |
| Val | His | Lys | Asp | Gly | Gly | Ile | Ser | Gln | Phe | Ile | Gly | Asp | Lys | Leu | Lys | |
| 575 | | | | | 580 | | | | | 585 | | | | | 590 | |
| CCG | AAA | ACT | GAG | TAT | GTA | ATC | CAA | TAT | ACT | GTT | AAA | GGA | AAA | CCT | TCT | 1826 |
| Pro | Lys | Thr | Glu | Tyr | Val | Ile | Gln | Tyr | Thr | Val | Lys | Gly | Lys | Pro | Ser | |
| | | | | 595 | | | | 600 | | | | | 605 | | | |
| ATT | CAT | TTA | AAA | GAT | GAA | AAT | ACT | GGA | TAT | ATT | CAT | TAT | GAA | GAT | ACA | 1874 |
| Ile | His | Leu | Lys | Asp | Glu | Asn | Thr | Gly | Tyr | Ile | His | Tyr | Glu | Asp | Thr | |
| | | | 610 | | | | 615 | | | | | 620 | | | | |
| AAT | AAT | AAT | TTA | GAA | GAT | TAT | CAA | ACT | ATT | AAT | AAA | CGT | TTT | ACT | ACA | 1922 |
| Asn | Asn | Asn | Leu | Glu | Asp | Tyr | Gln | Thr | Ile | Asn | Lys | Arg | Phe | Thr | Thr | |
| | | 625 | | | | | 630 | | | | | 635 | | | | |
| GGA | ACT | GAT | TTA | AAG | GGA | GTG | TAT | TTA | ATT | TTA | AAA | AGT | CAA | AAT | GGA | 1970 |
| Gly | Thr | Asp | Leu | Lys | Gly | Val | Tyr | Leu | Ile | Leu | Lys | Ser | Gln | Asn | Gly | |
| | 640 | | | | | 645 | | | | | 650 | | | | | |

| | | | | | | | | | | | | | | | | |
|---|---|---|---|---|---|---|---|---|---|---|---|---|---|---|---|---|
| GAT | GAA | GCT | TGG | GGA | GAT | AAC | TTT | ATT | ATT | TTG | GAA | ATT | AGT | CCT | TCT | 2018 |
| Asp | Glu | Ala | Trp | Gly | Asp | Asn | Phe | Ile | Ile | Leu | Glu | Ile | Ser | Pro | Ser | |
| 655 | | | | 660 | | | | | 665 | | | | | 670 | | |
| GAA | AAG | TTA | TTA | AGT | CCA | GAA | TTA | ATT | AAT | ACA | AAT | AAT | TGG | ACG | AGT | 2066 |
| Glu | Lys | Leu | Leu | Ser | Pro | Glu | Leu | Ile | Asn | Thr | Asn | Asn | Trp | Thr | Ser | |
| | | | | 675 | | | | 680 | | | | | 685 | | | |
| ACG | GGA | TCA | ACT | AAT | ATT | AGC | GGT | AAT | ACA | CTC | ACT | CTT | TAT | CAG | GGA | 2114 |
| Thr | Gly | Ser | Thr | Asn | Ile | Ser | Gly | Asn | Thr | Leu | Thr | Leu | Tyr | Gln | Gly | |
| | | | 690 | | | | | 695 | | | | | 700 | | | |
| GGA | CGA | GGG | ATT | CTA | AAA | CAA | AAC | CTT | CAA | TTA | GAT | AGT | TTT | TCA | ACT | 2162 |
| Gly | Arg | Gly | Ile | Leu | Lys | Gln | Asn | Leu | Gln | Leu | Asp | Ser | Phe | Ser | Thr | |
| | | 705 | | | | | 710 | | | | | 715 | | | | |
| TAT | AGA | GTG | TAT | TTT | TCT | GTG | TCC | GGA | GAT | GCT | AAT | GTA | AGG | ATT | AGA | 2210 |
| Tyr | Arg | Val | Tyr | Phe | Ser | Val | Ser | Gly | Asp | Ala | Asn | Val | Arg | Ile | Arg | |
| | 720 | | | | | 725 | | | | | 730 | | | | | |
| AAT | TCT | AGG | GAA | GTG | TTA | TTT | GAA | AAA | AGA | TAT | ATG | AGC | GGT | GCT | AAA | 2258 |
| Asn | Ser | Arg | Glu | Val | Leu | Phe | Glu | Lys | Arg | Tyr | Met | Ser | Gly | Ala | Lys | |
| 735 | | | | | 740 | | | | | 745 | | | | | 750 | |
| GAT | GTT | TCT | GAA | ATG | TTC | ACT | ACA | AAA | TTT | GAG | AAA | GAT | AAC | TTT | TAT | 2306 |
| Asp | Val | Ser | Glu | Met | Phe | Thr | Thr | Lys | Phe | Glu | Lys | Asp | Asn | Phe | Tyr | |
| | | | | 755 | | | | | 760 | | | | | 765 | | |
| ATA | GAG | CTT | TCT | CAA | GGG | AAT | AAT | TTA | TAT | GGT | GGT | CCT | ATT | GTA | CAT | 2354 |
| Ile | Glu | Leu | Ser | Gln | Gly | Asn | Asn | Leu | Tyr | Gly | Gly | Pro | Ile | Val | His | |
| | | | 770 | | | | | 775 | | | | | 780 | | | |
| TTT | TAC | GAT | GTC | TCT | ATT | AAG | TAA | | | | | | | | | 2378 |
| Phe | Tyr | Asp | Val | Ser | Ile | Lys | | | | | | | | | | |
| | | 785 | | | | | | | | | | | | | | |

( 2 ) INFORMATION FOR SEQ ID NO:29:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

| | | | | | | | | | | | | | | |
|---|---|---|---|---|---|---|---|---|---|---|---|---|---|---|
| Met | Asn | Lys | Asn | Asn | Thr | Lys | Leu | Ser | Thr | Arg | Ala | Leu | Pro | Ser | Phe |
| 1 | | | | 5 | | | | | 10 | | | | | 15 | |
| Ile | Asp | Tyr | Phe | Asn | Gly | Ile | Tyr | Gly | Phe | Ala | Thr | Gly | Ile | Lys | Asp |
| | | | 20 | | | | | 25 | | | | | 30 | | |
| Ile | Met | Asn | Met | Ile | Phe | Lys | Thr | Asp | Thr | Gly | Gly | Asp | Leu | Thr | Leu |
| | | 35 | | | | | 40 | | | | | 45 | | | |
| Asp | Glu | Ile | Leu | Lys | Asn | Gln | Gln | Leu | Leu | Asn | Asp | Ile | Ser | Gly | Lys |
| | 50 | | | | | 55 | | | | | 60 | | | | |
| Leu | Asp | Gly | Val | Asn | Gly | Ser | Leu | Asn | Asp | Leu | Ile | Ala | Gln | Gly | Asn |
| 65 | | | | | 70 | | | | | 75 | | | | | 80 |
| Leu | Asn | Thr | Glu | Leu | Ser | Lys | Glu | Ile | Leu | Lys | Ile | Ala | Asn | Glu | Gln |
| | | | | 85 | | | | | 90 | | | | | 95 | |
| Asn | Gln | Val | Leu | Asn | Asp | Val | Asn | Asn | Lys | Leu | Asp | Ala | Ile | Asn | Thr |
| | | | 100 | | | | | 105 | | | | | 110 | | |
| Met | Leu | Arg | Val | Tyr | Leu | Pro | Lys | Ile | Thr | Ser | Met | Leu | Ser | Asp | Val |
| | | 115 | | | | | 120 | | | | | 125 | | | |
| Met | Lys | Gln | Asn | Tyr | Ala | Leu | Ser | Leu | Gln | Ile | Glu | Tyr | Leu | Ser | Lys |
| | 130 | | | | | 135 | | | | | 140 | | | | |
| Gln | Leu | Gln | Glu | Ile | Ser | Asp | Lys | Leu | Asp | Ile | Ile | Asn | Val | Asn | Val |
| 145 | | | | | 150 | | | | | 155 | | | | | 160 |
| Leu | Ile | Asn | Ser | Thr | Leu | Thr | Glu | Ile | Thr | Pro | Ala | Tyr | Gln | Arg | Ile |
| | | | | 165 | | | | | 170 | | | | | 175 | |

-continued

```
Lys Tyr Val Asn Glu Lys Phe Glu Glu Leu Thr Phe Ala Thr Glu Thr
            180                 185                 190
Ser Ser Lys Val Lys Lys Asp Gly Ser Pro Ala Asp Ile Leu Asp Glu
        195                 200                 205
Leu Thr Glu Leu Thr Glu Leu Ala Lys Ser Val Thr Lys Asn Asp Val
    210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Thr Lys Glu Asn Val Lys Thr Ser Gly Glu Val Gly Asn Val Tyr
            260                 265                 270
Asn Phe Leu Ile Val Leu Thr Ala Leu Gln Ala Gln Ala Phe Leu Thr
            275                 280                 285
Leu Thr Thr Cys Arg Lys Leu Leu Gly Leu Ala Asp Ile Asp Tyr Thr
    290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Ile Gly Phe Glu Ile Ser Asn Asp Ser Ile Thr
            355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
    435                 440                 445
Glu Ile Asp Leu Asn Lys Lys Lys Val Glu Ser Ser Glu Ala Glu Tyr
    450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Ser Ile
    530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
```

```
                        595                       600                       605
Leu  Lys  Asp  Glu  Asn  Thr  Gly  Tyr  Ile  His  Tyr  Glu  Asp  Thr  Asn  Asn
     610                      615                      620

Asn  Leu  Glu  Asp  Tyr  Gln  Thr  Ile  Asn  Lys  Arg  Phe  Thr  Thr  Gly  Thr
625                           630                      635                      640

Asp  Leu  Lys  Gly  Val  Tyr  Leu  Ile  Leu  Lys  Ser  Gln  Asn  Gly  Asp  Glu
                    645                      650                      655

Ala  Trp  Gly  Asp  Asn  Phe  Ile  Ile  Leu  Glu  Ile  Ser  Pro  Ser  Glu  Lys
               660                      665                      670

Leu  Leu  Ser  Pro  Glu  Leu  Ile  Asn  Thr  Asn  Asn  Trp  Thr  Ser  Thr  Gly
          675                      680                      685

Ser  Thr  Asn  Ile  Ser  Gly  Asn  Thr  Leu  Thr  Leu  Tyr  Gln  Gly  Gly  Arg
     690                      695                      700

Gly  Ile  Leu  Lys  Gln  Asn  Leu  Gln  Leu  Asp  Ser  Phe  Ser  Thr  Tyr  Arg
705                           710                      715                      720

Val  Tyr  Phe  Ser  Val  Ser  Gly  Asp  Ala  Asn  Val  Arg  Ile  Arg  Asn  Ser
                    725                      730                      735

Arg  Glu  Val  Leu  Phe  Glu  Lys  Arg  Tyr  Met  Ser  Gly  Ala  Lys  Asp  Val
               740                      745                      750

Ser  Glu  Met  Phe  Thr  Thr  Lys  Phe  Glu  Lys  Asp  Asn  Phe  Tyr  Ile  Glu
          755                      760                      765

Leu  Ser  Gln  Gly  Asn  Asn  Leu  Tyr  Gly  Gly  Pro  Ile  Val  His  Phe  Tyr
     770                      775                      780

Asp  Val  Ser  Ile  Lys
785
```

( 2 ) INFORMATION FOR SEQ ID NO:30:

( i ) SEQUENCE CHARACTERISTICS:
        ( A ) LENGTH: 2403 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 11..2389
        ( D ) OTHER INFORMATION: /note= "maize optimized DNA
            sequence encoding VIP3A(a)"

( x i ) SEQUENCE DESCRIPTION: SEQ ID NO:30:

```
GGATCCACCA  ATGAACATGA  ACAAGAACAA  CACCAAGCTG  AGCACCCGCG  CCCTGCCGAG    60

CTTCATCGAC  TACTTCAACG  GCATCTACGG  CTTCGCCACC  GGCATCAAGG  ACATCATGAA   120

CATGATCTTC  AAGACCGACA  CCGGCGGCGA  CCTGACCCTG  GACGAGATCC  TGAAGAACCA   180

GCAGCTGCTG  AACGACATCA  GCGGCAAGCT  GGACGGCGTG  AACGGCAGCC  TGAACGACCT   240

GATCGCCCAG  GGCAACCTGA  ACACCGAGCT  GAGCAAGGAG  ATCCTTAAGA  TCGCCAACGA   300

GCAGAACCAG  GTGCTGAACG  ACGTGAACAA  CAAGCTGGAC  GCCATCAACA  CCATGCTGCG   360

CGTGTACCTG  CCGAAGATCA  CCAGCATGCT  GAGCGACGTG  ATGAAGCAGA  ACTACGCCCT   420

GAGCCTGCAG  ATCGAGTACC  TGAGCAAGCA  GCTGCAGGAG  ATCAGCGACA  GCTGGACAT    480

CATCAACGTG  AACGTCCTGA  TCAACAGCAC  CCTGACCGAG  ATCACCCCGG  CCTACCAGCG   540

CATCAAGTAC  GTGAACGAGA  AGTTCGAAGA  GCTGACCTTC  GCCACCGAGA  CCAGCAGCAA   600
```

| | | | | | |
|---|---|---|---|---|---|
| GGTGAAGAAG | GACGGCAGCC | CGGCCGACAT | CCTGGACGAG | CTGACCGAGC | TGACCGAGCT | 660 |
| GGCCAAGAGC | GTGACCAAGA | ACGACGTGGA | CGGCTTCGAG | TTCTACCTGA | ACACCTTCCA | 720 |
| CGACGTGATG | GTGGGCAACA | ACCTGTTCGG | CCGCAGCGCC | CTGAAGACCG | CCAGCGAGCT | 780 |
| GATCACCAAG | GAGAACGTGA | AGACCAGCGG | CAGCGAGGTG | GGCAACGTGT | ACAACTTCCT | 840 |
| GATCGTGCTG | ACCGCCCTGC | AGGCCCAGGC | CTTCCTGACC | CTGACCACCT | GTCGCAAGCT | 900 |
| GCTGGGCCTG | GCCGACATCG | ACTACACCAG | CATCATGAAC | GAGCACTTGA | ACAAGGAGAA | 960 |
| GGAGGAGTTC | CGCGTGAACA | TCCTGCCGAC | CCTGAGCAAC | ACCTTCAGCA | ACCCGAACTA | 1020 |
| CGCCAAGGTG | AAGGGCAGCG | ACGAGGACGC | CAAGATGATC | GTGGAGGCTA | AGCCGGGCCA | 1080 |
| CGCGTTGATC | GGCTTCGAGA | TCAGCAACGA | CAGCATCACC | GTGCTGAAGG | TGTACGAGGC | 1140 |
| CAAGCTGAAG | CAGAACTACC | AGGTGGACAA | GGACAGCTTG | AGCGAGGTGA | TCTACGGCGA | 1200 |
| CATGGACAAG | CTGCTGTGTC | CGGACCAGAG | CGAGCAAATC | TACTACACCA | ACAACATCGT | 1260 |
| GTTCCCGAAC | GAGTACGTGA | TCACCAAGAT | CGACTTCACC | AAGAAGATGA | AGACCCTGCG | 1320 |
| CTACGAGGTG | ACCGCCAACT | TCTACGACAG | CAGCACCGGC | GAGATCGACC | TGAACAAGAA | 1380 |
| GAAGGTGGAG | AGCAGCGAGG | CCGAGTACCG | CACCCTGAGC | GCGAACGACG | ACGGCGTCTA | 1440 |
| CATGCCACTG | GGCGTGATCA | GCGAGACCTT | CCTGACCCCG | ATCAACGGCT | TTGGCCTGCA | 1500 |
| GGCCGACGAG | AACAGCCGCC | TGATCACCCT | GACCTGTAAG | AGCTACCTGC | GCGAGCTGCT | 1560 |
| GCTAGCCACC | GACCTGAGCA | ACAAGGAGAC | CAAGCTGATC | GTGCCACCGA | GCGGCTTCAT | 1620 |
| CAGCAACATC | GTGGAGAACG | GCAGCATCGA | GGAGGACAAC | CTGGAGCCGT | GGAAGGCCAA | 1680 |
| CAACAAGAAC | GCCTACGTGG | ACCACACCGG | CGGCGTGAAC | GGCACCAAGG | CCCTGTACGT | 1740 |
| GCACAAGGAC | GGCGGCATCA | GCCAGTTCAT | CGGCGACAAG | CTGAAGCCGA | AGACCGAGTA | 1800 |
| CGTGATCCAG | TACACCGTGA | AGGGCAAGCC | ATCGATTCAC | CTGAAGGACG | AGAACACCGG | 1860 |
| CTACATCCAC | TACGAGGACA | CCAACAACAA | CCTGGAGGAC | TACCAGACCA | TCAACAAGCG | 1920 |
| CTTCACCACC | GGCACCGACC | TGAAGGGCGT | GTACCTGATC | CTGAAGAGCC | AGAACGGCGA | 1980 |
| CGAGGCCTGG | GGCGACAACT | TCATCATCCT | GGAGATCAGC | CCGAGCGAGA | AGCTGCTGAG | 2040 |
| CCCGGAGCTG | ATCAACACCA | ACAACTGGAC | CAGCACCGGC | AGCACCAACA | TCAGCGGCAA | 2100 |
| CACCCTGACC | CTGTACCAGG | GCGGCCGCGG | CATCCTGAAG | CAGAACCTGC | AGCTGGACAG | 2160 |
| CTTCAGCACC | TACCGCGTGT | ACTTCAGCGT | GAGCGGCGAC | GCCAACGTGC | GCATCCGCAA | 2220 |
| CAGCCGCGAG | GTGCTGTTCG | AGAAGAGGTA | CATGAGCGGC | GCCAAGGACG | TGAGCGAGAT | 2280 |
| GTTCACCACC | AAGTTCGAGA | AGGACAACTT | CTACATCGAG | CTGAGCCAGG | GCAACAACCT | 2340 |
| GTACGGCGGC | CCGATCGTGC | ACTTCTACGA | CGTGAGCATC | AAGTTAACGT | AGAGCTCAGA | 2400 |
| TCT | | | | | | 2403 |

( 2 ) INFORMATION FOR SEQ ID NO:31:

( i ) SEQUENCE CHARACTERISTICS:
  ( A ) LENGTH: 2612 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i x ) FEATURE:
  ( A ) NAME/KEY: CDS
  ( B ) LOCATION: 118..2484
  ( D ) OTHER INFORMATION: /note= "Native DNA sequence
   encoding VIP3A(b) from AB424"

( x i ) SEQUENCE DESCRIPTION: SEQ ID NO:31:

| | | | | | | | | | | |
|---|---|---|---|---|---|---|---|---|---|---|
| ATTGAAATTG | ATAAAAGTT | ATGAGTGTTT | AATAATCAGT | AATTACCAAT | AAAGAATTAA | | | | | 60 |
| GAATACAAGT | TTACAAGAAA | TAAGTGTTAC | AAAAAATAGC | TGAAAAGGAA | GATGAAC | | | | | 117 |

```
ATG  AAC  AAG  AAT  AAT  ACT  AAA  TTA  AGC  ACA  AGA  GCC  TTA  CCA  AGT  TTT      165
Met  Asn  Lys  Asn  Asn  Thr  Lys  Leu  Ser  Thr  Arg  Ala  Leu  Pro  Ser  Phe
790            795                 800                 805

ATT  GAT  TAT  TTC  AAT  GGC  ATT  TAT  GGA  TTT  GCC  ACT  GGT  ATC  AAA  GAC      213
Ile  Asp  Tyr  Phe  Asn  Gly  Ile  Tyr  Gly  Phe  Ala  Thr  Gly  Ile  Lys  Asp
                    810                 815                 820

ATT  ATG  AAC  ATG  ATT  TTT  AAA  ACG  GAT  ACA  GGT  GGT  GAT  CTA  ACC  CTA      261
Ile  Met  Asn  Met  Ile  Phe  Lys  Thr  Asp  Thr  Gly  Gly  Asp  Leu  Thr  Leu
               825                 830                 835

GAC  GAA  ATT  TTA  AAG  AAT  CAG  CAG  CTA  CTA  AAT  GAT  ATT  TCT  GGT  AAA      309
Asp  Glu  Ile  Leu  Lys  Asn  Gln  Gln  Leu  Leu  Asn  Asp  Ile  Ser  Gly  Lys
          840                 845                 850

TTG  GAT  GGG  GTG  AAT  GGA  AGC  TTA  AAT  GAT  CTT  ATC  GCA  CAG  GGA  AAC      357
Leu  Asp  Gly  Val  Asn  Gly  Ser  Leu  Asn  Asp  Leu  Ile  Ala  Gln  Gly  Asn
     855                 860                 865

TTA  AAT  ACA  GAA  TTA  TCT  AAG  GAA  ATA  TTA  AAA  ATT  GCA  AAT  GAA  CAA      405
Leu  Asn  Thr  Glu  Leu  Ser  Lys  Glu  Ile  Leu  Lys  Ile  Ala  Asn  Glu  Gln
870            875                 880                 885

AAT  CAA  GTT  TTA  AAT  GAT  GTT  AAT  AAC  AAA  CTC  GAT  GCG  ATA  AAT  ACG      453
Asn  Gln  Val  Leu  Asn  Asp  Val  Asn  Asn  Lys  Leu  Asp  Ala  Ile  Asn  Thr
                    890                 895                 900

ATG  CTT  CGG  GTA  TAT  CTA  CCT  AAA  ATT  ACC  TCT  ATG  TTG  AGT  GAT  GTA      501
Met  Leu  Arg  Val  Tyr  Leu  Pro  Lys  Ile  Thr  Ser  Met  Leu  Ser  Asp  Val
               905                 910                 915

ATG  AAA  CAA  AAT  TAT  GCG  CTA  AGT  CTG  CAA  ATA  GAA  TAC  TTA  AGT  AAA      549
Met  Lys  Gln  Asn  Tyr  Ala  Leu  Ser  Leu  Gln  Ile  Glu  Tyr  Leu  Ser  Lys
          920                 925                 930

CAA  TTG  CAA  GAG  ATT  TCT  GAT  AAG  TTG  GAT  ATT  ATT  AAT  GTA  AAT  GTA      597
Gln  Leu  Gln  Glu  Ile  Ser  Asp  Lys  Leu  Asp  Ile  Ile  Asn  Val  Asn  Val
     935                 940                 945

CTT  ATT  AAC  TCT  ACA  CTT  ACT  GAA  ATT  ACA  CCT  GCG  TAT  CAA  AGG  ATT      645
Leu  Ile  Asn  Ser  Thr  Leu  Thr  Glu  Ile  Thr  Pro  Ala  Tyr  Gln  Arg  Ile
950            955                 960                 965

AAA  TAT  GTG  AAC  GAA  AAA  TTT  GAG  GAA  TTA  ACT  TTT  GCT  ACA  GAA  ACT      693
Lys  Tyr  Val  Asn  Glu  Lys  Phe  Glu  Glu  Leu  Thr  Phe  Ala  Thr  Glu  Thr
                    970                 975                 980

AGT  TCA  AAA  GTA  AAA  AAG  GAT  GGC  TCT  CCT  GCA  GAT  ATT  CGT  GAT  GAG      741
Ser  Ser  Lys  Val  Lys  Lys  Asp  Gly  Ser  Pro  Ala  Asp  Ile  Arg  Asp  Glu
               985                 990                 995

TTA  ACT  GAG  TTA  ACT  GAA  CTA  GCG  AAA  AGT  GTA  ACA  AAA  AAT  GAT  GTG      789
Leu  Thr  Glu  Leu  Thr  Glu  Leu  Ala  Lys  Ser  Val  Thr  Lys  Asn  Asp  Val
          1000                1005                1010

GAT  GGT  TTT  GAA  TTT  TAC  CTT  AAT  ACA  TTC  CAC  GAT  GTA  ATG  GTA  GGA      837
Asp  Gly  Phe  Glu  Phe  Tyr  Leu  Asn  Thr  Phe  His  Asp  Val  Met  Val  Gly
     1015                1020                1025

AAT  AAT  TTA  TTC  GGG  CGT  TCA  GCT  TTA  AAA  ACT  GCA  TCG  GAA  TTA  ATT      885
Asn  Asn  Leu  Phe  Gly  Arg  Ser  Ala  Leu  Lys  Thr  Ala  Ser  Glu  Leu  Ile
1030           1035                1040                1045

ACT  AAA  GAA  AAT  GTG  AAA  ACA  AGT  GGC  AGT  GAG  GTC  GGA  AAT  GTT  TAT      933
Thr  Lys  Glu  Asn  Val  Lys  Thr  Ser  Gly  Ser  Glu  Val  Gly  Asn  Val  Tyr
                    1050                1055                1060

AAC  TTC  CTA  ATT  GTA  TTA  ACA  GCT  CTG  CAA  GCA  AAA  GCT  TTT  CTT  ACT      981
Asn  Phe  Leu  Ile  Val  Leu  Thr  Ala  Leu  Gln  Ala  Lys  Ala  Phe  Leu  Thr
               1065                1070                1075

TTA  ACA  CCA  TGC  CGA  AAA  TTA  TTA  GGC  TTA  GCA  GAT  ATT  GAT  TAT  ACT     1029
```

-continued

```
                Leu  Thr  Pro  Cys  Arg  Lys  Leu  Leu  Gly  Leu  Ala  Asp  Ile  Asp  Tyr  Thr
                     1080                1085                1090

TCT  ATT  ATG  AAT  GAA  CAT  TTA  AAT  AAG  GAA  AAA  GAG  GAA  TTT  AGA  GTA              1077
Ser  Ile  Met  Asn  Glu  His  Leu  Asn  Lys  Glu  Lys  Glu  Glu  Phe  Arg  Val
          1095                1100                1105

AAC  ATC  CTC  CCT  ACA  CTT  TCT  AAT  ACT  TTT  TCT  AAT  CCT  AAT  TAT  GCA              1125
Asn  Ile  Leu  Pro  Thr  Leu  Ser  Asn  Thr  Phe  Ser  Asn  Pro  Asn  Tyr  Ala
1110                1115                1120                     1125

AAA  GTT  AAA  GGA  AGT  GAT  GAA  GAT  GCA  AAG  ATG  ATT  GTG  GAA  GCT  AAA              1173
Lys  Val  Lys  Gly  Ser  Asp  Glu  Asp  Ala  Lys  Met  Ile  Val  Glu  Ala  Lys
               1130                1135                     1140

CCA  GGA  CAT  GCA  TTG  ATT  GGG  TTT  GAA  ATT  AGT  AAT  GAT  TCA  ATT  ACA              1221
Pro  Gly  His  Ala  Leu  Ile  Gly  Phe  Glu  Ile  Ser  Asn  Asp  Ser  Ile  Thr
                    1145                1150                1155

GTA  TTA  AAA  GTA  TAT  GAG  GCT  AAG  CTA  AAA  CAA  AAT  TAT  CAA  GTC  GAT              1269
Val  Leu  Lys  Val  Tyr  Glu  Ala  Lys  Leu  Lys  Gln  Asn  Tyr  Gln  Val  Asp
          1160                1165                1170

AAG  GAT  TCC  TTA  TCG  GAA  GTT  ATT  TAT  GGC  GAT  ATG  GAT  AAA  TTA  TTG              1317
Lys  Asp  Ser  Leu  Ser  Glu  Val  Ile  Tyr  Gly  Asp  Met  Asp  Lys  Leu  Leu
     1175                1180                1185

TGC  CCA  GAT  CAA  TCT  GGA  CAA  ATC  TAT  TAT  ACA  AAT  AAC  ATA  GTA  TTT              1365
Cys  Pro  Asp  Gln  Ser  Gly  Gln  Ile  Tyr  Tyr  Thr  Asn  Asn  Ile  Val  Phe
1190                1195                1200                     1205

CCA  AAT  GAA  TAT  GTA  ATT  ACT  AAA  ATT  GAT  TTC  ACT  AAA  AAA  ATG  AAA              1413
Pro  Asn  Glu  Tyr  Val  Ile  Thr  Lys  Ile  Asp  Phe  Thr  Lys  Lys  Met  Lys
               1210                1215                     1220

ACT  TTA  AGA  TAT  GAG  GTA  ACA  GCG  AAT  TTT  TAT  GAT  TCT  TCT  ACA  GGA              1461
Thr  Leu  Arg  Tyr  Glu  Val  Thr  Ala  Asn  Phe  Tyr  Asp  Ser  Ser  Thr  Gly
                    1225                1230                1235

GAA  ATT  GAC  TTA  AAT  AAG  AAA  AAA  GTA  GAA  TCA  AGT  GAA  GCG  GAG  TAT              1509
Glu  Ile  Asp  Leu  Asn  Lys  Lys  Lys  Val  Glu  Ser  Ser  Glu  Ala  Glu  Tyr
          1240                1245                1250

AGA  ACG  TTA  AGT  GCT  AAT  GAT  GAT  GGG  GTG  TAT  ATG  CCG  TTA  GGT  GTC              1557
Arg  Thr  Leu  Ser  Ala  Asn  Asp  Asp  Gly  Val  Tyr  Met  Pro  Leu  Gly  Val
     1255                1260                1265

ATC  AGT  GAA  ACA  TTT  TTG  ACT  CCG  ATT  AAT  GGG  TTT  GGC  CTC  CAA  GCT              1605
Ile  Ser  Glu  Thr  Phe  Leu  Thr  Pro  Ile  Asn  Gly  Phe  Gly  Leu  Gln  Ala
1270                1275                1280                     1285

GAT  GAA  AAT  TCA  AGA  TTA  ATT  ACT  TTA  ACA  TGT  AAA  TCA  TAT  TTA  AGA              1653
Asp  Glu  Asn  Ser  Arg  Leu  Ile  Thr  Leu  Thr  Cys  Lys  Ser  Tyr  Leu  Arg
               1290                1295                     1300

GAA  CTA  CTG  CTA  GCA  ACA  GAC  TTA  AGC  AAT  AAA  GAA  ACT  AAA  TTG  ATC              1701
Glu  Leu  Leu  Leu  Ala  Thr  Asp  Leu  Ser  Asn  Lys  Glu  Thr  Lys  Leu  Ile
                    1305                1310                1315

GTC  CCG  CCA  AGT  GGT  TTT  ATT  AGC  AAT  ATT  GTA  GAG  AAC  GGG  TCC  ATA              1749
Val  Pro  Pro  Ser  Gly  Phe  Ile  Ser  Asn  Ile  Val  Glu  Asn  Gly  Ser  Ile
          1320                1325                1330

GAA  GAG  GAC  AAT  TTA  GAG  CCG  TGG  AAA  GCA  AAT  AAT  AAG  AAT  GCG  TAT              1797
Glu  Glu  Asp  Asn  Leu  Glu  Pro  Trp  Lys  Ala  Asn  Asn  Lys  Asn  Ala  Tyr
     1335                1340                1345

GTA  GAT  CAT  ACA  GGC  GGA  GTG  AAT  GGA  ACT  AAA  GCT  TTA  TAT  GTT  CAT              1845
Val  Asp  His  Thr  Gly  Gly  Val  Asn  Gly  Thr  Lys  Ala  Leu  Tyr  Val  His
1350                1355                1360                     1365

AAG  GAC  GGA  GGA  ATT  TCA  CAA  TTT  ATT  GGA  GAT  AAG  TTA  AAA  CCG  AAA              1893
Lys  Asp  Gly  Gly  Ile  Ser  Gln  Phe  Ile  Gly  Asp  Lys  Leu  Lys  Pro  Lys
               1370                1375                     1380

ACT  GAG  TAT  GTA  ATC  CAA  TAT  ACT  GTT  AAA  GGA  AAA  CCT  TCT  ATT  CAT              1941
Thr  Glu  Tyr  Val  Ile  Gln  Tyr  Thr  Val  Lys  Gly  Lys  Pro  Ser  Ile  His
                    1385                1390                1395

TTA  AAA  GAT  GAA  AAT  ACT  GGA  TAT  ATT  CAT  TAT  GAA  GAT  ACA  AAT  AAT              1989
```

| | | | | | | | | | | | | | | | |
|---|---|---|---|---|---|---|---|---|---|---|---|---|---|---|---|
| Leu | Lys | Asp | Glu | Asn | Thr | Gly | Tyr | Ile | His | Tyr | Glu | Asp | Thr | Asn | Asn |
| | | | 1400 | | | | | 1405 | | | | | 1410 | | |

| AAT | TTA | GAA | GAT | TAT | CAA | ACT | ATT | AAT | AAA | CGT | TTT | ACT | ACA | GGA | ACT | 2037 |
|---|---|---|---|---|---|---|---|---|---|---|---|---|---|---|---|---|
| Asn | Leu | Glu | Asp | Tyr | Gln | Thr | Ile | Asn | Lys | Arg | Phe | Thr | Thr | Gly | Thr | |
| | 1415 | | | | 1420 | | | | | 1425 | | | | | | |

| GAT | TTA | AAG | GGA | GTG | TAT | TTA | ATT | TTA | AAA | AGT | CAA | AAT | GGA | GAT | GAA | 2085 |
|---|---|---|---|---|---|---|---|---|---|---|---|---|---|---|---|---|
| Asp | Leu | Lys | Gly | Val | Tyr | Leu | Ile | Leu | Lys | Ser | Gln | Asn | Gly | Asp | Glu | |
| 1430 | | | | | 1435 | | | | | 1440 | | | | | 1445 | |

| GCT | TGG | GGA | GAT | AAC | TTT | ATT | ATT | TTG | GAA | ATT | AGT | CCT | TCT | GAA | AAG | 2133 |
|---|---|---|---|---|---|---|---|---|---|---|---|---|---|---|---|---|
| Ala | Trp | Gly | Asp | Asn | Phe | Ile | Ile | Leu | Glu | Ile | Ser | Pro | Ser | Glu | Lys | |
| | | | | 1450 | | | | | 1455 | | | | | 1460 | | |

| TTA | TTA | AGT | CCA | GAA | TTA | ATT | AAT | ACA | AAT | AAT | TGG | ACG | AGT | ACG | GGA | 2181 |
|---|---|---|---|---|---|---|---|---|---|---|---|---|---|---|---|---|
| Leu | Leu | Ser | Pro | Glu | Leu | Ile | Asn | Thr | Asn | Asn | Trp | Thr | Ser | Thr | Gly | |
| | | | 1465 | | | | | 1470 | | | | | 1475 | | | |

| TCA | ACT | AAT | ATT | AGC | GGT | AAT | ACA | CTC | ACT | CTT | TAT | CAG | GGA | GGA | CGA | 2229 |
|---|---|---|---|---|---|---|---|---|---|---|---|---|---|---|---|---|
| Ser | Thr | Asn | Ile | Ser | Gly | Asn | Thr | Leu | Thr | Leu | Tyr | Gln | Gly | Gly | Arg | |
| | | 1480 | | | | | 1485 | | | | | 1490 | | | | |

| GGG | ATT | CTA | AAA | CAA | AAC | CTT | CAA | TTA | GAT | AGT | TTT | TCA | ACT | TAT | AGA | 2277 |
|---|---|---|---|---|---|---|---|---|---|---|---|---|---|---|---|---|
| Gly | Ile | Leu | Lys | Gln | Asn | Leu | Gln | Leu | Asp | Ser | Phe | Ser | Thr | Tyr | Arg | |
| | 1495 | | | | | 1500 | | | | | 1505 | | | | | |

| GTG | TAT | TTC | TCT | GTG | TCC | GGA | GAT | GCT | AAT | GTA | AGG | ATT | AGA | AAT | TCT | 2325 |
|---|---|---|---|---|---|---|---|---|---|---|---|---|---|---|---|---|
| Val | Tyr | Phe | Ser | Val | Ser | Gly | Asp | Ala | Asn | Val | Arg | Ile | Arg | Asn | Ser | |
| 1510 | | | | | 1515 | | | | | 1520 | | | | | 1525 | |

| AGG | GAA | GTG | TTA | TTT | GAA | AAA | AGA | TAT | ATG | AGC | GGT | GCT | AAA | GAT | GTT | 2373 |
|---|---|---|---|---|---|---|---|---|---|---|---|---|---|---|---|---|
| Arg | Glu | Val | Leu | Phe | Glu | Lys | Arg | Tyr | Met | Ser | Gly | Ala | Lys | Asp | Val | |
| | | | | 1530 | | | | | 1535 | | | | | 1540 | | |

| TCT | GAA | ATG | TTC | ACT | ACA | AAA | TTT | GAG | AAA | GAT | AAC | TTC | TAT | ATA | GAG | 2421 |
|---|---|---|---|---|---|---|---|---|---|---|---|---|---|---|---|---|
| Ser | Glu | Met | Phe | Thr | Thr | Lys | Phe | Glu | Lys | Asp | Asn | Phe | Tyr | Ile | Glu | |
| | | | | 1545 | | | | | 1550 | | | | | 1555 | | |

| CTT | TCT | CAA | GGG | AAT | AAT | TTA | TAT | GGT | GGT | CCT | ATT | GTA | CAT | TTT | TAC | 2469 |
|---|---|---|---|---|---|---|---|---|---|---|---|---|---|---|---|---|
| Leu | Ser | Gln | Gly | Asn | Asn | Leu | Tyr | Gly | Gly | Pro | Ile | Val | His | Phe | Tyr | |
| | | | 1560 | | | | | 1565 | | | | | 1570 | | | |

| GAT | GTC | TCT | ATT | AAG | TAAGATCGGG | ATCTAATATT | AACAGTTTTT | AGAAGCTAAT | 2524 |
|---|---|---|---|---|---|---|---|---|---|
| Asp | Val | Ser | Ile | Lys | | | | | |
| | | 1575 | | | | | | | |

TCTTGTATAA TGTCCTTGAT TATGGAAAAA CACAATTTTG TTTGCTAAGA TGTATATATA    2584

GCTCACTCAT TAAAAGGCAA TCAAGCTT    2612

( 2 ) INFORMATION FOR SEQ ID NO:32:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Met | Asn | Lys | Asn | Asn | Thr | Lys | Leu | Ser | Thr | Arg | Ala | Leu | Pro | Ser | Phe |
|---|---|---|---|---|---|---|---|---|---|---|---|---|---|---|---|
| 1 | | | | 5 | | | | | 10 | | | | | 15 | |

| Ile | Asp | Tyr | Phe | Asn | Gly | Ile | Tyr | Gly | Phe | Ala | Thr | Gly | Ile | Lys | Asp |
|---|---|---|---|---|---|---|---|---|---|---|---|---|---|---|---|
| | | | | 20 | | | | | 25 | | | | | 30 | |

| Ile | Met | Asn | Met | Ile | Phe | Lys | Thr | Asp | Thr | Gly | Gly | Asp | Leu | Thr | Leu |
|---|---|---|---|---|---|---|---|---|---|---|---|---|---|---|---|
| | | 35 | | | | | 40 | | | | | 45 | | | |

| Asp | Glu | Ile | Leu | Lys | Asn | Gln | Gln | Leu | Leu | Asn | Asp | Ile | Ser | Gly | Lys |
|---|---|---|---|---|---|---|---|---|---|---|---|---|---|---|---|
| | 50 | | | | | 55 | | | | | 60 | | | | |

| Leu | Asp | Gly | Val | Asn | Gly | Ser | Leu | Asn | Asp | Leu | Ile | Ala | Gln | Gly | Asn |
|---|---|---|---|---|---|---|---|---|---|---|---|---|---|---|---|
| 65 | | | | | 70 | | | | | 75 | | | | | 80 |

| Leu | Asn | Thr | Glu | Leu | Ser | Lys | Glu | Ile | Leu | Lys | Ile | Ala | Asn | Glu | Gln |
|---|---|---|---|---|---|---|---|---|---|---|---|---|---|---|---|
| | | | | 85 | | | | | 90 | | | | | 95 | |

```
Asn Gln Val Leu Asn Asp Val Asn Asn Lys Leu Asp Ala Ile Asn Thr
                100                 105                 110
Met Leu Arg Val Tyr Leu Pro Lys Ile Thr Ser Met Leu Ser Asp Val
        115                 120                 125
Met Lys Gln Asn Tyr Ala Leu Ser Leu Gln Ile Glu Tyr Leu Ser Lys
        130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
                180                 185                 190
Ser Ser Lys Val Lys Lys Asp Gly Ser Pro Ala Asp Ile Arg Asp Glu
        195                 200                 205
Leu Thr Glu Leu Thr Glu Leu Ala Lys Ser Val Thr Lys Asn Asp Val
    210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Thr Lys Glu Asn Val Lys Thr Ser Gly Ser Glu Val Gly Val Tyr
                260                 265                 270
Asn Phe Leu Ile Val Leu Thr Ala Leu Gln Ala Lys Ala Phe Leu Thr
        275                 280                 285
Leu Thr Pro Cys Arg Lys Leu Leu Gly Leu Ala Asp Ile Asp Tyr Thr
    290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
            340                 345                 350
Pro Gly His Ala Leu Ile Gly Phe Glu Ile Ser Asn Asp Ser Ile Thr
        355                 360                 365
Val Leu Lys Val Tyr Glu Ala Lys Leu Lys Gln Asn Tyr Gln Val Asp
    370                 375                 380
Lys Asp Ser Leu Ser Glu Val Ile Tyr Gly Asp Met Asp Lys Leu Leu
385                 390                 395                 400
Cys Pro Asp Gln Ser Gly Gln Ile Tyr Tyr Thr Asn Asn Ile Val Phe
                405                 410                 415
Pro Asn Glu Tyr Val Ile Thr Lys Ile Asp Phe Thr Lys Met Lys
            420                 425                 430
Thr Leu Arg Tyr Glu Val Thr Ala Asn Phe Tyr Asp Ser Ser Thr Gly
        435                 440                 445
Glu Ile Asp Leu Asn Lys Lys Lys Val Glu Ser Ser Glu Ala Glu Tyr
    450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
```

|     |     |     |     |     |     |     |     |     |     |     |     |     |
|-----|-----|-----|-----|-----|-----|-----|-----|-----|-----|-----|-----|-----|
|     |     | 515 |     |     |     | 520 |     |     |     | 525 |     |     |
| Val | Pro<br>530 | Pro | Ser | Gly | Phe | Ile<br>535 | Ser | Asn | Ile | Val | Glu<br>540 | Asn | Gly | Ser | Ile |
| Glu<br>545 | Glu | Asp | Asn | Leu | Glu<br>550 | Pro | Trp | Lys | Ala | Asn<br>555 | Asn | Lys | Asn | Ala | Tyr<br>560 |
| Val | Asp | His | Thr | Gly<br>565 | Gly | Val | Asn | Gly | Thr<br>570 | Lys | Ala | Leu | Tyr | Val<br>575 | His |
| Lys | Asp | Gly | Gly<br>580 | Ile | Ser | Gln | Phe | Ile<br>585 | Gly | Asp | Lys | Leu | Lys<br>590 | Pro | Lys |
| Thr | Glu | Tyr<br>595 | Val | Ile | Gln | Tyr | Thr<br>600 | Val | Lys | Gly | Lys | Pro<br>605 | Ser | Ile | His |
| Leu | Lys<br>610 | Asp | Glu | Asn | Thr | Gly<br>615 | Tyr | Ile | His | Tyr | Glu<br>620 | Asp | Thr | Asn | Asn |
| Asn<br>625 | Leu | Glu | Asp | Tyr | Gln<br>630 | Thr | Ile | Asn | Lys | Arg<br>635 | Phe | Thr | Thr | Gly | Thr<br>640 |
| Asp | Leu | Lys | Gly | Val<br>645 | Tyr | Leu | Ile | Leu | Lys<br>650 | Ser | Gln | Asn | Gly | Asp<br>655 | Glu |
| Ala | Trp | Gly | Asp<br>660 | Asn | Phe | Ile | Ile | Leu<br>665 | Glu | Ile | Ser | Pro | Ser<br>670 | Glu | Lys |
| Leu | Leu | Ser<br>675 | Pro | Glu | Leu | Ile | Asn<br>680 | Thr | Asn | Asn | Trp | Thr<br>685 | Ser | Thr | Gly |
| Ser | Thr<br>690 | Asn | Ile | Ser | Gly | Asn<br>695 | Thr | Leu | Thr | Leu | Tyr<br>700 | Gln | Gly | Gly | Arg |
| Gly<br>705 | Ile | Leu | Lys | Gln | Asn<br>710 | Leu | Gln | Leu | Asp | Ser<br>715 | Phe | Ser | Thr | Tyr | Arg<br>720 |
| Val | Tyr | Phe | Ser | Val<br>725 | Ser | Gly | Asp | Ala | Asn<br>730 | Val | Arg | Ile | Arg | Asn<br>735 | Ser |
| Arg | Glu | Val | Leu<br>740 | Phe | Glu | Lys | Arg | Tyr<br>745 | Met | Ser | Gly | Ala | Lys<br>750 | Asp | Val |
| Ser | Glu | Met<br>755 | Phe | Thr | Thr | Lys | Phe<br>760 | Glu | Lys | Asp | Asn | Phe<br>765 | Tyr | Ile | Glu |
| Leu | Ser<br>770 | Gln | Gly | Asn | Asn | Leu<br>775 | Tyr | Gly | Gly | Pro | Ile<br>780 | Val | His | Phe | Tyr |
| Asp<br>785 | Val | Ser | Ile | Lys |

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make pCIB5526"

( i i i ) HYPOTHETICAL: NO ( x i ) SEQUENCE DESCRIPTION: SEQ ID NO:33:

GGATCCACCA TGAAGACCAA CCAGATCAGC     30

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
( A ) DESCRIPTION: /desc = "reverse primer used to make pCIB5526"

( i i i ) HYPOTHETICAL: NO ( x i ) SEQUENCE DESCRIPTION: SEQ ID NO:34:

```
AAGCTTCAGC TCCTT                                                   15
```

( 2 ) INFORMATION FOR SEQ ID NO:35:

( i ) SEQUENCE CHARACTERISTICS:
( A ) LENGTH: 2576 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: CDS
( B ) LOCATION: 9..2564
( D ) OTHER INFORMATION: /note= "Maize optimized sequence encoding VIP1A(a) with the Bacillus secretion signal removed as contained in pCIB5526"

( x i ) SEQUENCE DESCRIPTION: SEQ ID NO:35:

```
GATCCACC ATG AAG ACC AAC CAG ATC AGC ACC ACC CAG AAG AAC CAG CAG     50
         Met Lys Thr Asn Gln Ile Ser Thr Thr Gln Lys Asn Gln Gln
                     825                 830                 835

AAG GAG ATG GAC CGC AAG GGC CTG CTG GGC TAC TAC TTC AAG GGC AAG      98
Lys Glu Met Asp Arg Lys Gly Leu Leu Gly Tyr Tyr Phe Lys Gly Lys
                840                 845                 850

GAC TTC AGC AAC CTG ACC ATG TTC GCC CCC ACG CGT GAC AGC ACC CTG     146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG     194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC     242
Glu Tyr Gln Ser Ile Arg Trp Ile Gly Leu Ile Gln Ser Lys Glu Thr
    885                 890                 895

GGC GAC TTC ACC TTC AAC CTG AGC GAG GAC GAG CAG GCC ATC ATC GAG     290
Gly Asp Phe Thr Phe Asn Leu Ser Glu Asp Glu Gln Ala Ile Ile Glu
900                 905                 910                 915

ATC AAC GGC AAG ATC ATC AGC AAC AAG GGC AAG GAG AAG CAG GTG GTG     338
Ile Asn Gly Lys Ile Ile Ser Asn Lys Gly Lys Glu Lys Gln Val Val
                920                 925                 930

CAC CTG GAG AAG GGC AAG CTG GTG CCC ATC AAG ATC GAG TAC CAG AGC     386
His Leu Glu Lys Gly Lys Leu Val Pro Ile Lys Ile Glu Tyr Gln Ser
            935                 940                 945

GAC ACC AAG TTC AAC ATC GAC AGC AAG ACC TTC AAG GAG CTG AAG CTT     434
Asp Thr Lys Phe Asn Ile Asp Ser Lys Thr Phe Lys Glu Leu Lys Leu
        950                 955                 960

TTC AAG ATC GAC AGC CAG AAC CAG CCC CAG CAG GTG CAG CAG GAC GAG     482
Phe Lys Ile Asp Ser Gln Asn Gln Pro Gln Gln Val Gln Gln Asp Glu
    965                 970                 975

CTG CGC AAC CCC GAG TTC AAC AAG AAG GAG AGC CAG GAG TTC CTG GCC     530
Leu Arg Asn Pro Glu Phe Asn Lys Lys Glu Ser Gln Glu Phe Leu Ala
980                 985                 990                 995

AAG CCC AGC AAG ATC AAC CTG TTC ACC CAG CAG ATG AAG CGC GAG ATC     578
Lys Pro Ser Lys Ile Asn Leu Phe Thr Gln Gln Met Lys Arg Glu Ile
```

-continued

```
                     1000                       1005                      1010
GAC  GAG  GAC  ACC  GAC  ACC  GAC  GGC  GAC  AGC  ATC  CCC  GAC  CTG  TGG  GAG         626
Asp  Glu  Asp  Thr  Asp  Thr  Asp  Gly  Asp  Ser  Ile  Pro  Asp  Leu  Trp  Glu
               1015                       1020                      1025

GAG  AAC  GGC  TAC  ACC  ATC  CAG  AAC  CGC  ATC  GCC  GTG  AAG  TGG  GAC  GAC         674
Glu  Asn  Gly  Tyr  Thr  Ile  Gln  Asn  Arg  Ile  Ala  Val  Lys  Trp  Asp  Asp
               1030                       1035                      1040

AGC  CTG  GCT  AGC  AAG  GGC  TAC  ACC  AAG  TTC  GTG  AGC  AAC  CCC  CTG  GAG         722
Ser  Leu  Ala  Ser  Lys  Gly  Tyr  Thr  Lys  Phe  Val  Ser  Asn  Pro  Leu  Glu
     1045                      1050                      1055

AGC  CAC  ACC  GTG  GGC  GAC  CCC  TAC  ACC  GAC  TAC  GAG  AAG  GCC  GCC  CGC         770
Ser  His  Thr  Val  Gly  Asp  Pro  Tyr  Thr  Asp  Tyr  Glu  Lys  Ala  Ala  Arg
1060                      1065                      1070                      1075

GAC  CTG  GAC  CTG  AGC  AAC  GCC  AAG  GAG  ACC  TTC  AAC  CCC  CTG  GTG  GCC         818
Asp  Leu  Asp  Leu  Ser  Asn  Ala  Lys  Glu  Thr  Phe  Asn  Pro  Leu  Val  Ala
                    1080                      1085                      1090

GCC  TTC  CCC  AGC  GTG  AAC  GTG  AGC  ATG  GAG  AAG  GTG  ATC  CTG  AGC  CCC         866
Ala  Phe  Pro  Ser  Val  Asn  Val  Ser  Met  Glu  Lys  Val  Ile  Leu  Ser  Pro
                    1095                      1100                      1105

AAC  GAG  AAC  CTG  AGC  AAC  AGC  GTG  GAG  AGC  CAC  TCG  AGC  ACC  AAC  TGG         914
Asn  Glu  Asn  Leu  Ser  Asn  Ser  Val  Glu  Ser  His  Ser  Ser  Thr  Asn  Trp
          1110                      1115                      1120

AGC  TAC  ACC  AAC  ACC  GAG  GGC  GCC  AGC  GTG  GAG  GCC  GGC  ATC  GGT  CCC         962
Ser  Tyr  Thr  Asn  Thr  Glu  Gly  Ala  Ser  Val  Glu  Ala  Gly  Ile  Gly  Pro
          1125                      1130                      1135

AAG  GGC  ATC  AGC  TTC  GGC  GTG  AGC  GTG  AAC  TAC  CAG  CAC  AGC  GAG  ACC        1010
Lys  Gly  Ile  Ser  Phe  Gly  Val  Ser  Val  Asn  Tyr  Gln  His  Ser  Glu  Thr
1140                      1145                      1150                      1155

GTG  GCC  CAG  GAG  TGG  GGC  ACC  AGC  ACC  GGC  AAC  ACC  AGC  CAG  TTC  AAC        1058
Val  Ala  Gln  Glu  Trp  Gly  Thr  Ser  Thr  Gly  Asn  Thr  Ser  Gln  Phe  Asn
                    1160                      1165                      1170

ACC  GCC  AGC  GCC  GGC  TAC  CTG  AAC  GCC  AAC  GTG  CGC  TAC  AAC  AAC  GTG        1106
Thr  Ala  Ser  Ala  Gly  Tyr  Leu  Asn  Ala  Asn  Val  Arg  Tyr  Asn  Asn  Val
               1175                      1180                      1185

GGC  ACC  GGC  GCC  ATC  TAC  GAC  GTG  AAG  CCC  ACC  ACC  AGC  TTC  GTG  CTG        1154
Gly  Thr  Gly  Ala  Ile  Tyr  Asp  Val  Lys  Pro  Thr  Thr  Ser  Phe  Val  Leu
          1190                      1195                      1200

AAC  AAC  GAC  ACC  ATC  GCC  ACC  ATC  ACC  GCC  AAG  TCG  AAT  TCC  ACC  GCC        1202
Asn  Asn  Asp  Thr  Ile  Ala  Thr  Ile  Thr  Ala  Lys  Ser  Asn  Ser  Thr  Ala
          1205                      1210                      1215

CTG  AAC  ATC  AGC  CCC  GGC  GAG  AGC  TAC  CCC  AAG  AAG  GGC  CAG  AAC  GGC        1250
Leu  Asn  Ile  Ser  Pro  Gly  Glu  Ser  Tyr  Pro  Lys  Lys  Gly  Gln  Asn  Gly
1220                      1225                      1230                      1235

ATC  GCC  ATC  ACC  AGC  ATG  GAC  GAC  TTC  AAC  AGC  CAC  CCC  ATC  ACC  CTG        1298
Ile  Ala  Ile  Thr  Ser  Met  Asp  Asp  Phe  Asn  Ser  His  Pro  Ile  Thr  Leu
                    1240                      1245                      1250

AAC  AAG  AAG  CAG  GTG  GAC  AAC  CTG  CTG  AAC  AAC  AAG  CCC  ATG  ATG  CTG        1346
Asn  Lys  Lys  Gln  Val  Asp  Asn  Leu  Leu  Asn  Asn  Lys  Pro  Met  Met  Leu
                    1255                      1260                      1265

GAG  ACC  AAC  CAG  ACC  GAC  GGC  GTC  TAC  AAG  ATC  AAG  GAC  ACC  CAC  GGC        1394
Glu  Thr  Asn  Gln  Thr  Asp  Gly  Val  Tyr  Lys  Ile  Lys  Asp  Thr  His  Gly
               1270                      1275                      1280

AAC  ATC  GTG  ACG  GGC  GGC  GAG  TGG  AAC  GGC  GTG  ATC  CAG  CAG  ATC  AAG        1442
Asn  Ile  Val  Thr  Gly  Gly  Glu  Trp  Asn  Gly  Val  Ile  Gln  Gln  Ile  Lys
     1285                      1290                      1295

GCC  AAG  ACC  GCC  AGC  ATC  ATC  GTC  GAC  GAC  GGC  GAG  CGC  GTG  GCC  GAG        1490
Ala  Lys  Thr  Ala  Ser  Ile  Ile  Val  Asp  Asp  Gly  Glu  Arg  Val  Ala  Glu
1300                      1305                      1310                      1315

AAG  CGC  GTG  GCC  GCC  AAG  GAC  TAC  GAG  AAC  CCC  GAG  GAC  AAG  ACC  CCC        1538
Lys  Arg  Val  Ala  Ala  Lys  Asp  Tyr  Glu  Asn  Pro  Glu  Asp  Lys  Thr  Pro
```

-continued

```
                      1320                        1325                       1330
AGC  CTG  ACC  CTG  AAG  GAC  GCC  CTG  AAG  CTG  AGC  TAC  CCC  GAC  GAG  ATC    1586
Ser  Leu  Thr  Leu  Lys  Asp  Ala  Leu  Lys  Leu  Ser  Tyr  Pro  Asp  Glu  Ile
               1335                    1340                    1345

AAG  GAG  ATC  GAG  GGC  TTG  CTG  TAC  TAC  AAG  AAC  AAG  CCC  ATC  TAC  GAG    1634
Lys  Glu  Ile  Glu  Gly  Leu  Leu  Tyr  Tyr  Lys  Asn  Lys  Pro  Ile  Tyr  Glu
               1350                    1355                    1360

AGC  AGC  GTG  ATG  ACC  TAT  CTA  GAC  GAG  AAC  ACC  GCC  AAG  GAG  GTG  ACC    1682
Ser  Ser  Val  Met  Thr  Tyr  Leu  Asp  Glu  Asn  Thr  Ala  Lys  Glu  Val  Thr
               1365                    1370                    1375

AAG  CAG  CTG  AAC  GAC  ACC  ACC  GGC  AAG  TTC  AAG  GAC  GTG  AGC  CAC  CTG    1730
Lys  Gln  Leu  Asn  Asp  Thr  Thr  Gly  Lys  Phe  Lys  Asp  Val  Ser  His  Leu
1380                    1385                    1390                    1395

TAC  GAC  GTG  AAG  CTG  ACC  CCC  AAG  ATG  AAC  GTG  ACC  ATC  AAG  CTG  AGC    1778
Tyr  Asp  Val  Lys  Leu  Thr  Pro  Lys  Met  Asn  Val  Thr  Ile  Lys  Leu  Ser
               1400                    1405                    1410

ATC  CTG  TAC  GAC  AAC  GCC  GAG  AGC  AAC  GAC  AAC  AGC  ATC  GGC  AAG  TGG    1826
Ile  Leu  Tyr  Asp  Asn  Ala  Glu  Ser  Asn  Asp  Asn  Ser  Ile  Gly  Lys  Trp
               1415                    1420                    1425

ACC  AAC  ACC  AAC  ATC  GTG  AGC  GGC  GGC  AAC  AAC  GGC  AAG  AAG  CAG  TAC    1874
Thr  Asn  Thr  Asn  Ile  Val  Ser  Gly  Gly  Asn  Asn  Gly  Lys  Lys  Gln  Tyr
               1430                    1435                    1440

AGC  AGC  AAC  AAC  CCC  GAC  GCC  AAC  CTG  ACC  CTG  AAC  ACC  GAC  GCC  CAG    1922
Ser  Ser  Asn  Asn  Pro  Asp  Ala  Asn  Leu  Thr  Leu  Asn  Thr  Asp  Ala  Gln
               1445                    1450                    1455

GAG  AAG  CTG  AAC  AAG  AAC  CGC  GAC  TAC  TAC  ATC  AGC  CTG  TAC  ATG  AAG    1970
Glu  Lys  Leu  Asn  Lys  Asn  Arg  Asp  Tyr  Tyr  Ile  Ser  Leu  Tyr  Met  Lys
1460                    1465                    1470                    1475

AGC  GAG  AAG  AAC  ACC  CAG  TGC  GAG  ATC  ACC  ATC  GAC  GGC  GAG  ATA  TAC    2018
Ser  Glu  Lys  Asn  Thr  Gln  Cys  Glu  Ile  Thr  Ile  Asp  Gly  Glu  Ile  Tyr
               1480                    1485                    1490

CCC  ATC  ACC  ACC  AAG  ACC  GTG  AAC  GTG  AAC  AAG  GAC  AAC  TAC  AAG  CGC    2066
Pro  Ile  Thr  Thr  Lys  Thr  Val  Asn  Val  Asn  Lys  Asp  Asn  Tyr  Lys  Arg
               1495                    1500                    1505

CTG  GAC  ATC  ATC  GCC  CAC  AAC  ATC  AAG  AGC  AAC  CCC  ATC  AGC  AGC  CTG    2114
Leu  Asp  Ile  Ile  Ala  His  Asn  Ile  Lys  Ser  Asn  Pro  Ile  Ser  Ser  Leu
               1510                    1515                    1520

CAC  ATC  AAG  ACC  AAC  GAC  GAG  ATC  ACC  CTG  TTC  TGG  GAC  GAC  ATA  TCG    2162
His  Ile  Lys  Thr  Asn  Asp  Glu  Ile  Thr  Leu  Phe  Trp  Asp  Asp  Ile  Ser
               1525                    1530                    1535

ATT  ACC  GAC  GTC  GCC  AGC  ATC  AAG  CCC  GAG  AAC  CTG  ACC  GAC  AGC  GAG    2210
Ile  Thr  Asp  Val  Ala  Ser  Ile  Lys  Pro  Glu  Asn  Leu  Thr  Asp  Ser  Glu
1540                    1545                    1550                    1555

ATC  AAG  CAG  ATA  TAC  AGT  CGC  TAC  GGC  ATC  AAG  CTG  GAG  GAC  GGC  ATC    2258
Ile  Lys  Gln  Ile  Tyr  Ser  Arg  Tyr  Gly  Ile  Lys  Leu  Glu  Asp  Gly  Ile
               1560                    1565                    1570

CTG  ATC  GAC  AAG  AAA  GGC  GGC  ATC  CAC  TAC  GGC  GAG  TTC  ATC  AAC  GAG    2306
Leu  Ile  Asp  Lys  Lys  Gly  Gly  Ile  His  Tyr  Gly  Glu  Phe  Ile  Asn  Glu
               1575                    1580                    1585

GCC  AGC  TTC  AAC  ATC  GAG  CCC  CTG  CAG  AAC  TAC  GTG  ACC  AAG  TAC  GAG    2354
Ala  Ser  Phe  Asn  Ile  Glu  Pro  Leu  Gln  Asn  Tyr  Val  Thr  Lys  Tyr  Glu
               1590                    1595                    1600

GTG  ACC  TAC  AGC  AGC  GAG  CTG  GGC  CCC  AAC  GTG  AGC  GAC  ACC  CTG  GAG    2402
Val  Thr  Tyr  Ser  Ser  Glu  Leu  Gly  Pro  Asn  Val  Ser  Asp  Thr  Leu  Glu
               1605                    1610                    1615

AGC  GAC  AAG  ATT  TAC  AAG  GAC  GGC  ACC  ATC  AAG  TTC  GAC  TTC  ACC  AAG    2450
Ser  Asp  Lys  Ile  Tyr  Lys  Asp  Gly  Thr  Ile  Lys  Phe  Asp  Phe  Thr  Lys
1620                    1625                    1630                    1635

TAC  AGC  AAG  AAC  GAG  CAG  GGC  CTG  TTC  TAC  GAC  AGC  GGC  CTG  AAC  TGG    2498
Tyr  Ser  Lys  Asn  Glu  Gln  Gly  Leu  Phe  Tyr  Asp  Ser  Gly  Leu  Asn  Trp
```

-continued

```
                     1640                         1645                         1650
GAC  TTC  AAG  ATC  AAC  GCC  ATC  ACC  TAC  GAC  GGC  AAG  GAG  ATG  AAC  GTG         2546
Asp  Phe  Lys  Ile  Asn  Ala  Ile  Thr  Tyr  Asp  Gly  Lys  Glu  Met  Asn  Val
               1655                         1660                         1665

TTC  CAC  CGC  TAC  AAC  AAG  TAGATCTGAG  CT                                            2576
Phe  His  Arg  Tyr  Asn  Lys
          1670
```

( 2 ) INFORMATION FOR SEQ ID NO:36:

( i ) SEQUENCE CHARACTERISTICS:
        ( A ) LENGTH: 852 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met  Lys  Thr  Asn  Gln  Ile  Ser  Thr  Thr  Gln  Lys  Asn  Gln  Gln  Lys  Glu
 1                        5                        10                       15

Met  Asp  Arg  Lys  Gly  Leu  Leu  Gly  Tyr  Tyr  Phe  Lys  Gly  Lys  Asp  Phe
                20                       25                       30

Ser  Asn  Leu  Thr  Met  Phe  Ala  Pro  Thr  Arg  Asp  Ser  Thr  Leu  Ile  Tyr
               35                       40                       45

Asp  Gln  Gln  Thr  Ala  Asn  Lys  Leu  Leu  Asp  Lys  Lys  Gln  Gln  Glu  Tyr
     50                       55                       60

Gln  Ser  Ile  Arg  Trp  Ile  Gly  Leu  Ile  Gln  Ser  Lys  Glu  Thr  Gly  Asp
 65                       70                       75                       80

Phe  Thr  Phe  Asn  Leu  Ser  Glu  Asp  Glu  Gln  Ala  Ile  Ile  Glu  Ile  Asn
                    85                       90                       95

Gly  Lys  Ile  Ile  Ser  Asn  Lys  Gly  Lys  Glu  Lys  Gln  Val  Val  His  Leu
              100                      105                      110

Glu  Lys  Gly  Lys  Leu  Val  Pro  Ile  Lys  Ile  Glu  Tyr  Gln  Ser  Asp  Thr
         115                      120                      125

Lys  Phe  Asn  Ile  Asp  Ser  Lys  Thr  Phe  Lys  Glu  Leu  Lys  Leu  Phe  Lys
         130                      135                      140

Ile  Asp  Ser  Gln  Asn  Gln  Pro  Gln  Gln  Val  Gln  Gln  Asp  Glu  Leu  Arg
145                      150                      155                      160

Asn  Pro  Glu  Phe  Asn  Lys  Lys  Glu  Ser  Gln  Glu  Phe  Leu  Ala  Lys  Pro
                   165                      170                      175

Ser  Lys  Ile  Asn  Leu  Phe  Thr  Gln  Gln  Met  Lys  Arg  Glu  Ile  Asp  Glu
              180                      185                      190

Asp  Thr  Asp  Thr  Asp  Gly  Asp  Ser  Ile  Pro  Asp  Leu  Trp  Glu  Glu  Asn
         195                      200                      205

Gly  Tyr  Thr  Ile  Gln  Asn  Arg  Ile  Ala  Val  Lys  Trp  Asp  Asp  Ser  Leu
     210                      215                      220

Ala  Ser  Lys  Gly  Tyr  Thr  Lys  Phe  Val  Ser  Asn  Pro  Leu  Glu  Ser  His
225                      230                      235                      240

Thr  Val  Gly  Asp  Pro  Tyr  Thr  Asp  Tyr  Glu  Lys  Ala  Ala  Arg  Asp  Leu
                   245                      250                      255

Asp  Leu  Ser  Asn  Ala  Lys  Glu  Thr  Phe  Asn  Pro  Leu  Val  Ala  Ala  Phe
              260                      265                      270

Pro  Ser  Val  Asn  Val  Ser  Met  Glu  Lys  Val  Ile  Leu  Ser  Pro  Asn  Glu
         275                      280                      285

Asn  Leu  Ser  Asn  Ser  Val  Glu  Ser  His  Ser  Ser  Thr  Asn  Trp  Ser  Tyr
     290                      295                      300

Thr  Asn  Thr  Glu  Gly  Ala  Ser  Val  Glu  Ala  Gly  Ile  Gly  Pro  Lys  Gly
```

|     |     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- | --- |
| Ile | Ser | Phe | Gly | Val | Ser | Val | Asn | Tyr | Gln | His | Ser | Glu | Thr | Val | Ala |
|     |     |     |     | 325 |     |     |     |     | 330 |     |     |     |     | 335 |     |
| Gln | Glu | Trp | Gly | Thr | Ser | Thr | Gly | Asn | Thr | Ser | Gln | Phe | Asn | Thr | Ala |
|     |     |     | 340 |     |     |     |     | 345 |     |     |     |     | 350 |     |     |
| Ser | Ala | Gly | Tyr | Leu | Asn | Ala | Asn | Val | Arg | Tyr | Asn | Asn | Val | Gly | Thr |
|     |     | 355 |     |     |     | 360 |     |     |     |     | 365 |     |     |     |     |
| Gly | Ala | Ile | Tyr | Asp | Val | Lys | Pro | Thr | Thr | Ser | Phe | Val | Leu | Asn | Asn |
|     | 370 |     |     |     |     | 375 |     |     |     |     | 380 |     |     |     |     |
| Asp | Thr | Ile | Ala | Thr | Ile | Thr | Ala | Lys | Ser | Asn | Ser | Thr | Ala | Leu | Asn |
| 385 |     |     |     |     | 390 |     |     |     |     | 395 |     |     |     |     | 400 |
| Ile | Ser | Pro | Gly | Glu | Ser | Tyr | Pro | Lys | Lys | Gly | Gln | Asn | Gly | Ile | Ala |
|     |     |     |     | 405 |     |     |     |     | 410 |     |     |     |     | 415 |     |
| Ile | Thr | Ser | Met | Asp | Asp | Phe | Asn | Ser | His | Pro | Ile | Thr | Leu | Asn | Lys |
|     |     |     | 420 |     |     |     |     | 425 |     |     |     |     | 430 |     |     |
| Lys | Gln | Val | Asp | Asn | Leu | Leu | Asn | Asn | Lys | Pro | Met | Met | Leu | Glu | Thr |
|     |     |     | 435 |     |     |     | 440 |     |     |     |     | 445 |     |     |     |
| Asn | Gln | Thr | Asp | Gly | Val | Tyr | Lys | Ile | Lys | Asp | Thr | His | Gly | Asn | Ile |
| 450 |     |     |     |     | 455 |     |     |     |     | 460 |     |     |     |     |     |
| Val | Thr | Gly | Gly | Glu | Trp | Asn | Gly | Val | Ile | Gln | Gln | Ile | Lys | Ala | Lys |
| 465 |     |     |     |     | 470 |     |     |     |     | 475 |     |     |     |     | 480 |
| Thr | Ala | Ser | Ile | Ile | Val | Asp | Asp | Gly | Glu | Arg | Val | Ala | Glu | Lys | Arg |
|     |     |     |     | 485 |     |     |     |     | 490 |     |     |     |     | 495 |     |
| Val | Ala | Ala | Lys | Asp | Tyr | Glu | Asn | Pro | Glu | Asp | Lys | Thr | Pro | Ser | Leu |
|     |     |     |     | 500 |     |     |     |     | 505 |     |     |     |     | 510 |     |
| Thr | Leu | Lys | Asp | Ala | Leu | Lys | Leu | Ser | Tyr | Pro | Asp | Glu | Ile | Lys | Glu |
|     |     |     | 515 |     |     |     |     | 520 |     |     |     |     | 525 |     |     |
| Ile | Glu | Gly | Leu | Leu | Tyr | Tyr | Lys | Asn | Lys | Pro | Ile | Tyr | Glu | Ser | Ser |
|     |     | 530 |     |     |     |     | 535 |     |     |     |     | 540 |     |     |     |
| Val | Met | Thr | Tyr | Leu | Asp | Glu | Asn | Thr | Ala | Lys | Glu | Val | Thr | Lys | Gln |
| 545 |     |     |     |     | 550 |     |     |     |     | 555 |     |     |     |     | 560 |
| Leu | Asn | Asp | Thr | Thr | Gly | Lys | Phe | Lys | Asp | Val | Ser | His | Leu | Tyr | Asp |
|     |     |     |     | 565 |     |     |     |     | 570 |     |     |     |     | 575 |     |
| Val | Lys | Leu | Thr | Pro | Lys | Met | Asn | Val | Thr | Ile | Lys | Leu | Ser | Ile | Leu |
|     |     |     |     | 580 |     |     |     |     | 585 |     |     |     |     | 590 |     |
| Tyr | Asp | Asn | Ala | Glu | Ser | Asn | Asp | Asn | Ser | Ile | Gly | Lys | Trp | Thr | Asn |
|     |     |     | 595 |     |     |     |     | 600 |     |     |     |     | 605 |     |     |
| Thr | Asn | Ile | Val | Ser | Gly | Gly | Asn | Asn | Gly | Lys | Lys | Gln | Tyr | Ser | Ser |
|     |     | 610 |     |     |     |     | 615 |     |     |     |     | 620 |     |     |     |
| Asn | Asn | Pro | Asp | Ala | Asn | Leu | Thr | Leu | Asn | Thr | Asp | Ala | Gln | Glu | Lys |
| 625 |     |     |     |     | 630 |     |     |     |     | 635 |     |     |     |     | 640 |
| Leu | Asn | Lys | Asn | Arg | Asp | Tyr | Tyr | Ile | Ser | Leu | Tyr | Met | Lys | Ser | Glu |
|     |     |     |     | 645 |     |     |     |     | 650 |     |     |     |     | 655 |     |
| Lys | Asn | Thr | Gln | Cys | Glu | Ile | Thr | Ile | Asp | Gly | Glu | Ile | Tyr | Pro | Ile |
|     |     |     | 660 |     |     |     |     | 665 |     |     |     |     | 670 |     |     |
| Thr | Thr | Lys | Thr | Val | Asn | Val | Asn | Lys | Asp | Asn | Tyr | Lys | Arg | Leu | Asp |
|     |     |     | 675 |     |     |     |     | 680 |     |     |     |     | 685 |     |     |
| Ile | Ile | Ala | His | Asn | Ile | Lys | Ser | Asn | Pro | Ile | Ser | Ser | Leu | His | Ile |
|     |     |     | 690 |     |     |     | 695 |     |     |     |     | 700 |     |     |     |
| Lys | Thr | Asn | Asp | Glu | Ile | Thr | Leu | Phe | Trp | Asp | Asp | Ile | Ser | Ile | Thr |
| 705 |     |     |     |     | 710 |     |     |     |     | 715 |     |     |     |     | 720 |
| Asp | Val | Ala | Ser | Ile | Lys | Pro | Glu | Asn | Leu | Thr | Asp | Ser | Glu | Ile | Lys |
|     |     |     |     | 725 |     |     |     |     | 730 |     |     |     |     | 735 |     |

| Gln | Ile | Tyr | Ser<br>740 | Arg | Tyr | Gly | Ile | Lys<br>745 | Leu | Glu | Asp | Gly | Ile<br>750 | Leu | Ile |

| Asp | Lys | Lys<br>755 | Gly | Gly | Ile | His | Tyr<br>760 | Gly | Glu | Phe | Ile | Asn<br>765 | Glu | Ala | Ser |

| Phe | Asn<br>770 | Ile | Glu | Pro | Leu | Gln<br>775 | Asn | Tyr | Val | Thr | Lys<br>780 | Tyr | Glu | Val | Thr |

| Tyr<br>785 | Ser | Ser | Glu | Leu | Gly<br>790 | Pro | Asn | Val | Ser | Asp<br>795 | Thr | Leu | Glu | Ser | Asp<br>800 |

| Lys | Ile | Tyr | Lys | Asp<br>805 | Gly | Thr | Ile | Lys | Phe<br>810 | Asp | Phe | Thr | Lys | Tyr<br>815 | Ser |

| Lys | Asn | Glu | Gln<br>820 | Gly | Leu | Phe | Tyr | Asp<br>825 | Ser | Gly | Leu | Asn | Trp<br>830 | Asp | Phe |

| Lys | Ile | Asn<br>835 | Ala | Ile | Thr | Tyr | Asp<br>840 | Gly | Lys | Glu | Met | Asn<br>845 | Val | Phe | His |

| Arg | Tyr | Asn<br>850 | Lys |

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make pCIB5527"

( i i i ) HYPOTHETICAL: NO ( x i ) SEQUENCE DESCRIPTION: SEQ ID NO:37:

GGATCCACCA TGCTGCAGAA CCTGAAGATC AC        32

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make pCIB5527"

( i i i ) HYPOTHETICAL: NO ( x i ) SEQUENCE DESCRIPTION: SEQ ID NO:38:

AAGCTTCCAC TCCTTCTC        18

( 2 ) INFORMATION FOR SEQ ID NO:39:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA -continued sequence encoding VIP2A(a) with the Bacillus secretion
signal removed as contained in pCIB5527"

( x i ) SEQUENCE DESCRIPTION: SEQ ID NO:39:

| GATCCACC | ATG | CTG | CAG | AAC | CTG | AAG | ATC | ACC | GAC | AAG | GTG | GAG | GAC | TTC | 50 |
| | Met | Leu | Gln | Asn | Leu | Lys | Ile | Thr | Asp | Lys | Val | Glu | Asp | Phe | |
| | | | 855 | | | | 860 | | | | | 865 | | | |

| AAG | GAG | GAC | AAG | GAG | AAG | GCC | AAG | GAG | TGG | GGC | AAG | GAG | AAG | GAG | AAG | 98 |
| Lys | Glu | Asp | Lys | Glu | Lys | Ala | Lys | Glu | Trp | Gly | Lys | Glu | Lys | Glu | Lys | |
| | | | 870 | | | | 875 | | | | | 880 | | | | |

| GAG | TGG | AAG | CTT | ACC | GCC | ACC | GAG | AAG | GGC | AAG | ATG | AAC | AAC | TTC | CTG | 146 |
| Glu | Trp | Lys | Leu | Thr | Ala | Thr | Glu | Lys | Gly | Lys | Met | Asn | Asn | Phe | Leu | |
| | | 885 | | | | 890 | | | | 895 | | | | | | |

| GAC | AAC | AAG | AAC | GAC | ATC | AAG | ACC | AAC | TAC | AAG | GAG | ATC | ACC | TTC | AGC | 194 |
| Asp | Asn | Lys | Asn | Asp | Ile | Lys | Thr | Asn | Tyr | Lys | Glu | Ile | Thr | Phe | Ser | |
| 900 | | | | | 905 | | | | | 910 | | | | | | |

| ATA | GCC | GGC | AGC | TTC | GAG | GAC | GAG | ATC | AAG | GAC | CTG | AAG | GAG | ATC | GAC | 242 |
| Ile | Ala | Gly | Ser | Phe | Glu | Asp | Glu | Ile | Lys | Asp | Leu | Lys | Glu | Ile | Asp | |
| 915 | | | | | 920 | | | | 925 | | | | | 930 | | |

| AAG | ATG | TTC | GAC | AAG | ACC | AAC | CTG | AGC | AAC | AGC | ATC | ATC | ACC | TAC | AAG | 290 |
| Lys | Met | Phe | Asp | Lys | Thr | Asn | Leu | Ser | Asn | Ser | Ile | Ile | Thr | Tyr | Lys | |
| | | | 935 | | | | 940 | | | | | 945 | | | | |

| AAC | GTG | GAG | CCC | ACC | ACC | ATC | GGC | TTC | AAC | AAG | AGC | CTG | ACC | GAG | GGC | 338 |
| Asn | Val | Glu | Pro | Thr | Thr | Ile | Gly | Phe | Asn | Lys | Ser | Leu | Thr | Glu | Gly | |
| | | | 950 | | | | 955 | | | | | 960 | | | | |

| AAC | ACC | ATC | AAC | AGC | GAC | GCC | ATG | GCC | CAG | TTC | AAG | GAG | CAG | TTC | CTG | 386 |
| Asn | Thr | Ile | Asn | Ser | Asp | Ala | Met | Ala | Gln | Phe | Lys | Glu | Gln | Phe | Leu | |
| | | 965 | | | | 970 | | | | 975 | | | | | | |

| GAC | CGC | GAC | ATC | AAG | TTC | GAC | AGC | TAC | CTG | GAC | ACC | CAC | CTG | ACC | GCC | 434 |
| Asp | Arg | Asp | Ile | Lys | Phe | Asp | Ser | Tyr | Leu | Asp | Thr | His | Leu | Thr | Ala | |
| | 980 | | | | | 985 | | | | | 990 | | | | | |

| CAG | CAG | GTG | AGC | AGC | AAG | GAG | CGC | GTG | ATC | CTG | AAG | GTG | ACC | GTC | CCC | 482 |
| Gln | Gln | Val | Ser | Ser | Lys | Glu | Arg | Val | Ile | Leu | Lys | Val | Thr | Val | Pro | |
| 995 | | | | | 1000 | | | | | 1005 | | | | | 1010 | |

| AGC | GGC | AAG | GGC | AGC | ACC | ACC | CCC | ACC | AAG | GCC | GGC | GTG | ATC | CTG | AAC | 530 |
| Ser | Gly | Lys | Gly | Ser | Thr | Thr | Pro | Thr | Lys | Ala | Gly | Val | Ile | Leu | Asn | |
| | | | | 1015 | | | | 1020 | | | | | 1025 | | | |

| AAC | AGC | GAG | TAC | AAG | ATG | CTG | ATC | GAC | AAC | GGC | TAC | ATG | GTG | CAC | GTG | 578 |
| Asn | Ser | Glu | Tyr | Lys | Met | Leu | Ile | Asp | Asn | Gly | Tyr | Met | Val | His | Val | |
| | | | 1030 | | | | 1035 | | | | | 1040 | | | | |

| GAC | AAG | GTG | AGC | AAG | GTG | GTG | AAG | AAG | GGC | GTG | GAG | TGC | CTC | CAG | ATC | 626 |
| Asp | Lys | Val | Ser | Lys | Val | Val | Lys | Lys | Gly | Val | Glu | Cys | Leu | Gln | Ile | |
| | | | 1045 | | | | 1050 | | | | | 1055 | | | | |

| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala | |
| | | | 1060 | | | | 1065 | | | | | 1070 | | | | |

| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp | |
| 1075 | | | | 1080 | | | | | 1085 | | | | | 1090 | | |

| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp | |
| | | | | 1095 | | | | 1100 | | | | | 1105 | | | |

| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn | |
| | | | | 1110 | | | | 1115 | | | | | 1120 | | | |

| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys | |
| | | | 1125 | | | | 1130 | | | | | 1135 | | | | |

| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro | |
| | | | 1140 | | | | 1145 | | | | | 1150 | | | | |

| | | | | | | | | | | | | | | | | |
|---|---|---|---|---|---|---|---|---|---|---|---|---|---|---|---|---|
| GAG | TTC | GGC | TAC | CAG | ATC | AGC | GAC | CCC | CTG | CCC | AGC | CTG | AAG | GAC | TTC | 962 |
| Glu | Phe | Gly | Tyr | Gln | Ile | Ser | Asp | Pro | Leu | Pro | Ser | Leu | Lys | Asp | Phe | |
| 1155 | | | | 1160 | | | | | 1165 | | | | | 1170 | | |
| GAG | GAG | CAG | TTC | CTG | AAC | ACC | ATC | AAG | GAG | GAC | AAG | GGC | TAC | ATG | AGC | 1010 |
| Glu | Glu | Gln | Phe | Leu | Asn | Thr | Ile | Lys | Glu | Asp | Lys | Gly | Tyr | Met | Ser | |
| | | | | 1175 | | | | | 1180 | | | | | 1185 | | |
| ACC | AGC | CTG | AGC | AGC | GAG | CGC | CTG | GCC | GCC | TTC | GGC | AGC | CGC | AAG | ATC | 1058 |
| Thr | Ser | Leu | Ser | Ser | Glu | Arg | Leu | Ala | Ala | Phe | Gly | Ser | Arg | Lys | Ile | |
| | | | 1190 | | | | | 1195 | | | | | 1200 | | | |
| ATC | CTG | CGC | CTG | CAG | GTG | CCC | AAG | GGC | AGC | ACT | GGT | GCC | TAC | CTG | AGC | 1106 |
| Ile | Leu | Arg | Leu | Gln | Val | Pro | Lys | Gly | Ser | Thr | Gly | Ala | Tyr | Leu | Ser | |
| | | 1205 | | | | | 1210 | | | | | 1215 | | | | |
| GCC | ATC | GGC | GGC | TTC | GCC | AGC | GAG | AAG | GAG | ATC | CTG | CTG | GAT | AAG | GAC | 1154 |
| Ala | Ile | Gly | Gly | Phe | Ala | Ser | Glu | Lys | Glu | Ile | Leu | Leu | Asp | Lys | Asp | |
| | 1220 | | | | | 1225 | | | | | 1230 | | | | | |
| AGC | AAG | TAC | CAC | ATC | GAC | AAG | GTG | ACC | GAG | GTG | ATC | ATC | AAG | GGC | GTG | 1202 |
| Ser | Lys | Tyr | His | Ile | Asp | Lys | Val | Thr | Glu | Val | Ile | Ile | Lys | Gly | Val | |
| 1235 | | | | | 1240 | | | | | 1245 | | | | | 1250 | |
| AAG | CGC | TAC | GTG | GTG | GAC | GCC | ACC | CTG | CTG | ACC | AAC | TAG | | | | 1241 |
| Lys | Arg | Tyr | Val | Val | Asp | Ala | Thr | Leu | Leu | Thr | Asn | | | | | |
| | | | | 1255 | | | | | 1260 | | | | | | | |

(2) INFORMATION FOR SEQ ID NO:40:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:40:

| | | | | | | | | | | | | | | |
|---|---|---|---|---|---|---|---|---|---|---|---|---|---|---|
| Met | Leu | Gln | Asn | Leu | Lys | Ile | Thr | Asp | Lys | Val | Glu | Asp | Phe | Lys | Glu |
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | 25 | | | | | 30 | | | |
| Lys | Leu | Thr | Ala | Thr | Glu | Lys | Gly | Lys | Met | Asn | Asn | Phe | Leu | Asp | Asn |
| | | 35 | | | | | 40 | | | | | 45 | | | |
| Lys | Asn | Asp | Ile | Lys | Thr | Asn | Tyr | Lys | Glu | Ile | Thr | Phe | Ser | Ile | Ala |
| | 50 | | | | | 55 | | | | | 60 | | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |
| | | | | 85 | | | | | 90 | | | | | 95 | |
| Glu | Pro | Thr | Thr | Ile | Gly | Phe | Asn | Lys | Ser | Leu | Thr | Glu | Gly | Asn | Thr |
| | | | 100 | | | | | 105 | | | | | 110 | | |
| Ile | Asn | Ser | Asp | Ala | Met | Ala | Gln | Phe | Lys | Glu | Gln | Phe | Leu | Asp | Arg |
| | | 115 | | | | | 120 | | | | | 125 | | | |
| Asp | Ile | Lys | Phe | Asp | Ser | Tyr | Leu | Asp | Thr | His | Leu | Thr | Ala | Gln | Gln |
| | 130 | | | | | 135 | | | | | 140 | | | | |
| Val | Ser | Ser | Lys | Glu | Arg | Val | Ile | Leu | Lys | Val | Thr | Val | Pro | Ser | Gly |
| 145 | | | | | 150 | | | | | 155 | | | | | 160 |
| Lys | Gly | Ser | Thr | Thr | Pro | Thr | Lys | Ala | Gly | Val | Ile | Leu | Asn | Asn | Ser |
| | | | | 165 | | | | | 170 | | | | | 175 | |
| Glu | Tyr | Lys | Met | Leu | Ile | Asp | Asn | Gly | Tyr | Met | Val | His | Val | Asp | Lys |
| | | | 180 | | | | | 185 | | | | | 190 | | |
| Val | Ser | Lys | Val | Val | Lys | Lys | Gly | Val | Glu | Cys | Leu | Gln | Ile | Glu | Gly |
| | | 195 | | | | | 200 | | | | | 205 | | | |

| Thr | Leu | Lys | Lys | Ser | Leu | Asp | Phe | Lys | Asn | Asp | Ile | Asn | Ala | Glu | Ala |
|---|---|---|---|---|---|---|---|---|---|---|---|---|---|---|---|
| 210 | | | | | 215 | | | | | 220 | | | | | |

| His | Ser | Trp | Gly | Met | Lys | Asn | Tyr | Glu | Glu | Trp | Ala | Lys | Asp | Leu | Thr |
|---|---|---|---|---|---|---|---|---|---|---|---|---|---|---|---|
| 225 | | | | | 230 | | | | | 235 | | | | | 240 |

| Asp | Ser | Gln | Arg | Glu | Ala | Leu | Asp | Gly | Tyr | Ala | Arg | Gln | Asp | Tyr | Lys |
|---|---|---|---|---|---|---|---|---|---|---|---|---|---|---|---|
| | | | | 245 | | | | | 250 | | | | | 255 | |

| Glu | Ile | Asn | Asn | Tyr | Leu | Arg | Asn | Gln | Gly | Gly | Ser | Gly | Asn | Glu | Lys |
|---|---|---|---|---|---|---|---|---|---|---|---|---|---|---|---|
| | | | 260 | | | | | 265 | | | | | 270 | | |

| Leu | Asp | Ala | Gln | Ile | Lys | Asn | Ile | Ser | Asp | Ala | Leu | Gly | Lys | Lys | Pro |
|---|---|---|---|---|---|---|---|---|---|---|---|---|---|---|---|
| | | 275 | | | | | 280 | | | | | 285 | | | |

| Ile | Pro | Glu | Asn | Ile | Thr | Val | Tyr | Arg | Trp | Cys | Gly | Met | Pro | Glu | Phe |
|---|---|---|---|---|---|---|---|---|---|---|---|---|---|---|---|
| | 290 | | | | | 295 | | | | | 300 | | | | |

| Gly | Tyr | Gln | Ile | Ser | Asp | Pro | Leu | Pro | Ser | Leu | Lys | Asp | Phe | Glu | Glu |
|---|---|---|---|---|---|---|---|---|---|---|---|---|---|---|---|
| 305 | | | | | 310 | | | | | 315 | | | | | 320 |

| Gln | Phe | Leu | Asn | Thr | Ile | Lys | Glu | Asp | Lys | Gly | Tyr | Met | Ser | Thr | Ser |
|---|---|---|---|---|---|---|---|---|---|---|---|---|---|---|---|
| | | | | 325 | | | | | 330 | | | | | 335 | |

| Leu | Ser | Ser | Glu | Arg | Leu | Ala | Ala | Phe | Gly | Ser | Arg | Lys | Ile | Ile | Leu |
|---|---|---|---|---|---|---|---|---|---|---|---|---|---|---|---|
| | | | 340 | | | | | 345 | | | | | 350 | | |

| Arg | Leu | Gln | Val | Pro | Lys | Gly | Ser | Thr | Gly | Ala | Tyr | Leu | Ser | Ala | Ile |
|---|---|---|---|---|---|---|---|---|---|---|---|---|---|---|---|
| | | 355 | | | | | 360 | | | | | 365 | | | |

| Gly | Gly | Phe | Ala | Ser | Glu | Lys | Glu | Ile | Leu | Leu | Asp | Lys | Asp | Ser | Lys |
|---|---|---|---|---|---|---|---|---|---|---|---|---|---|---|---|
| 370 | | | | | 375 | | | | | 380 | | | | | |

| Tyr | His | Ile | Asp | Lys | Val | Thr | Glu | Val | Ile | Ile | Lys | Gly | Val | Lys | Arg |
|---|---|---|---|---|---|---|---|---|---|---|---|---|---|---|---|
| 385 | | | | | 390 | | | | | 395 | | | | | 400 |

| Tyr | Val | Val | Asp | Ala | Thr | Leu | Leu | Thr | Asn |
|---|---|---|---|---|---|---|---|---|---|
| | | | | 405 | | | | | 410 |

( 2 ) INFORMATION FOR SEQ ID NO:41:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            eukaryotic secretion signal used to construct pCIB5527"

( i i i ) HYPOTHETICAL: NO ( x i ) SEQUENCE DESCRIPTION: SEQ ID NO:41:

| GGATCCACCA | TGGGCTGGAG | CTGGATCTTC | CTGTTCCTGC | TGAGCGGCGC | CGCGGGCGTG | 60 |
|---|---|---|---|---|---|---|
| CACTGCCTGC | AG | | | | | 72 |

( 2 ) INFORMATION FOR SEQ ID NO:42:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
            signal removed and the eukaryotic secretion signal inserted as contained in pCIB5528"

(xi) SEQUENCE DESCRIPTION: SEQ ID NO:42:

```
GATCCACC ATG CTG CAG AAC CTG AAG ATC ACC GAC AAG GTG GAG GAC TTC      50
         Met Leu Gln Asn Leu Lys Ile Thr Asp Lys Val Glu Asp Phe
             415                 420

AAG GAG GAC AAG GAG AAG GCC AAG GAG TGG GGC AAG GAG AAG GAG AAG       98
Lys Glu Asp Lys Glu Lys Ala Lys Glu Trp Gly Lys Glu Lys Glu Lys
425                 430                 435                 440

GAG TGG AAG CTT ACC GCC ACC GAG AAG GGC AAG ATG AAC AAC TTC CTG      146
Glu Trp Lys Leu Thr Ala Thr Glu Lys Gly Lys Met Asn Asn Phe Leu
                445                 450                 455

GAC AAC AAG AAC GAC ATC AAG ACC AAC TAC AAG GAG ATC ACC TTC AGC      194
Asp Asn Lys Asn Asp Ile Lys Thr Asn Tyr Lys Glu Ile Thr Phe Ser
            460                 465                 470

ATA GCC GGC AGC TTC GAG GAC GAG ATC AAG GAC CTG AAG GAG ATC GAC      242
Ile Ala Gly Ser Phe Glu Asp Glu Ile Lys Asp Leu Lys Glu Ile Asp
        475                 480                 485

AAG ATG TTC GAC AAG ACC AAC CTG AGC AAC AGC ATC ATC ACC TAC AAG      290
Lys Met Phe Asp Lys Thr Asn Leu Ser Asn Ser Ile Ile Thr Tyr Lys
    490                 495                 500

AAC GTG GAG CCC ACC ACC ATC GGC TTC AAC AAG AGC CTG ACC GAG GGC      338
Asn Val Glu Pro Thr Thr Ile Gly Phe Asn Lys Ser Leu Thr Glu Gly
505                 510                 515                 520

AAC ACC ATC AAC AGC GAC GCC ATG GCC CAG TTC AAG GAG CAG TTC CTG      386
Asn Thr Ile Asn Ser Asp Ala Met Ala Gln Phe Lys Glu Gln Phe Leu
                525                 530                 535

GAC CGC GAC ATC AAG TTC GAC AGC TAC CTG GAC ACC CAC CTG ACC GCC      434
Asp Arg Asp Ile Lys Phe Asp Ser Tyr Leu Asp Thr His Leu Thr Ala
            540                 545                 550

CAG CAG GTG AGC AGC AAG GAG CGC GTG ATC CTG AAG GTG ACC GTC CCC      482
Gln Gln Val Ser Ser Lys Glu Arg Val Ile Leu Lys Val Thr Val Pro
        555                 560                 565

AGC GGC AAG GGC AGC ACC ACC CCC ACC AAG GCC GGC GTG ATC CTG AAC      530
Ser Gly Lys Gly Ser Thr Thr Pro Thr Lys Ala Gly Val Ile Leu Asn
    570                 575                 580

AAC AGC GAG TAC AAG ATG CTG ATC GAC AAC GGC TAC ATG GTG CAC GTG      578
Asn Ser Glu Tyr Lys Met Leu Ile Asp Asn Gly Tyr Met Val His Val
585                 590                 595                 600

GAC AAG GTG AGC AAG GTG GTG AAG AAG GGC GTG GAG TGC CTC CAG ATC      626
Asp Lys Val Ser Lys Val Val Lys Lys Gly Val Glu Cys Leu Gln Ile
                605                 610                 615

GAG GGC ACC CTG AAG AAG AGT CTA GAC TTC AAG AAC GAC ATC AAC GCC      674
Glu Gly Thr Leu Lys Lys Ser Leu Asp Phe Lys Asn Asp Ile Asn Ala
            620                 625                 630

GAG GCC CAC AGC TGG GGC ATG AAG AAC TAC GAG GAG TGG GCC AAG GAC      722
Glu Ala His Ser Trp Gly Met Lys Asn Tyr Glu Glu Trp Ala Lys Asp
        635                 640                 645

CTG ACC GAC AGC CAG CGC GAG GCC CTG GAC GGC TAC GCC CGC CAG GAC      770
Leu Thr Asp Ser Gln Arg Glu Ala Leu Asp Gly Tyr Ala Arg Gln Asp
    650                 655                 660

TAC AAG GAG ATC AAC AAC TAC CTG CGC AAC CAG GGC GGC AGC GGC AAC      818
Tyr Lys Glu Ile Asn Asn Tyr Leu Arg Asn Gln Gly Gly Ser Gly Asn
665                 670                 675                 680

GAG AAG CTG GAC GCC CAG ATC AAG AAC ATC AGC GAC GCC CTG GGC AAG      866
Glu Lys Leu Asp Ala Gln Ile Lys Asn Ile Ser Asp Ala Leu Gly Lys
                685                 690                 695

AAG CCC ATC CCC GAG AAC ATC ACC GTG TAC CGC TGG TGC GGC ATG CCC      914
Lys Pro Ile Pro Glu Asn Ile Thr Val Tyr Arg Trp Cys Gly Met Pro
            700                 705                 710
```

| | | | | | | | | | | | | | | | | |
|---|---|---|---|---|---|---|---|---|---|---|---|---|---|---|---|---|
|GAG|TTC|GGC|TAC|CAG|ATC|AGC|GAC|CCC|CTG|CCC|AGC|CTG|AAG|GAC|TTC|962|
|Glu|Phe|Gly|Tyr|Gln|Ile|Ser|Asp|Pro|Leu|Pro|Ser|Leu|Lys|Asp|Phe| |
| | |715| | | |720| | | |725| | | | | | |
|GAG|GAG|CAG|TTC|CTG|AAC|ACC|ATC|AAG|GAG|GAC|AAG|GGC|TAC|ATG|AGC|1010|
|Glu|Glu|Gln|Phe|Leu|Asn|Thr|Ile|Lys|Glu|Asp|Lys|Gly|Tyr|Met|Ser| |
|730| | | | |735| | | | |740| | | | | | |
|ACC|AGC|CTG|AGC|AGC|GAG|CGC|CTG|GCC|GCC|TTC|GGC|AGC|CGC|AAG|ATC|1058|
|Thr|Ser|Leu|Ser|Ser|Glu|Arg|Leu|Ala|Ala|Phe|Gly|Ser|Arg|Lys|Ile| |
|745| | | | |750| | | | |755| | | | |760| |
|ATC|CTG|CGC|CTG|CAG|GTG|CCC|AAG|GGC|AGC|ACT|GGT|GCC|TAC|CTG|AGC|1106|
|Ile|Leu|Arg|Leu|Gln|Val|Pro|Lys|Gly|Ser|Thr|Gly|Ala|Tyr|Leu|Ser| |
| | | | |765| | | | |770| | | | |775| | |
|GCC|ATC|GGC|GGC|TTC|GCC|AGC|GAG|AAG|GAG|ATC|CTG|CTG|GAT|AAG|GAC|1154|
|Ala|Ile|Gly|Gly|Phe|Ala|Ser|Glu|Lys|Glu|Ile|Leu|Leu|Asp|Lys|Asp| |
| | | |780| | | | |785| | | | |790| | | |
|AGC|AAG|TAC|CAC|ATC|GAC|AAG|GTG|ACC|GAG|GTG|ATC|ATC|AAG|GGC|GTG|1202|
|Ser|Lys|Tyr|His|Ile|Asp|Lys|Val|Thr|Glu|Val|Ile|Ile|Lys|Gly|Val| |
| | |795| | | | |800| | | | |805| | | | |
|AAG|CGC|TAC|GTG|GTG|GAC|GCC|ACC|CTG|CTG|ACC|AAC|TAG| | | |1241|
|Lys|Arg|Tyr|Val|Val|Asp|Ala|Thr|Leu|Leu|Thr|Asn| | | | | |
| |810| | | | |815| | | | |820| | | | | |

( 2 ) INFORMATION FOR SEQ ID NO:43:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| | | | | | | | | | | | | | | |
|---|---|---|---|---|---|---|---|---|---|---|---|---|---|---|
|Met|Leu|Gln|Asn|Leu|Lys|Ile|Thr|Asp|Lys|Val|Glu|Asp|Phe|Lys|Glu|
|1| | | |5| | | |10| | | | |15| |
|Asp|Lys|Glu|Lys|Ala|Lys|Glu|Trp|Gly|Lys|Glu|Lys|Glu|Lys|Glu|Trp|
| | | |20| | | |25| | | | |30| | |
|Lys|Leu|Thr|Ala|Thr|Glu|Lys|Gly|Lys|Met|Asn|Asn|Phe|Leu|Asp|Asn|
| | |35| | | |40| | | | |45| | | |
|Lys|Asn|Asp|Ile|Lys|Thr|Asn|Tyr|Lys|Glu|Ile|Thr|Phe|Ser|Ile|Ala|
| |50| | | |55| | | |60| | | | | |
|Gly|Ser|Phe|Glu|Asp|Glu|Ile|Lys|Asp|Leu|Lys|Glu|Ile|Asp|Lys|Met|
|65| | | |70| | | |75| | | | |80| |
|Phe|Asp|Lys|Thr|Asn|Leu|Ser|Asn|Ser|Ile|Ile|Thr|Tyr|Lys|Asn|Val|
| | | |85| | | |90| | | | |95| | |
|Glu|Pro|Thr|Thr|Ile|Gly|Phe|Asn|Lys|Ser|Leu|Thr|Glu|Gly|Asn|Thr|
| | |100| | | |105| | | | |110| | | |
|Ile|Asn|Ser|Asp|Ala|Met|Ala|Gln|Phe|Lys|Glu|Gln|Phe|Leu|Asp|Arg|
| |115| | | |120| | | |125| | | | | |
|Asp|Ile|Lys|Phe|Asp|Ser|Tyr|Leu|Asp|Thr|His|Leu|Thr|Ala|Gln|Gln|
|130| | | |135| | | |140| | | | | | |
|Val|Ser|Ser|Lys|Glu|Arg|Val|Ile|Leu|Lys|Val|Thr|Val|Pro|Ser|Gly|
|145| | | |150| | | |155| | | | |160| |
|Lys|Gly|Ser|Thr|Thr|Pro|Thr|Lys|Ala|Gly|Val|Ile|Leu|Asn|Asn|Ser|
| | | |165| | | |170| | | | |175| | |
|Glu|Tyr|Lys|Met|Leu|Ile|Asp|Asn|Gly|Tyr|Met|Val|His|Val|Asp|Lys|
| | |180| | | |185| | | | |190| | | |
|Val|Ser|Lys|Val|Val|Lys|Lys|Gly|Val|Glu|Cys|Leu|Gln|Ile|Glu|Gly|
| |195| | | |200| | | |205| | | | | |
|Thr|Leu|Lys|Lys|Ser|Leu|Asp|Phe|Lys|Asn|Asp|Ile|Asn|Ala|Glu|Ala|

|  |  |  | 210 |  |  |  | 215 |  |  |  | 220 |  |  |  |
|---|---|---|---|---|---|---|---|---|---|---|---|---|---|---|
| His 225 | Ser | Trp | Gly | Met | Lys 230 | Asn | Tyr | Glu | Glu | Trp 235 | Ala | Lys | Asp | Leu 240 | Thr |
| Asp | Ser | Gln | Arg | Glu 245 | Ala | Leu | Asp | Gly | Tyr 250 | Ala | Arg | Gln | Asp | Tyr 255 | Lys |
| Glu | Ile | Asn | Asn 260 | Tyr | Leu | Arg | Asn | Gln 265 | Gly | Gly | Ser | Gly | Asn 270 | Glu | Lys |
| Leu | Asp | Ala 275 | Gln | Ile | Lys | Asn | Ile 280 | Ser | Asp | Ala | Leu | Gly 285 | Lys | Lys | Pro |
| Ile | Pro 290 | Glu | Asn | Ile | Thr | Val 295 | Tyr | Arg | Trp | Cys | Gly 300 | Met | Pro | Glu | Phe |
| Gly 305 | Tyr | Gln | Ile | Ser | Asp 310 | Pro | Leu | Pro | Ser | Leu 315 | Lys | Asp | Phe | Glu | Glu 320 |
| Gln | Phe | Leu | Asn | Thr 325 | Ile | Lys | Glu | Asp | Lys 330 | Gly | Tyr | Met | Ser | Thr 335 | Ser |
| Leu | Ser | Ser | Glu 340 | Arg | Leu | Ala | Ala | Phe 345 | Gly | Ser | Arg | Lys | Ile 350 | Ile | Leu |
| Arg | Leu | Gln 355 | Val | Pro | Lys | Gly | Ser 360 | Thr | Gly | Ala | Tyr | Leu 365 | Ser | Ala | Ile |
| Gly | Gly 370 | Phe | Ala | Ser | Glu | Lys 375 | Glu | Ile | Leu | Leu | Asp 380 | Lys | Asp | Ser | Lys |
| Tyr 385 | His | Ile | Asp | Lys | Val 390 | Thr | Glu | Val | Ile | Ile 395 | Lys | Gly | Val | Lys | Arg 400 |
| Tyr | Val | Val | Asp | Ala 405 | Thr | Leu | Leu | Thr | Asn 410 |  |  |  |  |  |  |

( 2 ) INFORMATION FOR SEQ ID NO:44:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
        vacuolar targetting peptide used to construct pCIB5533"

( i i i ) HYPOTHETICAL: NO ( x i ) SEQUENCE DESCRIPTION: SEQ ID NO:44:

```
CCGCGGGCGT GCACTGCCTC AGCAGCAGCA GCTTCGCCGA CAGCAACCCC ATCCGCGTGA      60

CCGACCGCGC CGCCAGCACC CTGCAG                                          86
```

( 2 ) INFORMATION FOR SEQ ID NO:45:

( i ) SEQUENCE CHARACTERISTICS:
        ( A ) LENGTH: 1358 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1355
        ( D ) OTHER INFORMATION: /note= "Maize optimized VIP2A(a)
    &nbs ( x i ) SEQUENCE DESCRIPTION: SEQ ID NO:45:

```
GATCCACC ATG GGC TGG AGC TGG ATC TTC CTG TTC CTG CTG AGC GGC GCC          50
         Met Gly Trp Ser Trp Ile Phe Leu Phe Leu Leu Ser Gly Ala
         415                 420

GCG GGC GTG CAC TGC CTC AGC AGC AGC AGC TTC GCC GAC AGC AAC CCC           98
Ala Gly Val His Cys Leu Ser Ser Ser Ser Phe Ala Asp Ser Asn Pro
425             430              435                 440

ATC CGC GTG ACC GAC CGC GCC GCC AGC ACC CTG CAG AAC CTG AAG ATC          146
Ile Arg Val Thr Asp Arg Ala Ala Ser Thr Leu Gln Asn Leu Lys Ile
                445              450                 455

ACC GAC AAG GTG GAG GAC TTC AAG GAG GAC AAG GAG AAG GCC AAG GAG          194
Thr Asp Lys Val Glu Asp Phe Lys Glu Asp Lys Glu Lys Ala Lys Glu
                460              465                 470

TGG GGC AAG GAG AAG GAG AAG GAG TGG AAG CTT ACC GCC ACC GAG AAG          242
Trp Gly Lys Glu Lys Glu Lys Glu Trp Lys Leu Thr Ala Thr Glu Lys
        475              480                 485

GGC AAG ATG AAC AAC TTC CTG GAC AAC AAG AAC GAC ATC AAG ACC AAC          290
Gly Lys Met Asn Asn Phe Leu Asp Asn Lys Asn Asp Ile Lys Thr Asn
        490              495                 500

TAC AAG GAG ATC ACC TTC AGC ATA GCC GGC AGC TTC GAG GAC GAG ATC          338
Tyr Lys Glu Ile Thr Phe Ser Ile Ala Gly Ser Phe Glu Asp Glu Ile
505             510              515                 520

AAG GAC CTG AAG GAG ATC GAC AAG ATG TTC GAC AAG ACC AAC CTG AGC          386
Lys Asp Leu Lys Glu Ile Asp Lys Met Phe Asp Lys Thr Asn Leu Ser
                525              530                 535

AAC AGC ATC ATC ACC TAC AAG AAC GTG GAG CCC ACC ACC ATC GGC TTC          434
Asn Ser Ile Ile Thr Tyr Lys Asn Val Glu Pro Thr Thr Ile Gly Phe
                540              545                 550

AAC AAG AGC CTG ACC GAG GGC AAC ACC ATC AAC AGC GAC GCC ATG GCC          482
Asn Lys Ser Leu Thr Glu Gly Asn Thr Ile Asn Ser Asp Ala Met Ala
        555              560                 565

CAG TTC AAG GAG CAG TTC CTG GAC CGC GAC ATC AAG TTC GAC AGC TAC          530
Gln Phe Lys Glu Gln Phe Leu Asp Arg Asp Ile Lys Phe Asp Ser Tyr
        570              575                 580

CTG GAC ACC CAC CTG ACC GCC CAG CAG GTG AGC AGC AAG GAG CGC GTG          578
Leu Asp Thr His Leu Thr Ala Gln Gln Val Ser Ser Lys Glu Arg Val
585             590              595                 600

ATC CTG AAG GTG ACC GTC CCC AGC GGC AAG GGC AGC ACC ACC CCC ACC          626
Ile Leu Lys Val Thr Val Pro Ser Gly Lys Gly Ser Thr Thr Pro Thr
                605              610                 615

AAG GCC GGC GTG ATC CTG AAC AAC AGC GAG TAC AAG ATG CTG ATC GAC          674
Lys Ala Gly Val Ile Leu Asn Asn Ser Glu Tyr Lys Met Leu Ile Asp
            620              625                 630

AAC GGC TAC ATG GTG CAC GTG GAC AAG GTG AGC AAG GTG GTG AAG AAG          722
Asn Gly Tyr Met Val His Val Asp Lys Val Ser Lys Val Val Lys Lys
                635              640                 645

GGC GTG GAG TGC CTC CAG ATC GAG GGC ACC CTG AAG AAG AGT CTA GAC          770
Gly Val Glu Cys Leu Gln Ile Glu Gly Thr Leu Lys Lys Ser Leu Asp
        650              655                 660

TTC AAG AAC GAC ATC AAC GCC GAG GCC CAC AGC TGG GGC ATG AAG AAC          818
Phe Lys Asn Asp Ile Asn Ala Glu Ala His Ser Trp Gly Met Lys Asn
665             670              675                 680

TAC GAG GAG TGG GCC AAG GAC CTG ACC GAC AGC CAG CGC GAG GCC CTG          866
Tyr Glu Glu Trp Ala Lys Asp Leu Thr Asp Ser Gln Arg Glu Ala Leu
                685              690                 695

GAC GGC TAC GCC CGC CAG GAC TAC AAG GAG ATC AAC AAC TAC CTG CGC          914
Asp Gly Tyr Ala Arg Gln Asp Tyr Lys Glu Ile Asn Asn Tyr Leu Arg
                700              705                 710

AAC CAG GGC GGC AGC GGC AAC GAG AAG CTG GAC GCC CAG ATC AAG AAC          962
```

|     |     |     |     |     |     |     |     |     |     |     |     |     |     |     |     |
|-----|-----|-----|-----|-----|-----|-----|-----|-----|-----|-----|-----|-----|-----|-----|-----|
| Asn | Gln | Gly | Gly | Ser | Gly | Asn | Glu | Lys | Leu | Asp | Ala | Gln | Ile | Lys | Asn |
|     |     | 715 |     |     |     | 720 |     |     |     |     | 725 |     |     |     |     |

| ATC | AGC | GAC | GCC | CTG | GGC | AAG | AAG | CCC | ATC | CCC | GAG | AAC | ATC | ACC | GTG | 1010 |
|-----|-----|-----|-----|-----|-----|-----|-----|-----|-----|-----|-----|-----|-----|-----|-----|------|
| Ile | Ser | Asp | Ala | Leu | Gly | Lys | Lys | Pro | Ile | Pro | Glu | Asn | Ile | Thr | Val |      |
|     | 730 |     |     |     |     | 735 |     |     |     |     | 740 |     |     |     |     |      |

| TAC | CGC | TGG | TGC | GGC | ATG | CCC | GAG | TTC | GGC | TAC | CAG | ATC | AGC | GAC | CCC | 1058 |
|-----|-----|-----|-----|-----|-----|-----|-----|-----|-----|-----|-----|-----|-----|-----|-----|------|
| Tyr | Arg | Trp | Cys | Gly | Met | Pro | Glu | Phe | Gly | Tyr | Gln | Ile | Ser | Asp | Pro |      |
| 745 |     |     |     |     | 750 |     |     |     |     | 755 |     |     |     |     | 760 |      |

| CTG | CCC | AGC | CTG | AAG | GAC | TTC | GAG | GAG | CAG | TTC | CTG | AAC | ACC | ATC | AAG | 1106 |
|-----|-----|-----|-----|-----|-----|-----|-----|-----|-----|-----|-----|-----|-----|-----|-----|------|
| Leu | Pro | Ser | Leu | Lys | Asp | Phe | Glu | Glu | Gln | Phe | Leu | Asn | Thr | Ile | Lys |      |
|     |     |     |     | 765 |     |     |     |     | 770 |     |     |     |     | 775 |     |      |

| GAG | GAC | AAG | GGC | TAC | ATG | AGC | ACC | AGC | CTG | AGC | AGC | GAG | CGC | CTG | GCC | 1154 |
|-----|-----|-----|-----|-----|-----|-----|-----|-----|-----|-----|-----|-----|-----|-----|-----|------|
| Glu | Asp | Lys | Gly | Tyr | Met | Ser | Thr | Ser | Leu | Ser | Ser | Glu | Arg | Leu | Ala |      |
|     |     |     | 780 |     |     |     |     | 785 |     |     |     |     | 790 |     |     |      |

| GCC | TTC | GGC | AGC | CGC | AAG | ATC | ATC | CTG | CGC | CTG | CAG | GTG | CCC | AAG | GGC | 1202 |
|-----|-----|-----|-----|-----|-----|-----|-----|-----|-----|-----|-----|-----|-----|-----|-----|------|
| Ala | Phe | Gly | Ser | Arg | Lys | Ile | Ile | Leu | Arg | Leu | Gln | Val | Pro | Lys | Gly |      |
|     |     | 795 |     |     |     |     | 800 |     |     |     |     | 805 |     |     |     |      |

| AGC | ACT | GGT | GCC | TAC | CTG | AGC | GCC | ATC | GGC | GGC | TTC | GCC | AGC | GAG | AAG | 1250 |
|-----|-----|-----|-----|-----|-----|-----|-----|-----|-----|-----|-----|-----|-----|-----|-----|------|
| Ser | Thr | Gly | Ala | Tyr | Leu | Ser | Ala | Ile | Gly | Gly | Phe | Ala | Ser | Glu | Lys |      |
|     | 810 |     |     |     |     | 815 |     |     |     |     | 820 |     |     |     |     |      |

| GAG | ATC | CTG | CTG | GAT | AAG | GAC | AGC | AAG | TAC | CAC | ATC | GAC | AAG | GTG | ACC | 1298 |
|-----|-----|-----|-----|-----|-----|-----|-----|-----|-----|-----|-----|-----|-----|-----|-----|------|
| Glu | Ile | Leu | Leu | Asp | Lys | Asp | Ser | Lys | Tyr | His | Ile | Asp | Lys | Val | Thr |      |
| 825 |     |     |     |     | 830 |     |     |     |     | 835 |     |     |     |     | 840 |      |

| GAG | GTG | ATC | ATC | AAG | GGC | GTG | AAG | CGC | TAC | GTG | GTG | GAC | GCC | ACC | CTG | 1346 |
|-----|-----|-----|-----|-----|-----|-----|-----|-----|-----|-----|-----|-----|-----|-----|-----|------|
| Glu | Val | Ile | Ile | Lys | Gly | Val | Lys | Arg | Tyr | Val | Val | Asp | Ala | Thr | Leu |      |
|     |     |     |     | 845 |     |     |     |     | 850 |     |     |     |     | 855 |     |      |

| CTG | ACC | AAC | TAG | 1358 |
|-----|-----|-----|-----|------|
| Leu | Thr | Asn |     |      |

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

| Met | Gly | Trp | Ser | Trp | Ile | Phe | Leu | Phe | Leu | Leu | Ser | Gly | Ala | Ala | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | His | Cys | Leu | Ser | Ser | Ser | Phe | Ala | Asp | Ser | Asn | Pro | Ile | Arg |
|-----|-----|-----|-----|-----|-----|-----|-----|-----|-----|-----|-----|-----|-----|-----|
|     |     |     | 20  |     |     |     | 25  |     |     |     | 30  |     |     |     |

| Val | Thr | Asp | Arg | Ala | Ala | Ser | Thr | Leu | Gln | Asn | Leu | Lys | Ile | Thr | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Val | Glu | Asp | Phe | Lys | Glu | Asp | Lys | Glu | Lys | Ala | Lys | Glu | Trp | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Glu | Lys | Glu | Lys | Glu | Trp | Lys | Leu | Thr | Ala | Thr | Glu | Lys | Gly | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Asn | Asn | Phe | Leu | Asp | Asn | Lys | Asn | Asp | Ile | Lys | Thr | Asn | Tyr | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Ile | Thr | Phe | Ser | Ile | Ala | Gly | Ser | Phe | Glu | Asp | Glu | Ile | Lys | Asp |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Lys | Glu | Ile | Asp | Lys | Met | Phe | Asp | Lys | Thr | Asn | Leu | Ser | Asn | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ile | Ile | Thr | Tyr | Lys | Asn | Val | Glu | Pro | Thr | Thr | Ile | Gly | Phe | Asn | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Leu | Thr | Glu | Gly | Asn | Thr | Ile | Asn | Ser | Asp | Ala | Met | Ala | Gln | Phe |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| | | | | | | | | | | | | | | |
|---|---|---|---|---|---|---|---|---|---|---|---|---|---|---|
| Lys | Glu | Gln | Phe | Leu<br>165 | Asp | Arg | Asp | Ile | Lys<br>170 | Phe | Asp | Ser | Tyr | Leu<br>175 | Asp |
| Thr | His | Leu | Thr<br>180 | Ala | Gln | Gln | Val | Ser<br>185 | Ser | Lys | Glu | Arg | Val<br>190 | Ile | Leu |
| Lys | Val | Thr<br>195 | Val | Pro | Ser | Gly | Lys<br>200 | Gly | Ser | Thr | Thr | Pro<br>205 | Thr | Lys | Ala |
| Gly | Val<br>210 | Ile | Leu | Asn | Asn | Ser<br>215 | Glu | Tyr | Lys | Met | Leu<br>220 | Ile | Asp | Asn | Gly |
| Tyr<br>225 | Met | Val | His | Val | Asp<br>230 | Lys | Val | Ser | Lys | Val<br>235 | Val | Lys | Lys | Gly | Val<br>240 |
| Glu | Cys | Leu | Gln | Ile<br>245 | Glu | Gly | Thr | Leu | Lys<br>250 | Lys | Ser | Leu | Asp | Phe<br>255 | Lys |
| Asn | Asp | Ile | Asn<br>260 | Ala | Glu | Ala | His | Ser<br>265 | Trp | Gly | Met | Lys | Asn<br>270 | Tyr | Glu |
| Glu | Trp | Ala<br>275 | Lys | Asp | Leu | Thr | Asp<br>280 | Ser | Gln | Arg | Glu | Ala<br>285 | Leu | Asp | Gly |
| Tyr | Ala<br>290 | Arg | Gln | Asp | Tyr | Lys<br>295 | Glu | Ile | Asn | Asn | Tyr<br>300 | Leu | Arg | Asn | Gln |
| Gly<br>305 | Gly | Ser | Gly | Asn | Glu<br>310 | Lys | Leu | Asp | Ala | Gln<br>315 | Ile | Lys | Asn | Ile | Ser<br>320 |
| Asp | Ala | Leu | Gly | Lys<br>325 | Lys | Pro | Ile | Pro | Glu<br>330 | Asn | Ile | Thr | Val | Tyr<br>335 | Arg |
| Trp | Cys | Gly | Met<br>340 | Pro | Glu | Phe | Gly | Tyr<br>345 | Gln | Ile | Ser | Asp | Pro<br>350 | Leu | Pro |
| Ser | Leu | Lys<br>355 | Asp | Phe | Glu | Glu | Gln<br>360 | Phe | Leu | Asn | Thr | Ile<br>365 | Lys | Glu | Asp |
| Lys | Gly<br>370 | Tyr | Met | Ser | Thr | Ser<br>375 | Leu | Ser | Ser | Glu | Arg<br>380 | Leu | Ala | Ala | Phe |
| Gly<br>385 | Ser | Arg | Lys | Ile | Ile<br>390 | Leu | Arg | Leu | Gln | Val<br>395 | Pro | Lys | Gly | Ser | Thr<br>400 |
| Gly | Ala | Tyr | Leu | Ser<br>405 | Ala | Ile | Gly | Gly | Phe<br>410 | Ala | Ser | Glu | Lys | Glu<br>415 | Ile |
| Leu | Leu | Asp | Lys<br>420 | Asp | Ser | Lys | Tyr | His<br>425 | Ile | Asp | Lys | Val | Thr<br>430 | Glu | Val |
| Ile | Ile | Lys<br>435 | Gly | Val | Lys | Arg | Tyr<br>440 | Val | Val | Asp | Ala | Thr<br>445 | Leu | Leu | Thr |
| Asn | | | | | | | | | | | | | | | |

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Peptide
        (B) LOCATION: 1..16
        (D) OTHER INFORMATION: /note= "linker peptide for fusion
            of VIP1A(a) and VIP2A(a) used to construct pCIB5533"

(x) SEQUENCE DESCRIPTION: SEQ ID NO:47:

| | | | | | | | | | | | | | | |
|---|---|---|

( 2 ) INFORMATION FOR SEQ ID NO:48:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA encoding linker peptide used to construct pCIB5533"

( i i i ) HYPOTHETICAL: NO ( x i ) SEQUENCE DESCRIPTION: SEQ ID NO:48:

```
CCCGGGCCTT CTACTCCCCC AACTCCCTCT CCTAGCACGC CTCCGACACC TAGCGATATC    60

GGATCC                                                               66
```

( 2 ) INFORMATION FOR SEQ ID NO:49:

( i ) SEQUENCE CHARACTERISTICS:
( A ) LENGTH: 4031 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: CDS
( B ) LOCATION: 6..4019
( D ) OTHER INFORMATION: /note= "Maize optimized DNA sequence encoding a VIP2A(a) - VIP1A(a) fusion protein as contained in pCIB5531"

( x i ) SEQUENCE DESCRIPTION: SEQ ID NO:49:

```
GATCC ATG AAG CGC ATG GAG GGC AAG CTG TTC ATG GTG AGC AAG AAG     47
      Met Lys Arg Met Glu Gly Lys Leu Phe Met Val Ser Lys Lys
      450                     455                 460

CTC CAG GTG GTG ACC AAG ACC GTG CTG CTG AGC ACC GTG TTC AGC ATC   95
Leu Gln Val Val Thr Lys Thr Val Leu Leu Ser Thr Val Phe Ser Ile
    465                 470                 475

AGC CTG CTG AAC AAC GAG GTG ATC AAG GCC GAG CAG CTG AAC ATC AAC  143
Ser Leu Leu Asn Asn Glu Val Ile Lys Ala Glu Gln Leu Asn Ile Asn
480                 485                 490                 495

AGC CAG AGC AAG TAC ACC AAC CTC CAG AAC CTG AAG ATC ACC GAC AAG  191
Ser Gln Ser Lys Tyr Thr Asn Leu Gln Asn Leu Lys Ile Thr Asp Lys
                500                 505                 510

GTG GAG GAC TTC AAG GAG GAC AAG GAG AAG GCC AAG GAG TGG GGC AAG  239
Val Glu Asp Phe Lys Glu Asp Lys Glu Lys Ala Lys Glu Trp Gly Lys
            515                 520                 525

GAG AAG GAG AAG GAG TGG AAG CTT ACC GCC ACC GAG AAG GGC AAG ATG  287
Glu Lys Glu Lys Glu Trp Lys Leu Thr Ala Thr Glu Lys Gly Lys Met
        530                 535                 540

AAC AAC TTC CTG GAC AAC AAG AAC GAC ATC AAG ACC AAC TAC AAG GAG  335
Asn Asn Phe Leu Asp Asn Lys Asn Asp Ile Lys Thr Asn Tyr Lys Glu
    545                 550                 555

ATC ACC TTC AGC ATA GCC GGC AGC TTC GAG GAC GAG ATC AAG GAC CTG  383
Ile Thr Phe Ser Ile Ala Gly Ser Phe Glu Asp Glu Ile Lys Asp Leu
560                 565                 570                 575

AAG GAG ATC GAC AAG ATG TTC GAC AAG ACC AAC CTG AGC AAC AGC ATC  431
Lys Glu Ile Asp Lys Met Phe Asp Lys Thr Asn Leu Ser Asn Ser Ile
                580                 585                 590
```

| | | | | | | | | | | | | | | | | |
|---|---|---|---|---|---|---|---|---|---|---|---|---|---|---|---|---|
| ATC | ACC | TAC | AAG | AAC | GTG | GAG | CCC | ACC | ACC | ATC | GGC | TTC | AAC | AAG | AGC | 479 |
| Ile | Thr | Tyr | Lys | Asn | Val | Glu | Pro | Thr | Thr | Ile | Gly | Phe | Asn | Lys | Ser | |
| | | 595 | | | | 600 | | | | | 605 | | | | | |
| CTG | ACC | GAG | GGC | AAC | ACC | ATC | AAC | AGC | GAC | GCC | ATG | GCC | CAG | TTC | AAG | 527 |
| Leu | Thr | Glu | Gly | Asn | Thr | Ile | Asn | Ser | Asp | Ala | Met | Ala | Gln | Phe | Lys | |
| | 610 | | | | | 615 | | | | | 620 | | | | | |
| GAG | CAG | TTC | CTG | GAC | CGC | GAC | ATC | AAG | TTC | GAC | AGC | TAC | CTG | GAC | ACC | 575 |
| Glu | Gln | Phe | Leu | Asp | Arg | Asp | Ile | Lys | Phe | Asp | Ser | Tyr | Leu | Asp | Thr | |
| 625 | | | | | 630 | | | | | 635 | | | | | | |
| CAC | CTG | ACC | GCC | CAG | CAG | GTG | AGC | AGC | AAG | GAG | CGC | GTG | ATC | CTG | AAG | 623 |
| His | Leu | Thr | Ala | Gln | Gln | Val | Ser | Ser | Lys | Glu | Arg | Val | Ile | Leu | Lys | |
| 640 | | | | | 645 | | | | 650 | | | | | | 655 | |
| GTG | ACC | GTC | CCC | AGC | GGC | AAG | GGC | AGC | ACC | ACC | CCC | ACC | AAG | GCC | GGC | 671 |
| Val | Thr | Val | Pro | Ser | Gly | Lys | Gly | Ser | Thr | Thr | Pro | Thr | Lys | Ala | Gly | |
| | | | | 660 | | | | | 665 | | | | | 670 | | |
| GTG | ATC | CTG | AAC | AAC | AGC | GAG | TAC | AAG | ATG | CTG | ATC | GAC | AAC | GGC | TAC | 719 |
| Val | Ile | Leu | Asn | Asn | Ser | Glu | Tyr | Lys | Met | Leu | Ile | Asp | Asn | Gly | Tyr | |
| | | | 675 | | | | | 680 | | | | 685 | | | | |
| ATG | GTG | CAC | GTG | GAC | AAG | GTG | AGC | AAG | GTG | GTG | AAG | AAG | GGC | GTG | GAG | 767 |
| Met | Val | His | Val | Asp | Lys | Val | Ser | Lys | Val | Val | Lys | Lys | Gly | Val | Glu | |
| | | 690 | | | | | 695 | | | | | 700 | | | | |
| TGC | CTC | CAG | ATC | GAG | GGC | ACC | CTG | AAG | AAG | AGT | CTA | GAC | TTC | AAG | AAC | 815 |
| Cys | Leu | Gln | Ile | Glu | Gly | Thr | Leu | Lys | Lys | Ser | Leu | Asp | Phe | Lys | Asn | |
| 705 | | | | | 710 | | | | | 715 | | | | | | |
| GAC | ATC | AAC | GCC | GAG | GCC | CAC | AGC | TGG | GGC | ATG | AAG | AAC | TAC | GAG | GAG | 863 |
| Asp | Ile | Asn | Ala | Glu | Ala | His | Ser | Trp | Gly | Met | Lys | Asn | Tyr | Glu | Glu | |
| 720 | | | | | 725 | | | | | 730 | | | | | 735 | |
| TGG | GCC | AAG | GAC | CTG | ACC | GAC | AGC | CAG | CGC | GAG | GCC | CTG | GAC | GGC | TAC | 911 |
| Trp | Ala | Lys | Asp | Leu | Thr | Asp | Ser | Gln | Arg | Glu | Ala | Leu | Asp | Gly | Tyr | |
| | | | | 740 | | | | | 745 | | | | | 750 | | |
| GCC | CGC | CAG | GAC | TAC | AAG | GAG | ATC | AAC | AAC | TAC | CTG | CGC | AAC | CAG | GGC | 959 |
| Ala | Arg | Gln | Asp | Tyr | Lys | Glu | Ile | Asn | Asn | Tyr | Leu | Arg | Asn | Gln | Gly | |
| | | | 755 | | | | | 760 | | | | | 765 | | | |
| GGC | AGC | GGC | AAC | GAG | AAG | CTG | GAC | GCC | CAG | ATC | AAG | AAC | ATC | AGC | GAC | 1007 |
| Gly | Ser | Gly | Asn | Glu | Lys | Leu | Asp | Ala | Gln | Ile | Lys | Asn | Ile | Ser | Asp | |
| | | 770 | | | | | 775 | | | | | 780 | | | | |
| GCC | CTG | GGC | AAG | AAG | CCC | ATC | CCC | GAG | AAC | ATC | ACC | GTG | TAC | CGC | TGG | 1055 |
| Ala | Leu | Gly | Lys | Lys | Pro | Ile | Pro | Glu | Asn | Ile | Thr | Val | Tyr | Arg | Trp | |
| | 785 | | | | | 790 | | | | | 795 | | | | | |
| TGC | GGC | ATG | CCC | GAG | TTC | GGC | TAC | CAG | ATC | AGC | GAC | CCC | CTG | CCC | AGC | 1103 |
| Cys | Gly | Met | Pro | Glu | Phe | Gly | Tyr | Gln | Ile | Ser | Asp | Pro | Leu | Pro | Ser | |
| 800 | | | | | 805 | | | | | 810 | | | | | 815 | |
| CTG | AAG | GAC | TTC | GAG | GAG | CAG | TTC | CTG | AAC | ACC | ATC | AAG | GAG | GAC | AAG | 1151 |
| Leu | Lys | Asp | Phe | Glu | Glu | Gln | Phe | Leu | Asn | Thr | Ile | Lys | Glu | Asp | Lys | |
| | | | | 820 | | | | | 825 | | | | | 830 | | |
| GGC | TAC | ATG | AGC | ACC | AGC | CTG | AGC | AGC | GAG | CGC | CTG | GCC | GCC | TTC | GGC | 1199 |
| Gly | Tyr | Met | Ser | Thr | Ser | Leu | Ser | Ser | Glu | Arg | Leu | Ala | Ala | Phe | Gly | |
| | | | 835 | | | | | 840 | | | | | 845 | | | |
| AGC | CGC | AAG | ATC | ATC | CTG | CGC | CTG | CAG | GTG | CCC | AAG | GGC | AGC | ACT | GGT | 1247 |
| Ser | Arg | Lys | Ile | Ile | Leu | Arg | Leu | Gln | Val | Pro | Lys | Gly | Ser | Thr | Gly | |
| | | 850 | | | | | 855 | | | | | 860 | | | | |
| GCC | TAC | CTG | AGC | GCC | ATC | GGC | GGC | TTC | GCC | AGC | GAG | AAG | GAG | ATC | CTG | 1295 |
| Ala | Tyr | Leu | Ser | Ala | Ile | Gly | Gly | Phe | Ala | Ser | Glu | Lys | Glu | Ile | Leu | |
| | 865 | | | | | 870 | | | | | 875 | | | | | |
| CTG | GAT | AAG | GAC | AGC | AAG | TAC | CAC | ATC | GAC | AAG | GTG | ACC | GAG | GTG | ATC | 1343 |
| Leu | Asp | Lys | Asp | Ser | Lys | Tyr | His | Ile | Asp | Lys | Val | Thr | Glu | Val | Ile | |
| 880 | | | | | 885 | | | | | 890 | | | | | 895 | |
| ATC | AAG | GGC | GTG | AAG | CGC | TAC | GTG | GTG | GAC | GCC | ACC | CTG | CTG | ACC | AAC | 1391 |
| Ile | Lys | Gly | Val | Lys | Arg | Tyr | Val | Val | Asp | Ala | Thr | Leu | Leu | Thr | Asn | |
| | | | | 900 | | | | | 905 | | | | | 910 | | |

```
TCC CGG GGG CCT TCT ACT CCC CCA ACT CCC TCT CCT AGC ACG CCT CCG        1439
Ser Arg Gly Pro Ser Thr Pro Pro Thr Pro Ser Pro Ser Thr Pro Pro
        915                     920                 925

ACA CCT AGC GAT ATC GGA TCC ACC ATG AAG ACC AAC CAG ATC AGC ACC        1487
Thr Pro Ser Asp Ile Gly Ser Thr Met Lys Thr Asn Gln Ile Ser Thr
    930                     935                     940

ACC CAG AAG AAC CAG CAG AAG GAG ATG GAC CGC AAG GGC CTG CTG GGC        1535
Thr Gln Lys Asn Gln Gln Lys Glu Met Asp Arg Lys Gly Leu Leu Gly
945                     950                     955

TAC TAC TTC AAG GGC AAG GAC TTC AGC AAC CTG ACC ATG TTC GCC CCC        1583
Tyr Tyr Phe Lys Gly Lys Asp Phe Ser Asn Leu Thr Met Phe Ala Pro
960                     965                     970                     975

ACG CGT GAC AGC ACC CTG ATC TAC GAC CAG CAG ACC GCC AAC AAG CTG        1631
Thr Arg Asp Ser Thr Leu Ile Tyr Asp Gln Gln Thr Ala Asn Lys Leu
                980                     985                     990

CTG GAC AAG AAG CAG CAG GAG TAC CAG AGC ATC CGC TGG ATC GGC CTG        1679
Leu Asp Lys Lys Gln Gln Glu Tyr Gln Ser Ile Arg Trp Ile Gly Leu
            995                     1000                    1005

ATC CAG AGC AAG GAG ACC GGC GAC TTC ACC TTC AAC CTG AGC GAG GAC        1727
Ile Gln Ser Lys Glu Thr Gly Asp Phe Thr Phe Asn Leu Ser Glu Asp
        1010                    1015                    1020

GAG CAG GCC ATC ATC GAG ATC AAC GGC AAG ATC ATC AGC AAC AAG GGC        1775
Glu Gln Ala Ile Ile Glu Ile Asn Gly Lys Ile Ile Ser Asn Lys Gly
    1025                    1030                    1035

AAG GAG AAG CAG GTG GTG CAC CTG GAG AAG GGC AAG CTG GTG CCC ATC        1823
Lys Glu Lys Gln Val Val His Leu Glu Lys Gly Lys Leu Val Pro Ile
1040                    1045                    1050                    1055

AAG ATC GAG TAC CAG AGC GAC ACC AAG TTC AAC ATC GAC AGC AAG ACC        1871
Lys Ile Glu Tyr Gln Ser Asp Thr Lys Phe Asn Ile Asp Ser Lys Thr
                1060                    1065                    1070

TTC AAG GAG CTG AAG CTT TTC AAG ATC GAC AGC CAG AAC CAG CCC CAG        1919
Phe Lys Glu Leu Lys Leu Phe Lys Ile Asp Ser Gln Asn Gln Pro Gln
            1075                    1080                    1085

CAG GTG CAG CAG GAC GAG CTG CGC AAC CCC GAG TTC AAC AAG AAG GAG        1967
Gln Val Gln Gln Asp Glu Leu Arg Asn Pro Glu Phe Asn Lys Lys Glu
        1090                    1095                    1100

AGC CAG GAG TTC CTG GCC AAG CCC AGC AAG ATC AAC CTG TTC ACC CAG        2015
Ser Gln Glu Phe Leu Ala Lys Pro Ser Lys Ile Asn Leu Phe Thr Gln
    1105                    1110                    1115

CAG ATG AAG CGC GAG ATC GAC GAG GAC ACC GAC ACC GAC GGC GAC AGC        2063
Gln Met Lys Arg Glu Ile Asp Glu Asp Thr Asp Thr Asp Gly Asp Ser
1120                    1125                    1130                    1135

ATC CCC GAC CTG TGG GAG GAG AAC GGC TAC ACC ATC CAG AAC CGC ATC        2111
Ile Pro Asp Leu Trp Glu Glu Asn Gly Tyr Thr Ile Gln Asn Arg Ile
                1140                    1145                    1150

GCC GTG AAG TGG GAC GAC AGC CTG GCT AGC AAG GGC TAC ACC AAG TTC        2159
Ala Val Lys Trp Asp Asp Ser Leu Ala Ser Lys Gly Tyr Thr Lys Phe
            1155                    1160                    1165

GTG AGC AAC CCC CTG GAG AGC CAC ACC GTG GGC GAC CCC TAC ACC GAC        2207
Val Ser Asn Pro Leu Glu Ser His Thr Val Gly Asp Pro Tyr Thr Asp
        1170                    1175                    1180

TAC GAG AAG GCC GCC CGC GAC CTG GAC CTG AGC AAC GCC AAG GAG ACC        2255
Tyr Glu Lys Ala Ala Arg Asp Leu Asp Leu Ser Asn Ala Lys Glu Thr
    1185                    1190                    1195

TTC AAC CCC CTG GTG GCC GCC TTC CCC AGC GTG AAC GTG AGC ATG GAG        2303
Phe Asn Pro Leu Val Ala Ala Phe Pro Ser Val Asn Val Ser Met Glu
1200                    1205                    1210                    1215

AAG GTG ATC CTG AGC CCC AAC GAG AAC CTG AGC AAC AGC GTG GAG AGC        2351
Lys Val Ile Leu Ser Pro Asn Glu Asn Leu Ser Asn Ser Val Glu Ser
                1220                    1225                    1230
```

| | | | | | | | | | | | | | | | |
|---|---|---|---|---|---|---|---|---|---|---|---|---|---|---|---|
| CAC | TCG | AGC | ACC | AAC | TGG | AGC | TAC | ACC | AAC | ACC | GAG | GGC | GCC | AGC | GTG |
| His | Ser | Ser | Thr | Asn | Trp | Ser | Tyr | Thr | Asn | Thr | Glu | Gly | Ala | Ser | Val |
| | | | 1235 | | | | 1240 | | | | | 1245 | | | | 2399

| GAG | GCC | GGC | ATC | GGT | CCC | AAG | GGC | ATC | AGC | TTC | GGC | GTG | AGC | GTG | AAC |
| Glu | Ala | Gly | Ile | Gly | Pro | Lys | Gly | Ile | Ser | Phe | Gly | Val | Ser | Val | Asn |
| 1250 | | | | | 1255 | | | | | 1260 | | | | | | 2447

| TAC | CAG | CAC | AGC | GAG | ACC | GTG | GCC | CAG | GAG | TGG | GGC | ACC | AGC | ACC | GGC |
| Tyr | Gln | His | Ser | Glu | Thr | Val | Ala | Gln | Glu | Trp | Gly | Thr | Ser | Thr | Gly |
| | 1265 | | | | 1270 | | | | 1275 | | | | | | | 2495

| AAC | ACC | AGC | CAG | TTC | AAC | ACC | GCC | AGC | GCC | GGC | TAC | CTG | AAC | GCC | AAC |
| Asn | Thr | Ser | Gln | Phe | Asn | Thr | Ala | Ser | Ala | Gly | Tyr | Leu | Asn | Ala | Asn |
| 1280 | | | | 1285 | | | | 1290 | | | | | 1295 | | | 2543

| GTG | CGC | TAC | AAC | AAC | GTG | GGC | ACC | GGC | GCC | ATC | TAC | GAC | GTG | AAG | CCC |
| Val | Arg | Tyr | Asn | Asn | Val | Gly | Thr | Gly | Ala | Ile | Tyr | Asp | Val | Lys | Pro |
| | | 1300 | | | | 1305 | | | | 1310 | | | | | | 2591

| ACC | ACC | AGC | TTC | GTG | CTG | AAC | AAC | GAC | ACC | ATC | GCC | ACC | ATC | ACC | GCC |
| Thr | Thr | Ser | Phe | Val | Leu | Asn | Asn | Asp | Thr | Ile | Ala | Thr | Ile | Thr | Ala |
| | | | 1315 | | | | 1320 | | | | 1325 | | | | | 2639

| AAG | TCG | AAT | TCC | ACC | GCC | CTG | AAC | ATC | AGC | CCC | GGC | GAG | AGC | TAC | CCC |
| Lys | Ser | Asn | Ser | Thr | Ala | Leu | Asn | Ile | Ser | Pro | Gly | Glu | Ser | Tyr | Pro |
| | | 1330 | | | | 1335 | | | | 1340 | | | | | | 2687

| AAG | AAG | GGC | CAG | AAC | GGC | ATC | GCC | ATC | ACC | AGC | ATG | GAC | GAC | TTC | AAC |
| Lys | Lys | Gly | Gln | Asn | Gly | Ile | Ala | Ile | Thr | Ser | Met | Asp | Asp | Phe | Asn |
| 1345 | | | | | 1350 | | | | | 1355 | | | | | | 2735

| AGC | CAC | CCC | ATC | ACC | CTG | AAC | AAG | AAG | CAG | GTG | GAC | AAC | CTG | CTG | AAC |
| Ser | His | Pro | Ile | Thr | Leu | Asn | Lys | Lys | Gln | Val | Asp | Asn | Leu | Leu | Asn |
| 1360 | | | | | 1365 | | | | | 1370 | | | | | 1375 | 2783

| AAC | AAG | CCC | ATG | ATG | CTG | GAG | ACC | AAC | CAG | ACC | GAC | GGC | GTC | TAC | AAG |
| Asn | Lys | Pro | Met | Met | Leu | Glu | Thr | Asn | Gln | Thr | Asp | Gly | Val | Tyr | Lys |
| | | | | 1380 | | | | | 1385 | | | | | 1390 | | 2831

| ATC | AAG | GAC | ACC | CAC | GGC | AAC | ATC | GTG | ACG | GGC | GGC | GAG | TGG | AAC | GGC |
| Ile | Lys | Asp | Thr | His | Gly | Asn | Ile | Val | Thr | Gly | Gly | Glu | Trp | Asn | Gly |
| | | | | 1395 | | | | 1400 | | | | | 1405 | | | 2879

| GTG | ATC | CAG | CAG | ATC | AAG | GCC | AAG | ACC | GCC | AGC | ATC | ATC | GTC | GAC | GAC |
| Val | Ile | Gln | Gln | Ile | Lys | Ala | Lys | Thr | Ala | Ser | Ile | Ile | Val | Asp | Asp |
| | 1410 | | | | | 1415 | | | | | 1420 | | | | | 2927

| GGC | GAG | CGC | GTG | GCC | GAG | AAG | CGC | GTG | GCC | GCC | AAG | GAC | TAC | GAG | AAC |
| Gly | Glu | Arg | Val | Ala | Glu | Lys | Arg | Val | Ala | Ala | Lys | Asp | Tyr | Glu | Asn |
| | 1425 | | | | | 1430 | | | | | 1435 | | | | | 2975

| CCC | GAG | GAC | AAG | ACC | CCC | AGC | CTG | ACC | CTG | AAG | GAC | GCC | CTG | AAG | CTG |
| Pro | Glu | Asp | Lys | Thr | Pro | Ser | Leu | Thr | Leu | Lys | Asp | Ala | Leu | Lys | Leu |
| 1440 | | | | | 1445 | | | | | 1450 | | | | | 1455 | 3023

| AGC | TAC | CCC | GAC | GAG | ATC | AAG | GAG | ATC | GAG | GGC | TTG | CTG | TAC | TAC | AAG |
| Ser | Tyr | Pro | Asp | Glu | Ile | Lys | Glu | Ile | Glu | Gly | Leu | Leu | Tyr | Tyr | Lys |
| | | | | 1460 | | | | | 1465 | | | | | 1470 | | 3071

| AAC | AAG | CCC | ATC | TAC | GAG | AGC | AGC | GTG | ATG | ACC | TAT | CTA | GAC | GAG | AAC |
| Asn | Lys | Pro | Ile | Tyr | Glu | Ser | Ser | Val | Met | Thr | Tyr | Leu | Asp | Glu | Asn |
| | | | 1475 | | | | | 1480 | | | | | 1485 | | | 3119

| ACC | GCC | AAG | GAG | GTG | ACC | AAG | CAG | CTG | AAC | GAC | ACC | ACC | GGC | AAG | TTC |
| Thr | Ala | Lys | Glu | Val | Thr | Lys | Gln | Leu | Asn | Asp | Thr | Thr | Gly | Lys | Phe |
| | | 1490 | | | | | 1495 | | | | | 1500 | | | | 3167

| AAG | GAC | GTG | AGC | CAC | CTG | TAC | GAC | GTG | AAG | CTG | ACC | CCC | AAG | ATG | AAC |
| Lys | Asp | Val | Ser | His | Leu | Tyr | Asp | Val | Lys | Leu | Thr | Pro | Lys | Met | Asn |
| | | 1505 | | | | 1510 | | | | | 1515 | | | | | 3215

| GTG | ACC | ATC | AAG | CTG | AGC | ATC | CTG | TAC | GAC | AAC | GCC | GAG | AGC | AAC | GAC |
| Val | Thr | Ile | Lys | Leu | Ser | Ile | Leu | Tyr | Asp | Asn | Ala | Glu | Ser | Asn | Asp |
| 1520 | | | | | 1525 | | | | | 1530 | | | | | 1535 | 3263

| AAC | AGC | ATC | GGC | AAG | TGG | ACC | AAC | ACC | AAC | ATC | GTG | AGC | GGC | GGC | AAC |
| Asn | Ser | Ile | Gly | Lys | Trp | Thr | Asn | Thr | Asn | Ile | Val | Ser | Gly | Gly | Asn |
| | | | 1540 | | | | | 1545 | | | | | 1550 | | | 3311

| | | | | | | | | | | | | | | | |
|---|---|---|---|---|---|---|---|---|---|---|---|---|---|---|---|
| AAC | GGC | AAG | AAG | CAG | TAC | AGC | AGC | AAC | AAC | CCC | GAC | GCC | AAC | CTG | ACC | 3359
| Asn | Gly | Lys | Lys | Gln | Tyr | Ser | Ser | Asn | Asn | Pro | Asp | Ala | Asn | Leu | Thr |
| | | | 1555 | | | | 1560 | | | | | 1565 | | | |
| CTG | AAC | ACC | GAC | GCC | CAG | GAG | AAG | CTG | AAC | AAG | AAC | CGC | GAC | TAC | TAC | 3407
| Leu | Asn | Thr | Asp | Ala | Gln | Glu | Lys | Leu | Asn | Lys | Asn | Arg | Asp | Tyr | Tyr |
| | 1570 | | | | | 1575 | | | | | 1580 | | | | |
| ATC | AGC | CTG | TAC | ATG | AAG | AGC | GAG | AAG | AAC | ACC | CAG | TGC | GAG | ATC | ACC | 3455
| Ile | Ser | Leu | Tyr | Met | Lys | Ser | Glu | Lys | Asn | Thr | Gln | Cys | Glu | Ile | Thr |
| | 1585 | | | | | 1590 | | | | | 1595 | | | | |
| ATC | GAC | GGC | GAG | ATA | TAC | CCC | ATC | ACC | ACC | AAG | ACC | GTG | AAC | GTG | AAC | 3503
| Ile | Asp | Gly | Glu | Ile | Tyr | Pro | Ile | Thr | Thr | Lys | Thr | Val | Asn | Val | Asn |
| 1600 | | | | | 1605 | | | | | 1610 | | | | | 1615 |
| AAG | GAC | AAC | TAC | AAG | CGC | CTG | GAC | ATC | ATC | GCC | CAC | AAC | ATC | AAG | AGC | 3551
| Lys | Asp | Asn | Tyr | Lys | Arg | Leu | Asp | Ile | Ile | Ala | His | Asn | Ile | Lys | Ser |
| | | | | 1620 | | | | | 1625 | | | | | 1630 | |
| AAC | CCC | ATC | AGC | AGC | CTG | CAC | ATC | AAG | ACC | AAC | GAC | GAG | ATC | ACC | CTG | 3599
| Asn | Pro | Ile | Ser | Ser | Leu | His | Ile | Lys | Thr | Asn | Asp | Glu | Ile | Thr | Leu |
| | | | 1635 | | | | 1640 | | | | | 1645 | | | |
| TTC | TGG | GAC | GAC | ATA | TCG | ATT | ACC | GAC | GTC | GCC | AGC | ATC | AAG | CCC | GAG | 3647
| Phe | Trp | Asp | Asp | Ile | Ser | Ile | Thr | Asp | Val | Ala | Ser | Ile | Lys | Pro | Glu |
| | | 1650 | | | | | 1655 | | | | | 1660 | | | |
| AAC | CTG | ACC | GAC | AGC | GAG | ATC | AAG | CAG | ATA | TAC | AGT | CGC | TAC | GGC | ATC | 3695
| Asn | Leu | Thr | Asp | Ser | Glu | Ile | Lys | Gln | Ile | Tyr | Ser | Arg | Tyr | Gly | Ile |
| | 1665 | | | | | 1670 | | | | | 1675 | | | | |
| AAG | CTG | GAG | GAC | GGC | ATC | CTG | ATC | GAC | AAG | AAA | GGC | GGC | ATC | CAC | TAC | 3743
| Lys | Leu | Glu | Asp | Gly | Ile | Leu | Ile | Asp | Lys | Lys | Gly | Gly | Ile | His | Tyr |
| 1680 | | | | | 1685 | | | | | 1690 | | | | | 1695 |
| GGC | GAG | TTC | ATC | AAC | GAG | GCC | AGC | TTC | AAC | ATC | GAG | CCC | CTG | CAG | AAC | 3791
| Gly | Glu | Phe | Ile | Asn | Glu | Ala | Ser | Phe | Asn | Ile | Glu | Pro | Leu | Gln | Asn |
| | | | | 1700 | | | | | 1705 | | | | | 1710 | |
| TAC | GTG | ACC | AAG | TAC | GAG | GTG | ACC | TAC | AGC | AGC | GAG | CTG | GGC | CCC | AAC | 3839
| Tyr | Val | Thr | Lys | Tyr | Glu | Val | Thr | Tyr | Ser | Ser | Glu | Leu | Gly | Pro | Asn |
| | | | 1715 | | | | | 1720 | | | | | 1725 | | |
| GTG | AGC | GAC | ACC | CTG | GAG | AGC | GAC | AAG | ATT | TAC | AAG | GAC | GGC | ACC | ATC | 3887
| Val | Ser | Asp | Thr | Leu | Glu | Ser | Asp | Lys | Ile | Tyr | Lys | Asp | Gly | Thr | Ile |
| | | | 1730 | | | | | 1735 | | | | | 1740 | | |
| AAG | TTC | GAC | TTC | ACC | AAG | TAC | AGC | AAG | AAC | GAG | CAG | GGC | CTG | TTC | TAC | 3935
| Lys | Phe | Asp | Phe | Thr | Lys | Tyr | Ser | Lys | Asn | Glu | Gln | Gly | Leu | Phe | Tyr |
| | 1745 | | | | | 1750 | | | | | 1755 | | | | |
| GAC | AGC | GGC | CTG | AAC | TGG | GAC | TTC | AAG | ATC | AAC | GCC | ATC | ACC | TAC | GAC | 3983
| Asp | Ser | Gly | Leu | Asn | Trp | Asp | Phe | Lys | Ile | Asn | Ala | Ile | Thr | Tyr | Asp |
| 1760 | | | | | 1765 | | | | | 1770 | | | | | 1775 |
| GGC | AAG | GAG | ATG | AAC | GTG | TTC | CAC | CGC | TAC | AAC | AAG | TAGATCTGAG | | | | 4029
| Gly | Lys | Glu | Met | Asn | Val | Phe | His | Arg | Tyr | Asn | Lys | | | | |
| | | | | 1780 | | | | | 1785 | | | | | | |
| CT | | | | | | | | | | | | | | | | 4031

( 2 ) INFORMATION FOR SEQ ID NO:50:

( i ) SEQUENCE CHARACTERISTICS:
        ( A ) LENGTH: 1338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| | | | | | | | | | | | | | | |
|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 |
| Val | Val | Thr | Lys | Thr | Val | Leu | Leu | Ser | Thr | Val | Phe | Ser | Ile | Ser | Leu |
| | | | 20 | | | | | 25 | | | | | 30 | |

Leu Asn Asn Glu Val Ile Lys Ala Glu Gln Leu Asn Ile Asn Ser Gln
            35                  40                  45

Ser Lys Tyr Thr Asn Leu Gln Asn Leu Lys Ile Thr Asp Lys Val Glu
    50                  55                  60

Asp Phe Lys Glu Asp Lys Glu Lys Ala Lys Glu Trp Gly Lys Glu Lys
65                  70                  75                  80

Glu Lys Glu Trp Lys Leu Thr Ala Thr Glu Lys Gly Lys Met Asn Asn
                85                  90                  95

Phe Leu Asp Asn Lys Asn Asp Ile Lys Thr Asn Tyr Lys Glu Ile Thr
                100                 105                 110

Phe Ser Ile Ala Gly Ser Phe Glu Asp Glu Ile Lys Asp Leu Lys Glu
            115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
    195                 200                 205

Val Pro Ser Gly Lys Gly Ser Thr Thr Pro Thr Lys Ala Gly Val Ile
210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Lys Gly Val Glu Cys Leu
                245                 250                 255

Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
    275                 280                 285

Lys Asp Leu Thr Asp Ser Gln Arg Glu Ala Leu Asp Gly Tyr Ala Arg
290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
    355                 360                 365

Asp Phe Glu Glu Gln Phe Leu Asn Thr Ile Lys Glu Asp Lys Gly Tyr
370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
    435                 440                 445

Gly Val Lys Arg Tyr Val Val Asp Ala Thr Leu Leu Thr Asn Ser Arg
450                 455                 460

```
Gly  Pro  Ser  Thr  Pro  Pro  Thr  Pro  Ser  Pro  Ser  Thr  Pro  Pro  Thr  Pro
465                      470                      475                      480

Ser  Asp  Ile  Gly  Ser  Thr  Met  Lys  Thr  Asn  Gln  Ile  Ser  Thr  Thr  Gln
                    485                 490                      495

Lys  Asn  Gln  Gln  Lys  Glu  Met  Asp  Arg  Lys  Gly  Leu  Leu  Gly  Tyr  Tyr
               500                      505                      510

Phe  Lys  Gly  Lys  Asp  Phe  Ser  Asn  Leu  Thr  Met  Phe  Ala  Pro  Thr  Arg
          515                      520                      525

Asp  Ser  Thr  Leu  Ile  Tyr  Asp  Gln  Gln  Thr  Ala  Asn  Lys  Leu  Leu  Asp
     530                      535                      540

Lys  Lys  Gln  Gln  Glu  Tyr  Gln  Ser  Ile  Arg  Trp  Ile  Gly  Leu  Ile  Gln
545                      550                      555                      560

Ser  Lys  Glu  Thr  Gly  Asp  Phe  Thr  Phe  Asn  Leu  Ser  Glu  Asp  Glu  Gln
                    565                      570                      575

Ala  Ile  Ile  Glu  Ile  Asn  Gly  Lys  Ile  Ile  Ser  Asn  Lys  Gly  Lys  Glu
               580                      585                      590

Lys  Gln  Val  Val  His  Leu  Glu  Lys  Gly  Lys  Leu  Val  Pro  Ile  Lys  Ile
          595                      600                      605

Glu  Tyr  Gln  Ser  Asp  Thr  Lys  Phe  Asn  Ile  Asp  Ser  Lys  Thr  Phe  Lys
     610                      615                      620

Glu  Leu  Lys  Leu  Phe  Lys  Ile  Asp  Ser  Gln  Asn  Gln  Pro  Gln  Gln  Val
625                      630                      635                      640

Gln  Gln  Asp  Glu  Leu  Arg  Asn  Pro  Glu  Phe  Asn  Lys  Lys  Glu  Ser  Gln
                    645                      650                      655

Glu  Phe  Leu  Ala  Lys  Pro  Ser  Lys  Ile  Asn  Leu  Phe  Thr  Gln  Gln  Met
               660                      665                      670

Lys  Arg  Glu  Ile  Asp  Glu  Asp  Thr  Asp  Thr  Asp  Gly  Asp  Ser  Ile  Pro
          675                      680                      685

Asp  Leu  Trp  Glu  Glu  Asn  Gly  Tyr  Thr  Ile  Gln  Asn  Arg  Ile  Ala  Val
     690                      695                      700

Lys  Trp  Asp  Asp  Ser  Leu  Ala  Ser  Lys  Gly  Tyr  Thr  Lys  Phe  Val  Ser
705                      710                      715                      720

Asn  Pro  Leu  Glu  Ser  His  Thr  Val  Gly  Asp  Pro  Tyr  Thr  Asp  Tyr  Glu
                    725                      730                      735

Lys  Ala  Ala  Arg  Asp  Leu  Asp  Leu  Ser  Asn  Ala  Lys  Glu  Thr  Phe  Asn
               740                      745                      750

Pro  Leu  Val  Ala  Ala  Phe  Pro  Ser  Val  Asn  Val  Ser  Met  Glu  Lys  Val
          755                      760                      765

Ile  Leu  Ser  Pro  Asn  Glu  Asn  Leu  Ser  Asn  Ser  Val  Glu  Ser  His  Ser
     770                      775                      780

Ser  Thr  Asn  Trp  Ser  Tyr  Thr  Asn  Thr  Glu  Gly  Ala  Ser  Val  Glu  Ala
785                      790                      795                      800

Gly  Ile  Gly  Pro  Lys  Gly  Ile  Ser  Phe  Gly  Val  Ser  Val  Asn  Tyr  Gln
                    805                      810                      815

His  Ser  Glu  Thr  Val  Ala  Gln  Glu  Trp  Gly  Thr  Ser  Thr  Gly  Asn  Thr
               820                      825                      830

Ser  Gln  Phe  Asn  Thr  Ala  Ser  Ala  Gly  Tyr  Leu  Asn  Ala  Asn  Val  Arg
          835                      840                      845

Tyr  Asn  Asn  Val  Gly  Thr  Gly  Ala  Ile  Tyr  Asp  Val  Lys  Pro  Thr  Thr
     850                      855                      860

Ser  Phe  Val  Leu  Asn  Asn  Asp  Thr  Ile  Ala  Thr  Ile  Thr  Ala  Lys  Ser
865                      870                      875                      880

Asn  Ser  Thr  Ala  Leu  Asn  Ile  Ser  Pro  Gly  Glu  Ser  Tyr  Pro  Lys  Lys
```

-continued

```
                              885                      890                      895

Gly  Gln  Asn  Gly  Ile  Ala  Ile  Thr  Ser  Met  Asp  Asp  Phe  Asn  Ser  His
               900                      905                      910

Pro  Ile  Thr  Leu  Asn  Lys  Lys  Gln  Val  Asp  Asn  Leu  Leu  Asn  Asn  Lys
               915                      920                      925

Pro  Met  Met  Leu  Glu  Thr  Asn  Gln  Thr  Asp  Gly  Val  Tyr  Lys  Ile  Lys
               930                      935                      940

Asp  Thr  His  Gly  Asn  Ile  Val  Thr  Gly  Gly  Glu  Trp  Asn  Gly  Val  Ile
945                      950                      955                      960

Gln  Gln  Ile  Lys  Ala  Lys  Thr  Ala  Ser  Ile  Ile  Val  Asp  Asp  Gly  Glu
               965                      970                      975

Arg  Val  Ala  Glu  Lys  Arg  Val  Ala  Ala  Lys  Asp  Tyr  Glu  Asn  Pro  Glu
               980                      985                      990

Asp  Lys  Thr  Pro  Ser  Leu  Thr  Leu  Lys  Asp  Ala  Leu  Lys  Leu  Ser  Tyr
               995                     1000                     1005

Pro  Asp  Glu  Ile  Lys  Glu  Ile  Glu  Gly  Leu  Leu  Tyr  Lys  Asn  Lys
              1010                     1015                     1020

Pro  Ile  Tyr  Glu  Ser  Ser  Val  Met  Thr  Tyr  Leu  Asp  Glu  Asn  Thr  Ala
1025                    1030                     1035                     1040

Lys  Glu  Val  Thr  Lys  Gln  Leu  Asn  Asp  Thr  Thr  Gly  Lys  Phe  Lys  Asp
                    1045                     1050                     1055

Val  Ser  His  Leu  Tyr  Asp  Val  Lys  Leu  Thr  Pro  Lys  Met  Asn  Val  Thr
                    1060                     1065                     1070

Ile  Lys  Leu  Ser  Ile  Leu  Tyr  Asp  Asn  Ala  Glu  Ser  Asn  Asp  Asn  Ser
                    1075                     1080                     1085

Ile  Gly  Lys  Trp  Thr  Asn  Thr  Asn  Ile  Val  Ser  Gly  Gly  Asn  Asn  Gly
     1090                     1095                     1100

Lys  Lys  Gln  Tyr  Ser  Ser  Asn  Asn  Pro  Asp  Ala  Asn  Leu  Thr  Leu  Asn
1105                     1110                     1115                     1120

Thr  Asp  Ala  Gln  Glu  Lys  Leu  Asn  Lys  Asn  Arg  Asp  Tyr  Tyr  Ile  Ser
                    1125                     1130                     1135

Leu  Tyr  Met  Lys  Ser  Glu  Lys  Asn  Thr  Gln  Cys  Glu  Ile  Thr  Ile  Asp
                    1140                     1145                     1150

Gly  Glu  Ile  Tyr  Pro  Ile  Thr  Thr  Lys  Thr  Val  Asn  Val  Asn  Lys  Asp
                    1155                     1160                     1165

Asn  Tyr  Lys  Arg  Leu  Asp  Ile  Ile  Ala  His  Asn  Ile  Lys  Ser  Asn  Pro
1170                     1175                     1180

Ile  Ser  Ser  Leu  His  Ile  Lys  Thr  Asn  Asp  Glu  Ile  Thr  Leu  Phe  Trp
1185                     1190                     1195                     1200

Asp  Asp  Ile  Ser  Ile  Thr  Asp  Val  Ala  Ser  Ile  Lys  Pro  Glu  Asn  Leu
                    1205                     1210                     1215

Thr  Asp  Ser  Glu  Ile  Lys  Gln  Ile  Tyr  Ser  Arg  Tyr  Gly  Ile  Lys  Leu
                    1220                     1225                     1230

Glu  Asp  Gly  Ile  Leu  Ile  Asp  Lys  Lys  Gly  Gly  Ile  His  Tyr  Gly  Glu
                    1235                     1240                     1245

Phe  Ile  Asn  Glu  Ala  Ser  Phe  Asn  Ile  Glu  Pro  Leu  Gln  Asn  Tyr  Val
                    1250                     1255                     1260

Thr  Lys  Tyr  Glu  Val  Thr  Tyr  Ser  Ser  Glu  Leu  Gly  Pro  Asn  Val  Ser
1265                     1270                     1275                     1280

Asp  Thr  Leu  Glu  Ser  Asp  Lys  Ile  Tyr  Lys  Asp  Gly  Thr  Ile  Lys  Phe
                    1285                     1290                     1295

Asp  Phe  Thr  Lys  Tyr  Ser  Lys  Asn  Glu  Gln  Gly  Leu  Phe  Tyr  Asp  Ser
                    1300                     1305                     1310
```

| | | | | | | | | | | | | | |
|---|---|---|---|---|---|---|---|---|---|---|---|---|---|
| Gly | Leu | Asn | Trp | Asp | Phe | Lys | Ile | Asn | Ala | Ile | Thr | Tyr | Asp | Gly | Lys |
| | | 1315 | | | | | 1320 | | | | | 1325 | | |
| Glu | Met | Asn | Val | Phe | His | Arg | Tyr | Asn | Lys | | | | | |
| | | 1330 | | | | 1335 | | | | | | | | |

NUCLEOTIDE SEQUENCES ENCODING PESTICIDAL PROTEINS

The present application is a divisional application of U.S. application Ser. No. 08/463,483, filed Jun. 5, 1995, which is a continuation-in-part application of U.S. application Ser. No. 08/314,594 filed Sep. 28, 1994, now abandoned, which is a continuation-in-part application of U.S. application Ser. No. 08/218,018 filed Mar. 23, 1994, now abandoned, which is a continuation-in-part application of U.S. application Ser. No. 08/037,057 filed Mar. 25, 1993, now abandoned, the disclosures of which are herein incorporated by reference.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (Bt). Bt is a gram-positive spore forming Bacillus which produces an insecticidal crystal protein (ICP) during sporulation.

Numerous varieties of Bt are known that produce more than 25 different but related ICP's. The majority of ICP's made by Bt are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

Bacillus cereus (Bc) is closely related to Bt. A major distinguishing characteristic is the absence of a parasporal crystal in Bc. Bc is a widely distributed bacterium that is commonly found in soil and has been isolated from a variety of foods and drugs. The organism has been implicated in the spoilage of food.

Although Bt has been very useful in controlling insect pests, there is a need to expand the number of potential biological control agents.

BRIEF DESCRIPTION OF THE FIGURE

FIG. 1: Characterization of pCIB6022. Boxed regions represent the extent of VIP1A(a) and VIP2A(a). White box represents the portion of VIP1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI-Eco RI; B-Bgl II; RV-Eco RV.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from Bacillus sphaericus SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

| Lepidoptera (Butterflies and Moths) | |
|---|---|
| Maize | Sunflower |
| *Ostrinia nubilalis*, European corn borer | *Suleima helianthana*, sunflower bud moth |
| *Agrotis ipsilon*, black cutworm | *Homoeosoma electellum*, sunflower moth |
| *Helicoverpa zea*, corn earworm | |
| *Spodoptera frugiperda*, fall armyworm | Cotton |
| *Diatraea grandiosella*, southwestern corn borer | *Heliothis virescens*, cotton boll worm |
| | *Helicoverpa zea*, cotton bollworm |
| | *Spodoptera exigua*, beet armyworm |

TABLE 1-continued

Lepidoptera (Butterflies and Moths)

| | |
|---|---|
| *Elasmopalpus lignosellus*, lesser cornstalk borer | *Pectinophora gossypiella*, pink bollworm |
| *Diatraea saccharalis*, sugarcane borer | Rice |
| Sorghum | *Diatraea saccharalis*, sugarcane borer |
| *Chilo partellus*, sorghum borer | *Spodoptera frugiperda*, fall armyworm |
| *Spodoptera frugiperda*, fall armyworm | Helicoverpa zea, corn earworm |
| *Helicoverpa zea*, corn earworm | Soybean |
| *Elasmopalpus lignosellus*, lesser cornstalk borer | *Pseudoplusia includens*, soybean looper |
| *Feltia subterranea*, granulate cutworm | *Anticarsia gemmatalis*, velvetbean caterpillar |
| Wheat | *Plathypena scabra*, green cloverworm |
| *Pseudaletia unipunctata*, army worm | *Ostrinia nubilalis*, European corn borer |
| *Spodoptera frugiperda*, fall armyworm | *Agrotis ipsilon*, black cutworm |
| *Elasmopalpus lignosellus*, lesser cornstalk borer | *Spodoptera exigua*, beet armyworm |
| | *Heliothis virescens*, cotton boll worm |
| *Agrotis orthogonia*, pale western cutworm | *Helicoverpa zea*, cotton bollworm |
| | Barley |
| *Elasmopalpus lignosellus*, lesser cornstalk borer | *Ostrinia nubilalis*, European corn borer |
| | *Agrotis ipsilon*, black cutworm |

TABLE 2

Coleoptera (Beetles)

Maize

*Diabrotica virgifera virgifera*, western corn rootworm
*Diabrotica longicornis barberi*, northern corn rootworm
*Diabrotica undecimpunctata howardi*, southern corn rootworm
Melanotus spp., wireworms
*Cyclocephala borealis*, northern masked chafer (white grub)
*Cyclocephala immaculata*, southern masked chafer (white grub)
*Popillia japonica*, Japanese beetle
*Chaetocnema pulicaria*, corn flea beetle
*Sphenophorus maidis*, maize billbug
Sorghum

*Phyllophaga crinita*, white grub
Eleodes, Conoderus, and Aeolus spp., wireworms
*Oulema melanopus*, cereal leaf beetle
*Chaetocnema pulicaria*, corn flea beetle
*Sphenophorus maidis*, maize billbug
Wheat

*Oulema melanopus*, cereal leaf beetle
*Hypera punctata*, clover leaf weevil
*Diabrotica undecimpunctata howardi*, southern corn rootworm
Sunflower

*Zygogramma exclamationis*, sunflower beetle
*Bothyrus gibbosus*, carrot beetle
Cotton

*Anthonomus grandis*, boll weevil
Rice

*Colaspis brunnea*, grape colaspis
*Lissorhoptrus oryzophilus*, rice water weevil
*Sitophilus oryzae*, rice weevil
Soybean

*Epilachna varivestis*, Mexican bean beetle

TABLE 3

Homoptera (Whiteflies, Aphids etc.)

Maize

*Rhopalosiphum maidis*, corn leaf aphid
*Anuraphis maidiradicis*, corn root aphid
Sorghum

*Rhopalosiphum maidis*, corn leaf aphid
*Sipha flava*, yellow sugarcane aphid
Wheat Russian wheat aphid
*Schizaphis graminum*, greenbug
*Macrosiphum avenae*, English grain aphid
Cotton

*Aphis gossypii*, cotton aphid
*Pseudatomoscelis seriatus*, cotton fleahopper
*Trialeurodes abutilonea*, bandedwinged whitefly
Rice

*Nephotettix nigropictus*, rice leafhopper
Soybean

*Myzus persicae*, green peach aphid
*Empoasca fabae*, potato leafhopper
Barley

*Schizaphis graminum*, greenbug
Oil Seed Rape

*Brevicoryne brassicae*, cabbage aphid

TABLE 4

Hemiptera (Bugs)

Maize

*Blissus leucopterus leucopterus*, chinch bug
Sorghum

*Blissus leucopterus leucopterus*, chinch bug
Cotton

*Lygus lineolaris*, tarnished plant bug
Rice

*Blissus leucopterus leucopterus*, chinch bug
*Acrosternum hilare*, green stink bug
Soybean

*Acrosternum hilare*, green stink bug
Barley

*Blissus leucopterus leucopterus*, chinch bug
*Acrosternum hilare*, green stink bug
*Euschistus servus*, brown stink bug

TABLE 5

Orthoptera (Grasshoppers. Crickets and Cockroaches)

Maize

*Melanoplus femurrubrum*, redlegged grasshopper
*Melanoplus sanguinipes*, migratory grasshopper
Wheat

*Melanoplus femurrubrum*, redlegged grasshopper
*Melanoplus differentialis*, differential grasshopper
*Melanoplus sanguinipes*, migratory grasshopper

TABLE 5-continued

Orthoptera (Grasshoppers. Crickets and Cockroaches)

Cotton

*Melanoplus femurrubrum*, redlegged grasshopper
*Melanoplus differentialis*, differential grasshopper
Soybean

*Melanoplus femurrubrum*, redlegged grasshopper
*Melanoplus differentialis*, differential grasshopper
Structural/Household

*Periplaneta americana*, American cockroach
*Blattella germanica*, German cockroach
*Blatta orientalis*, oriental cockroach

TABLE 6

Diptera (Flies and Mosquitoes)

Maize

*Hylemya platura*, seedcorn maggot
*Agromyza parvicornis*, corn blotch leafminer
Sorghum

*Contarinia sorghicola*, sorghum midge
Wheat

*Mayetiola destructor*, Hessian fly
*Sitodiplosis mosellana*, wheat midge
*Meromyza americana*, wheat stem maggot
*Hylemya coarctata*, wheat bulb fly
Sunflower

*Neolasioptera murtfeldtiana*, sunflower seed midge
Soybean

*Hylemya platura*, seedcorn maggot
Barley

*Hylemya platura*, seedcorn maggot
*Mayetiola destructor*, Hessian fly
Insects attacking humans and animals and disease carriers

*Aedes aegypti*, yellowfever mosquito
*Aedes albopictus*, forest day mosquito
*Phlebotomus papatasii*, sand fly
*Musca domestica*, house fly
*Tabanus atratus*, black horse fly
*Cochliomyia hominivorax*, screwworm fly

TABLE 7

Thysanoptera (Thrips)

Maize

*Anaphothrips obscurus*, grass thrips
Wheat
*Frankliniella fusca*, tobacco thrips
Cotton

*Thrips tabaci*, onion thrips
*Frankliniella fusca*, tobacco thrips
Soybean

*Sericothrips variabilis*, soybean thrips
*Thrips tabaci*, onion thrips

TABLE 8

Hymenoptera (Sawflies, Ants, Wasps, etc.)

Maize

*Solenopsis milesta*, thief ant
Wheat

*Cephus cinctus*, wheat stem sawfly

TABLE 9

Other Orders and Representative Species

Dermaptera (Earwigs)

*Forficula auricularia*, European earwig
Isoptera (Termites)

*Reticulitermes flavipes*, eastern subterranean termite
Mallophaga (Chewing Lice)

*Cuclotogaster heterographa*, chicken head louse
*Bovicola bovis*, cattle biting louse
Anoplura (Sucking Lice)

Pediculus humanus, head and body louse
Siphonaptera (Fleas)

*Ctenocephalides felis*, cat flea

TABLE 10

Acari (Mites and Ticks)

Maize

*Tetranychus urticae*, twospotted spider mite
Sorghum

*Tetranychus cinnabarinus*, carmine spider mite
*Tetranychus urticae*, twospotted spider mite
Wheat

*Aceria tulipae*, wheat curl mite
Cotton

*Tetranychus cinnabarinus*, carmine spider mite
*Tetranychus urticae*, twospotted spider mite
Soybean

*Tetranychus turkestani*, strawberry spider mite
*Tetranychus urticae*, twospotted spider mite
Barley

*Petrobia latens*, brown wheat mite
Important human and animal Acari

*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al.

(1981) "The genera Bacillus and Sporolactobacillus," In Starr et al. (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| Morphological Group 1 | Unassigned Strains |
|---|---|
| *B. megaterium* | Subgroup A |
| *B. cereus** | *B. apiarus** |
| *B. cereus* var. mycoides | *B. filicolonicus* |
| *B. thuringiensis** | *B. thiaminolyticus* |
| *B. licheniformis* | *B. alcalophilus* |
| *B. subtilis** | Subgroup B |
| *B. pumilus* | *B. cirroflagellosus* |
| *B. firmus** | *B. chitinosporus* |
| *B. coagulans* | *B. lentus* |
| Morphological Group 2 | Subgroup C |
| *B. polymyxa* | *B. badius* |
| *B. macerans* | *B. aneurinolyticus* |
| *B. circulans* | *B. macroides* |
| *B. stearothermophilus* | *B. freundenreichii* |
| *B. alvei** | Subgroup D |
| *B. laterosporus** | *B. pantothenticus* |
| *B. brevis* | *B. epiphytus* |
| *B. pulvifaciens* | Subgroup E1 |
| *B. popilliae** | *B. aminovorans* |
| *B. lentimorbus** | *B. globisporus* |
| *B. larvae** | *B. insolitus* |
| Morphological Group 3 | *B. psychrophilus* |
| *B. sphaericus** | Subgroup E2 |
| *B. pasteurii* | *B. psychrosaccharolyticus* |
| | *B. macquariensis* |

*= Those Bacillus strains that have been previously found associated with insects Grouping according to Parry, J. M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, NY (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. application Ser. No. 07/951,715, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*. J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff (1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP 1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, pesticidal protein. Such a pesticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. application Ser. No. 07/951,715; EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), Nucleic Acids Research 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) Gene 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327:70–73; Howell et al., (1980) *Science* 208:1265; Horsch et al., (1985) *Science*

227:1229–1231; DeBlock et al., (1989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also US patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al., (1989) *Nucleic Acids Research* 17:477498; and WO 91/16432.

The construct may also include any other necessary regulators such as terminators, (Guerineau et al., (1991), *Mol. Gen. Genet.,* 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al et al., (1989), *Nucleic Acids Res.,* 17:7891–7903; Joshi et al., (1987), *Nucleic Acid Res.,* 15:9627–9639); plant translational consensus sequences (Joshi, C. P., (1987), *Nucleic Acids Research,* 15:6643–6653), introns (Luehrsen and Walbot, (1991), *Mol. Gen. Genet.,* 225:81–93) and the like, operably linked to the nucleotide sequence. It may be beneficial to include 5' leader sequences in the expression cassette construct. Such leader sequences can act to enhance translation. Translational leaders are known in the art and include:

- Picornavirus leaders, for example, EMCV leader (encephalomyocarditis 5' noncoding region) (Elroy-Stein, O., Fuerst, T. R., and Moss, B. (1989) *PNAS USA* 86:6126–6130);
- Potyvirus leaders, for example, TEV leader (Tobacco Etch Virus) (Allison et al., (1986); MDMV leader (Maize Dwarf Mosaic Virus); *Virology,* 154:9–20), and
- Human immunoglobulin heavy-chain binding protein (BiP), (Macejak, D. G., and Sarnow, P., (1991), *Nature,* 353:90–94;
- Untranslated leader from the coat protein mRNA of alfalfa mosaic virus (AMV RNA 4), (Jobling, S. A., and Gehrke, L., (1987), *Nature,* 325:622–625;
- Tobacco mosaic virus leader (TMV), (Gallie, D. R. et al., (1989), *Molecular Biology of RNA pages* 237–256; and
- Maize Chlorotic Mottle Virus leader (MCMV) (Lommel, S. A. et al., (1991), *Virology,* 81:382–385. See also, Della-Cioppa et al., (1987), *Plant Physiology,* 84:965–968.
- A plant terminator may be utilized in the expression cassette. See, Rosenberg et al., (1987), *Gene,* 56:125; Guerineau et al., (1991), *Mol. Gen. Genet.,* 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al., (1989), *Nucleic Acids Res.,* 17:7891–7903; Joshi et al., (1987), *Nucleic Acid Res.,* 15:9627–9639.

For tissue specific expression, the nucleotide sequences of the invention can be operably linked to tissue specific promoters. See, for example, U.S. application Ser. No. 07/951,715 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli and Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonasfluorescens, Saccharomyces cerevisiae, Bacillus thuringiensis, Escherichia coli, Bacillus subtilis*, and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from Bacillus cereus strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.*, 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.*, 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology.* 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, *EMBO J.*, 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in *E. coli* would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that *Bacillus thuringiensis* strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such Bt strains produce endotoxin protein(s) as well as VIPs. Alternatively, such strains can produce only VIPs. A sporulation deficient strain of *Bacillus subtilis* has been shown to produce high levels of the CryIIIA endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", *J. Bacteriol.* 176:4734–4741 (1994)). A similar spoOA mutant can be prepared in *Bacillus thuringiensis* and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne, *J. Mol. Biol.* 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP 1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that multiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide) -producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a *Bacillus cereus* microorganism has been isolated which is capable of killing *Diabrotica virgifera virgifera*, and *Diabrotica longicornis barberi*. The novel *B. cereus* strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the *B. cereus* strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: $NH_2$-Lys-Arg-Glu-Ile-Asp-Glu-Asp-Thr-Asp-Thr-Asx-Gly-Asp-Ser-Ile-Pro-(SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the $NH_2$-terminus has been generated. The probe was synthesized based on the codon usage of a *Bacillus thuringiensis* (Bt) δ-endotoxin gene. The nucleotide sequence of the oligonucleotide probe used for Southern hybridizations was as follows:

5'-GAA ATT GAT CAA GAT ACN GAT-3' (SEQ ID NO:9)

where N represents any base.

In addition, the DNA probe for the Bc AB78 VIP1 gene described herein, permits the screening of any Bacillus strain or other organisms to determine whether the VIP 1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
|---|---|---|
| VIP1A(a) | VIP1 | VIP1 from strain AB78 as disclosed in SEQ ID NO: 5. |
| VIP2A(a) | VIP2 | VIP2 from strain AB78 as disclosed in SEQ ID NO: 2. |

-continued

| Gene/Protein Name under Standard Nomenclature | Gene/Protein Name in Parent | Description of Protein |
|---|---|---|
| VIP1A(b) | VIP1 homolog | VIP1 from *Bacillus thuringiensis* var. *tenebrionis* as disclosed in SEQ ID NO: 21. |
| VIP2A(b) | VIP2 homolog | VIP2 from *Bacillus thuringiensis* var. *tenebrionis* as disclosed in SEQ ID NO: 20. |
| VIP3A(a) | — | VIP from strain AB88 as disclosed in SEQ ID NO: 28 of the present application |
| VIP3A(b) | — | VIP from strain AB424 as disclosed in SEQ ID NO: 31 of the present application |

Experimental

EXAMPLE 1

AB78 Isolation and Characterization

*Bacillus cereus* strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g $MnCl_2$; Travers, R. S. 1983). During log phase growth, AB78 gave significant activity against western corn rootworm. Antibiotic activity against gram-positive Bacillus spp. was also demonstrated (Table 12).

TABLE 12

Antibiotic activity of AB78 culture supernatant

| | Zone of inhibition (cm) | |
|---|---|---|
| Bacteria tested | AB78 | Streptomycin |
| *E. coli* | 0.0 | 3.0 |
| *B. megaterium* | 1.1 | 2.2 |
| *B. mycoides* | 1.3 | 2.1 |
| *B. cereus* CB | 1.0 | 2.0 |
| *B. cereus* 11950 | 1.3 | 2.1 |
| *B. cereus* 14579 | 1.0 | 2.4 |
| *B. cereus* AB78 | 0.0 | 2.2 |
| Bt var. *israelensis* | 1.1 | 2.2 |
| Bt var. *tenebrionis* | 0.9 | 2.3 |

Morphological characteristics of AB78 are as follows: Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl.

Table 13 provides the biochemical profile of AB78.

TABLE 13

Biochemical characteristics of *B. cereus* strain AB78.

| Acid from L-arabinose | – | Methylene blue reoxidized | + |
| Gas from L-arabinose | – | Nitrate reduced | + |

TABLE 13-continued

Biochemical characteristics of *B. cereus* strain AB78.

| Acid from D-xylose | – | $NO_3$ reduced to $NO_2$ | + |
|---|---|---|---|
| Gas from D-xylose | – | VP | + |
| Acid from D-glucose | + | $H_2O_2$ decomposed | + |
| Gas from D-glucose | – | Indole | – |
| Acid from lactose | – | Tyrosine decomposed | + |
| Gas from lactose | – | Dihydroxyacetone | – |
| Acid from sucrose | – | Litmus milk acid | – |
| Gas from sucrose | – | Litmus milk coagulated | – |
| Acid from D-mannitol | – | Litmus milk alkaline | – |
| Gas from D-mannitol | – | Litmus milk peptonized | – |
| Proprionate utilization | + | Litmus milk reduced | – |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

EXAMPLE 2

Bacterial Culture

A subculture of Bc strain AB78 was used to inoculate the following medium, known as TB broth:

| Tryptone | 12 g/l |
|---|---|
| Yeast Extract | 24 g/l |
| Glycerol | 4 ml/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3

Insect Bioassays

*B. cereus* strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli* clone bioassay: *E. coli* cells were grown overnight in broth containing 100 μg/ml ampicillin at 37° C. Ten ml culture was sonicated 3× for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five $cm^2$ potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 $\mu$l was pipetted onto the surface of 18 $cm^2$ of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 $\mu$l was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
|---|---|---|
| Western corn rootworm (*Diabrotica virgifera virgifera*) | Col | +++ |
| Northern corn rootworm (*Diabrotica longicornis barberi*) | Col | +++ |
| Southern corn rootworm (*Diabrotica undecimpunctata howardi*) | Col | – |
| Colorado potato beetle (*Leptinotarsa decemlineata*) | Col | – |
| Yellow mealworm (*Tenebrio molitor*) | Col | – |
| European corn borer (*Ostrinia nubilalis*) | Lep | – |
| Tobacco budworm (*Heliothis virescens*) | Lep | – |
| Tobacco hornworm (Manduca sexta) | Lep | – |
| Beet armyworm (Spodoptera exigua) | Lep | – |
| Black cutworm (Agrotis ipsilon) | Lep | – |
| Northern house mosquito (*Culex pipiens*) | Dip | – |

The newly discovered *B. cereus* strain AB78 showed a significantly different spectrum of insecticidal activity as compared to known coleopteran active δ-endotoxins from Bt. In particular, AB78 showed more selective activity against beetles than known coleopteran-active Bt strains in that it was specifically active against Diabrotica spp. More specifically, it was most active against *D. virgifera virgifera* and *D. longicornis barberi* but not *D. undecimpunctata howardi.*

A number of Bacillus strains were bioassayed for activity during vegetative growth (Table 15) against western corn rootworm. The results demonstrate that AB78 is unique in that activity against western corn rootworm is not a general phenomenon.

TABLE 15

Activity of culture supernatants from various Bacillus spp. against western corn rootworm

| Bacillus strain | Percent WCRW mortality |
|---|---|
| *B. cereus* AB78 (Bat. 1) | 100 |
| *B. cereus* AB78 (Bat. 2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis isrealensis* | 24 |
| Water Control | 4 |

Specific activity of AB78 against western corn rootworm is provided in Table 16.

TABLE 16

Activity of AB78 culture supernatant against neonate western corn rootworm

| Culture supernatant concentration ($\mu$l/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 $\mu$l of culture supernatant per ml of western corn rootworm diet.

The cell pellet was also bioassayed and had no activity against WCRW. Thus, the presence of activity only in the supernatant indicates that this VIP is an exotoxin.

EXAMPLE 4

Isolation and Purification of Corn Rootworm Active Proteins from AB78.

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

Sequence Analysis of the Corn Rootworm Active Protein

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be: NH2-Lys-Arg-Glu-Ile-Asp-Glu-Asp-Thr-Asp-Thr-Asx-Gly-Asp-Ser-Ile-Pro-(SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

Construction of DNA Probe

An oligonucleotide probe for the region of the gene encoding amino acids 3–9 of the N-terminal sequence (Example 5) was generated. The probe was synthesized based on the codon usage of a *Bacillus thuringiensis* (Bt) δ-endotoxin gene. The nucleotide sequence

5'-GAA ATT GAT CAA GAT ACN GAT-3' (SEQ ID NO:9)

was used as a probe in Southern hybridizations. The oligonucleotide was synthesized using standard procedures and equipment.

EXAMPLE 7

Isoelectric Point Determination of the Corn Rootworm Active Protein

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR Data on AB78

PCR analysis (See, for example U.S. patent application Ser. No. 08/008,006; and, Carozzi et al. (1991) *Appl. Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

Bacillus insecticidal crystal protein gene primers tested by PCR against AB78 DNA.

| Primers Tested | Product Produced |
|---|---|
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |
| CryIC specific | Negative |
| CryIE specific | Negative |
| 2 sets specific for *B. sphaericus* | Negative |
| 2 sets specific for CryIV | Negative |
| Bacillus control (PI-PLC) | Positive |

EXAMPLE 9

Cosmid Cloning of Total DNA from *B. Cereus* Strain AB78

The VIP1A(a) gene was cloned from total DNA prepared from strain AB78 as follows:

Isolation of AB78 DNA was as follows:

1. Grow bacteria in 10 ml L-broth overnight. (Use 50 ml sterile centrifuge tube)
2. Add 25 ml of fresh L-broth and ampicillin (30 μg/ml).
3. Grow cells 2–6 h. at 30° C. with shaking;
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 μl 20% SDS and 400 μl Proteinase K stock (20 mg/ml). Incubate at 37° C.
8. Add 200 μl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h.
14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.

16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:

A. Sau 3A partial digestion of the AB78 DNA.

B. Preparation of vector DNA

C. Ligation and packaging of DNA

D. Tittering the cosmid library
1. Start a culture of HB101 cells by placing 50 ml of an overnight culture in 5 mls of TB with 0.2% maltose. Incubate 3.5 hrs. at 37° C.
2. Spin out cells and resuspend in 0.5 ml 10 mM MgSO$_4$.
3. Add together: 100 µl cells 100 µl diluted packaging mixture 100 µl 10 mM MgSO$_4$ 30 µl TB
4. Adsorb at room temperature for 30 minutes with no shaking.
5. Add 1 ml TB and mix gently. Incubate 30 minutes at 37° C.
6. Plate 200 µl onto L-amp plates. Incubate at 37° C overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
|---|---|
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

EXAMPLE 10

Identification of a 6 KB Region Active against Western Corn Rootworm

DNA from P3-12 was partially digested with restriction enzyme Sau 3A, and ligated into the *E. coli* vector pUC 19 and transformed into *E. coli*. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the *E. coli*-Bacillus shuttle vector pHT 3101 (Lereclus, D. et al., *FEMS Microbiology Letters* 60:211–218 (1989)) to yield pCIB6201. This construct confers anti-western corn rootworm activity upon both Bacillus and *E.coli* strains, in either orientation. pCIB6022 contains this same 6 kb Cla I fragment in pBluescript SK(+) (Stratagene), produces equivalent VIP1A(a) protein (by western blot), and is also active against western corn rootworm.

The nucleotide sequence of pCIB6022 was determined by the dideoxy termination method of Sanger et al., *Proc. Natl. Acad. Sci. USA,* 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in FIG. 1. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11

Functional Dissection of the VIP1A(a) DNA REGION

To confirm that the VIP1A(a) open reading frame (ORF) is necessary for insecticidal activity a translational frameshift mutation was created in the gene. The restriction enzyme Bg1 II recognizes a unique site located 857 bp into the coding region of VIP1A(a). pCIB6201 was digested with Bg1 II, and the single-stranded ends filled-in with DNA polymerase (Klenow fragment) and dNTPS. The plasmid was re-ligated and transformed into *E. coli*. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm. (See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) regions in combination with VIP1A (a), to confer maximal western corn rootworm activity. (See FIG. 1)

EXAMPLE 12

AB78 Antibody Production

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3x63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on nitrocellulose in DMSO for ELISA screening:

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 μl of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:
1. Coat with AB78/DMSO in BBS. Incubate overnight at 4° C.
2. Wash plate 3× with 1×ELISA wash buffer.
3. Block (1% BSA & 0.05% Tween 20 in PBS) for 30 minutes at Room Temperature.
4. Wash plate 3× with 1×ELISA wash buffer.
5. Add rat serum. Incubate 1.5 hours at 37° C.
6. Wash plate 3× with 1×ELISA wash buffer.
7. Add goat anti-rat at a concentration of 2 μg/ml in ELISA diluent. Incubate 1 hr. at 37° C.
8. Wash plate 3× with 1×ELISA wash buffer.
9. Add rabbit anti-goat alkaline phosphatase at 2 μg/ml in ELISA diluent. Incubate 1 hr. at 37° C.
10. Wash 3× with 1×ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

EXAMPLE 13

Activation of Insecticidal Activity of Non-Active BT Strains with AB78 VIP Clones Adding pCIB6203 together with a 24 h culture (early to mid-log phase) supernatant from Bt strain GC91 produces 100% mortality in *Diabrotica virgifera virgifera*. Neither pCIB6203 nor GC91 is active on *Diabrotica virgifera virgifera* by itself. Data are shown below:

| Test material | Percent Diabrotica mortality |
| --- | --- |
| pCIB6203 | 0 |
| GC91 | 16 |
| pCIB6203 + GC91 | 100 |
| Control | 0 |

EXAMPLE 14

Isolation and Biological Activity of *B. cereus* AB81

A second *B. cereus* strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
|---|---|
| Ostrinia nubilalis | 0 |
| Agrotis ipsilon | 0 |
| Diabrotica virgifera virgifera | 55 |

EXAMPLE 15

Isolation and Biological Activity of B. thuringiensis AB6

A B. thuringiensis strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
|---|---|
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal activity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16

Isolation and Biological Characterization of B. Thuringiensis AB88

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| Insect species tested | Order | Percent mortality of culture supernatant | |
|---|---|---|---|
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virgifera | Coleoptera | 0 | 5 |

The reduction of insecticidal activity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against Agrotis ipsilon.

EXAMPLE 17

Purification of VIPS from strain AB88

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromatography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins.

anion exchange fraction 23 (smaller): xEPFVSAxxxQxxx (SEQ ID NO:10)

anion exchange fraction 28 (larger): xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18

Characterization of AB88 VIP

Fractions containing the various lepidopteran active vegetative proteins were generated as described in Example 17.

Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa |
| | MDNNPNINE |
| | (SEQ ID NO: 14) |
| 80 kDa | 80 kDa |
| MNKNNTKLPTRALP | MDNNPNINE |
| (SEQ ID NO: 12) | (SEQ ID NO: 15) |
| | 60 kDa |
| | MNVLNSGRTTI |
| | (SEQ ID NO: 16) |
| 35 kDa | |
| ALSENTGKDGGYIVP | |
| (SEQ ID NO: 13) | |

The *Ostrinia nubilalis* activity is due to a 60 kDa VIP and the *Spodoptera frugperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A

Isolation and Biological Activity of *B. Thuringiensis* AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| *Ostrinia nubilalis* | 100 |
| *Agrotis ipsilon* | 100 |
| *Diabrotica virgifera virgifera* | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

EXAMPLE 18B

Cloning of the VIP3A(a) and VIP3A(b) Genes which Encode Proteins Active against Black Cutworm DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis ipsilon* (black cutworm). Four out of 400 recombinant clones were positive. Insect bioassays of the positive recombinants exhibited toxicity to black cutworm larvae comparable to that of AB88 or AB424 supernatants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C

Identification of Novel VIP3-like Genes by Hybridization

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D

Characterization of A *B. thuringiensis* Strain M2194 containing a Cryptic VIP3-like Gene A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19

Isolation and Biological Activity of other Bacillus SP.

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
| --- | --- | --- |
| AB6 | + | 100 |
| AB53 | – | 80 |
| AB88 | + | 100 |
| AB195 | – | 60 |
| AB211 | – | 70 |
| AB217 | – | 83 |
| AB272 | – | 80 |
| AB279 | – | 70 |
| AB289 | + | 100 |
| AB292 | + | 80 |
| AB294 | – | 100 |
| AB300 | – | 80 |
| AB359 | – | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
| --- | --- | --- |
| AB52 | – | 50 |
| AB59 | – | 71 |
| AB68 | + | 60 |
| AB78 | – | 100 |
| AB122 | – | 57 |
| AB218 | – | 64 |
| AB256 | – | 64 |

Isolates AB59 and AB256 have been deposited in the Agricultural Research Service, Patent Culture Collection (NRRL), Northern Regional Research Center, 1815 North University Street, Peoria, Ill. 61604, USA, and given the Accession Numbers NRRL B-21228 and NRRL B-21230, respectively.

EXAMPLE 20

Identification of Novel VIP1/VIP2 like Genes by Hybridization

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis* var *tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21

Cloning of a VIP1A(a)/VIP2A(a) Homolog from *Bacillus thuringiensis* var. *tenebrionis*

Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)VIP2A(a) like sequences. DNA from Bt strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)VIP2A(a) homologs. In contrast, *Bacillus thuringiensis* var. *tenebrionis* (Btt) contained sequences that hybridized to the VIP1A(a)/VIP2A(a) region. Further analysis confirmed that Btt contains VIP1A (a)/VIP2A(a) like sequences.

To characterize the Btt homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria, Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria, Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77% amino acid identity to VIP1A(a) from AB78. An alignment of these two VIP1 proteins is provided in Table 20. The alignment shown in Table 20 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20) of the two proteins exhibit 91% identity, while the carboxy-terminal third (from aa 619–833 of VIP1A(b)) exhibit only 35% identity.

Western blot analysis indicated that *Bacillus thuringiensis* var. *tenebrionis* (Btt) produces both VIP1A(a) like and VIP2A(a) like proteins. However, these proteins do not appear to have activity against western corn rootworm. Bioassay for activity against western corn rootworm was performed using either a 24 h culture supernatant from Btt or *E. coli* clone pCIB7100 (which contains the entire region of the VIP1A(a)/VIP2A(a) homologs). No activity against western corn rootworm was detected in either case.

Given the similarity between the VIP2 proteins from Btt and AB78, the ability of VIP2A(b) from Btt to substitute for VIP2A(a) from AB78 was tested. Cells containing pCIB6206 (which produces AB78 VIP1A(a) but not VIP2A(a) protein) were mixed with Btt culture supernatant, and tested for activity against western corn rootworm. While neither Btt culture supernatant nor cells containing pCIB6206 had activity on WCRW, the mixture of Btt and pCIB6206 gave high activity against WCRW. Furthermore, additional bioassay showed that the Btt clone pCIB7100, which contains the Btt VIP1A(b)/VIP2A(b) genes in *E. coli*, also confers activity against WCRW when mixed with pCIB6206. Thus, the VIP2A(b) protein produced by Btt is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences from *Bacillus thuringiensis* var. *tenebrionis*
(VIP2A(b)) vs. AB78 (VIP2A(a))

```
Btt    1  M Q R M E G K L F V V S K T L Q V V T R T V L L S T V Y S I T L L N N V V I K A D Q L N I N S Q S K  50   SEQ ID NO: 20
          | . | | | | | | | : | | | . | | | | | : | | | | | | | | : | | . | | | | | | | | | : | | | | | | | | |
AB78   1  M K R M E G K L F M V S K K L Q V V T K T V L L S T V F S I S L L N N E V I K A E Q L N I N S Q S K  50   SEQ ID NO: 2

51 Y T N L Q N L K I P D N A E D F K E D K G K A K E W G K E K G E E W R P P A T E K G E M N N F L D N  100
          | | | | | | | | | . | . . | | | | | | | | : | | | | | | | | | | | | : . | | :   . | | | | | . | | | | | | |
       51 Y T N L Q N L K I T D K V E D F K E D K E K A K E W G K E K E K E W K L T A T E K G K M N N F L D N  100

101 K N D I K T N Y K E I T F S M A G S C E D E I K D L E E I D K I F D K A N L S S S I I T Y K N V E P  150
          | | | |   | | | | | | | | | | | | | | | | | | | | | | | | . | | | | : | | | . | | | . | | | | | | | | | | |
      101 K N D I X T N Y K E I T F S M A G S F E D E I K D L K E I D K M F D K T N L S N S I I T Y K N V E P  150

151 A T I G F N K S L T E G N T I N S D A M A Q F K E Q F L G K D M K F D S Y L D T H L T A Q Q V S S K  200
          . | | | | | | | | | | | | | | | | | | | | | | | | | | | : : | : | | | | | | | | | | | | | | | | | | |
      151 T T I G F N K S L T E G N T I N S D A M A Q F K E Q F L D R D I K F D S Y L D T H L T A Q Q V S S K  200
```

TABLE 19-continued

Alignment of VIP2 Amino Acid Sequences from *Bacillus thuringiensis* var. *tenebrionis* (VIP2A(b)) vs. AB78 (VIP2A(a))

```
201 K R V I L K V T V P S G K G S T T P T K A G V I L N N N E Y K M L I D N G Y V L H V D K V S K V V K 250
    . | | | | | | | | | | | | | | | | | | | | | | | | | . | | | | | | | | | | : : | | | | | | | | | |
201 E R V I L K V T V P S G K G S T T P T K A G V I L N N S E Y K M L I D N G Y M V H V D K V S K V V K 250

251 K G M E C L Q V E G T L K K S L D F K N D I N A E A H S W G M K I Y E D W A K N L T A S Q R E A L D 300
    | | : | | | | : | | | | | | | | | | | | | | | | | | | | | | : | | | : | | . | | | | | | |
251 K G V E C L Q I E G T L K K S L D F K N D I N A E A H S W G M K N Y E E W A K D L T D S Q R E A L D 300

301 G Y A R Q D Y K E I N N Y L R N Q G G S G N E K L D A Q L K N I S D A L G K K P I P E N I T V Y R W 350
    | | | | | | | | | | | | | | | | | | | | | | | | : | | | | | | | | | | | | | | | | | | | | | | | |
301 G Y A R Q D Y K E I N N Y L R N Q G G S G N E K L D A Q I K N I S D A L G K K P I P E N I T V Y R W 350

351 C G M P E F G Y Q I S D P L P S L K D F E E Q F L N T I K E D K G Y M S T S L S S E R L A A F G S R 400
    | | | | | | | | | | | | | | | | | | | | | | | | | | | | | | | | | | | | | | | | | | | | | | | | |
351 C G M P E F G Y Q I S D P L P S L K D F E E Q F L N T I K E D K G Y M S T S L S S E R L A A F G S R 400

401 K I I L R L Q V P K G S T G A Y L S A I G G F A S E K E I L L D K D S K Y H I D K A T E V I I K G V 450
    | | | | | | | | | | | | | | | | | | | | | | | | | | | | | | | | | | | | | | | . | | | | | | | |
401 K I I L R L Q V P K G S T G A Y L S A I G G F A S E K E I L L D K D S K Y H I D K V T E V I I K G V 450

451 K R Y V V D A T L L T N 462
    | | | | | | | | | | | |
451 K R Y V V D A T L L T N 462
```

TABLE 20

Alignment of VIP1 Amino Acid Sequences from *Bacillus thuringiensis* var. *tenebrionis* (VIP1A(b)) vs. AB78 (VIP1A(a))

```
Btt    1 M K N M K K K L A S V V T C M L L A P M F L N G N V N A V N A D S K I N Q I S T T Q E N Q Q K E M D 50   SEQ ID NO: 21
         | | | | | | | | | | | | | | | | | | | | | | | | | | . | | | | | | | | . | | | | | | | |
Ab78   1 M K N M K K K L A S V V T C T L L A P M F L N G N V N A V Y A D S K T N Q I S T T Q K N Q Q K E M D 50   SEQ ID NO: 5

51 R K G L L G Y Y F K G K D F N N L T M F A P T R D N T L M Y D Q Q T A N A L L D K K Q Q E Y Q S I R 100
         | | | | | | | | | | | | | | . | | | | | | | | | . | | : | | | | | | | | | | | | | | | | | |
      51 R K G L L G Y Y F K G K D F S N L T M F A P T R D S T L I Y D Q Q T A N K L L D K K Q Q E Y Q S I R 100

101 W I G L I Q R K E T G D F T F N L S K D E Q A I I E I D G K I I S N K G K E K Q V V H L E K E K L V 150
         | | | | | | . | | | | | | | | | . | | | | | | | | : | | | | | | | | | | | | | | | | | : | | |
     101 W I G L I Q S K E T G D F T F N L S E D E Q A I I E I N G K I I S N K G K E K Q V V H L E K G K L V 150

151 P I K I E Y Q S D T K F N I D S K T F K E L K L F K I D S Q N Q S Q Q V Q . . . L R N P E F N K K E 197
         | | | | | | | | | | | | | | | | | | | | | | | | | | | | | | . | | | |    | | | | | | | | |
     151 P I K I E Y Q S D T K F N I D S K T F K E L K L F K I D S Q N Q P Q Q V Q Q D E L R N P E F N K K E 200

198 S Q E F L A K A S K T N L F K Q K M K R D I D E D T D T D G D S I P D L W E E N G Y T I Q N K V A V 247
         | | | | | | | : | | . | | | . | | | | | : | | | | | | | | | | | | | | | | | | | | | | | : : | |
     201 S Q E F L A K P S K I N L F T Q K M K R E I D E D T D T D G D S I P D L W E E N G Y T I Q N R I A V 250

248 K W D D S L A S K G Y T K F V S N P L D S H T V G D P Y T D Y E K A A R D L D L S N A K E T F N P L 297
         | | | | | | | | | | | | | | | | : | | | | | | | | | | | | | | | | | | | | | | | | | | | | | |
     251 K W D D S L A S K G Y T K F V S N P L E S H T V G D P Y T D Y E K A A R D L D L S N A K E T F N P L 300

298 V A A F P S V N V S M E K V I L S P N E N L S N S V E S H S S T N W S Y T N T E G A S I E A G G G P 347
         | | | | | | | | | | | | | | | | | | | | | | | | | | | | | | | | | | | | | | | | : | | | | |
     301 V A A F P S V N V S M E K V I L S P N E N L S N S V E S H S S T N W S Y T N T E G A S V E A G I G P 350

348 L G L S F G V S V T Y Q H S E T V A Q E W G T S T G N T S Q F N T A S A G Y L N A N V R Y N N V G T 397
         | : | | | | | | . | | | | | | | | | | | | | | | | | | | | | | | | | | | | | | | | | | | | | |
     351 K G I S F G V S V N Y Q H S E T V A Q E W G T S T G N T S Q F N T A S A G Y L N A N V R Y N N V G T 400

398 G A I Y D V K P T T S F V L N N N T I A T I T A K S N S T A L R I S P G D S Y P E I G E N A I A I T 447
         | | | | | | | | | | | | | | | | : | | | | | | | | | | | | | | | . | | | | : | | | . | : | : | | | |
     401 G A I Y D V K P T T S F V L N N D T I A T I T A K S N S T A L N I S P G E S Y P K K G Q N G I A I T 450

448 S M D D F N S H P I T L N K Q Q V N Q L I N N K P I M L E T D Q T D G V Y K I R D T H G N I V T G G 497
         | | | | | | | | | | | | | . | | : . | : | | | | : | | | | : | | | | | | | | | : | | | | | | | | |
     451 S M D D F N S H P I T L N K K Q V D N L L N N K P M M L E T N Q T D G V Y K I K D T H G N I V T G G 500

498 E W N G V T Q Q I K A K T A S I I V D D G K Q V A E K R V A A K D Y G H P E D K T P P L T L K D T L 547
         | | | | | . | | | | | | | | | | | | | | . . | | | | | | | | | | | | | : : | | | | | . | | | | . |
     501 E W N G V I Q Q I K A K T A S I I V D D G E R V A E K R V A A K D Y E N P E D K T P S L T L K D A L 550
```

TABLE 20-continued

Alignment of VIP1 Amino Acid Sequences from Bacillus thuringiensis var. tenebrionis
(VIP1A(b)) vs. AB78 (VIP1A(a))

```
     548 K L S Y P D E I K E T N G L L Y Y D D K P I Y E S S V M T Y L D E N T A K E V K K Q I N D T T G K F 597
         | | | | | | | | | | . : | | | | | . : | | | | | | | | | | | | | | | | | | | . | | : | | | | | | |
     551 K L S Y P D E I K E I E G L L Y Y K N K P I Y E S S V M T Y L D E N T A K E V T K Q L N D T T G K F 600

Btt  598 K D V N H L Y D V K L T P K M N F T I K M A S L Y D G A E N N H N S L G T W Y L T Y N V A G G N T G 647 SEQ ID NO: 21
         | | | . | | | | | | | | | | | . | | | : .   | | | . | | . | . | | : | . |   |   | . | | | . |
Ab78 601 K D V S H L Y D V K L T P K M N V T I K L S I L Y D N A E S N D N S I G K W T N T N I V S G G N N G 650 SEQ ID NO: 5

648 K R Q Y R S A H S C A H V A L S S E A K K K L N Q N A N Y Y L S M Y M K A D S T T E P T I E V A G E 697
         | : | | . | . : .   | : : . | . . : | . . | | | . |   : | | : | : | | | . : . . | : . . | . : . | |
     651 K K Q Y S S N N P D A N L T L N T D A Q E K L N K N R D Y Y I S L Y M K S E K N T Q C E I T I D G E 700

698 K S A I T S K K V K L N N Q N Y Q R V D I L V K N S E R N P M D K I Y I R G N G T T N V Y G D D V T 747
         : | | . | . | . : | . : | | . | : | | : . . |   . . | | : . . : . | : . | : . . . . : :   | | : .
     701 I Y P I T T K T V N V N K D N Y K R L D I I A H N I K S N P I S S L H I K T N D E I T L F W D D I S 750

748 I P E V S A I N P A S L S D E E I Q E I F K D S T I E Y G N P S F V A D A V T F K . . . . . . . . . 788
         | . . : | . . | . | . . | . | . | | . : | : .     . | . . . : : .   : : . . .   . . : .
     751 I T D V A S I K P E N L T D S E I K Q I Y S R Y G I K L E D G I L I D K K G G I H Y G E F I N E A S 800

789 . N I K P L Q N Y V K E Y E I Y H K . . . . . . . S H R Y E K K T V F D I M G V H Y E Y S I A R E Q 830
         | | . | | | | | | . . | . :   . .           | . . | . . . . : : .     . : . : : : .   . . .
     801 F N I E P L Q N Y V T K Y K V T Y S S E L G Q N V S D T L E S D K I Y K D G T I K F D F T K Y S K N 850

831 K K A 833
         . . :
     851 E Q G 853
```

EXAMPLE 22

Fusion of VIP Proteins to make a Single Polypeptide

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the $NH_2$ terminus of the fusion protein, or they can be fused to produce the larger of the polypeptides as the $NH_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example patent application U.S. Ser. No. 07/951,715 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-<u>CCCGGG</u> CCT TCT ACT CCC CCA ACT CCC TCT CCT AGC ACG CCT CCG ACA CCT AGC <u>GAT ATC GGA TC C</u>-3' (SEQ ID NO:48). Oligonucleotides were synthesized to represent both the upper and lower strands and cloned into a pUC vector following hybridization and phosphorylation using standard procedures. The stop codon in VIP2A(a) was removed using PCR and replaced by the BglII restriction site with a SmaI site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23

Targeting of VIP2 to Plant Organelles

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263:15104–15109 (1988)). These signal sequences can be fused to heterologous gene products such as VIP2 to effect the import of those products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13:411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad. Sci. USA 82:6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al Mol. Gen. Genet. 205:446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell,* 1:381–390 (1989), Denecke et al., *The Plant Cell,* 2:51–59 (1990). Amino-terminal sequences have been identified that are responsible for targeting to the ER, the apoplast, and extracellular secretion from aleurone cells (Koehler & Ho, Plant Cell 2:769–783 (1990)).

The presence of additional signals are required for the protein to be retained in the endoplasmic reticulum or the vacuole. The peptide sequence KDEL/HDEL at the carboxy-terminal of a protein is required for its retention in the endoplasmic reticulum (reviewed by Pelham, *Annual Review Cell Biol.,* 5:1–23 (1989). The signals for retention of proteins in the vacuole have also been characterized. Vacuolar targeting signals may be present either at the amino-terminal portion, (Holwerda et al., *The Plant Cell,* 4:307–318 (1992), Nakamura et al., *Plant Physiol.,* 101:1–5 (1993)), carboxy-terminal portion, or in the internal sequence of the targeted protein. (Tague et al., *The Plant Cell,* 4:307–318 (1992), Saalbach et al. *The Plant Cell,* 3:695–708 (1991)). Additionally, amino-terminal sequences in conjunction with carboxy-terminal sequences are responsible for vacuolar targeting of gene products (Shinshi et al. Plant Molec. Biol. 14:357–368 (1990)). Similarly, proteins may be targeted to the mitochondria or plastids using specific carboxy terminal signal peptide fusions (Heijne et al., *Eur. J. Biochem.,* 180:535–545 (1989), Archer and Keegstra, *Plant Molecular Biology,* 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLSGAAGVHCL (SEQ ID NO:25) from U.S. patent application Ser. No. 08/267,641 or any other described in the literature (Itirriaga et al., *The Plant Cell,* 1:381–390 (1989), Denecke, et al., *The Plant Cell*, 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant Cell*, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-<u>GGATCC</u>ACC ATG GGC TGG AGC TGG ATC TTC CTG TTC CTG CTG AGC GGC G<u>CC GCGG</u> GGC GTG CAC TGC <u>CTGCAG</u>-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-<u>CCG CGG</u> GCG TGC ACT GCC TCA GCA GCA GCA GCT TCG CCG ACA GCA ACC CCA TCC GCG TGA CCG ACC GCG CCG CCA GCA C<u>CC TGC AG</u>-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A

Removal of Bacillus Secretion Signal from VIP1A (a) and VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucleotide position 507. A 527 bp amplification product was obtained containing the restriction sites BamHI at the 5' end and HindIII site at the 3' end. The amplification product was cloned into a T- vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A (a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC -3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T-vector, sequenced and ligated to a BamHI/HindIII digested root-preferred promoter cassette containing the maize optimized VIP2A(a). The construct obtained was designated pCIB5527. The maize optimized coding region for VIP2A (a) with the Bacillus secretion signal removed is disclosed as SEQ ID NO:39 and the encoded protein is disclosed as SEQ ID NO:40.

EXAMPLE 24

Construction and Cloning of the VIP1A(a) and VIP2A(a) Maize Optimized Genes

Design: The maize optimized genes were designed by reverse translation of the native VIP1A(a) and VIP2A(a)

protein sequences using codons that are used most often in maize (Murray et al., *Nucleic Acid Research,* 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever necessary, nucleotides were changed to decrease the stability of the secondary structure without changing the amino acid sequence of the protein. A plant ribosomal binding site consensus sequence, TAAACA<u>ATG</u> (Joshi et al., *Nucleic Acid Res.,* 15:6643–6653 (1987)) or eukaryotic ribosomal binding site concensus sequence CCACC<u>ATG</u> (Kozak, *Nucleic Acid Research,* 12:857–872 (1984)) was inserted at the translational start codon of the gene.

Cloning: Oligos were synthesized by IDT Inc., and were supplied as lyophilized powders. They were resuspended at a concentration of 200 $\mu$M. To 30 $\mu$l of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in $dH_2O$ at a concentration of 2.5 $\mu$M. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation: Homologous double stranded oligo pairs were obtained by mixing 5 $\mu$l of the upper and of the lower oligo for each oligo pair with buffer containing 1×polynucleotide kinase (PNK) buffer (70 mM Tris-HCl (pH 7.6), 10 mM $MgCl_2$, 5 mM dithiothreitol (DTT)), 50 mM KCl, and 5% formamide in a final volume of 50 $\mu$l. The oligos were boiled for 10 minutes and slow cooled to 37° C. or room temperature. 10 $\mu$l was removed for analysis on a 4% agarose in a TAE buffer system (Metaphore®; FMC). Each hybridized oligo pair was kinased by the addition of ATP at a final concentration of 1 mM, BSA at a final concentration of 100 $\mu$g per ml and 200 units of polynucleotide kinase and 1 $\mu$l of 10×PNK buffer in a volume of 10 $\mu$l. Following hybridization and phosphorylation, the reaction was incubated at 37° C. for 2 hours to overnight. 10 $\mu$l of each of the oligo pairs for a particular fragment, were mixed in a final volume of 50 $\mu$l. The oligo pairs were hybridized by heating at 80° C. for 10 minutes and slow cooling to 37° C. 2 $\mu$l of oligos was mixed with about 100 ng of an appropriate vector and ligated using a buffer containing 50 mM Tris-HCl (pH 7.8), 10 mM $MgCl_2$, 10 mM DTT, 1 mM ATP. The reaction was incubated at room temp. for 2 hours to overnight and transformed into DH5$\alpha$ strain of *E.coli*, plated on L-plates containing ampicillin at a concentration of 100 $\mu$g/ml using standard procedures. Positive clones were further characterized and confirmed by PCR miniscreen described in detail in U.S. patent application Ser. No. 07/951,715 using the universal primers "Reverse" and M13 "−20" as primers. Positive clones were identified by digestion of DNA with appropriate enzymes followed by sequencing. Recombinants that had the expected DNA sequence were then selected for further work.

PCR Amplification and cloning Into T-vector:

PCR amplification was carried out by using a mixture of all the oligomers that represented the upper and the lower strand of a particular fragment (final concentration 5 mM each) as template, specific end primers for the particular fragment (final concentration 2 $\mu$M) 200 $\mu$M of each dATP, dTTP, dCTP and dGTP, 10 mM Tris-HCl (pH 8.3), 50 mM KCl, 1.5 mM $MgCl_2$,0.01% gelatin and 5 units of Taq polymerase in a final reaction volume of 50 $\mu$l. The amplification reaction was carried out in a Perkin Elmer thermocycler 9600 by incubation at 95° C. for 1 min (1 cycle ), followed by 20 cycles of 95° C. for 45 sec., 50 ° C. for 45 sec., 72° C. for 30 sec. Finally the reaction was incubated for 5 min at 72° C. before analyzing the product. 10 $\mu$l of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research.* 19:1154 (1991). pBluescriptsk+ (Stratagene®, Calif.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. patent application Ser. No. 08/017,209, herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC 19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

EXAMPLE 25

NAD Affinity Chromatography

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon –10. Yield is typically about 7–15 µg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

EXAMPLE 26

Expression of Maize Optimized VIP1A(a) and VIP2A(a)

*E. coli* strains containing different plasmids comprising VIP genes were assayed for expression of VIPs. *E. coli* strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

Expression of VIPs in *E. coli*

| Extract of *E. coli* Strain Harboring Indicated Plasmid | Assay No. 1 | Assay No. 2 | Protein Detected |
|---|---|---|---|
| | % Mortality | | |
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed 10 by a standard direct gene transfer method using approximately 75 μg plasmid DNA and PEG-40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

Expression of VIPs in Plant Protoplasts

| Extracts Tested | Assay No. 1 | Assay No. 2 | Protein Detected |
|---|---|---|---|
| | % Mortality | | |
| No DNA Control | 27 | 10 | no |
| pCIB552I (p) (maize optimized VIP1A(a)) | 20(0) | 30 | yes |
| pCIB5522 (p) (maize optimized VIP2A(a)) | 20(0) | 20 | yes |
| Extracts pCIB5521 (p) + pCIB5522 (p) combined | 87(82) | 90 | |
| Extracts pCIB5521 (p) + pCIB5522 (e) combined | 100 | — | |
| Extracts pCIB5522 (p) + pCIB5521 (e) combined | 53(36) | — | |
| Extracts pCIB5521 (p) + pCIB6024 (e) combined | 100 | — | |
| Extracts pCIB5522 (p) + pCIB6206 (e) combined | 100 | — | |
| pCIB6024 (e) (native VIP2A(a)) | 0 | — | yes |
| pCIB6206 (e) (native VIP1A(a)) | 20 | — | yes |
| pCIB5521 + pCIB5522 (plasmids delivered by cotransformation) | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern, Regional Research Center, 1815 North University Street, Peoria, Ill. 61604, USA:

1. *E. coli* PL2 Accession No. NRRL B-21221N
2. *E. coli* pCIB6022 Accession No. NRRL B-21222
3. *E. coli* pCIB6023 Accession No. NRRL B-21223N
4. *Bacillus thuringiensis* HD73-78VIP Accession No. NRRL B-21224
5. *Bacillus thuringiensis* AB88 Accession No. NRRL B-21225
6. *Bacillus thuringiensis* AB359 Accession No. NRRL B-21226
7. *Bacillus thuringiensis AB*289 Accession No. NRRL B-21227
8. Bacillus sp. AB59 Accession No. NRRL B-21228
9. Bacillus sp. AB294 Accession No. NRRL B-21229
10. Bacillus sp. AB256 Accession No. NRRL B-21230
11. *E. coli* P5-4 Accession No. NRRL B-21059

12. *E. coli* P3-12 Accession No. NRRL B-21061
13. *Bacillus cereus* AB78 Accession No. NRRL B-21058
14. *Bacillus thuringiensis* AB6 Accession No. NRRL B-21060
15. *E. coli* pCIB6202 Accession No. NRRL B-21321
16. *E. coli* pCIB7100 Accession No. NRRL B-21322
17. *E. coli* pCIB7101 Accession No. NRRL B-21323
18. *E. coli* pCIB7102 Accession No. NRRL B-21324
19. *E. coli* pCIB7102 Accession No. NRRL B-21325
20. *E. coli* pCIB7104 Accession No. NRRL B-21422
21. *E. coli* pCIB7107 Accession No. NRRL B-21423
22. *E. coli* pCIB7108 Accession No. NRRL B-21438
23. *Bacillus thuringiensis* AB424 Accession No. NRRL B-21439

Although the foregoing invention has been described in some detail by way of illustration and example for purposes of clarity of understanding, it will be obvious that certain changes and modifications may be practiced within the scope of the appended claims.

What is claimed is:

1. A substantially pure nucleotide sequence which encodes an insecticidal protein secreted during the vegetative growth phase of Bacillus spp. and components thereof, wherein said protein is not the mosquitocidal toxin from *B. spaericus* SSII-1.

2. The nucleotide sequence of claim 1 wherein said sequence has been optimized for expression in a microorganism.

3. The nucleotide sequence of claim 1, wherein said sequence is optimized for expression in a plant.

4. The nucleotide sequence of claim 1, wherein said sequence lacks the Bacillus secretion signal.

5. The nucleotide sequence of claim 1, wherein said Bacillus is selected from a *Bacillus thuringensis* and *B. cereus*.

6. The nucleotide sequence of claim 1, wherein said Bacillus is *Bacillus cereus* having Accession No. NRRL B-21058.

7. The nucleotide sequence of claim 5, wherein said sequence is optimized for expression in a plant.

8. The nucleotide sequence of claim 6, wherein said sequence is optimized for expression in a plant.

9. A nucleotide sequence encoding an insecticidal protein, wherein said sequence is selected from the group consisting of SEQ ID NO:4, SEQ ID NO:6, SEQ ID NO:17, SEQ ID NO:18, SEQ ID NO:24, SEQ ID NO:26, SEQ ID NO:27, SEQ ID NO:28, SEQ ID NO:30, SEQ ID NO:31, SEQ ID NO:35, SEQ ID NO:39, SEQ ID NO:42 and SEQ ID NO:45.

10. A nucleotide sequence encoding an insecticidal protein, wherein said protein has the sequence selected from the group consisting of SEQ ID NO:7, SEQ ID NO:5, SEQ ID NO:2, SEQ ID NO:20, SEQ ID NO:21, SEQ ID NO:29, SEQ ID NO:32, SEQ ID NO:36, SEQ ID NO:40, SEQ ID NO:43, SEQ ID NO:46 and SEQ ID NO:50.

11. The nucleotide sequence of claim 10, wherein said sequence is optimized for expression in a plant.

* * * * *